United States Patent
Knobelsdorf et al.

(10) Patent No.: US 6,875,765 B2
(45) Date of Patent: Apr. 5, 2005

(54) ARYLSULFONAMIDE ETHERS, AND METHODS OF USE THEREOF

(75) Inventors: James Knobelsdorf, Knoblesville, IN (US); Sheryl Hays, Ann Arbor, MI (US); Charles J. Stankovic, Saline, MI (US); Kimberly S. Para, Ann Arbor, MI (US); Michael K. Connolly, Ypsilanti, MI (US); Paul Galatsis, Ann Arbor, MI (US); William Harter, Chelsea, MI (US); Aurash B. Shahripour, Ann Arbor, MI (US); Mark Stephen Plummer, Dexter, MI (US); Beth Lunney, San Diego, CA (US); Bernd Janssen, Marlborough, MA (US); Jay Bradford Fell, Longmont, CO (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/143,675

(22) Filed: May 10, 2002

(65) Prior Publication Data

US 2003/0096826 A1 May 22, 2003

Related U.S. Application Data

(60) Provisional application No. 60/289,950, filed on May 10, 2001.

(51) Int. Cl.[7] .................. C07D 295/14; C07D 407/12; C07D 487/04; A61K 31/495; A61P 19/02
(52) U.S. Cl. .............................. 514/238.2; 514/252.12; 514/303; 514/311; 514/312; 514/307; 514/331; 514/365; 514/368; 514/394; 514/400; 514/405; 514/562; 544/159; 544/399; 546/118; 546/149; 546/157; 546/172; 546/235; 548/154; 548/204; 548/308.7; 548/309.7; 548/338.5; 548/362.5; 562/430

(58) Field of Search .................. 514/238.2, 252.12, 514/303, 307, 311, 312, 331, 365, 388, 394, 400, 405, 562; 544/159, 199; 546/118, 149, 157, 172; 548/275, 154, 204, 308.7, 309.5, 338.5, 362.5; 562/430

(56) References Cited

FOREIGN PATENT DOCUMENTS

| WO | WO 98/16504 A3 | 4/1998 |
|---|---|---|
| WO | WO 98/16504 A2 | 4/1998 |

OTHER PUBLICATIONS

Wolff, Manfred E. "Burger's Medicinal Chemistry, 5ed, Part I", John Wiley & Sons, 1995, pp. 975–977.*

(Continued)

*Primary Examiner*—Thomas C. McKenzie
(74) *Attorney, Agent, or Firm*—Charles W. Ashbrook; Claude F. Purchase, Jr.

(57) ABSTRACT

The novel arylsulfonamide ether compounds, pharmaceutical compositions and uses thereof as inhibitors of interleukin-1β converting enzyme and other cysteine proteases in the ICE family are described. In one embodiment, the compound is described by the generalized structure:

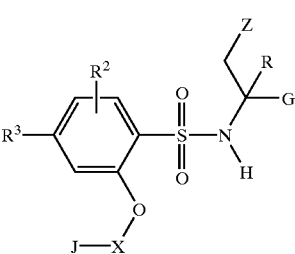

and pharmaceutically acceptable salts, esters, amides, and prodrugs thereof. In addition, methods of treating stroke, inflammatory diseases, septic shock, repurfusion injury, Alzheimer's disease, and shigellosis, using a compound of the invention or a pharmaceutical composition thereof, are described.

29 Claims, 30 Drawing Sheets

OTHER PUBLICATIONS

Banker, G.S. et al, "Modern Pharmaceutics, 3ed.", Marcel Dekker, New York, 1996, pp. 451 and 596.*

Randle, J.C. et al, Expert Opin. Investig. Drugs, 2001, vol. 10(7), pp. 1207–1209, Medline Abstract 11772244.*

Giegel, D.A. et al, Ann. Reports Med. Chem., 33, 1998, 183–192.*

Siegmund, B., Biochem. Pharmacol., vol. 64(1), 2002, pp. 1–8, Medline Abstract 12106600.*

Alnemri, E.S. et al. "Human ICE/CED–3 Protease Nomenclature." *Cell* 87:171 (Oct. 18, 1996).

Berge, S.M. et al. "Pharmaceutical Salts." *Journal of Pharmaceutical Sciences* 66(1):1–19 (Jan. 1977).

Ghayur, T. et al. "Caspase–1 Processes IFN–γ–inducing Factor and Regulates LPS–induced IFN–γ Production." *Nature* 386:619–23 (Apr. 10, 1997).

Harvey, R.G. et al. "Synthesis of the Dihydrodiol and Diol Epoxide Metabolites of Chrysene and 5–Methylcrhysene." *J. Org. Chem* 51:1407–1412 (1986).

Kouzai, Hiroaki et al. "Polymerization of 1–(1–Naphthyl)–1–Propyne by Nb and Ta Catalysts and Polymer Properties: Effects of the 1–Naphthyl Group." *Bull. Chem. Soc. Jpn.* 68:398–402 (1995).

Lai, G. et al. "A Concise Synthesis of a Benzimidazole Analogue of Mycophenolic Acid using a $BF_3$–$Et_2O$ catalyzed amino–Claisen rearrangement." *Tetrahedron Letters* 34(43):6849–52 (1993).

Thornberry, N.A. et al. "Interleukin–1β–converting enzyme and related proteases as potential targets in inflammation and apoptosis." *Perspectives in Drug Discovery and Design* 2:389–99 (1994).

* cited by examiner

Route A

Route B

Route E

From Route C

Route H

Route I

Route K

Route L

Route M

Route N

Route O

Route Q

ARYLSULFONAMIDE ETHERS, AND METHODS OF USE THEREOF

RELATED APPLICATIONS

This application claims priority to U.S. Provisional Patent Application No. 60/289,950 filed May 10, 2001 entitled "Arylsulfonamide Ethers, and Methods of Use Thereof". The entire content of the foregoing provisional patent application is incorporated herein by reference.

FIELD OF THE INVENTION

The invention relates to compounds that are inhibitors of interleukin-1β converting enzyme. The invention also relates to pharmaceutical compositions comprising a compound of the present invention. The invention also relates to methods of treating stroke, inflammatory diseases, septic shock, repurfusion injury, Alzheimer's disease, and shigellosis using a compound of the invention or a pharmaceutical composition thereof.

BACKGROUND OF THE INVENTION

Interleukin-1β converting enzyme (ICE) acts on pro-interleukin-1β (pro-IL-1β) to produce interleukin-1β (IL-1β), an inflammatory cytokine. In fact, ICE (also known as Caspase-1) regulates at least four cytokines: ICE activates IL-1β and IL-18, and indirectly regulates the production of IL-1α and IFNγ.

Several diseases are associated with abnormal interleukin-1 activity. Examples of diseases in which interleukin-1 is involved include, but are not limited to, inflammatory diseases such as rheumatoid arthritis and inflammatory bowel disease, and neuroinflammatory disorders such as stroke. Other diseases in which interleukin-1 is involved include septic shock, reperfasion injury, Alzheimer's disease, and shigellosis.

Agents that modulate IL-1β activity have been shown to have beneficial effects in vivo. For example, compounds that are interleukin-1 receptor antagonists have been shown to inhibit ischaemic and excitotoxic damage in rat brains. See, e.g., Relton, J. K. et al., *Brain Research Bulletin*, 1992; 29:243–246. Additionally, ICE inhibitors have been shown to reduce inflammation and pyrexia in rats. See Elford, P R et al., *British Journal of Pharmacology*, 1995; 115:601–606.

In addition to its effects on IL-1β production, ICE has been shown to play a role in the production of the inflammatory mediator interferon-γ (Ghayur et al., *Nature*, 1997; 386(6625):619–623). ICE processes the inactive pro-interferon-γ inducing factor (pro-IGIF) to active IGIF (also known as Interleukin-18), a protein which induces production of interferon-γ by T-cells and natural killer cells. Interferon-γ has been implicated in the pathogenesis of diseases such as inflammatory disorders and septic shock. Therefore, ICE inhibitors should also have beneficial effects in certain disease states due to their effects on interferon-γ.

Recently, the nomenclature of the cysteine proteases in the ICE family (also known as Caspases with ICE being known as Caspase-1) has been further defined. According to the nomenclature described in Alnemri et al., *Cell*, 1996; 87:171, members of this class of enzymes are referred to as Caspase-2 (also known as Ich-1); Caspase-3 (also known as CPP32, Yama, and apopain); Caspase-4 (also known as TX, Ich-2, and ICE rel-II; Caspase-5 (also known as ICE rel-III); Caspase-6 (also known as Mch2); Caspase-7 (also known as Mch3); Caspase-8 (also known as FLICE and Mch5); Caspase-9 (also known as ICE-LAP6 and Mch6); and Caspase-10 (also known as Mch4).

SUMMARY OF THE INVENTION

In certain embodiments, the compounds of the present invention are represented by generalized structure 1:

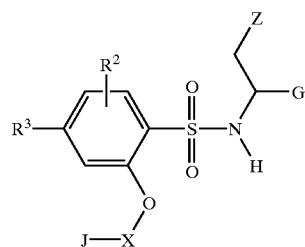

wherein

Z represents carboxylate, alkoxycarbonyl, aryloxycarbonyl, or cycloester;

G represents formyl, acyl, or —CN;

J represents optionally substituted naphthyl, benzimidazolyl, quinolinyl, isoquinolinyl, tetrahydroquinolinyl, adamantyl, azabenzimidazolyl, or indazolyl;

X represents $(C(R)_2)_f$ or $(C(R)_2)_f(C(R)_3)$;

R represents independently for each occurrence H or alkyl;

$R_2$ is absent or present 1, 2, or 3 times;

$R_2$ represents independently for each occurrence alkyl, alkenyl, alkynyl, halogen, formyl, acyl, carboxylate, alkoxycarbonyl, aryloxycarbonyl, carboxamido, alkylamino, acylamino, hydroxyl, alkoxyl, acyloxy, hydroxyalkyl, alkoxyalkyl, aminoalkyl, (alkylamino)alkyl, thio, alkylthio, thioalkyl, (alkylthio)alkyl, carbamoyl, urea, thiourea, sulfonyl, sulfonate, sulfonamido, sulfonylamino, or sulfonyloxy;

$R_3$ represents hydrogen, alkoxyl, amino, alkylamino, dialkylamino, (aminoalkyl)amino, ((alkylamino)alkyl)amino, ((dialkylamino)alkyl)amino, acylamino, (aminoacyl)amino, ((alkylamino)acyl)amino, ((dialkylamino)acyl)amino, (heterocyclyl)acylamino, carboxamido, (aminoalkyl)carboxamido, ((alkylamino)alkyl)carboxamido, ((dialkylamino)alkyl)carboxamido, sulfonylamino, urea, thiourea, —C(O)N(R)N(R)$_2$, —C(O)N(R)C(R)$_2$CO$_2$H, or —C(O)N(R)C(R)$_2$C(O)N(R)$_2$;

f represents 1, 2, or 3; and the stereochemical configuration at any stereocenter of a compound represented by 1 may be R, S, or a mixture of these configurations, and the pharmaceutically acceptable salts, esters, amides, and prodrugs thereof.

In certain embodiments, the compounds of the present invention are represented by generalized structure 2:

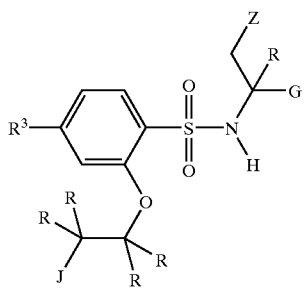

wherein
- Z represents carboxylate, alkoxycarbonyl, or aryloxycarbonyl;
- G represents formyl, acyl, or —CN;
- J represents optionally substituted 1-naphthyl, 1-, 4-, or 7-benzimidazolyl, 4-, or 5-quinolinyl, 4-isoquinolinyl, 5-tetrahydroquinolinyl, 1-adamantyl, 4-azabenzimidazol-3-yl, or 1-indazolyl;
- R represents independently for each occurrence H or alkyl;
- $R_3$ represents hydrogen, alkoxyl, amino, alkylamino, dialkylamino, (aminoalkyl)amino, ((alkylamino)alkyl)amino, ((dialkylamino)alkyl)amino, acylamino, (aminoacyl)amino, ((alkylamino)acyl)amino, ((dialkylamino)acyl)amino, (heterocyclyl)acylamino, carboxamido, (aminoalkyl)carboxamido, ((alkylamino)alkyl)carboxamido, ((dialkylamino)alkyl)carboxamido, sulfonylamino, urea, thiourea, —C(O)N(R)N(R)$_2$, —C(O)N(R)C(R)$_2$CO$_2$H, or —C(O)N(R)C(R)$_2$C(O)N(R)$_2$; and
- the stereochemical configuration at any stereocenter of a compound represented by 2 may be R, S, or a mixture of these configurations,
- and the pharmaceutically acceptable salts, esters, amides, and prodrugs thereof.

In certain assays based on ICE, certain compounds according to general structure 1 or 2 have IC$_{50}$ values less than 1 μM, more preferably less than 500 nM, and most preferably less than 250 nM.

In certain embodiments, the present invention provides a formulation, comprising a compound of the present invention and a pharmaceutically acceptable excipient.

In certain embodiments, the present invention provides a method of inhibiting an interleukin converting enzyme in a patient, comprising the step of administering to a patient in need of inhibition of interleukin-1β converting enzyme a therapeutically effective amount of a compound or formulation of the present invention.

In certain embodiments, the present invention provides a method of inhibiting interleukin-1β converting enzyme in a patient, comprising the step of administering to a patient in need of inhibition of interleukin-1β converting enzyme a therapeutically effective amount of a compound or formulation of the present invention.

In certain embodiments, the present invention provides a method of treating stroke in a patient, comprising the step of administering to a patient having a stroke or which had a stroke a therapeutically effective amount of a compound or formulation of the present invention.

In certain embodiments, the present invention provides a method of treating an inflammatory disease in a patient, comprising the step of administering to a patient having an inflammatory disease a therapeutically effective amount of a compound or formulation of the present invention.

In certain embodiments, the present invention provides a method of treating arthritis or inflammatory bowel disease in a patient, comprising the step of administering to a patient having arthritis or inflammatory bowel disease a therapeutically effective amount of a compound or formulation of the present invention.

In certain embodiments, the present invention provides a method of treating septic shock in a patient, comprising the step of administering to a patient having septic shock a therapeutically effective amount of a compound or formulation of the present invention.

In certain embodiments, the present invention provides a method of treating repurfusion injury in a patient, comprising the step of administering to a patient having repurfusion injury a therapeutically effective amount of a compound or formulation of the present invention.

In certain embodiments, the present invention provides a method of treating Alzheimer's disease in a patient, comprising the step of administering to a patient having Alzheimer's disease a therapeutically effective amount of a compound or formulation of the present invention.

In certain embodiments, the present invention provides a method of treating shigellosis in a patient, comprising the step of administering to a patient having shigellosis a therapeutically effective amount of a compound or formulation of the present invention.

DETAILED DESCRIPTION OF THE INVENTION

Figure 1:
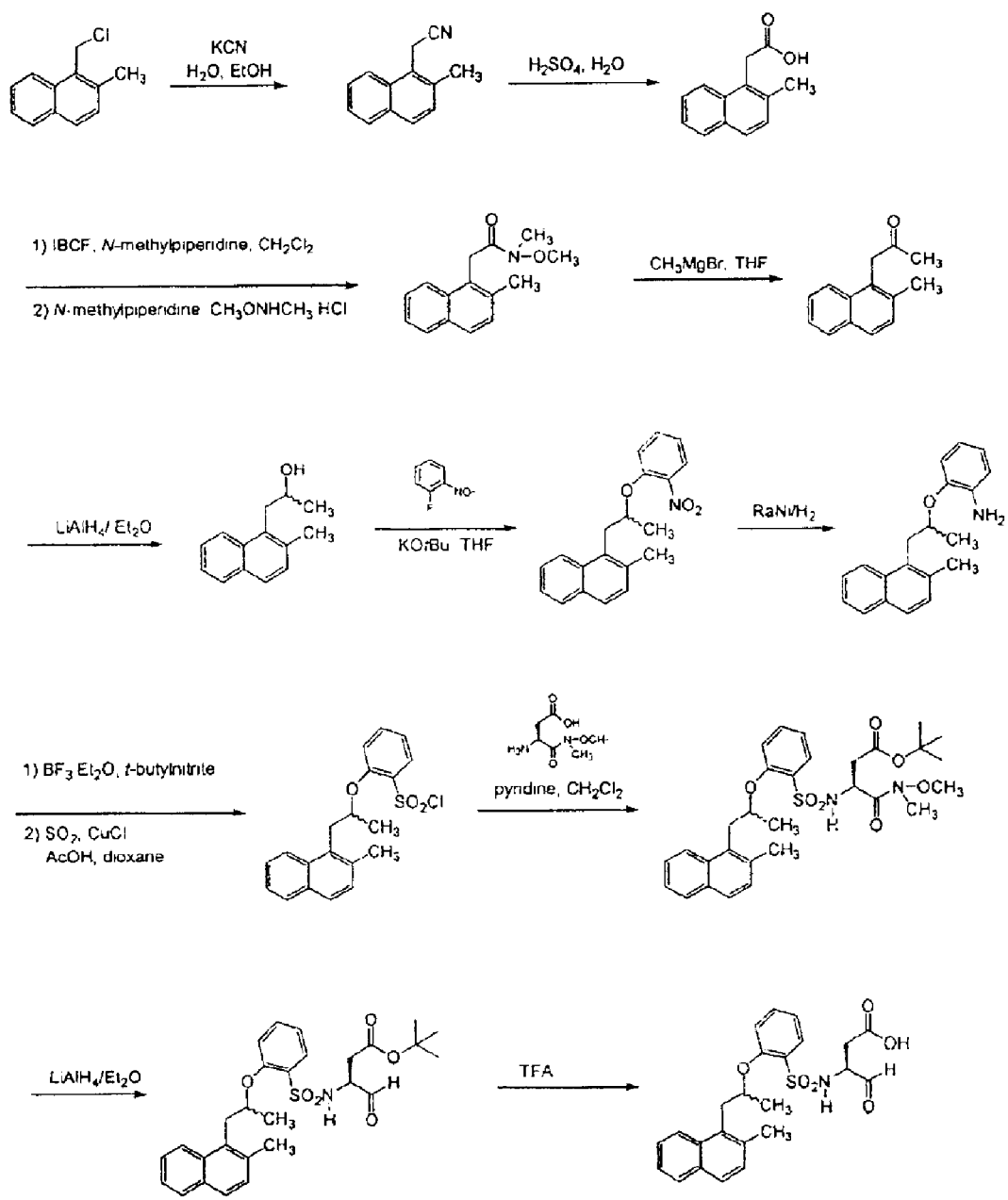
FIG. 1 depicts Route A for the synthesis of certain compounds of the present invention (See Example 1).

The compounds of the present invention are inhibitors of interleukin-1β converting enzyme (ICE) and are useful in treating diseases in which interleukin-1 plays a role. Additionally, the compounds of the present invention are inhibitors of other cysteine proteases in the ICE family. Many of these proteases have only recently been described in the literature. It is recognized that members of this enzyme family play key biological roles in both inflammation and apoptosis (programmed cell death). In particular, Caspase-4 can activate both IL-β and IL-18. It has been shown that a murine homolog of Caspase-4 can activate ICE. Thus, inhibition of Caspase-4 will act to inhibit ICE. See Thornberry, N. A. et al., *Perspectives in Drug Discovery and Design*, 1994; 2:389–399.

Definitions

For convenience, certain terms employed in the specification, examples, and appended claims are collected here.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl"

have similar chain lengths. Preferred alkyl groups are lower alkyls. In preferred embodiments, a substituent designated herein, as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $-CF_3$, $-CN$, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, tetrahydroquinoline, tetrahydroisoquinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The term "carbocycle", as used herein, refers to an aromatic or non-aromatic ring in which each atom of the ring is carbon.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

The terms "amine" and "amino" are art-recognized and refer to both unsubstituted and substituted amines, e.g., a moiety that can be represented by the general formula:

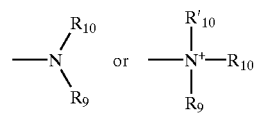

wherein $R_9$, $R_{10}$ and $R'_{10}$ each independently represent a hydrogen permitted by the rules of valence.

The term "acylamino" is art-recognized and refers to a moiety that can be represented by the general formula:

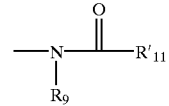

wherein $R_9$ is as defined above, and $R'_{11}$ represents a hydrogen, an alkyl, an alkenyl or $-(CH_2)_m-R_8$, where m and $R_8$ are as defined above.

The term "amido" is art recognized as an amino-substituted carbonyl and includes a moiety that can be represented by the general formula:

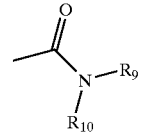

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of $-S$-alkyl, $-S$-alkenyl, $-S$-alkynyl, and $-S-(CH_2)_m-R_8$, wherein m and $R_8$ are defined above. Representative alkylthio groups include methylthio, ethyl thio, and the like.

The term "carbonyl" is art recognized and includes such moieties as can be represented by the general formula:

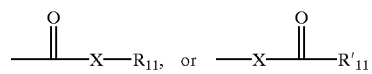

wherein X is a bond or represents an oxygen or a sulfur, and $R_{11}$ represents a hydrogen, an alkyl, an alkenyl, $-(CH_2)_m-R_8$ or a pharmaceutically acceptable salt, $R'_{11}$ represents a hydrogen, an alkyl, an alkenyl or $-(CH_2)_m-R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group.

Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

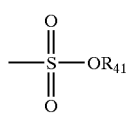

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

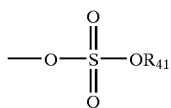

in which $R_{41}$ is as defined above.

The term "sulfonylamino" is art recognized and includes a moiety that can be represented by the general formula:

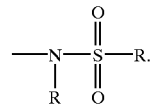

The term "sulfamoyl" is art-recognized and includes a moiety that can be represented by the general formula:

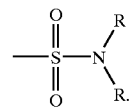

The term "sulfonyl", as used herein, refers to a moiety that can be represented by the general formula:

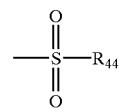

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

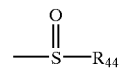

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as antiinflammatory agents), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Compounds of the Invention

In certain embodiments, the compounds of the present invention are represented by generalized structure 1:

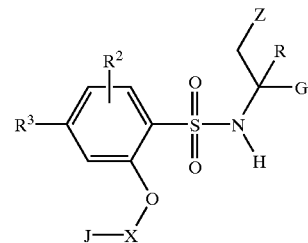

wherein
Z represents carboxylate, alkoxycarbonyl, or aryloxycarbonyl;
G represents formyl, acyl, or —CN;
J represents optionally substituted naphthyl, benzimidazolyl, quinolinyl, isoquinolinyl, tetrahydroquinolinyl, adamantyl, azabenzimidazolyl, or indazolyl;
X represents $(C(R)_2)_f$;
R represents independently for each occurrence H or alkyl;
$R_2$ is absent or present 1, 2 or 3 times;
$R_2$ represents independently for each occurrence alkyl, alkenyl, alkynyl, halogen, formyl, acyl, carboxylate, alkoxycarbonyl, aryloxycarbonyl, carboxamido, alkylamino, acylamino, hydroxyl, alkoxyl, acyloxy, hydroxyalkyl, alkoxyalkyl, aminoalkyl, (alkylamino)alkyl, thio, alkylthio, thioalkyl, (alkylthio)alkyl, carbamoyl, urea, thiourea, sulfonyl, sulfonate, sulfonamido, sulfonylamino, or sulfonyloxy;
$R_3$ represents hydrogen, alkoxyl, amino, alkylamino, dialkylamino, (aminoalkyl)amino, ((alkylamino)alkyl)amino, ((dialkylamino)alkyl)amino, acylamino, (aminoacyl)amino, ((alkylamino)acyl)amino, ((dialkylamino)acyl)amino, (heterocyclyl)acylamino, carboxamido, (aminoalkyl)carboxamido, (alkylamino)alkyl)carboxamido, (dialkylamino)alkyl)carboxamido, sulfonylamino, urea, thiourea, —C(O)N(R)N(R)$_2$, —C(O)N(R)C(R)$_2$CO$_2$H, or —C(O)N(R)C(R)$_2$C(O)N(R)$_2$;
f represents 1, 2, or 3; and
the stereochemical configuration at any stereocenter of a compound represented by 1 may be R, S, or a mixture of these configurations,
and the pharmaceutically acceptable salts, esters, amides, and prodrugs thereof.

In certain embodiments, the compounds of the present invention are represented by generalized structure 1 and the attendant definitions, wherein Z represents carboxylate.

In certain embodiments, the compounds of the present invention are represented by generalized structure 1 and the attendant definitions, wherein G represents formyl.

In certain embodiments, the compounds of the present invention are represented by generalized structure 1 and the attendant definitions, wherein X represents $(CH(R))_f$.

In certain embodiments, the compounds of the present invention are represented by generalized structure 1 and the attendant definitions, wherein $R^2$ is absent.

In certain embodiments, the compounds of the present invention are represented by generalized structure 1 and the attendant definitions, wherein f is 2.

In certain embodiments, the compounds of the present invention are represented by generalized structure 1 and the attendant definitions, wherein Z represents carboxylate; and G represents formyl.

In certain embodiments, the compounds of the present invention are represented by generalized structure 1 and the attendant definitions, wherein Z represents carboxylate; G represents formyl; and X represents $(CH(R))_f$.

In certain embodiments, the compounds of the present invention are represented by generalized structure 1 and the attendant definitions, wherein Z represents carboxylate; G represents formyl; and $R^2$ is absent.

In certain embodiments, the compounds of the present invention are represented by generalized structure 1 and the attendant definitions, wherein Z represents carboxylate; G represents formyl; and f is 2.

In certain embodiments, the compounds of the present invention are represented by generalized structure 1 and the attendant definitions, wherein Z represents carboxylate; G represents formyl; X represents $(CH(R))_f$; and $R^2$ is absent.

In certain embodiments, the compounds of the present invention are represented by generalized structure 1 and the attendant definitions, wherein Z represents carboxylate; G represents formyl; X represents $(CH(R))_f$; and f is 2.

In certain embodiments, the compounds of the present invention are represented by generalized structure 1 and the attendant definitions, wherein Z represents carboxylate; G represents formyl; $R^2$ is absent; and f is 2.

In certain embodiments, the compounds of the present invention are represented by generalized structure 1 and the attendant definitions, wherein Z represents carboxylate; G represents formyl; X represents $(CH(R))_f$; $R^2$ is absent; and f is 2.

In certain assays based on ICE, certain compounds according to general structure 1 have $IC_{50}$ values less than 1 μM, more preferably less than 500 nM, and most preferably less than 250 nM.

In certain embodiments, the compounds of the present invention are represented by generalized structure 2:

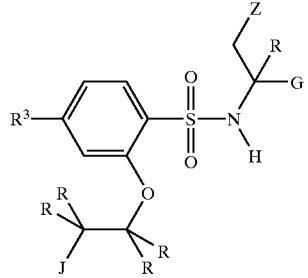

wherein
Z represents carboxylate, alkoxycarbonyl, or aryloxycarbonyl;
G represents formyl, acyl, or —CN;
J represents optionally substituted 1-naphthyl, 1-, 4-, or 7-benzimidazolyl, 4-, or 5-quinolinyl, 4-isoquinolinyl, 5-tetrahydroquinolinyl, 1-adamantyl, 4-azabenzimidazol-3-yl, or 1-indazolyl;
R represents independently for each occurrence H or alkyl;
$R_3$ represents hydrogen, alkoxyl, amino, alkylamino, dialkylamino, (aminoalkyl)amino, ((alkylamino)alkyl) amino, ((dialkylamino)alkyl)amino, acylamino, (aminoacyl)amino, ((alkylamino)acyl)amino, ((dialkylamino)acyl)amino, (heterocyclyl)acylamino, carboxamido, (aminoalkyl)carboxamido, ((alkylamino) alkyl)carboxamido, ((dialkylamino)alkyl) carboxamido, sulfonylamino, urea, thiourea, —C(O)N (R)N(R)$_2$, —C(O)N(R)C(R)$_2$CO$_2$H, or —C(O)N(R)C (R)$_2$C(O)N(R)$_2$; and the stereochemical configuration at any stereocenter of a compound represented by 2 may be R, S, or a mixture of these configurations, and the pharmaceutically acceptable salts, esters, amides, and prodrugs thereof.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems", Vol. 14 of the A.C.S. Symposium Series, and in *Bioreversible Carriers in Drug Design*, ed. Edward B. Roche, Amercian Pharmaceutical Associatioin and Pergamon Press, 1987, both of which are incorporated herein by reference.

In certain embodiments, the compounds of the present invention are represented by generalized structure 2 and the attendant definitions, wherein Z represents carboxylate.

In certain embodiments, the compounds of the present invention are represented by generalized structure 2 and the attendant definitions, wherein G represents formyl.

In certain embodiments, the compounds of the present invention are represented by generalized structure 2 and the attendant definitions, wherein R represents independently for each occurrence hydrogen or methyl.

In certain embodiments, the compounds of the present invention are represented by generalized structure 2 and the attendant definitions, wherein $R^3$ is selected from the group consisting of:

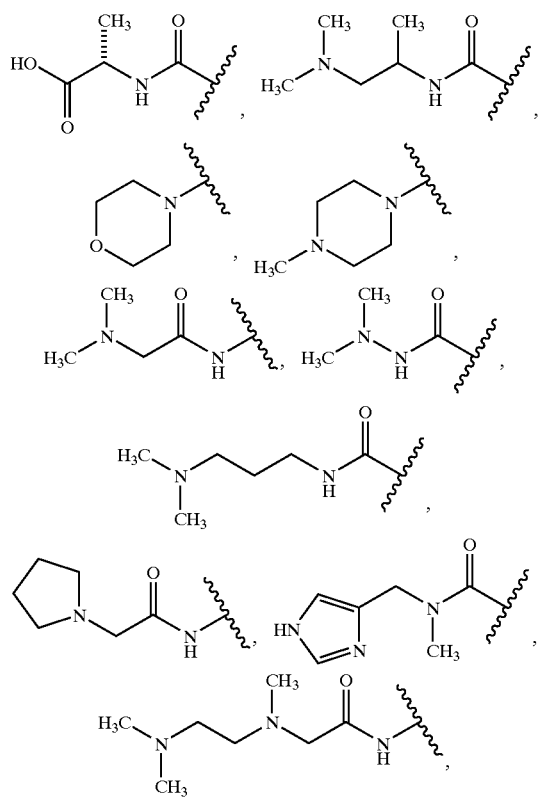

-continued
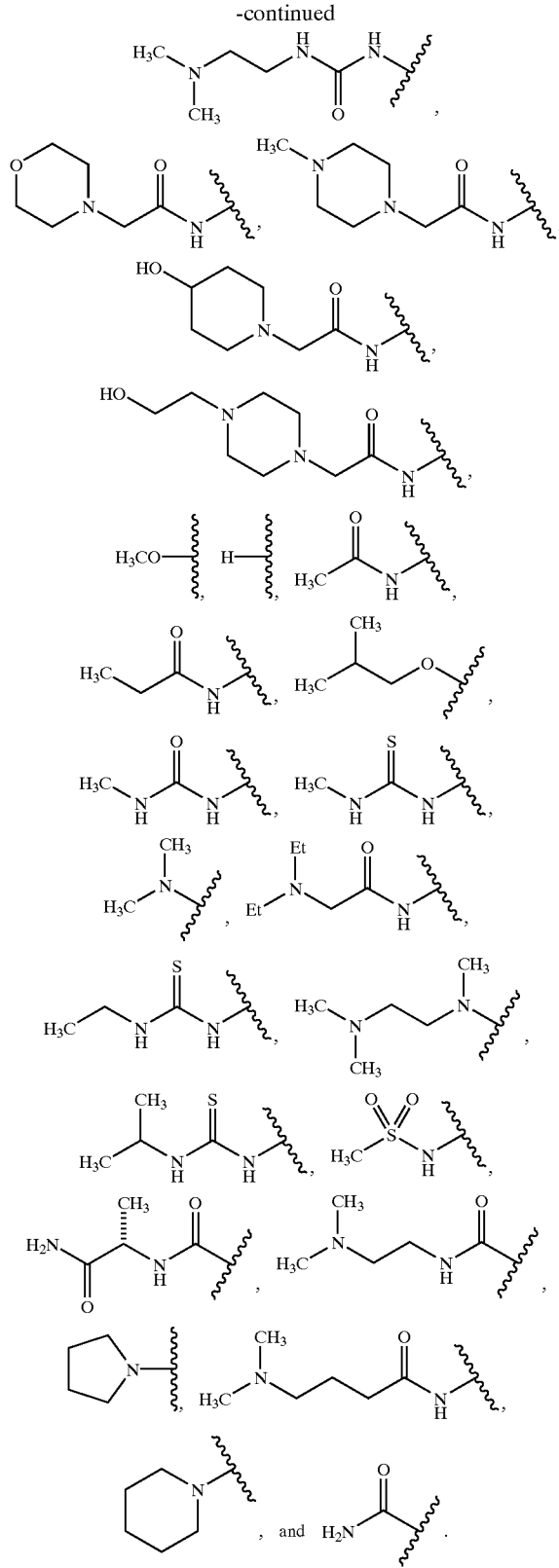
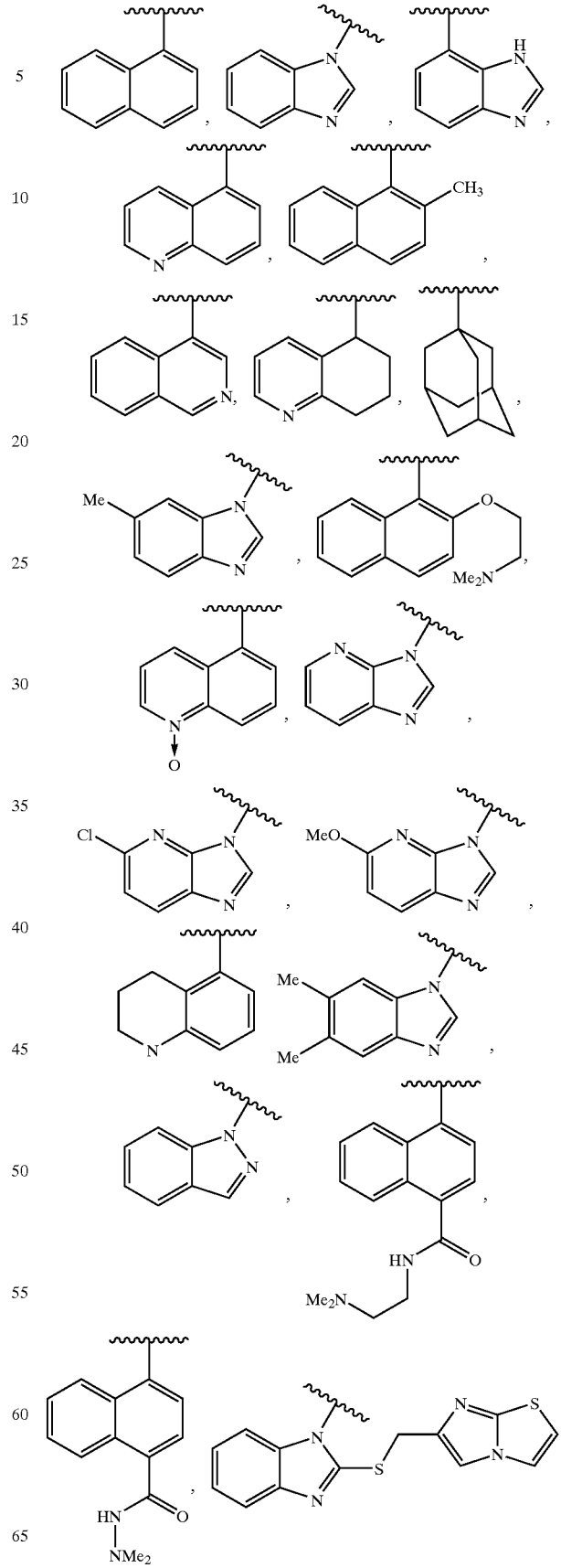
In certain embodiments, the compounds of the present invention are represented by generalized structure 2 and the attendant definitions, wherein J is selected from the group consisting of:

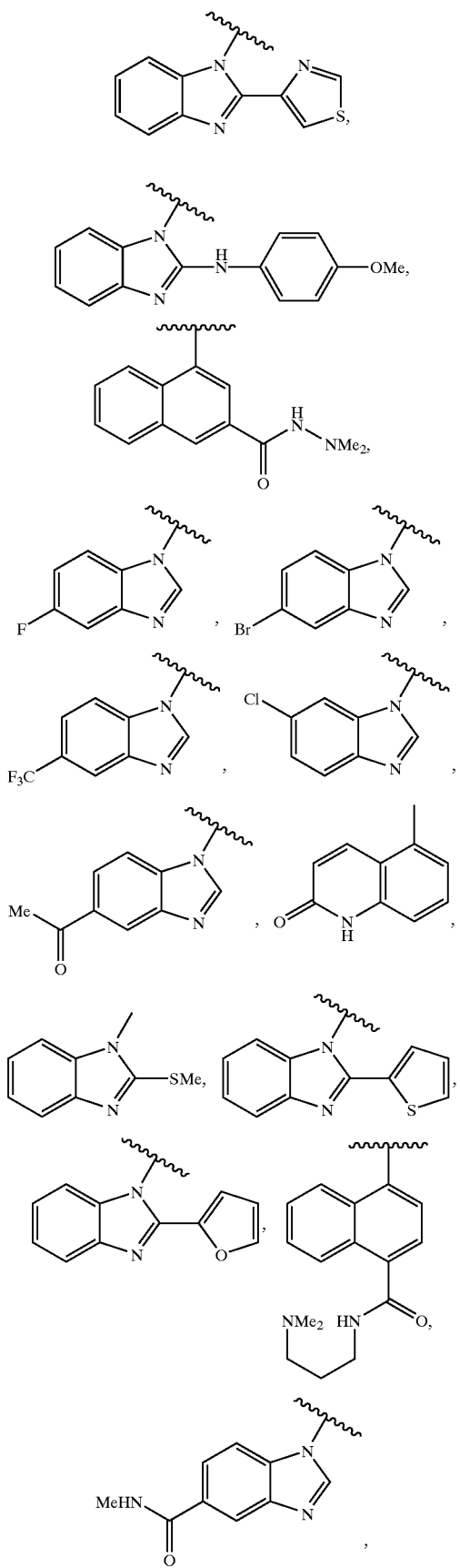
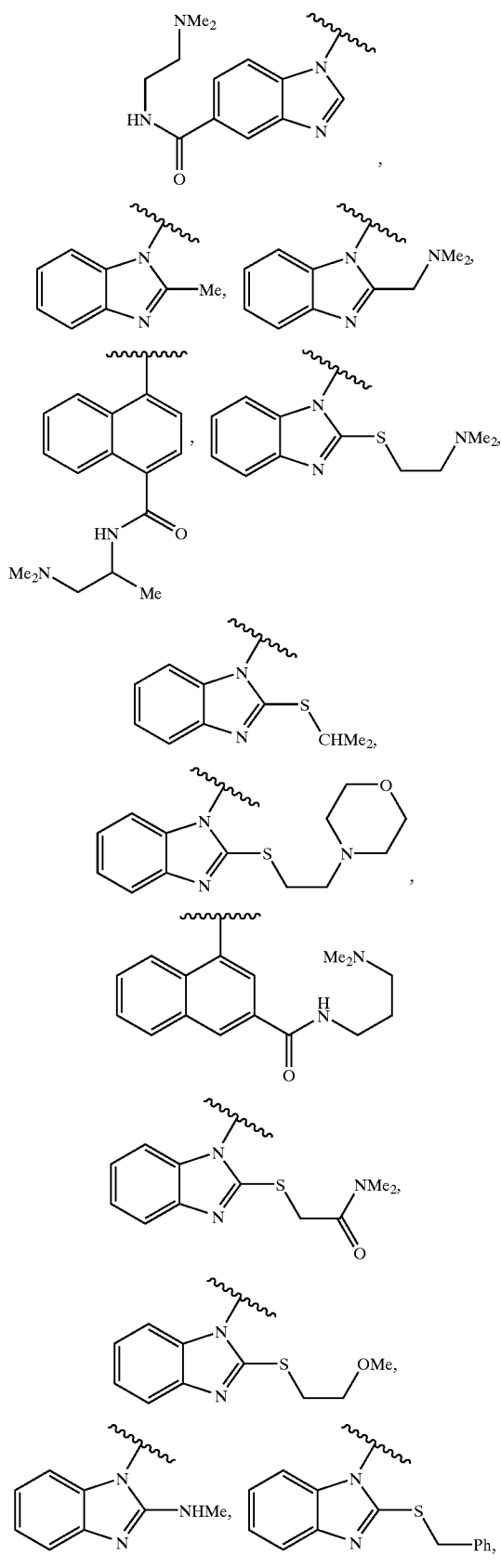

-continued

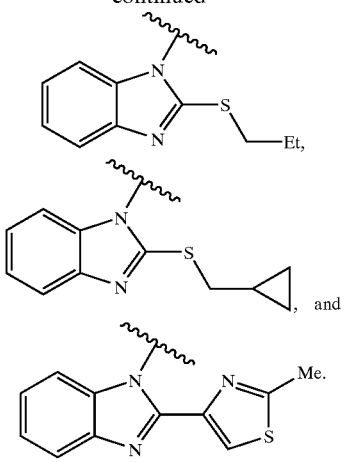

In certain embodiments, the compounds of the present invention are represented by generalized structure 2 and the attendant definitions, wherein Z represents carboxylate; and G represents formyl.

In certain embodiments, the compounds of the present invention are represented by generalized structure 2 and the attendant definitions, wherein Z represents carboxylate; G represents formyl; and R represents independently for each occurrence hydrogen or methyl.

In certain assays based on ICE, certain compounds according to general structure 2 have $IC_{50}$ values less than 1 μM, more preferably less than 500 nM, and most preferably less than 250 nM.

In certain embodiments, the present invention relates to a formulation, comprising a compound represented by generalized structure 1 or 2, and a pharmaceutically acceptable excipient.

The present invention also provides a method of inhibiting an interleukin converting enzyme in a mammal, comprising the step of administering to a mammal a therapeutically effective amount of a compound represented by generalized structure 1 or 2, or a formulation comprising a compound represented by generalized structure 1 or 2. In certain embodiments of this method, the mammal is a primate, equine, canine or feline. In certain embodiments of this method, the mammal is a human. In certain embodiments of this method, the compound or formulation is administered orally. In certain embodiments of this method, the compound or formulation is administered intravenously. In certain embodiments of this method, the compound or formulation is administered sublingually. In certain embodiments of this method, the compound or formulation is administered ocularly.

The present invention also provides a method of inhibiting interleukin-1β converting enzyme in a mammal, comprising the step of administering to a mammal a therapeutically effective amount of a compound represented by generalized structure 1 or 2, or a formulation comprising a compound represented by generalized structure 1 or 2. In certain embodiments of this method, the mammal is a primate, equine, canine or feline. In certain embodiments of this method, the mammal is a human. In certain embodiments of this method, the compound or formulation is administered orally. In certain embodiments of this method, the compound or formulation is administered intravenously. In certain embodiments of this method, the compound or formulation is administered sublingually. In certain embodiments of this method, the compound or formulation is administered ocularly.

The present invention also provides a method of treating stroke, comprising administering to a patient having a stroke or having had a stroke a therapeutically effective amount of a compound represented by generalized structure 1 or 2, or a formulation comprising a compound represented by generalized structure 1 or 2.

The present invention also provides a method of treating inflammatory diseases, comprising administering to a patient having an inflammatory disease a therapeutically effective amount of a compound represented by generalized structure 1 or 2, or a formulation comprising a compound represented by generalized structure 1 or 2. In certain embodiments of this method, the inflammatory disease is arthritis or inflammatory bowel disease.

The present invention also provides a method of treating septic shock, comprising administering to a patient having septic shock a therapeutically effective amount of a compound represented by generalized structure 1 or 2, or a formulation comprising a compound represented by generalized structure 1 or 2.

The present invention also provides a method of treating reperfusion injury, comprising administering to a patient having reperfusion injury a therapeutically effective amount of a compound represented by generalized structure 1 or 2, or a formulation comprising a compound represented by generalized structure 1 or 2.

The present invention also provides a method of treating Alzheimer's disease, comprising administering to a patient having Alzheimer's disease a therapeutically effective amount of a compound represented by generalized structure 1 or 2, or a formulation comprising a compound represented by generalized structure 1 or 2.

The present invention also provides a method of treating shigellosis, comprising administering to a patient having shigellosis a therapeutically effective amount of a compound represented by generalized structure 1 or 2, or a formulation comprising a compound represented by generalized structure 1 or 2.

Inhibition Studies

As noted above, the compounds of the invention are useful for inhibiting interleukin converting enzymes. Thus, in certain embodiments of the invention, methods for inhibiting interleukin converting enzymes in mammals in need thereof are provided.

Measurements of $K_i$ (μM) and $IC_{50}$ (μM) using the protocol described herein demonstrated that the compounds of the present invention are inhibitors of ICE. ICE (0.24 nM final concentration) was added to 400 μL of HGDE buffer (100 mM HEPES, 20% glycerol, 5 mM DTT, 0.5 mM EDTA) containing 15 μM substrate (Ac-Tyr-Val-Ala-Asp-AMC; $K_M$=15 μM) plus vehicle (DMSO) or inhibitor at concentrations bracketing the $K_i$. Substrate hydrolysis was monitored for 300 seconds by observing the fluorescence of released AMC using excitation at 380 nm. and emission at 460 nm. Mean rates of substrate hydrolysis were evaluated by linear-regression analysis of the fluorescence vs. time traces. To evaluate $K_i$, plots of percent inhibition vs. inhibitor concentration were fit by non-linear regression to a reversible, competitive model:

$$\% \text{ Inhibition} = \frac{100 * [I]}{[I] + Ki * \left(1 + \frac{[S]}{KM}\right)}$$

where the competition factor $(I+[S]/K_M)$=2.

ICE Colorimetric Dose-Response ($IC_{50}$) Assay

Diluted inhibitor stocks were prepared by two-fold serial dilution from a primary stock whose concentration was selected (based on screening results or on prior attempts at $IC_{50}$ evaluation) to achieve approximately 95% inhibition in the most concentrated well. Aliquots of each dilution were transferred to a microtitre plate in triplicate.

ICE enzyme was diluted to approximately 24 nM in HGE buffer (100 mM Hepes pH 7.5, 0.5 mM EDTA, 20% glycerol, 0.1% Bovine Serum Albumin (BSA), and activated by adding dithiothreitol (DTT) to a final concentration of 5 mM. The activated enzyme was then aliquoted into wells containing inhibitor or vehicle, and the plate was preincubated for 60 minutes at ambient temperature. Substrate (Ac-Tyr-Val-Ala-Asp-pNA) was added to each well to a final concentration of 50 µM, and plates were placed in the microtitre plate-reader thermostated to 25° C. Beginning 5 minutes after addition of substrate, absorbance (405 nm) of wells was monitored for 1 hour, and activity was calculated as the mean rate of change in absorbance during this interval.

PBMC Cellular Assay ($IC_{50}$) Determinations

Further evidence that compounds of the present invention are inhibitors of ICE was provided by their ability to inhibit IL-1β production in human peripheral blood mononuclear cells (PBMCs) as described herein. PBMCs were isolated from heparinized blood by centrifugation over a ficoll cushion, then washed three times with phosphate-buffered saline. PBMCs were suspended in a medium containing RPMI 1640 with glutamine, penicillin, streptomycin, and 2% human AB serum, then plated at $10^6$ cells per well in 96 well flat-bottom plates. PBMCs were stimulated overnight with 10 ng/mL of lipopolysaccharide (LPS, E. coli strain 0111:B4; Calbiochem) in the presence or absence of a compound of the present invention. Medium was harvested and the level of mature IL-1β was determined using an ELISA kit. Compound inhibition was assessed by determining the concentration of agent which reduced IL-1β levels by 50%. Cells were cultured for an additional four hours in the presence of 3-(4,5-dimethylthiazol-2-yl)-2,5-diphenyltetrazolium bromide (MTT) to determine viability. Compound toxicity can, therefore, be assessed by determining the concentration of agent which kills 50% of the cells ($IC_{50}$).

Ich-2 (Caspase-4) Colorimetric Dose-Response $IC_{50}$ Assay

Inhibition of Ich-2 enzyme was assayed as described above for ICE, except that enzyme was used at 64 nM, and 60 µM of the Ich-2-specific substrate Ac-Leu-Glu-Val-Asp-pNA was used instead of the ICE substrate, Ac-Tyr-Val-Ala-Asp-pNA.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or nonaqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject co,pounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "*Applied Animal Nutrition*", W.H. Freedman and CO., San Francisco, U.S.A., 1969 or "*Livestock Feeds and Feeding*" O and B books, Corvallis, Oreg., U.S.A., 1977).

Exemplification

The invention now being generally described, it will be more readily understood by reference to the following examples, which are included merely for purposes of illustration of certain aspects and embodiments of the present invention, and are not intended to limit the invention.

EXAMPLE 1

Route A (See FIG. 1)

An appropriate alcohol is/was treated with base, including but not limited to bases such as potassium t-butoxide and sodium hydride, in a solvent such as tetrahydrofuran or dimethylformamide. Ortho-fluoronitrobenzene is/was added to the mixture of base and alcohol to afford the ether product. The nitro group of the ether is/was subsequently reduced, either catalytically, using hydrogen and a catalyst like Raney nickel or Pd/C, or by using chemical reducing agents, e.g., Fe/HCl. The resulting aniline is/was diazotized, for example, by treatment with sodium nitrite/HCl/AcOH or t-butyl nitrite/boron trifluoride etherate. The diazonium product can be converted into a sulfonyl chloride with a sulfur dioxide/acid/solvent mixture. The resulting sulfonyl chloride is/was reacted with (S)-3-amino-N-methoxy-N-methyl-succinamic acid tert-butyl ester in the presence of an amine or other acid scavenger. The Weinreb amide is/was then reduced with lithium aluminum hydride or other reducing agent to afford the corresponding aldehyde. The t-butyl ester is/was cleaved with trifluoroacetic acid in solvent or another acidic reagent in solvent to provide the final product.

EXAMPLE 2

Figure 2:
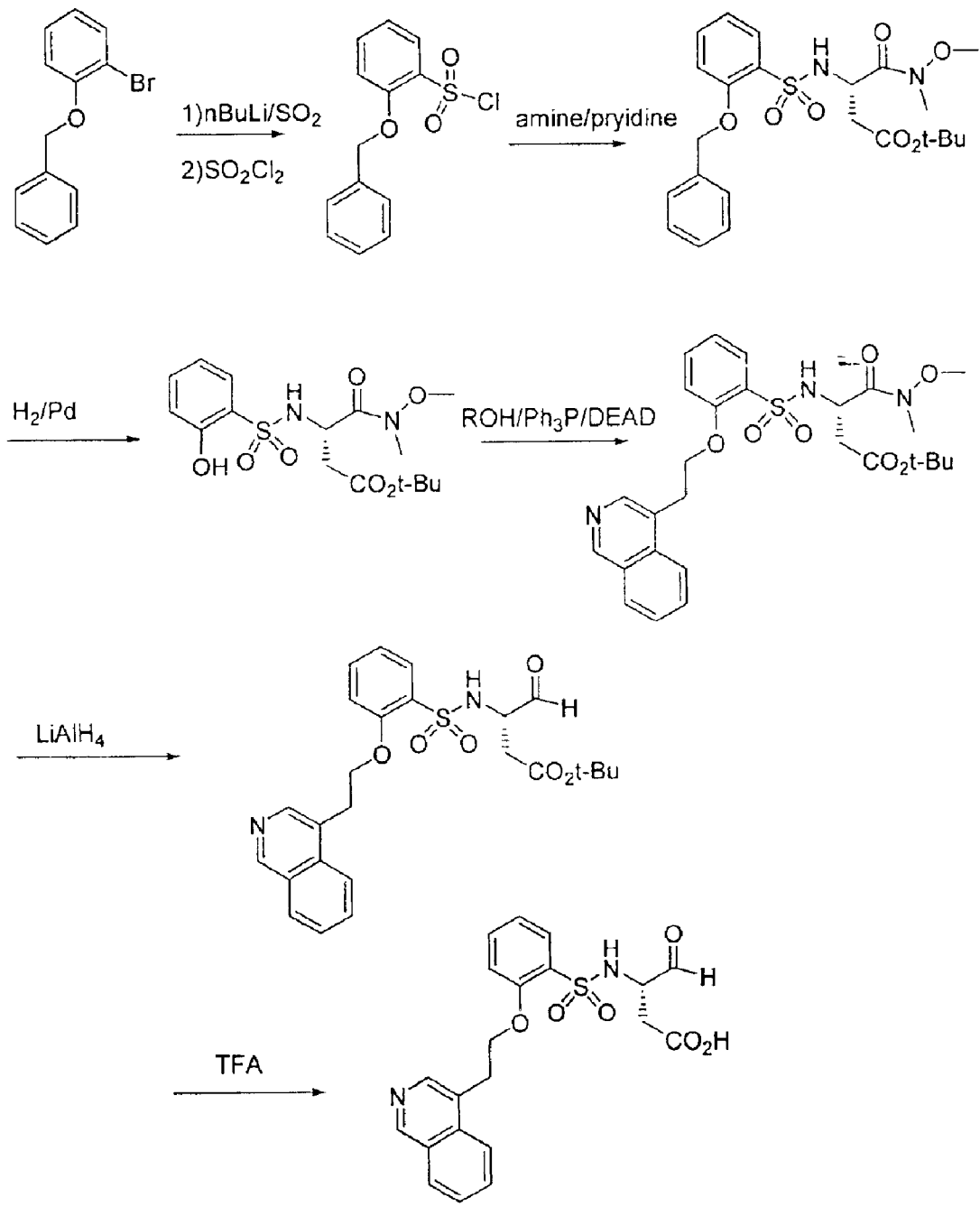
FIG. 2 depicts Route B for the synthesis of certain compounds of the present invention (See Example 2).

Route B (See FIG. 2)

2-Benzyloxy-bromobenzene in an ethereal solvent is/was transmetalated with n-butyllithium or other metalating agent, then sulfur dioxide is/was added to provide the sulfinate salt. This salt is/was converted to the sulfonyl chloride by use of a chlorinating agent such as sulfuryl chloride or N-chlorosuccinamide. The resulting sulfonyl chloride is/was reacted with (S)-3-amino-N-methoxy-N-methyl-succinamic acid tert-butyl ester in the presence of an amine or other acid scavenger. The benzyl protecting group is/was removed catalytically with a catalyst like Pd/C and hydrogen to provide the corresponding phenol. This phenol then is/was reacted with an appropriate alcohol in a polar aprotic solvent in the presence of a tertiary phosphine such as triphenylphosphine and a reagent like diethyl azodicarboxylate, to provide the ether. The Weinreb amide is/was reduced with lithium aluminum hydride or other reducing agent to afford the corresponding aldehyde. The t-butyl ester is/was cleaved with trifluoroacetic acid in solvent or another acidic reagent in solvent to provide the final product.

EXAMPLE 3

Figure 3:
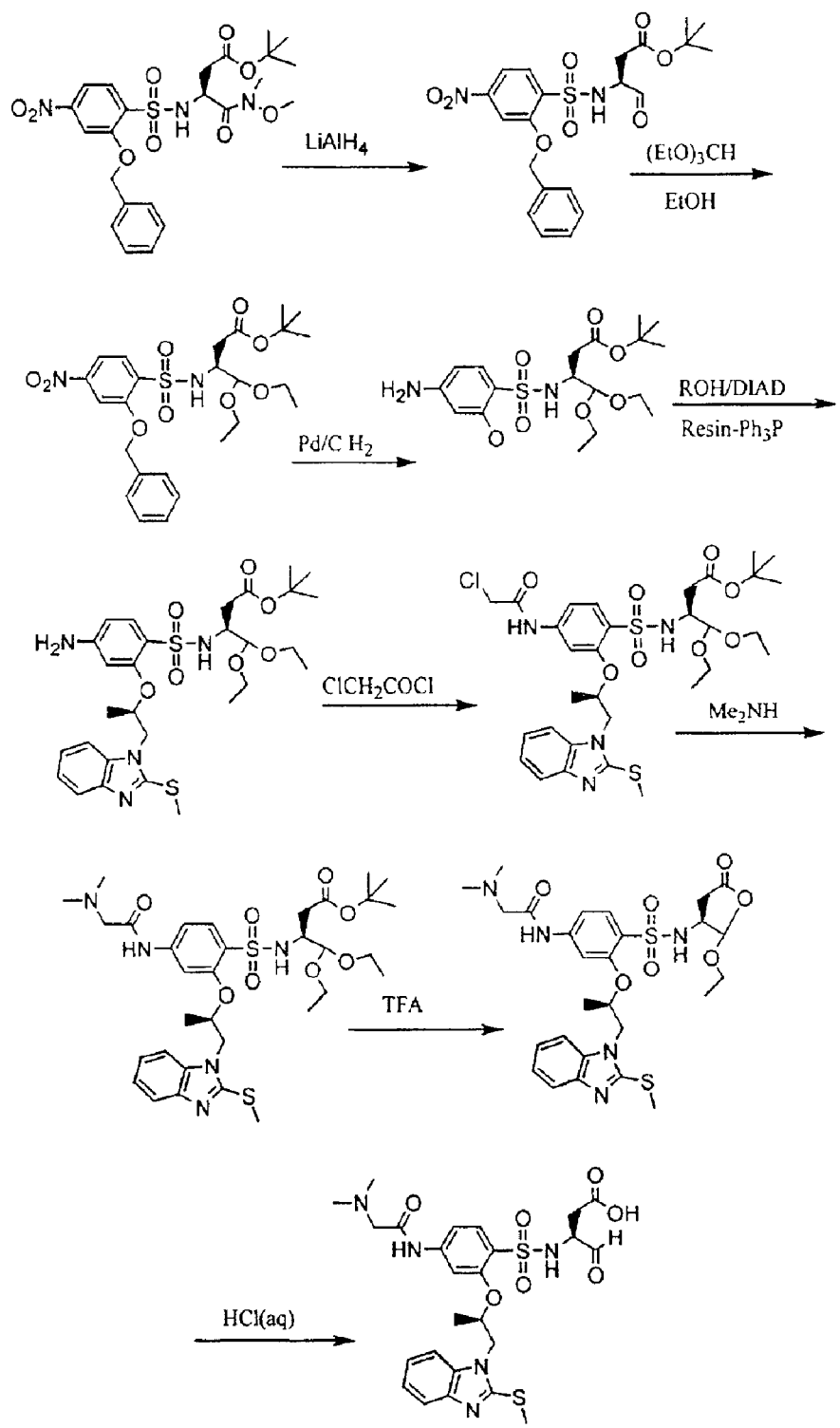
FIG. 3 depicts Route C for the synthesis of certain compounds of the present invention (See Example 3).

Route C (See FIG. 3)

(S)-3-(2-Benzyloxy-4-nitro-benzenesulfonylamino)-N-methoxy-N-methyl succinamic acid tert-butyl ester (see Route D) is/was reduced with lithium aluminum hydride or other reducing agent to afford the aldehyde. The aldehyde is/was transformed to the corresponding acetal using ethanol and a dehydrating agent, e.g., triethylorthoformate, and an acid catalyst. Reduction with, e.g., Pd/C and hydrogen, affords the aminophenol. This phenol then is/was reacted with an appropriate alcohol in a polar aprotic solvent in the presence of a tertiary phosphine, such as polymer bound triphenylphosphine, and a reagent like diisopropyl azodicarboxylate, to provide the ether. Treatment of the aniline with an acid chloride, like chloroacetyl chloride, in the presence of a tertiary amine base gives the chloroamide. This acyl chloride reacts with a variety of primary and secondary amines like dimethyl amine to provide a new amine. This amine is/was treated with an acid reagent like trifluoroacetic acid to provide the cyclic acetal prodrug. This prodrug could be further deprotected with aqueous acid to provide the acid aldehyde.

EXAMPLE 4

Figure 4:
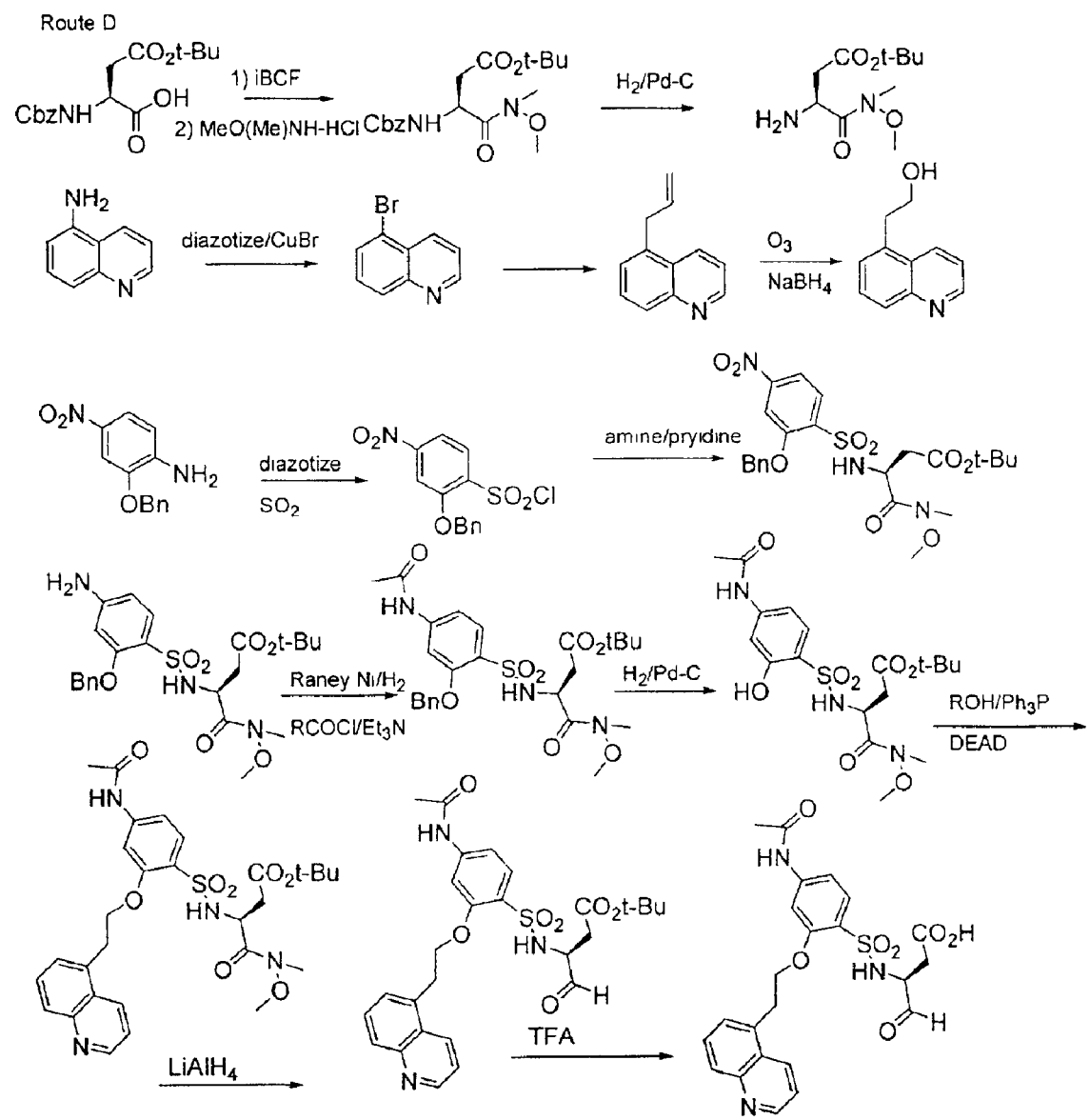
FIG. 4 depicts Route D for the synthesis of certain compounds of the present invention (See Example 4).

Route D (See FIG. 4)

2-Benzyloxy-4-nitro-phenylamine is/was diazotized, for example, by treatment with sodium nitrite/HCl/AcOH or t-butyl nitrite/boron trifluoride etherate. The diazonium product can be converted into a sulfonyl chloride with a sulfur dioxide/acid/solvent mixture. The resulting sulfonyl chloride is/was reacted with (S)-3-amino-N-methoxy-N-methyl-succinamic acid tert-butyl ester in the presence of an amine or other acid scavenger. The nitro group is/was subsequently reduced catalytically, using hydrogen and a catalyst like Raney nickel, or chemically, e.g., using Fe/HCl. The aniline is/was then treated with an acid chloride in the presence of a tertiary amine base to give the amide. The benzyl protecting group is/was removed with a catalyst like Pd/C and hydrogen to provide the phenol. This phenol then is/was reacted with an appropriate alcohol in a polar aprotic solvent in the presence of a tertiary phosphine, such as triphenylphosphine, and a reagent like diethyl azodicarboxylate, to provide the ether. The Weinreb amide is/was reduced with lithium aluminum hydride or other reducing agent to afford the aldehyde. The t-butyl ester is/was cleaved with trifluoroacetic acid in solvent or another acidic reagent in solvent to provide the final product.

EXAMPLE 5

Figure 5:
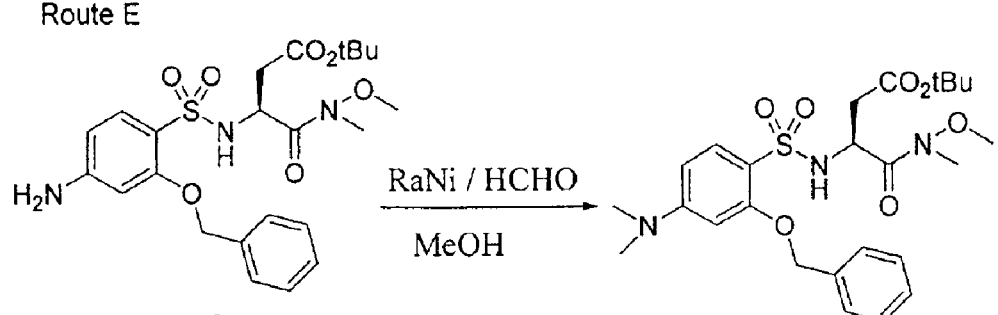
FIG. 5 depicts Route E for the synthesis of certain compounds of the present invention (See Example 5).
Figure 5:
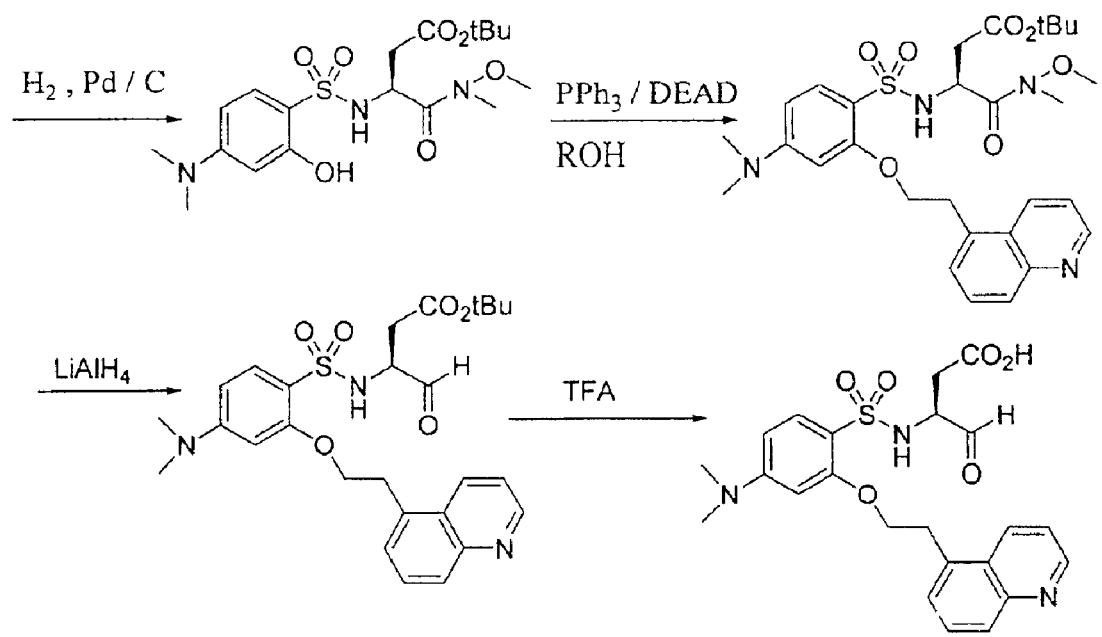

Route E (See FIG. 5)

The aniline functionality of 3-(4-amino-2-benzyloxy-benzenesulfonylamino)-N-methoxy-N-methyl succinamic acid t-butyl ester (Route D; Example 4) is/was reductively alkylated with an aldehyde such as formaldehyde using Raney nickel and hydrogen or by other commonly employed reducing reagents to provide a tertiary amine. The benzyl protecting group is/was then removed with a catalyst like Pd/C and hydrogen to provide the phenol. This phenol is/was then reacted with an appropriate alcohol in a polar aprotic solvent in the presence of a tertiary phosphine, such as triphenylphosphine, and a reagent like diethyl azodicarboxylate, to provide the ether. The Weinreb amide is/was reduced with lithium aluminum hydride or other reducing agent to afford the aldehyde. The t-butyl ester is/was cleaved with trifluoroacetic acid in solvent or another acidic reagent in solvent to provide the final product.

EXAMPLE 6

Figure 6:
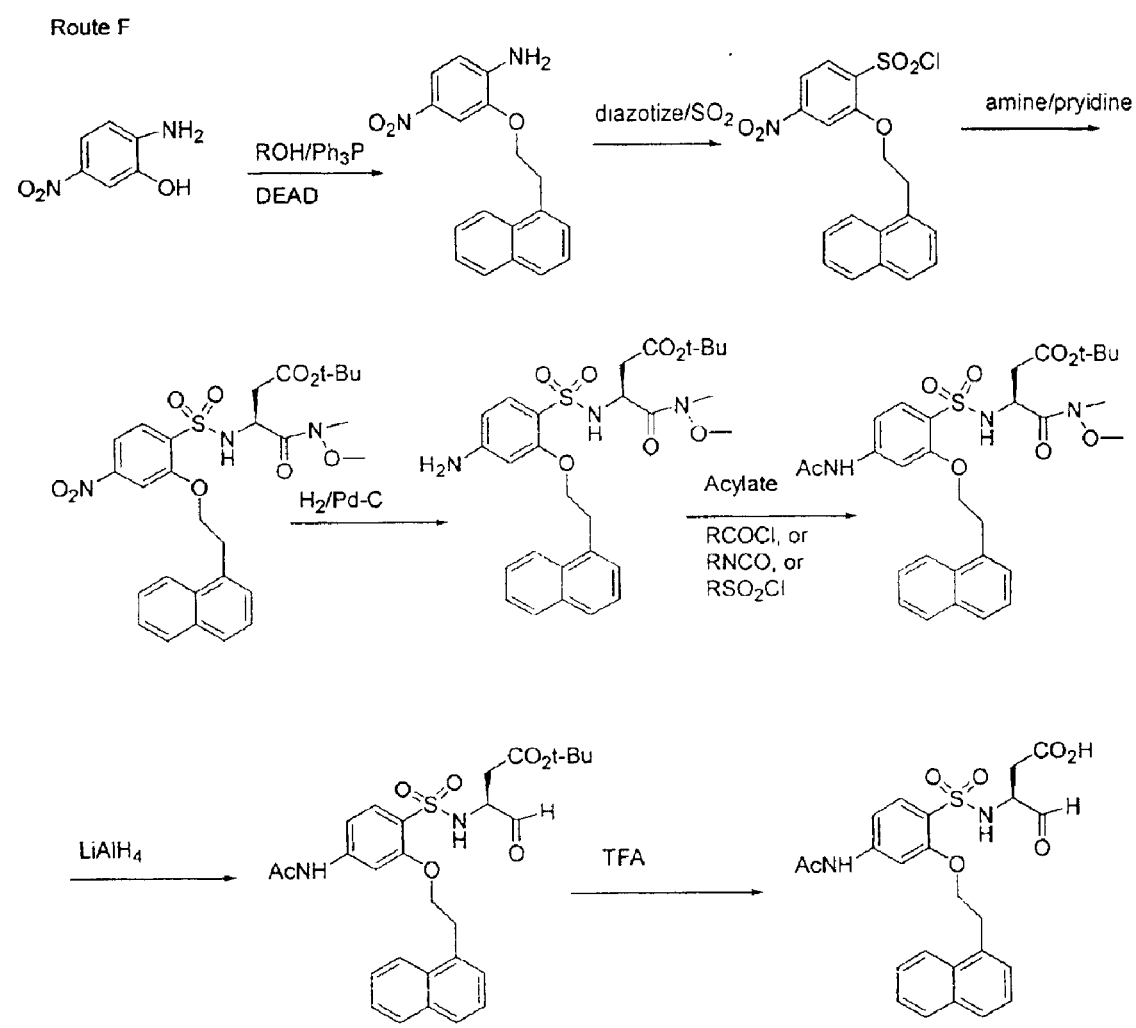
FIG. 6 depicts Route F for the synthesis of certain compounds of the present invention (See Example 6).

Route F (See FIG. 6)

2-Hydroxy-4-nitroaniline is/was reacted with an appropriate alcohol in a polar aprotic solvent in the presence of a tertiary phosphine, such as triphenylphosphine, and a reagent like diethyl azodicarboxylate, to provide the corresponding ether. Diazotization of the aniline occurs by treatment with sodium nitrite/HCl/AcOH or t-butyl nitrite/boron trifluoride etherate. The diazonium product can be converted into a sulfonyl chloride with a sulfur dioxide/acid/solvent mixture. The nitro group is/was subsequently reduced catalytically, using hydrogen and a catalyst like Raney nickel or Pd/C, or chemically, e.g., using Fe/HCl. The aniline can then be acylated with reagents like an acid chloride, isocyanate or sulfonyl chloride to provide an amide, urea or sulfonamide, respectively. The Weinreb amide is/was reduced with lithium aluminum hydride or other reducing agent to afford the aldehyde. The t-butyl ester is/was cleaved with trifluoroacetic acid in solvent or another acidic reagent in solvent to provide the final product.

EXAMPLE 7

Figure 7:
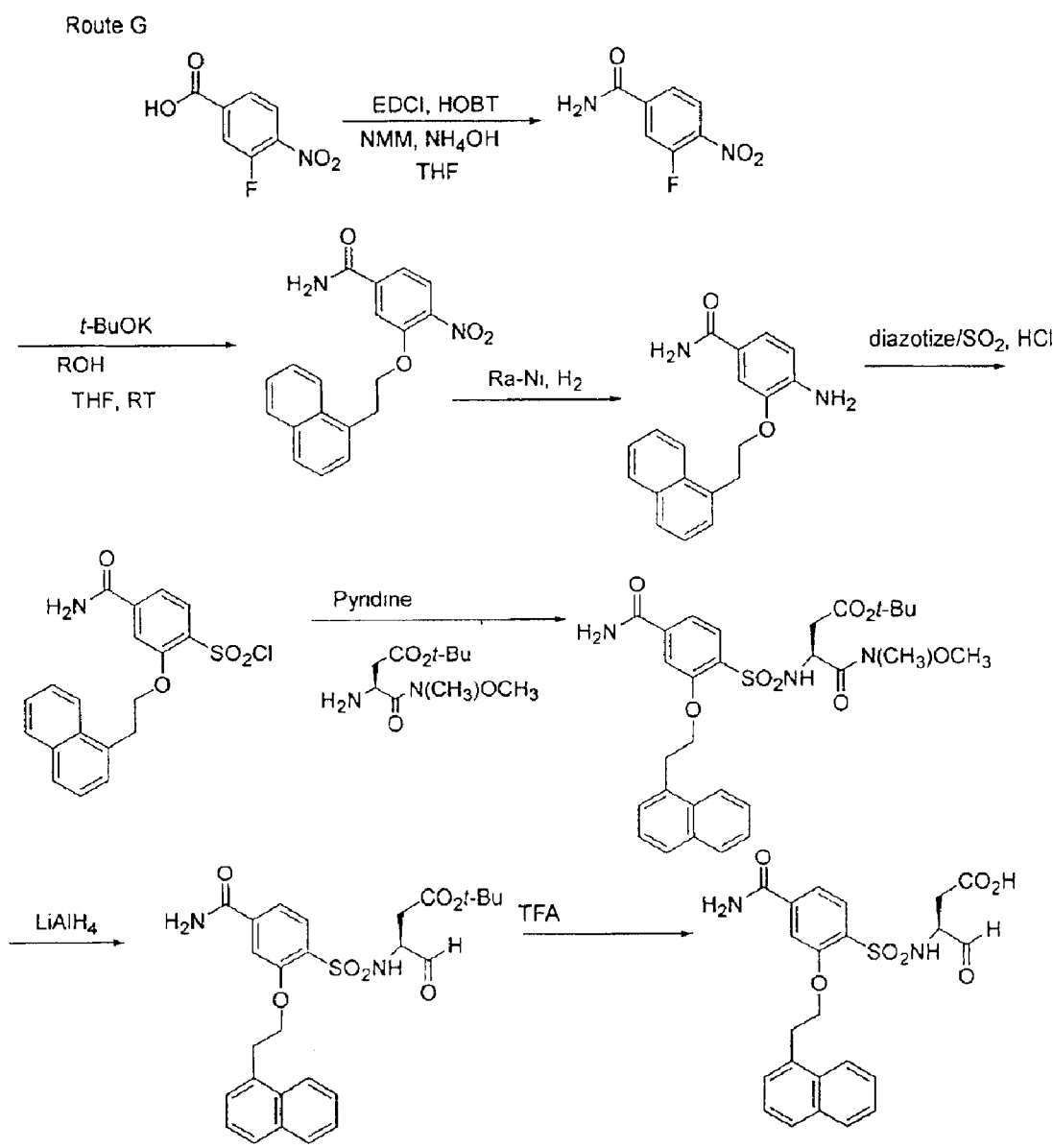
FIG. 7 depicts Route G for the synthesis of certain compounds of the present invention (See Example 7).

Route G (See FIG. 7)

3-Fluoro-4-nitro-benzoic acid and an amine, like ammonium hydroxide, were coupled in a polar aprotic solvent, using an activating agent like a carbodiimide and hydroxybenzotriazole, to provide an amide. An appropriate alcohol is/was treated with base, including but not limited to potassium t-butoxide and sodium hydride, in a solvent such as tetrahydrofuran or dimethylformamide. The 3-fluoro-4-nitro-benzamide is/was added to the solution of base and alcohol to afford the ether product. The nitro group is/was subsequently reduced catalytically, e.g., using hydrogen and a catalyst like Raney nickel or Pd/C, or chemically, e.g., with Fe/HCl. Diazotization of the aniline occurs by treatment with sodium nitrite/HCl/AcOH or t-butyl nitrite/boron trifluoride etherate. The diazonium product can be converted into a sulfonyl chloride with a sulfur dioxide/acid/solvent mixture. The resulting sulfonyl chloride is/was reacted with (S)-3-amino-N-methoxy-N-methyl-succinamic acid tert-butyl ester in the presence of an amine or other acid scavenger. The Weinreb amide is/was reduced with lithium aluminum hydride or other reducing agent to afford the aldehyde. The t-butyl ester is/was cleaved with trifluoroacetic acid in solvent or another acidic reagent in solvent to provide the final product.

Figure 8:
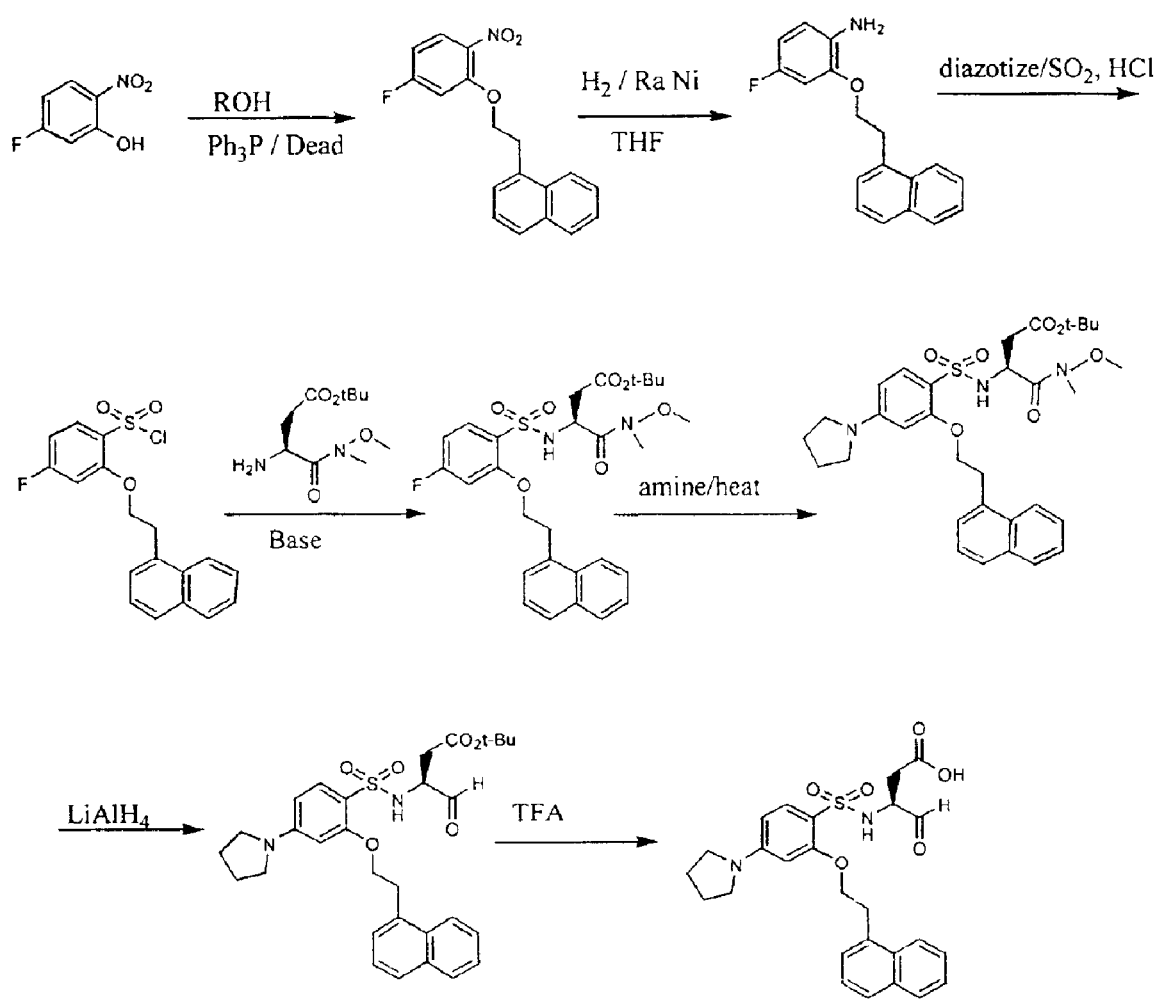
FIG. 8 depicts Route H for the synthesis of certain compounds of the present invention (See Example 8).

EXAMPLE 8
Route H (See FIG. 8)

4-Fluoro-2-nitrophenol is/was reacted with an appropriate alcohol in a polar aprotic solvent in the presence of a tertiary phosphine, such as triphenylphosphine, and a reagent like diethyl azodicarboxylate, to provide the ether. The nitro group is/was subsequently reduced catalytically, using hydrogen and a catalyst like Raney nickel or Pd/C, or chemically, e.g., with Fe/HCl. Diazotization of the aniline occurs by treatment with sodium nitrite/HCl/AcOH or t-butyl nitrite/boron trifluoride etherate. The diazonium product can be converted into a sulfonyl chloride with a sulfur dioxide/acid/solvent mixture. The resulting sulfonyl chloride is/was reacted with (S)-3-amino-N-methoxy-N-methyl-succinamic acid tert-butyl ester in the presence of an amine or other acid scavenger. Treatment with a secondary amine followed by heating provided the aniline. The Weinreb amide is/was reduced with lithium aluminum hydride or other reducing agent to afford the aldehyde. The t-butyl ester is/was cleaved with trifluoroacetic acid in solvent or another acidic reagent in solvent to provide the final product.

Figure 9:
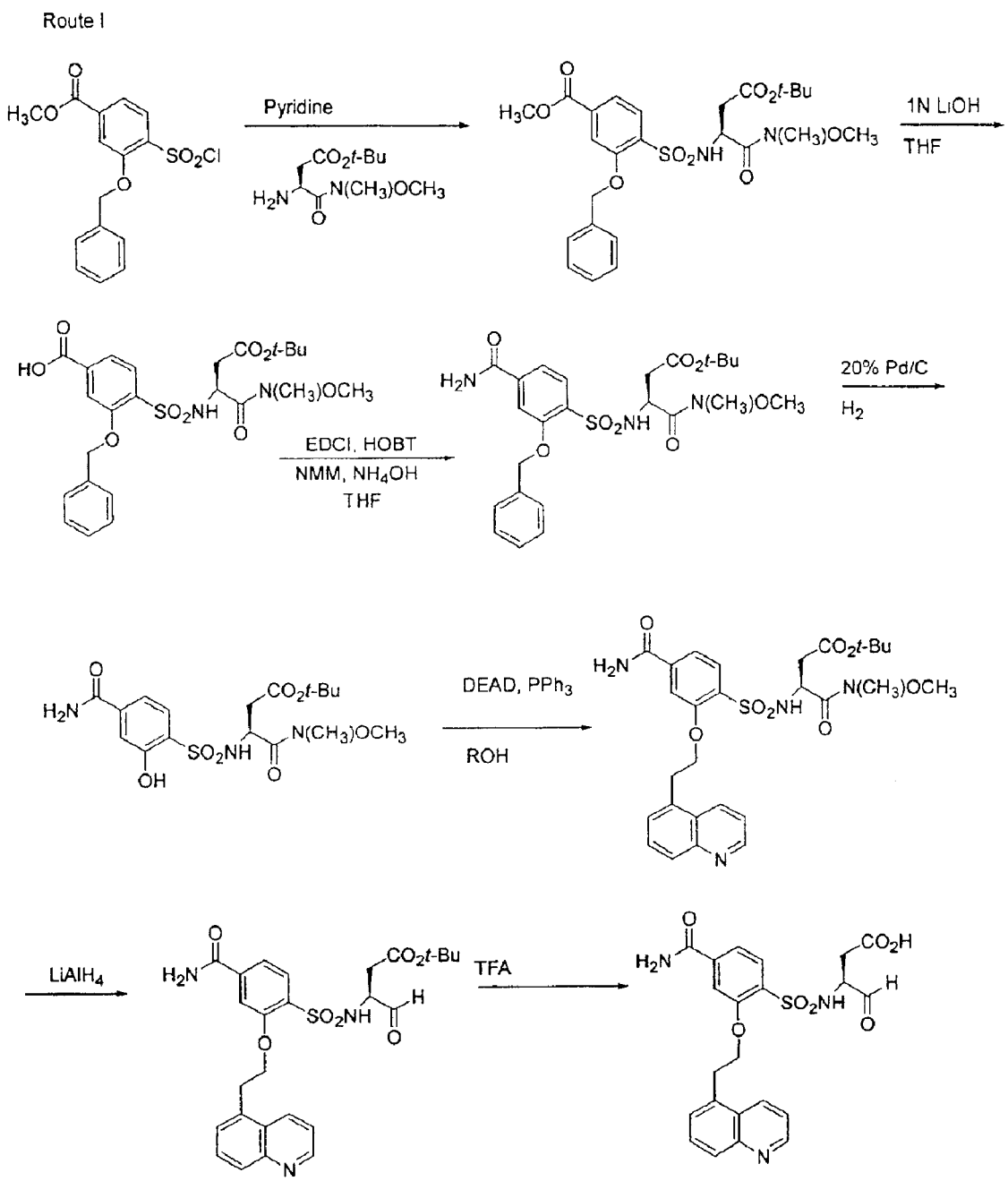
FIG. 9 depicts Route I for the synthesis of certain compounds of the present invention (See Example 9).

EXAMPLE 9
Route I (See FIG. 9)

3-Benzyloxy-4-chlorosulfonyl-benzoic acid methyl ester (Route P; Example 16) is/was reacted with (S)-3-amino-N-methoxy-N-methyl-succinamic acid tert-butyl ester in the presence of an amine or other acid scavenger. The methyl ester is/was hydrolyzed with base, such as lithium hydroxide. The resulting acid in a polar aprotic solvent is/was treated with an activating agent, like a carbodiimide and hydroxybenzotriazole, and is/was coupled with an amine like ammonia to provide an amide. The benzyl protecting group is/was removed with a catalyst like Pd/C and hydrogen to provide the phenol. The resulting phenol is/was reacted with an appropriate alcohol in a polar aprotic solvent in the presence of a tertiary phosphine, such as triphenylphosphine, and a reagent like diethyl azodicarboxylate, to provide the ether. The Weinreb amide is/was reduced with lithium aluminum hydride or another reducing agent to afford the aldehyde. The t-butyl ester is/was cleaved with trifluoroacetic acid in solvent or another acidic reagent in solvent to provide the final product.

Figure 10:
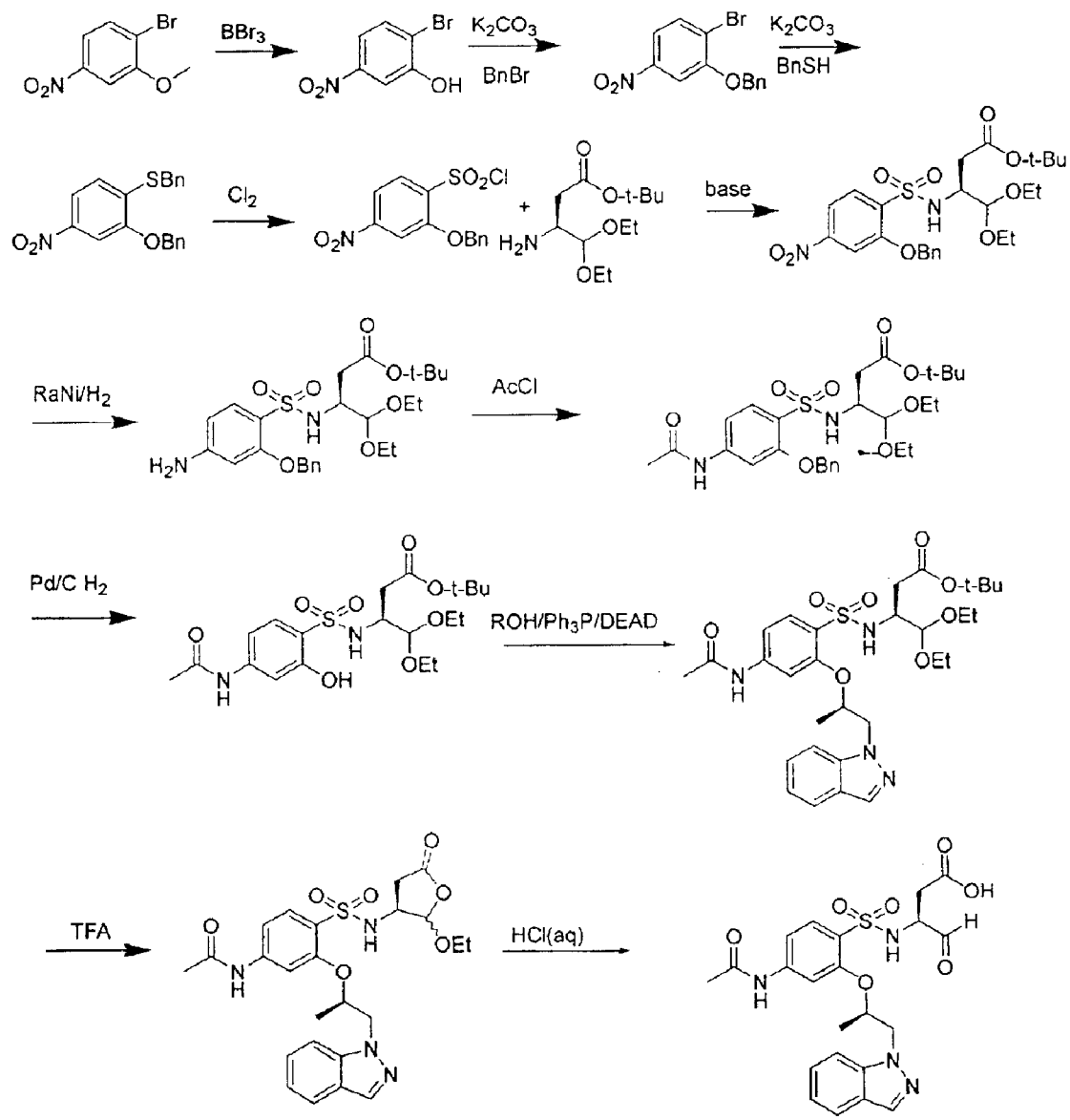
FIG. 10 depicts Route J for the synthesis of certain compounds of the present invention (See Example 10).

EXAMPLE 10
Route J (See FIG. 10)

2-Bromo-5-nitroanisole is/was demethylated with reagents known to demethylate anisoles, such as boron tribromide, trimethylsilyl iodide or sodium ethanethiolate, to provide the phenol. The phenol is/was alkylated using a benzyl halide and a base, such as potassium carbonate or cesium carbonate, to provide an ether. Treatment of the bromide with a base, like potassium carbonate or cesium carbonate, and a benzyl mercaptan provides a thioether. This thioether can then be oxidized with chlorine to provide the sulfonyl chloride. The sulfonyl chloride is/was reacted with (S)-3-amino-4,4-diethoxy-butyric acid tert-butyl ester in the presence of an amine or other acid scavenger. The nitro group is/was subsequently reduced catalytically, using hydrogen and a catalyst like Raney nickel or Pd/C, or by chemically, e.g., using Fe/HCl. The aniline can then be acylated with reagents like an acid chloride, isocyanate or sulfonyl chloride to provide an amide, urea or sulfonamide, respectively. The benzyl protecting group is/was removed with a catalyst like Pd/C and hydrogen to provide the phenol. The resulting phenol is/was reacted with an appropriate alcohol in a polar aprotic solvent in the presence of a tertiary phosphine, such as triphenylphosphine, and a reagent like diethyl azodicarboxylate, to provide the ether. This ether is/was treated with an acid reagent like trifluoroacetic acid to provide the cyclic acetal prodrug. This prodrug could be further deprotected with aqueous acid to provide the acid aldehyde.

Figure 11:
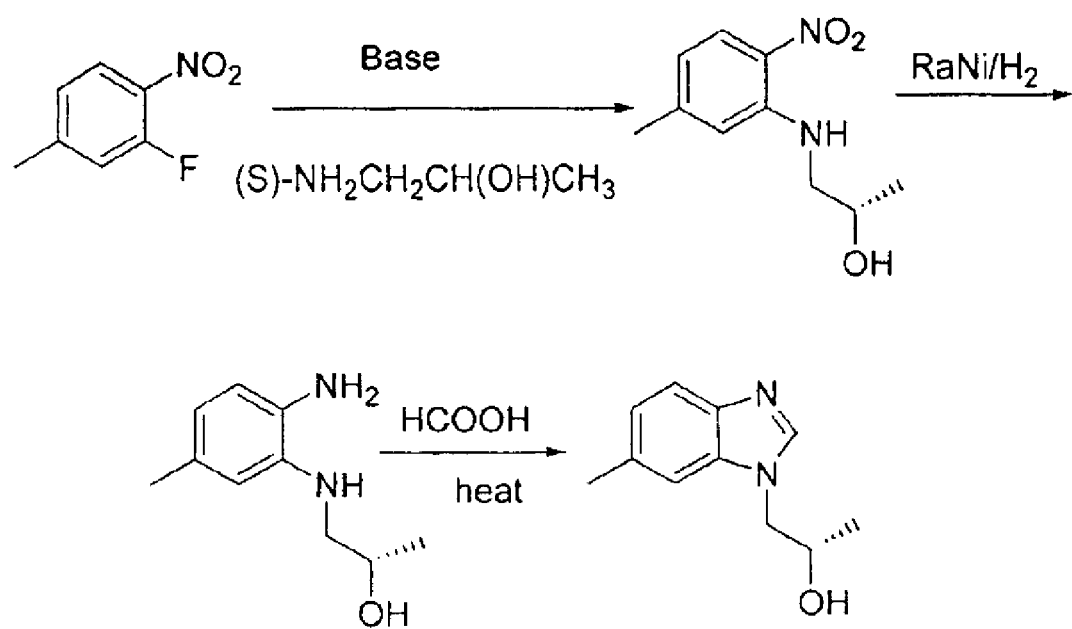
FIG. 11 depicts Route K for the synthesis of certain compounds of the present invention (See Example 11).

EXAMPLE 11
Route K (See FIG. 11)

Intermediate benzimidazole ethanols may be prepared by reaction of the appropriately substituted ortho-fluoronitrobenzene with the appropriately substituted aminoethanol derivative in the presence of base. Reduction of the nitro group catalytically, using hydrogen and a catalyst like Raney nickel or Pd/C, or by chemically, e.g., with Fe/HCl, followed by cyclization (for example by heating in the appropriately substituted carboxylic acid or by other methods well known in the literature) gives the required benzimidazole.

Figure 12:
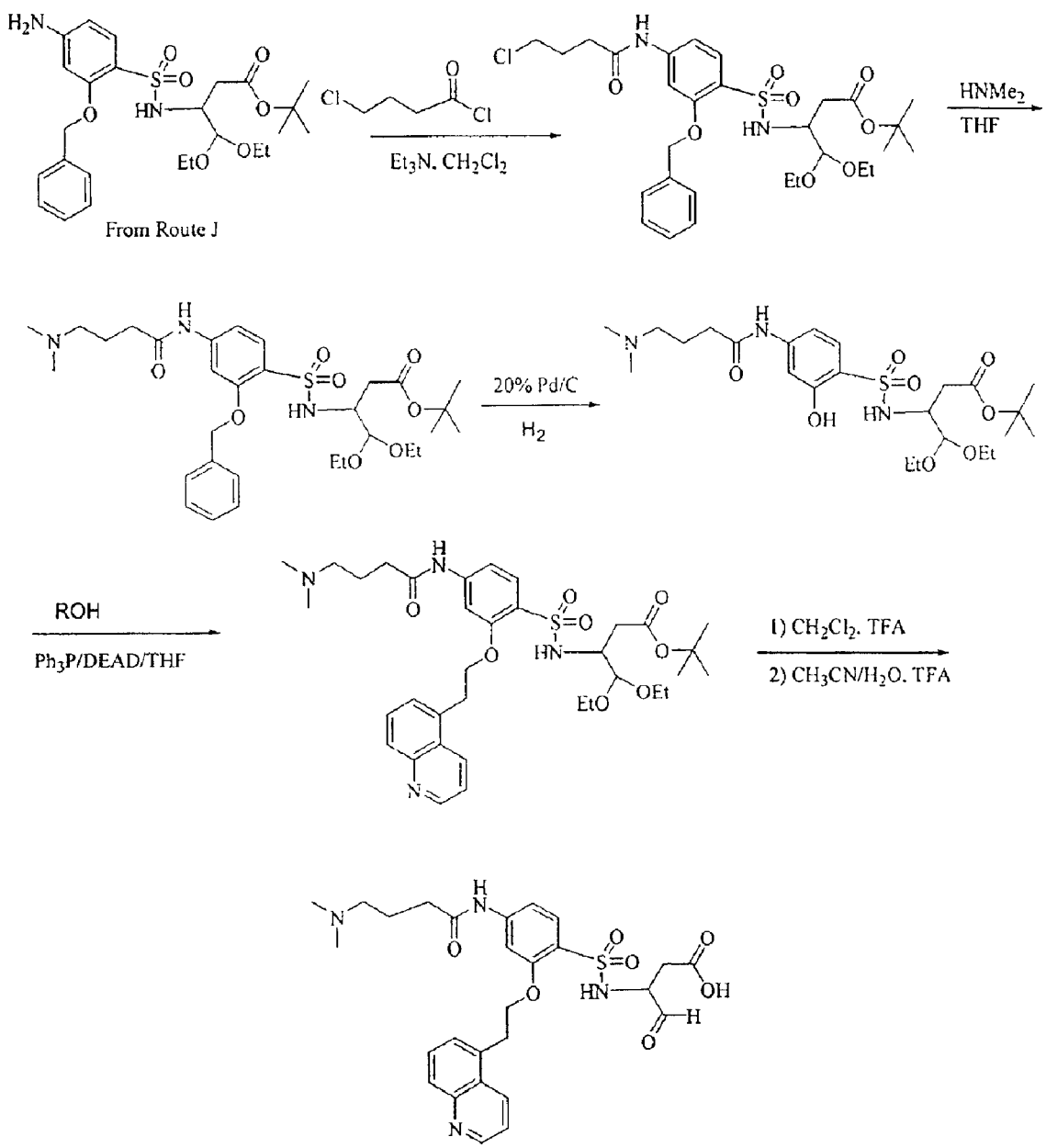
FIG. 12 depicts Route L for the synthesis of certain compounds of the present invention (See Example 12).

EXAMPLE 12
Route L (See FIG. 12)

Acylation of the aniline derivative (prepared as described in Route J; Example 10) with a halosubstituted acyl chloride, such as chloro butyrylchloride, in the presence of a base, such as triethylamine, followed by displacement of halide with a secondary amine, such as dimethylamine or a nitrogen heterocycle, such as imidazole, gives the intermediate amine-amide. The benzyl protecting group may then be removed using a catalyst like Pd/C and hydrogen to provide the phenol. The resulting phenol may be reacted with an appropriate alcohol in the presence of a tertiary phosphine, such as triphenylphosphine, and a reagent like diethyl azodicarboxylate, to provide the ether. This ether may then be treated with an acid reagent like trifluoroacetic acid to provide the cyclic acetal prodrug. This prodrug could be further deprotected with aqueous acid to provide the acid-aldehyde.

Figure 13:
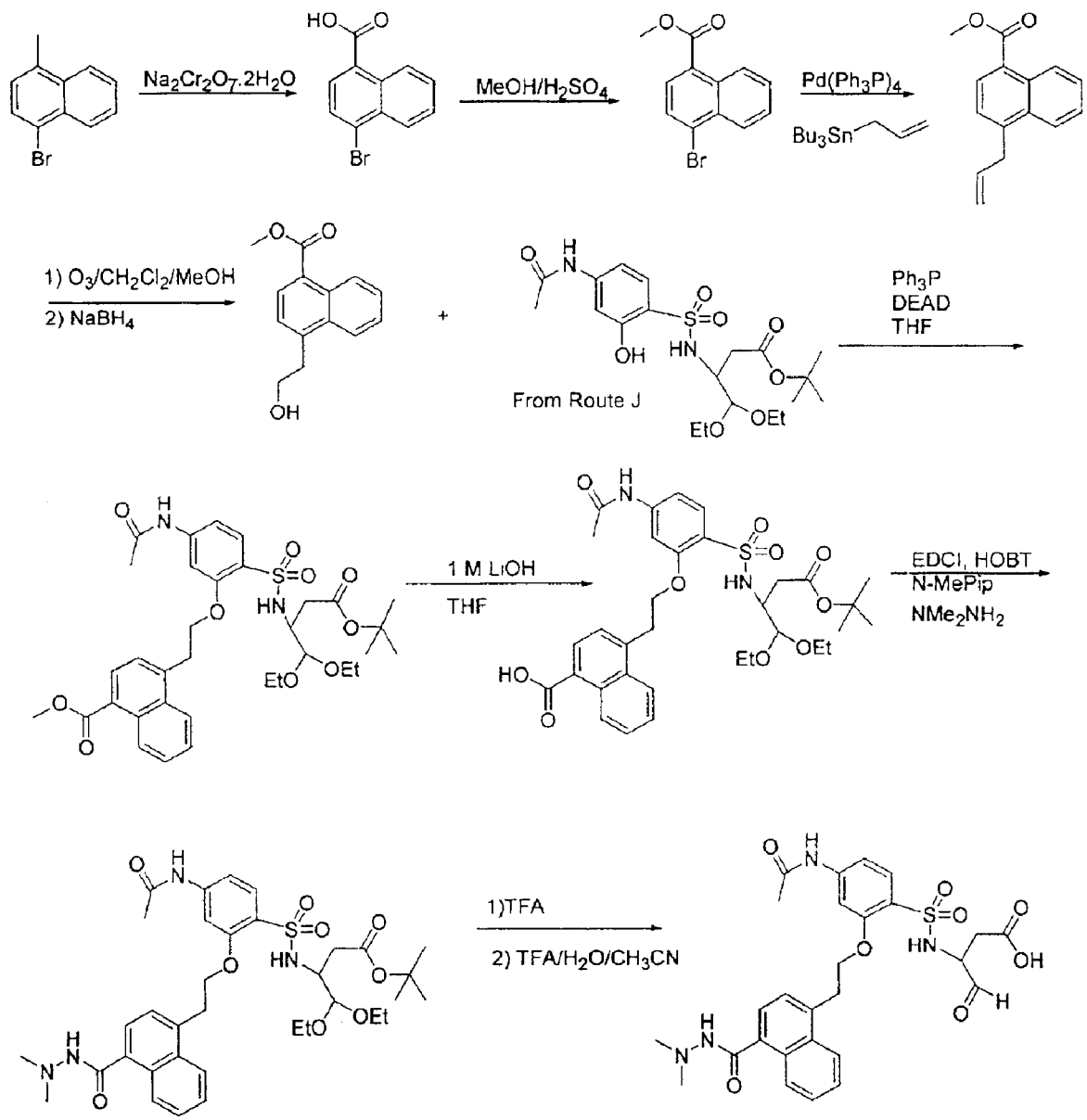
FIG. 13 depicts Route M for the synthesis of certain compounds of the present invention (See Example 13).

EXAMPLE 13
Route M (See FIG. 13)

N-acylated phenol intermediates, such as those prepared according to the procedure of Route J (Example 10), may be reacted with arylethanols, e.g., substituted on the aryl group with an ester of a carboxylic acid, in the presence of a tertiary phosphine, such as triphenylphosphine, and a reagent like diethyl azodicarboxylate, to provide the corresponding ether. Hydrolysis of the ester, e.g., using aqueous base, followed by coupling with an appropriately substituted amine or hydrazine, using standard coupling reagents such as carbodiimides or other reagents known in the literature, provides the intermediate amides or hydrazides. This intermediate may then be treated with an acid reagent like trifluoroacetic acid to provide the cyclic acetal prodrug. This prodrug may be further deprotected with aqueous acid to provide the acid aldehyde.

EXAMPLE 14

Figure 14:
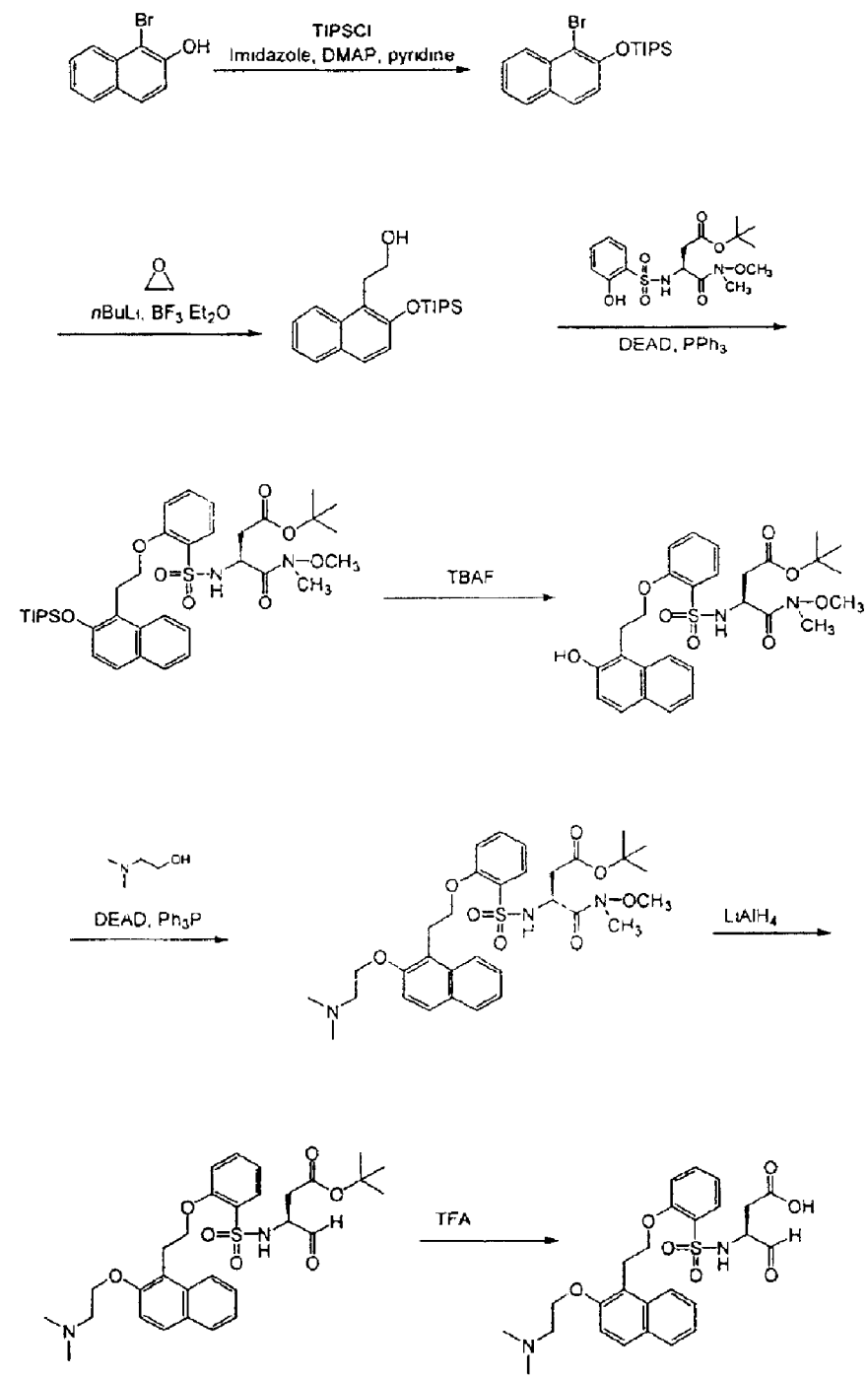
FIG. 14 depicts Route N for the synthesis of certain compounds of the present invention (See Example 14).

Route N (See FIG. 14)

The intermediate phenol (prepared as described in Route A; Example 1) may be reacted with an aryl alcohol, substituted on the aryl group by a suitably protected hydroxyl group, in the presence of a tertiary phosphine, such as triphenylphosphine, and a reagent like diethyl azodicarboxylate, to provide the ether. Deprotection, followed by reaction with an alcohol (preferably an alcohol substituted with a tertiary amino group, such as dimethyamino ethanol) in the presence of a tertiary phosphine, such as triphenylphosphine, and a reagent like diethyl azodicarboxylate, provides the ether. The Weinreb amide may then be reduced with lithium aluminum hydride or another reducing agent to afford the aldehyde. The t-butyl ester may then be cleaved with trifluoroacetic acid in solvent or another acidic reagent in solvent to provide the final product.

EXAMPLE 15

Figure 15:
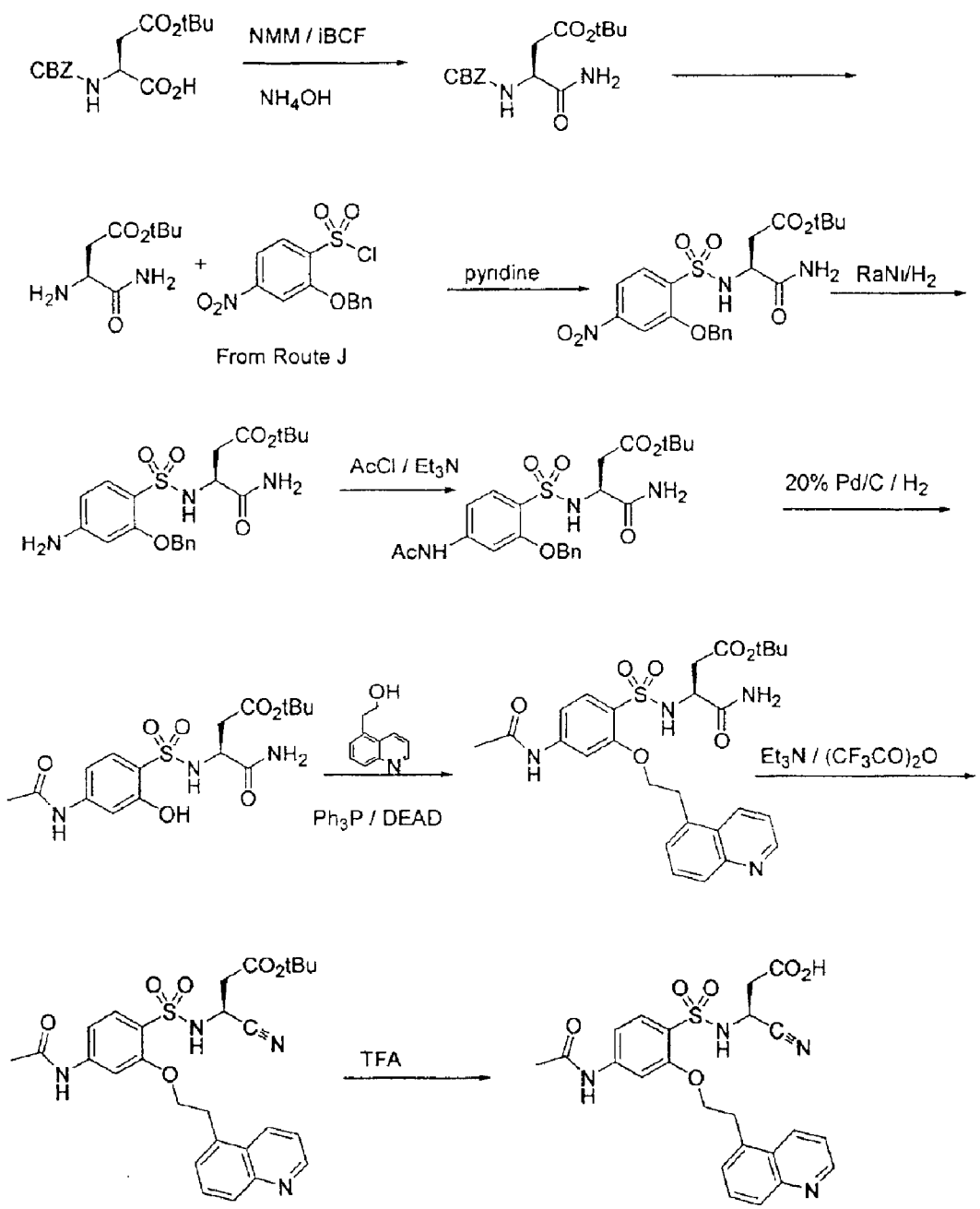
FIG. 15 depicts Route O tether for the synthesis of certain compounds of the present invention (See Example 15).

Route O (See FIG. 15)

Nitriles may be prepared by reaction of the of aspartic acid β-t-butyl ester α-amide with nitrobenzyloxysulfonyl chloride (prepared as described in Route J; Example 10). The nitro group is subsequently reduced catalytically, using hydrogen and a catalyst like Raney nickel or Pd/C, or chemically, e.g., with Fe/HCl. The aniline can then be acylated with reagents like an acid chloride, isocyanate or sulfonyl chloride to provide an amide, urea or sulfonamide, respectively. The benzyl protecting group may then be removed using a catalyst like Pd/C and hydrogen to provide the phenol. The resulting phenol may be reacted with an appropriate alcohol in the presence of a tertiary phosphine, such as triphenylphosphine, and a reagent like diethyl azodicarboxylate, to provide the ether. Dehydration of the amide using a reagent such as trifluoroacetic anhydride provides the corresponding nitrile. The t-butyl ester may then be cleaved with trifluoroacetic acid in solvent or another acidic reagent in solvent to provide the final product.

EXAMPLE 16

Figure 16:
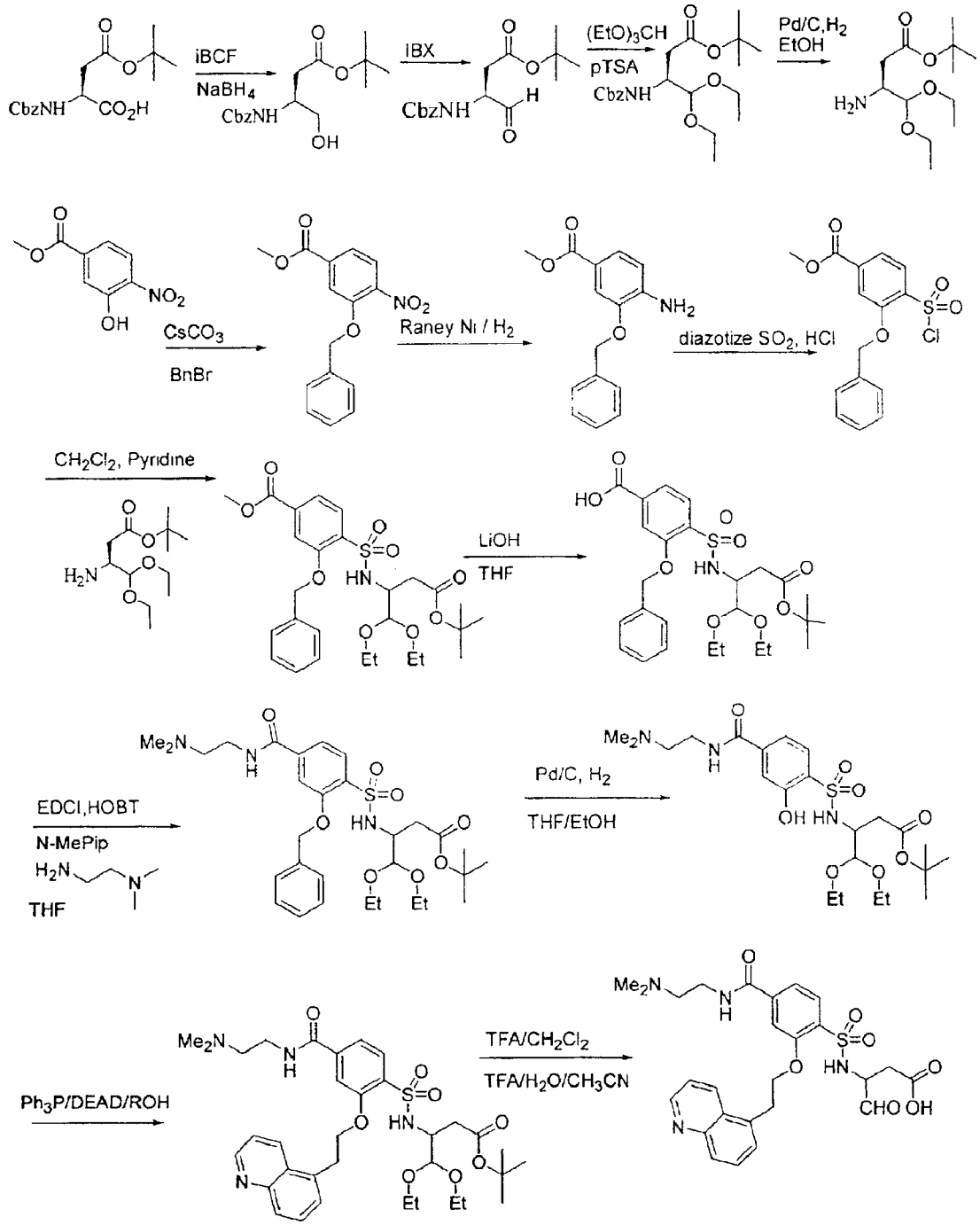
FIG. 16 depicts Route P for the synthesis of certain compounds of the present invention (See Example 16).

Route P (See FIG. 16)

Benzylation of the starting carboalkoxynitrophenol with a reagent such as benzyl bromide in the presence of a base or acid scavenger, followed by reduction of the nitro group catalytically, using hydrogen and a catalyst like Raney nickel or Pd/C, or chemically, e.g., with Fe/HCl, may be used to provide the intermediate aniline. Diazotization of the aniline may be achieved by treatment with sodium nitrite/HCl/AcOH or t-butyl nitrite/boron trifluoride etherate. The diazonium product can be converted into a sulfonyl chloride with a sulfur dioxide/acid/solvent mixture. The resulting sulfonyl chloride may then be reacted with the protected aspartic acid acetal. Hydrolysis of the ester, e.g., using aqueous base, followed by coupling with an appropriately substituted amine or hydrazine using standard coupling reagents, such as carbodiimides or other reagents known in the literature, provides the desired intermediate amides or hydrazides. The benzyl protecting group may then be removed using a catalyst like Pd/C and hydrogen to provide the phenol. The resulting phenol may be reacted with an appropriate alcohol in the presence of a tertiary phosphine, such as triphenylphosphine, and a reagent like diethyl azodicarboxylate, to provide the ether. This intermediate may then be treated with an acid reagent like trifluoroacetic acid to provide the cyclic acetal prodrug. This prodrug could be further deprotected with aqueous acid to provide the acid aldehyde.

EXAMPLE 17

Figure 17:
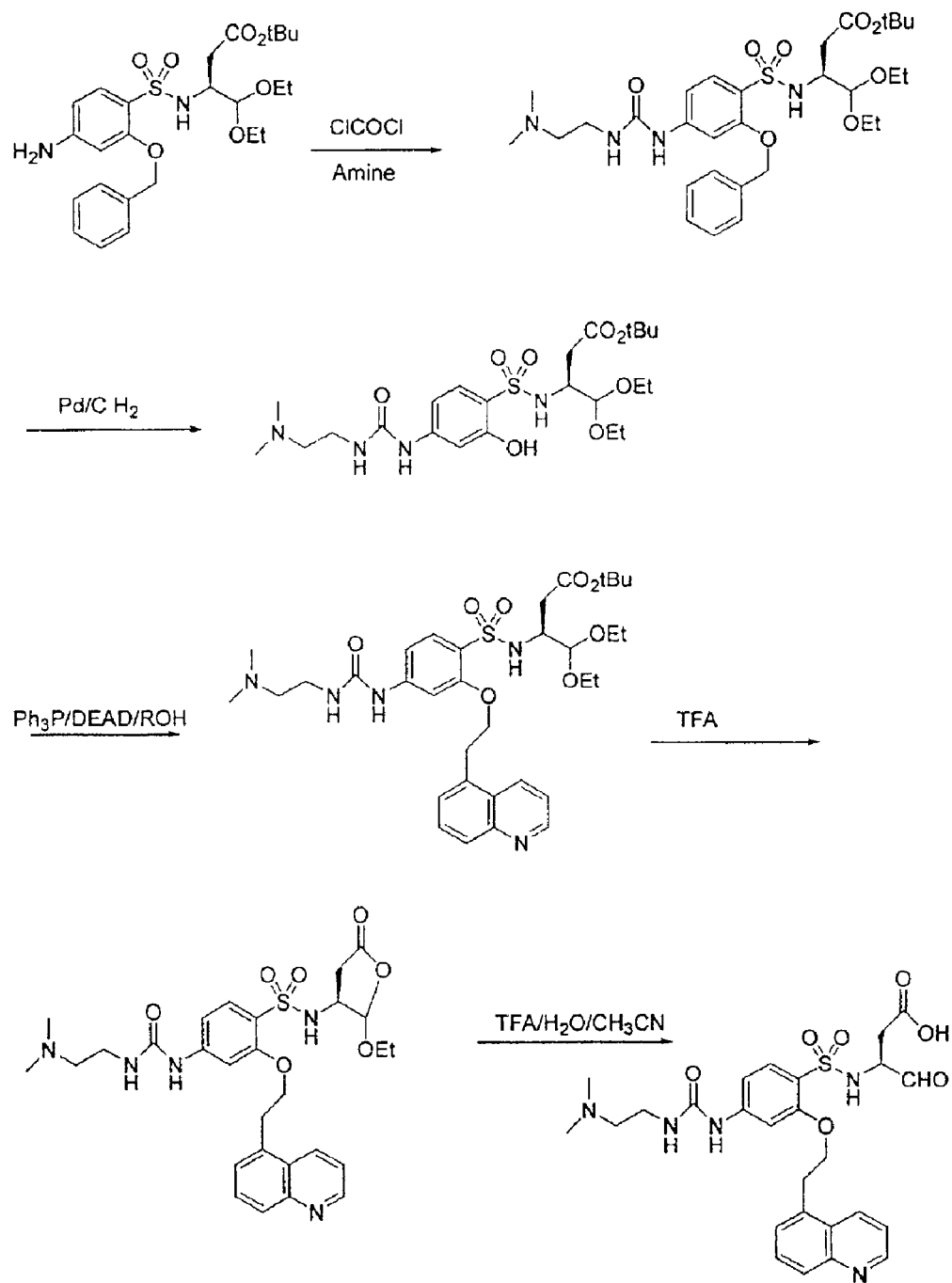
FIG. 17 depicts Route Q for the synthesis of certain compounds of the present invention (See Example 17).

Route Q (See FIG. 17)

The aniline derivative (prepared as described in Route J; Example 10) may be converted to the corresponding isocyanate, using a reagent such as phosgene in the presence of an appropriate base. Reaction with an amine provides the urea. The benzyl protecting group may then be removed using a catalyst like Pd/C and hydrogen to provide the phenol. The resulting phenol may be reacted with an appropriate alcohol in the presence of a tertiary phosphine, such as triphenylphosphine, and a reagent like diethyl azodicarboxylate, to provide the ether. This intermediate may then be treated with an acid reagent like trifluoroacetic acid to provide the cyclic acetal prodrug. This prodrug could be further deprotected with aqueous acid to provide the acid aldehyde.

EXAMPLE 18

Figure 18:
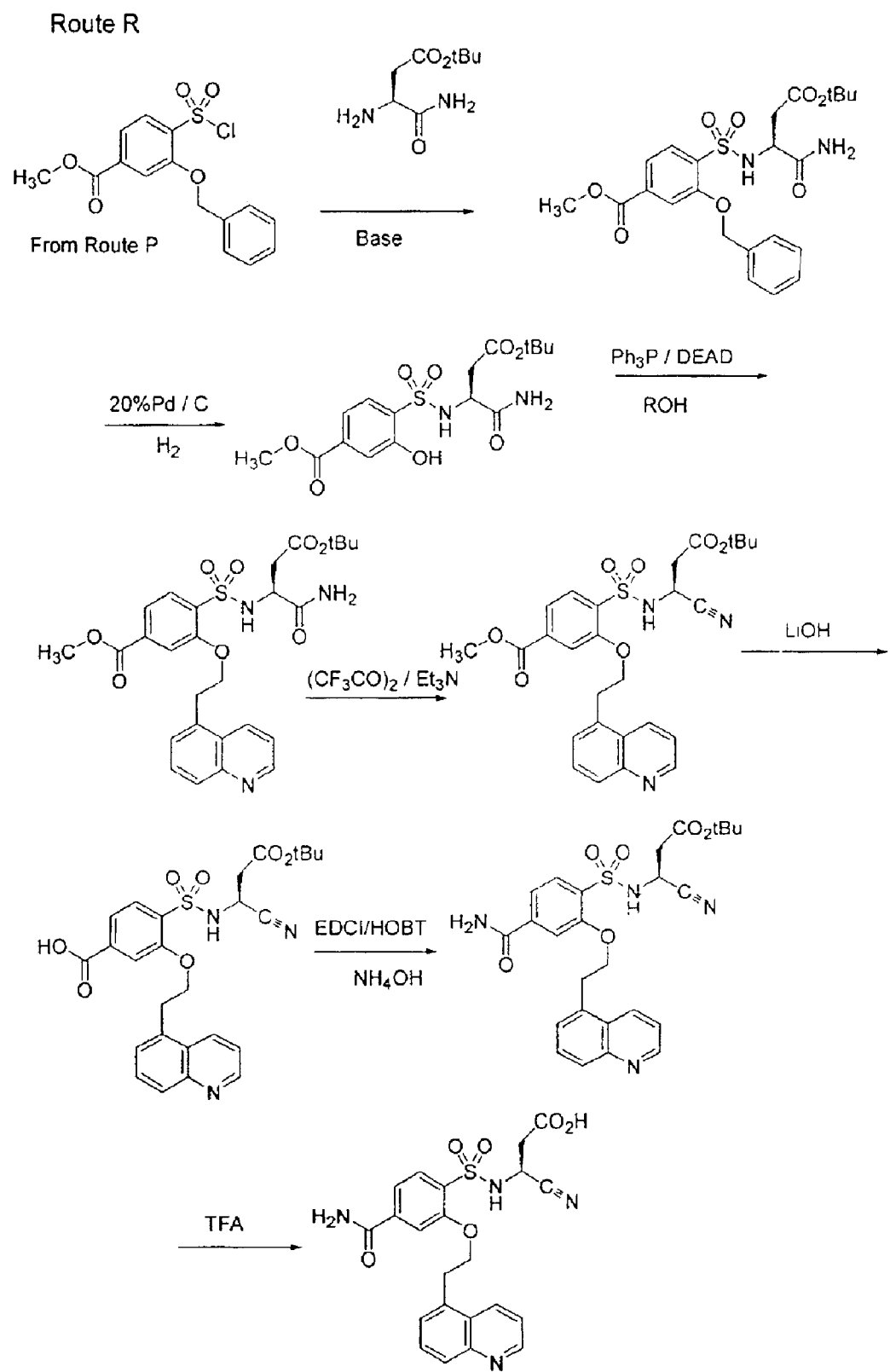
FIG. 18 depicts Route R for the synthesis of certain compounds of the present invention (See Example 18).
Figure 19:
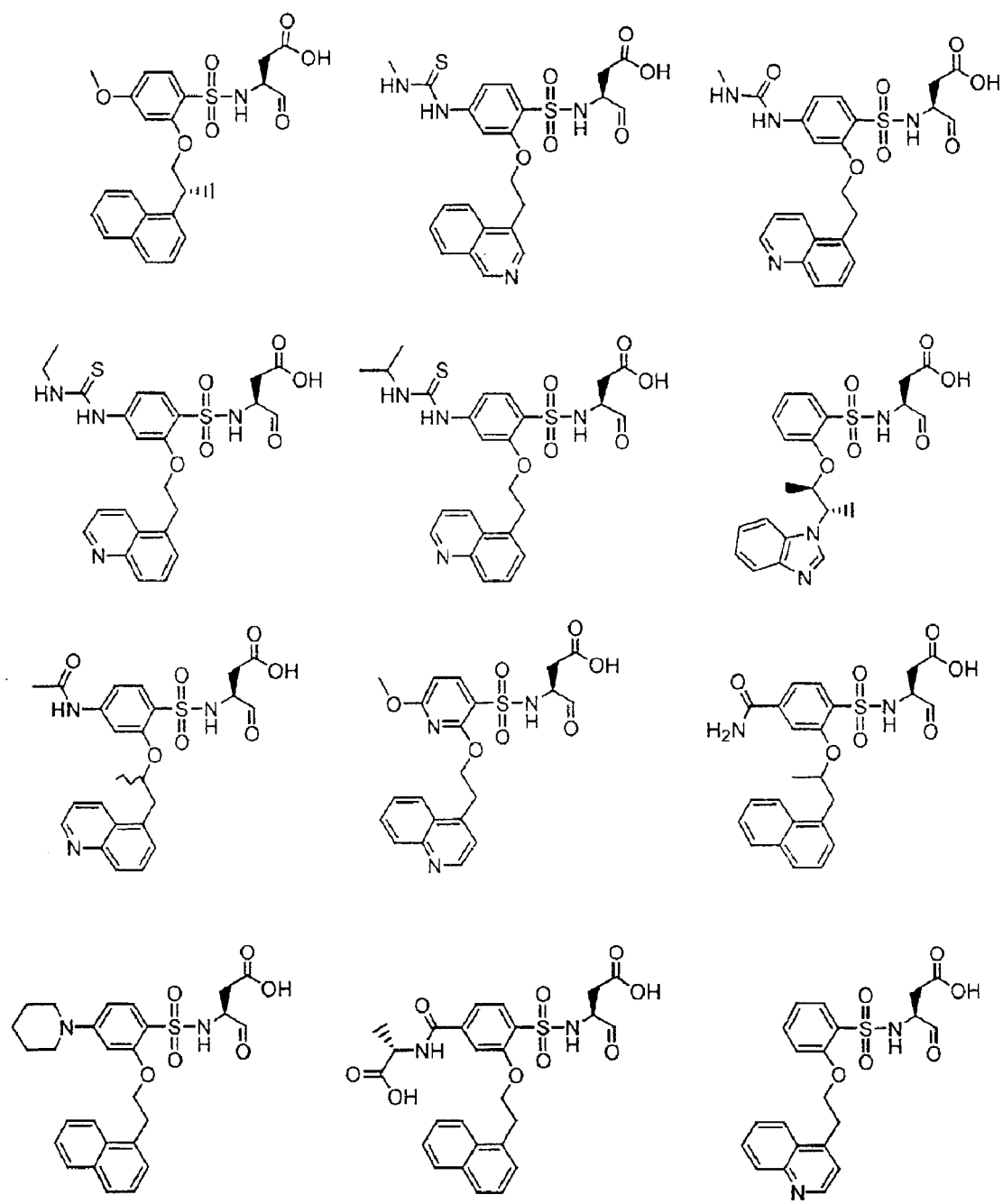
FIG. 19 depicts certain compounds of the present invention that were synthesized and subjected to inhibition studies.
Figure 20:
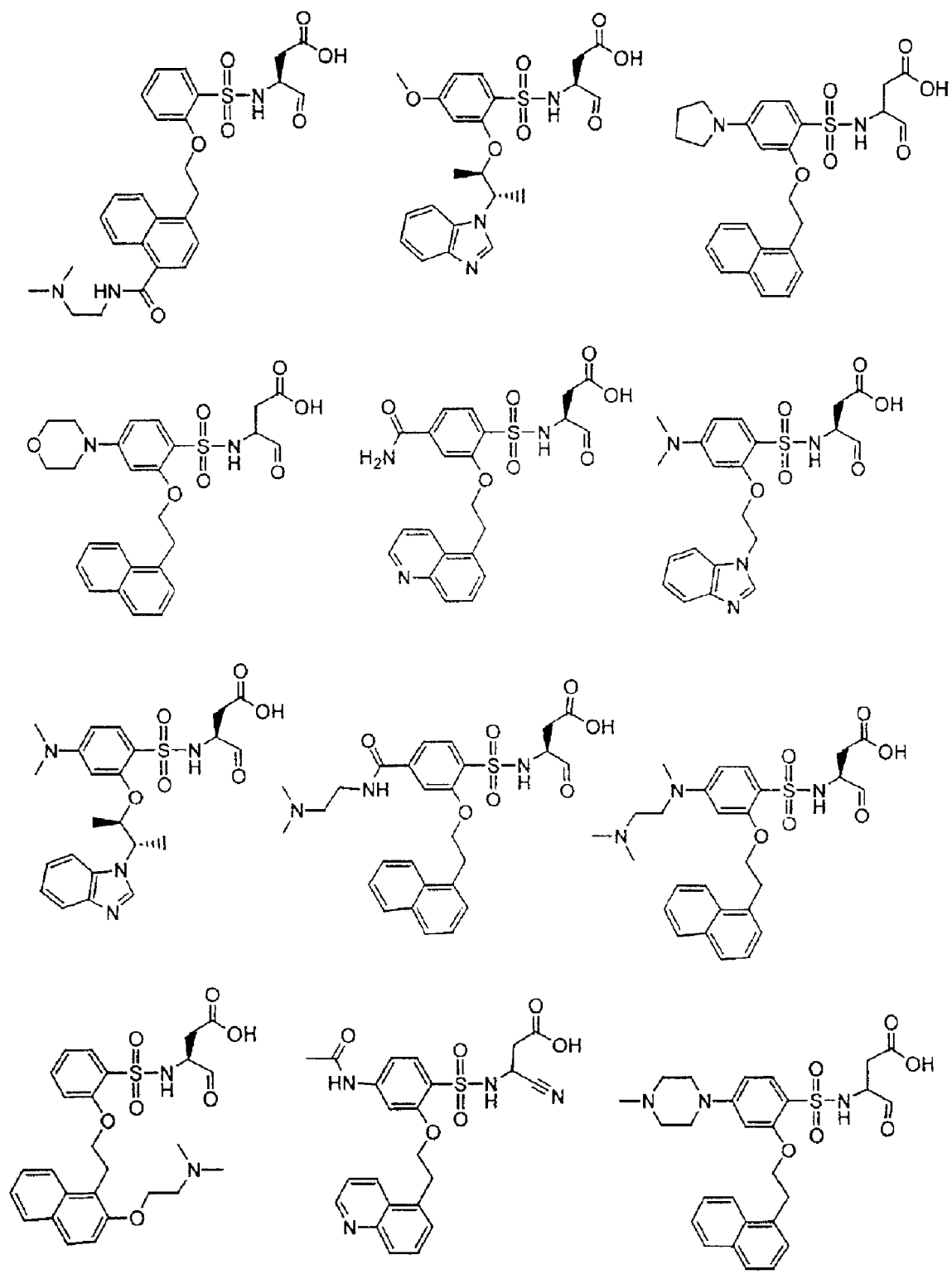
FIG. 20 depicts certain compounds of the present invention that were synthesized and subjected to inhibition studies.
Figure 21:
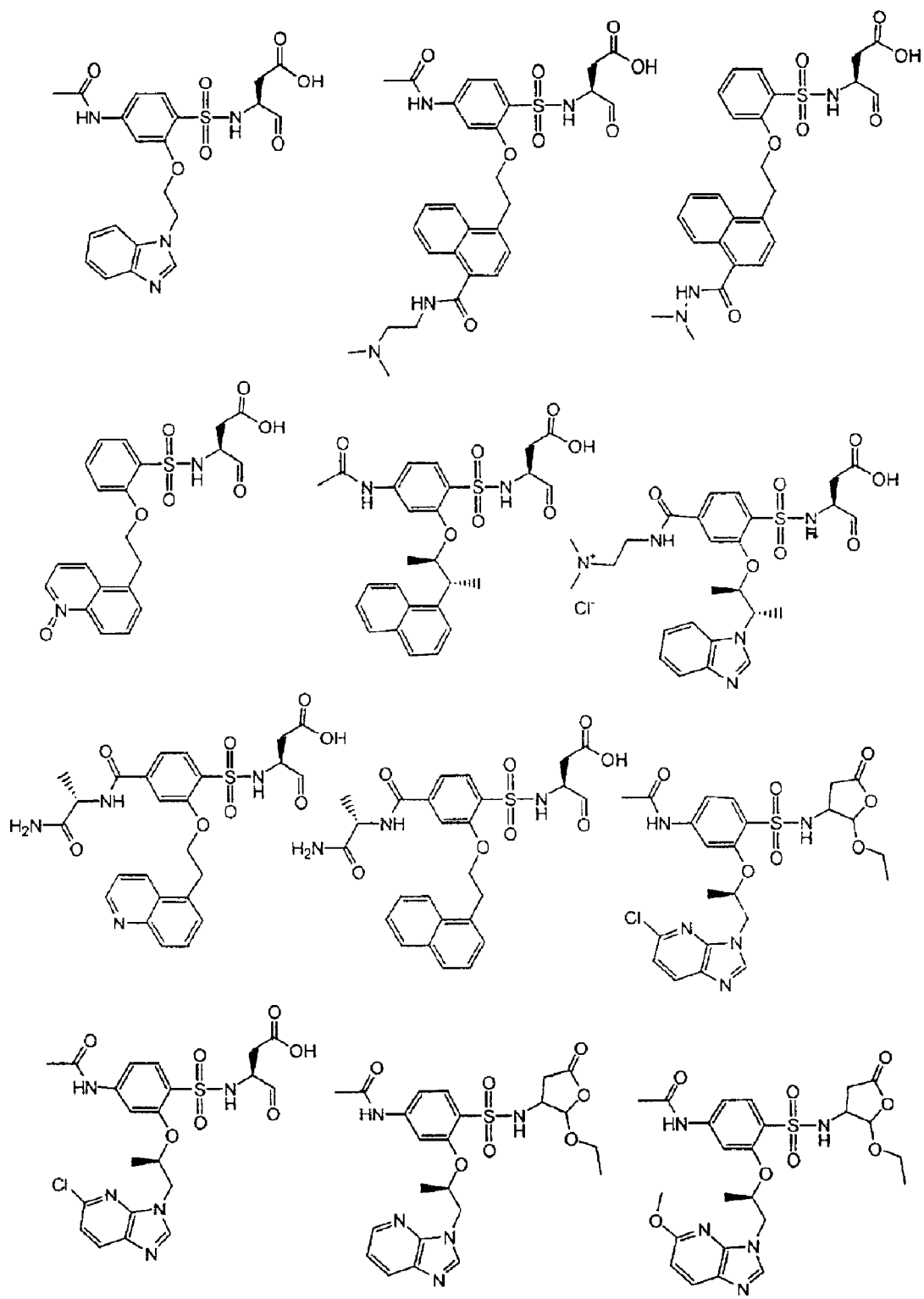
FIG. 21 depicts certain compounds of the present invention that were synthesized and subjected to inhibition studies.
Figure 22:
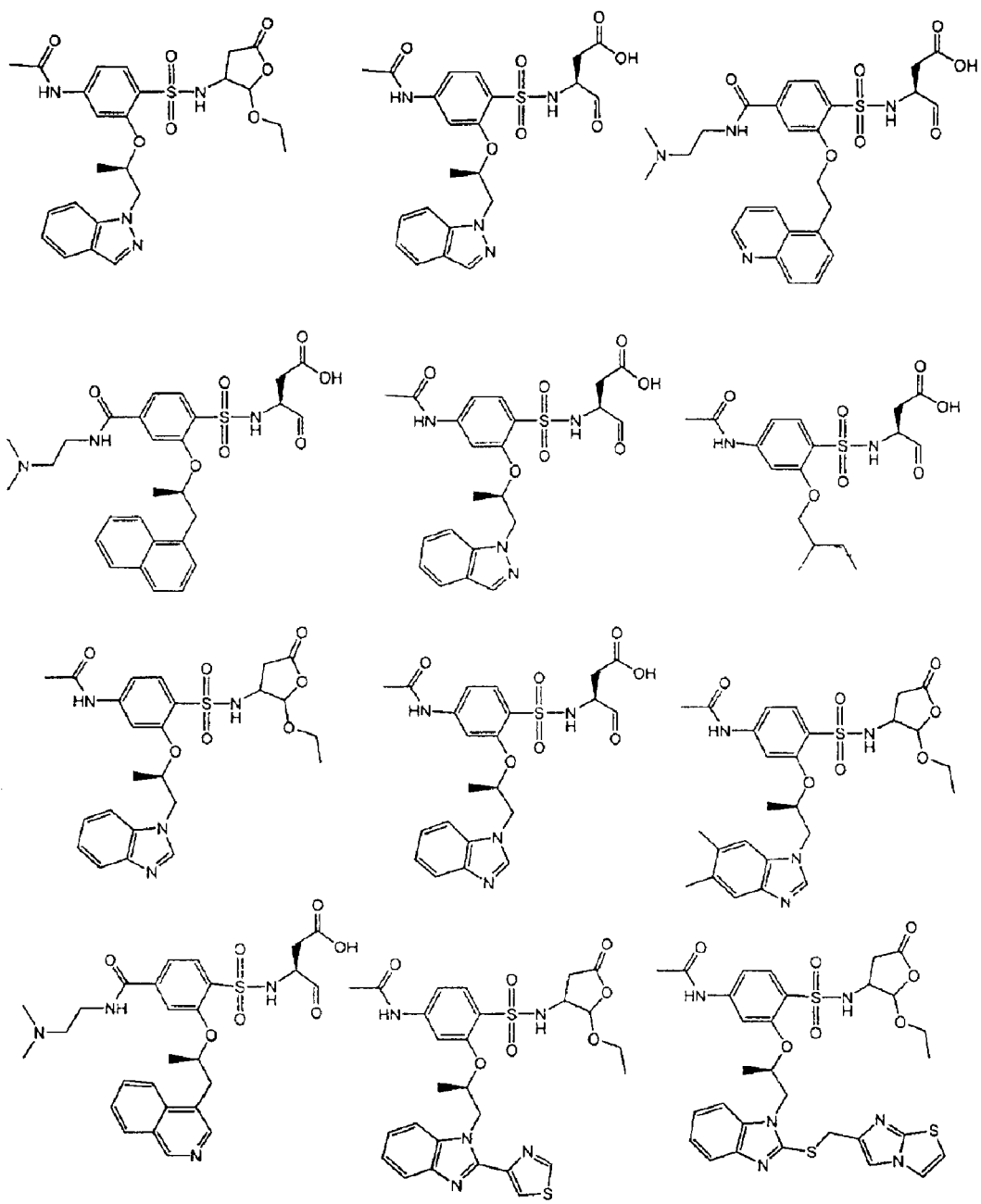
FIG. 22 depicts certain compounds of the present invention that were synthesized and subjected to inhibition studies.
Figure 23:
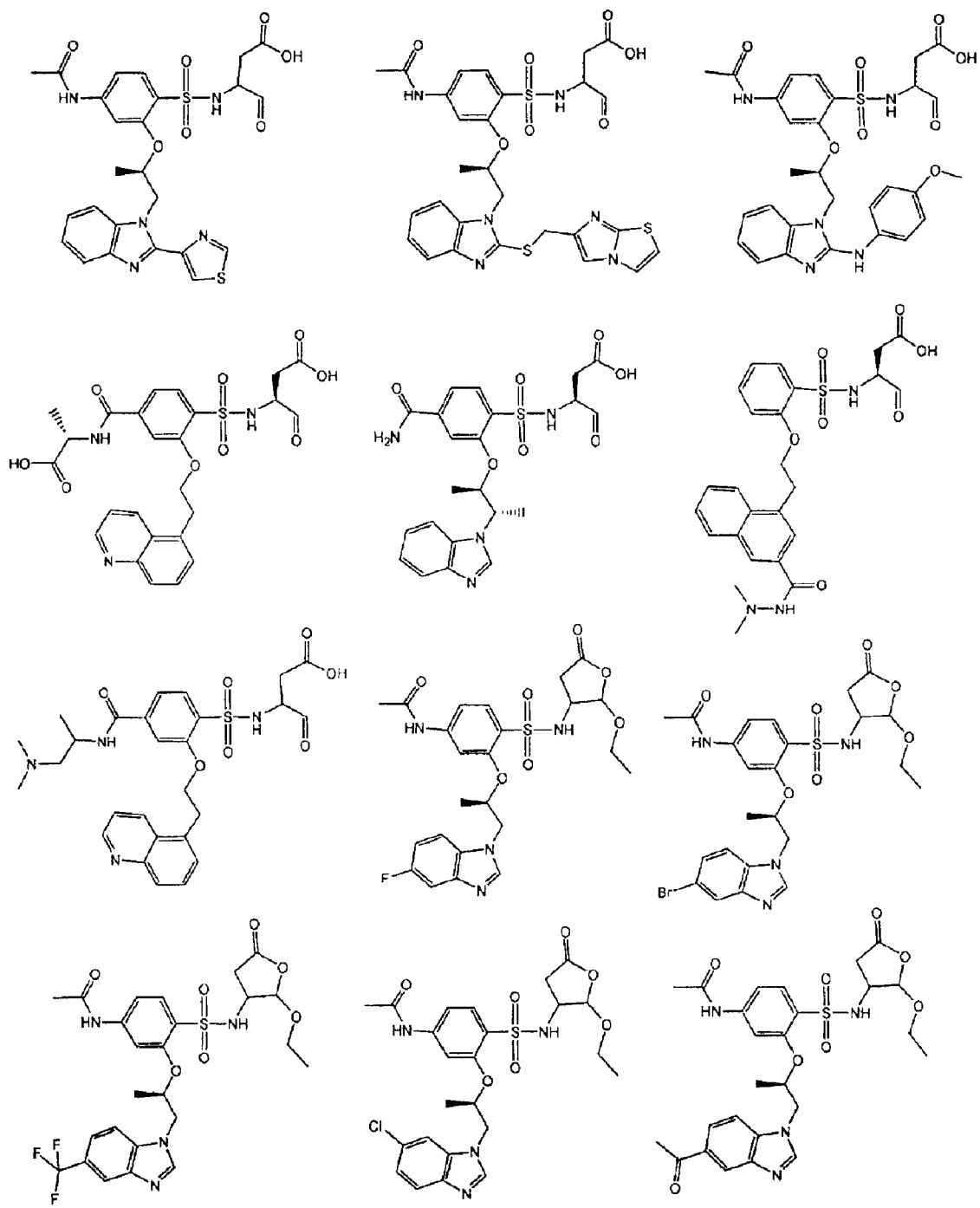
FIG. 23 depicts certain compounds of the present invention that were synthesized and subjected to inhibition studies.
Figure 24:
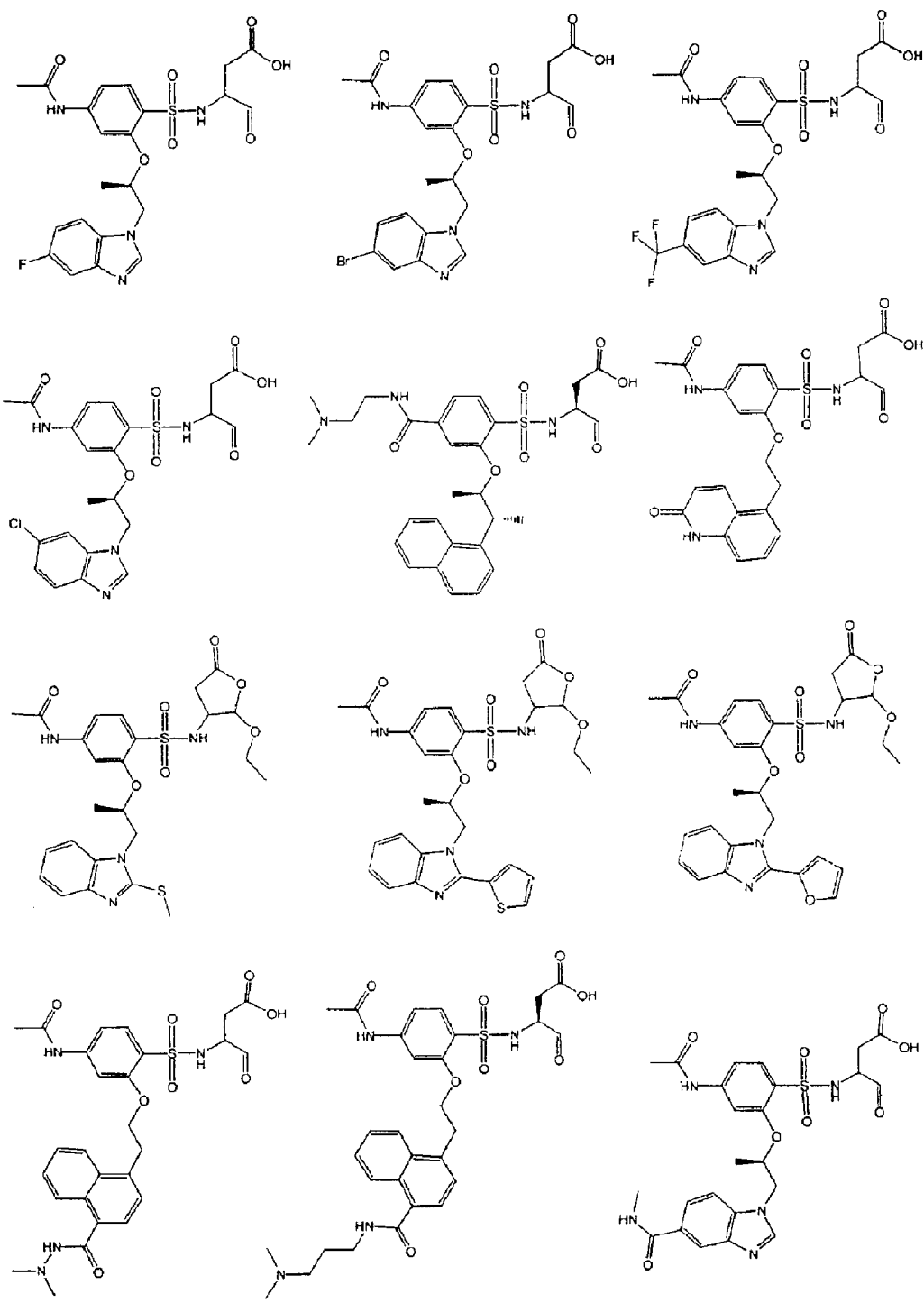
FIG. 24 depicts certain compounds of the present invention that were synthesized and subjected to inhibition studies.
Figure 25:
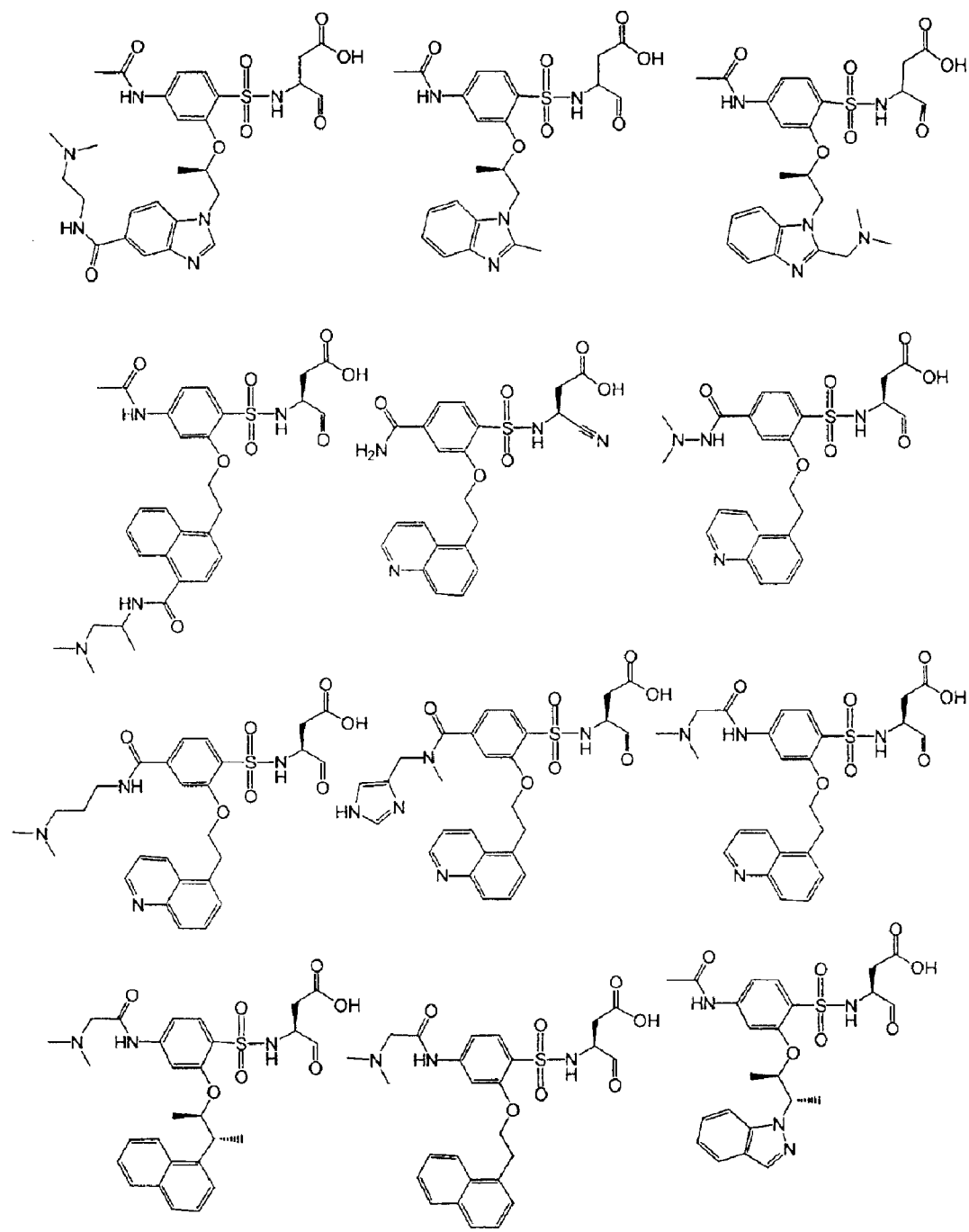
FIG. 25 depicts certain compounds of the present invention that were synthesized and subjected to inhibition studies.
Figure 26:
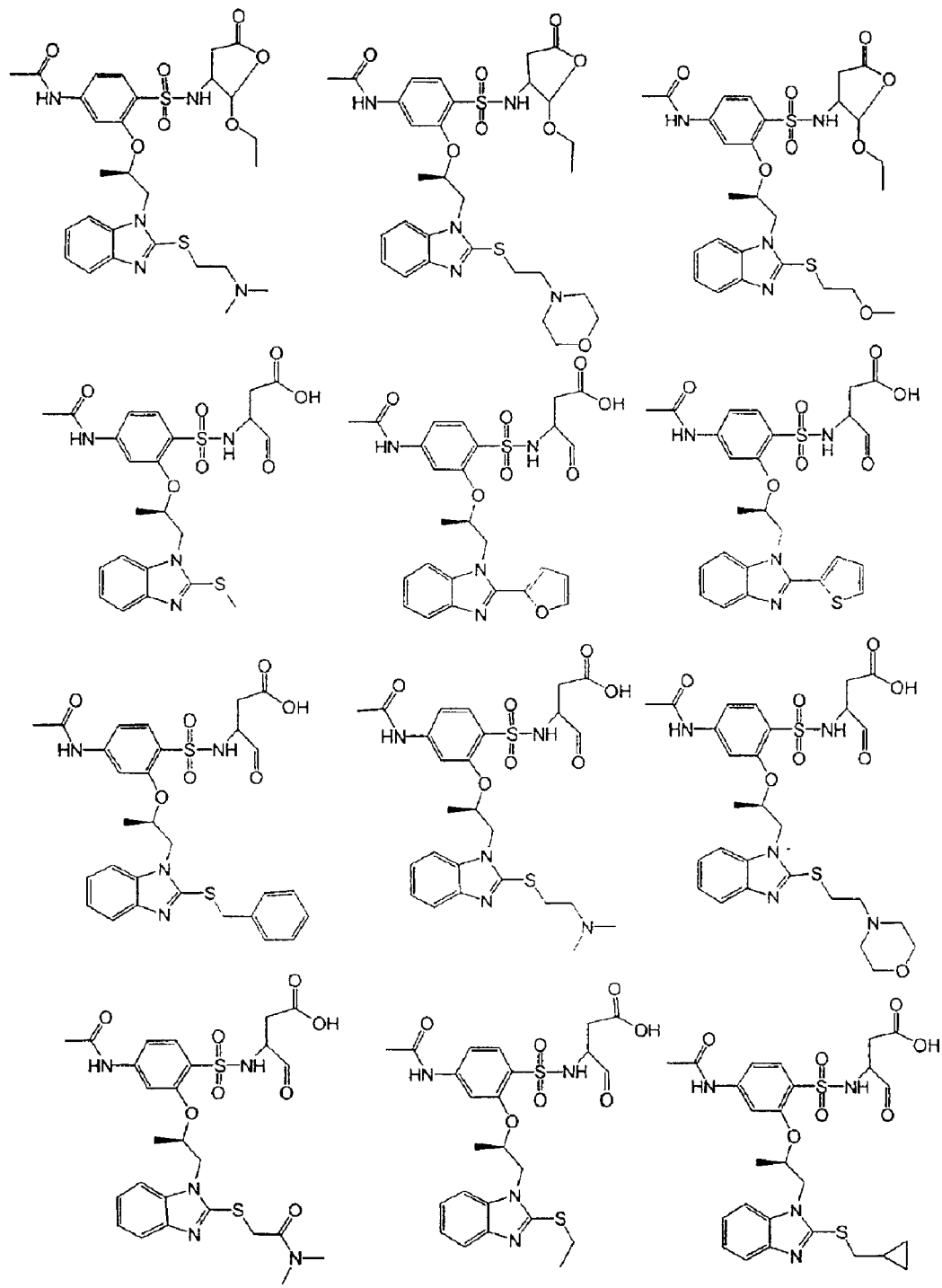
FIG. 26 depicts certain compounds of the present invention that were synthesized and subjected to inhibition studies.
Figure 27:
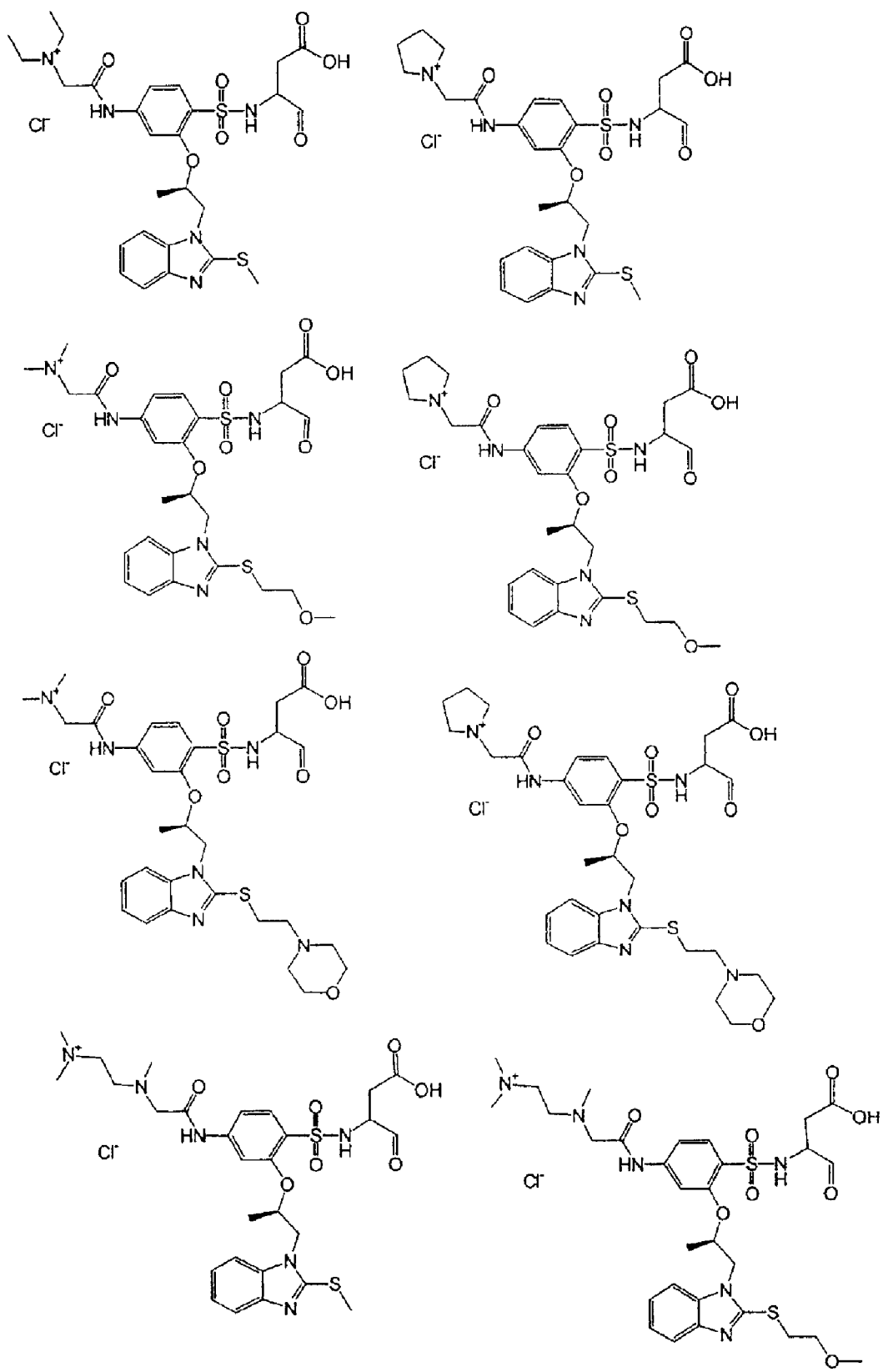
FIG. 27 depicts certain compounds of the present invention that were synthesized and subjected to inhibition studies.
Figure 28:
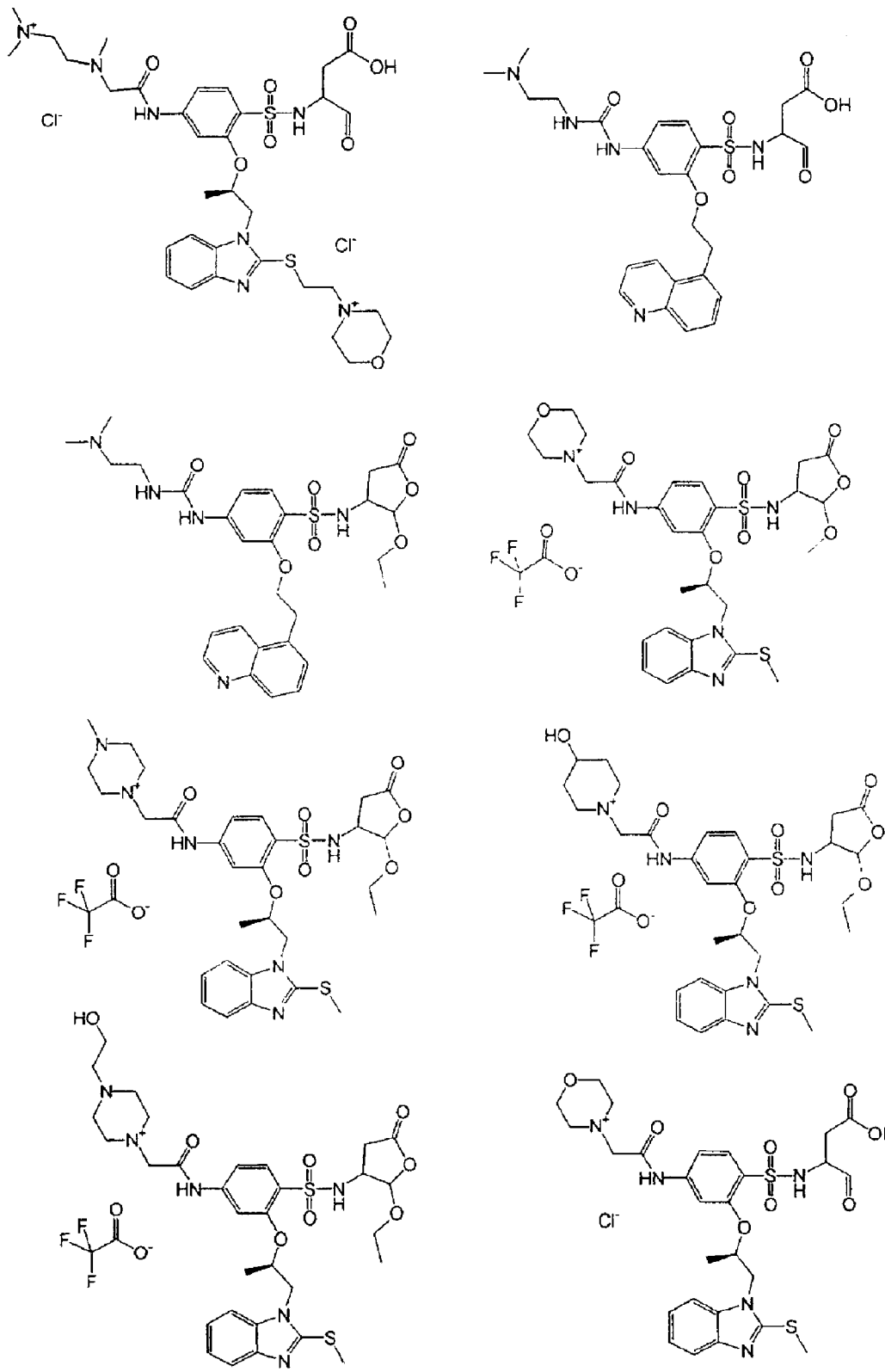
FIG. 28 depicts certain compounds of the present invention that were synthesized and subjected to inhibition studies.
Figure 29:
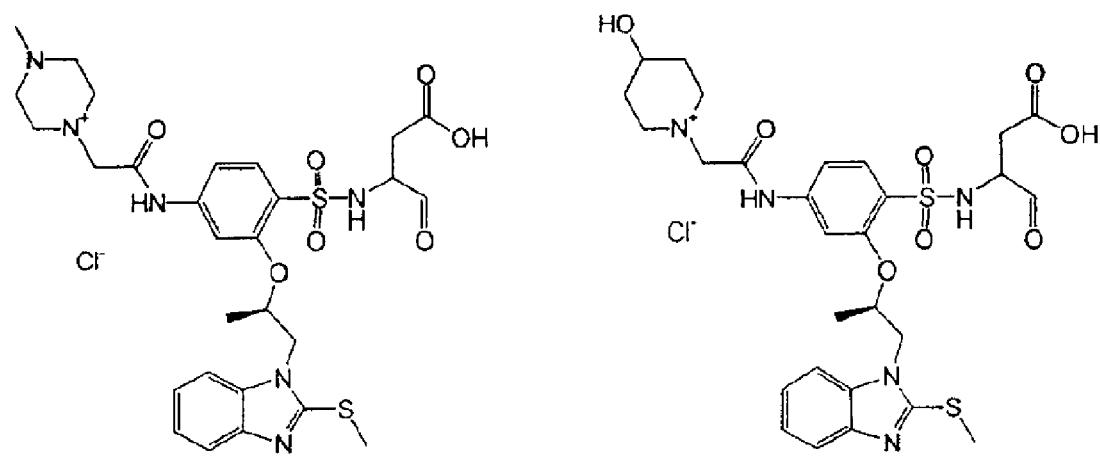
FIG. 29 depicts certain compounds of the present invention that were synthesized and subjected to inhibition studies.
Figure 29:
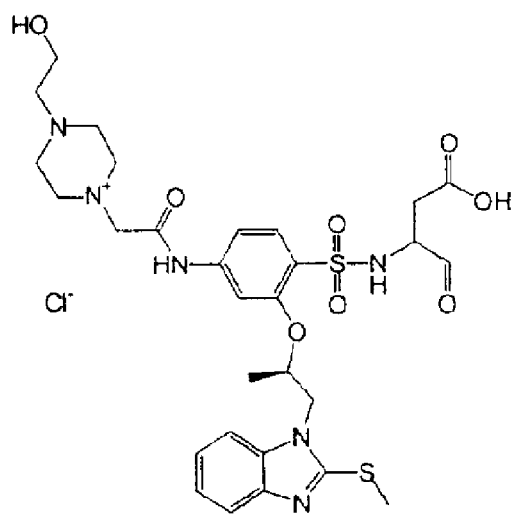
Figure 30:
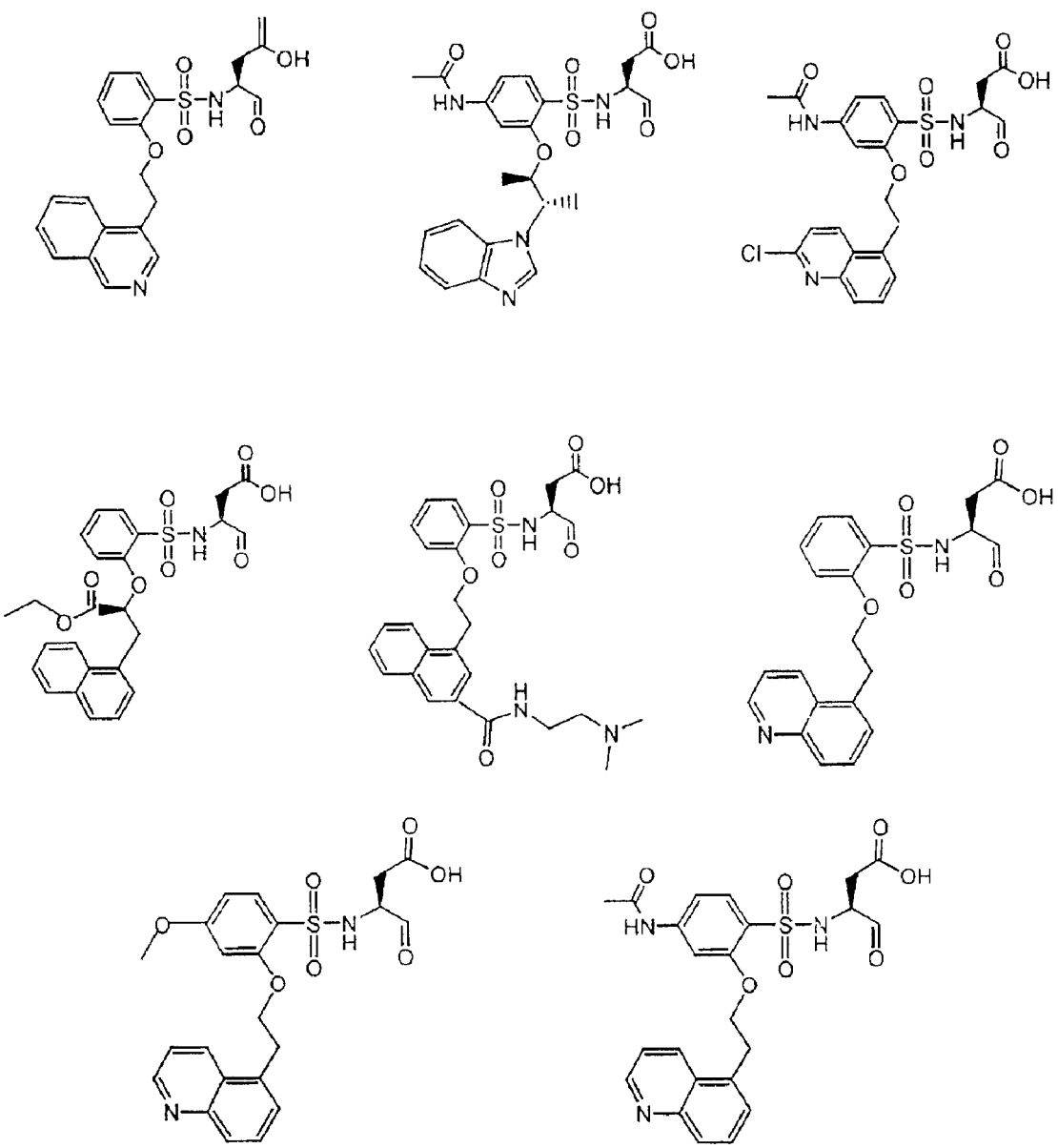
FIG. 30 depicts certain compounds of the present invention that were synthesized and subjected to inhibition studies.

Route R (See FIG. 18)

The sulfonyl chloride (prepared as described in Route P; Example 16) may be reacted with aspartic acid β-t-butyl ester α-amide to give the corresponding sulfonamide. The benzyl protecting group may then be removed using a catalyst like Pd/C and hydrogen to provide the phenol. The resulting phenol may be reacted with an appropriate alcohol in the presence of a tertiary phosphine, such as triphenylphosphine, and a reagent like diethyl azodicarboxylate, to provide the ether. Dehydration of the amide using a reagent such as trifluoroacetic anhydride provides the nitrite. Hydrolysis of the methyl ester, e.g., using aqueous base, followed by coupling with an appropriately substituted amine, using standard coupling reagents, such as carbodiimides or other reagents known in the literature, provides the desired amide. The t-butyl ester may then be cleaved with trifluoroacetic acid in solvent or other acidic reagent in solvent to provide the final product.

EXAMPLE 19

3-[4-Methoxy-2-(2-naphthalen-1-yl-propoxy)-benzenesulfonylamino]-4-oxo-butyric acid Route A using the $BF_3$ etherate/tert-butyl nitrite diazotization described in Route D. Low $R_f$ diastereomer, as a colorless foam 64 mg. The alcohol, 2-(1-naphthyl)-propan-1-ol, used in the synthesis of this compound is known: Harvey, R. G., Pataki, J. L., Hongmee, L. *J. Org. Chem.* 1986, 51, 1407–1412.

Analysis calculated for $C_{25}H_{27}N_1O_7S_1$. 0.12 toluene. 0.07 TFA anion:C, 61.84; H, 5.60; N, 2.78.

Found: C, 61.84; H, 5.60; N, 2.88.

EXAMPLE 20

3-[2-(1-Naphthalen-1-ylmethyl-propoxy)-benzenesulfonylamino]-4-oxo-butyric acid trifloroacetate salt (1:X).

Route A; MS (APCI) m/z 454.1 (M−1).

Step 1: Synthesis of: 1-Naphthalen-1-ylmethyl-propanol

1-Naphthylacetylchloride was synthesized from 1-naphthylacetic acid (20.0 g, 107.4 mmol) which was dissolved in $CH_2Cl_2$ (200 mL) and the solution was cooled to 0° C. Oxalylchloride (11.20 mL, 128.90 mmol) was added to the solution dropwise over 20 min. under the atmosphere of $N_2$ then followed by one drop of DMF. The mixture was then allowed to warm to room temperature where it was stirred for 12 hours. The reaction mixture was concentrated under vacuum, the resulting residue was redissolved in CH$_2$Cl$_2$ (200 mL) and the solvents were evaporated in vacuo to give 1-naphthylacetylchloride 21.90 g (99%) as a dark oil: $^1$H-NMR (400 MHz, CDCl$_3$) δ 7.92–7.84 (m, 3H), 7.61–7.42 (m, 4H), 4.58 (s, 2H).

Step 2: N-Methoxy-N-methyl-2-naphthalen-1-yl-acetamide

To a solution of the 1-naphthylacetylchloride (21.90 g, 107.0 mmol) in CH$_2$Cl$_2$ (100 mL) was added dimethylhydroxyl amine hydrochloride (13.57 g, 139.1 mmol) and the solution cooled to 0° C. Et$_3$N (43.20 mL, 31.32 mmol) was added to the solution dropwise under an atmosphere of N$_2$. The mixture was then allowed to warm to room temperature where it was stirred for 12 hours and then filtered to remove a white solid. The filtrate was concentrated under vacuum and the residue was diluted with EtOAc (100 mL) and then was washed with 1 N HCl (50 mL), saturated NaHCO$_3$ (50 mL) and brine (50 mL). The organic layer was dried (MgSO$_4$) and then stripped of solvent under vacuum. The crude product was subjected to silica gel chromatography (EtOAc/Hexanes, 1:9) to give N-methoxy-N-methyl-2-naphthalen-1-yl-acetamide 16.90 g (69%) as a white solid: $^1$H-NMR (400 MHz, CDCl$_3$) δ 8.06 (dd, 1 H), 7.87 (dd, 2H), 7.77 (dd, 1 H), 7.56–7.39 (m, 4 H), 4.22 (s, 2H), 3.60 (s, 3H), 3.22 (s, 2H).

Step 3: 1-Naphthyl-2-butanone

To a solution of EtMgBr (3 M in toluene, 15 mL, 45 mmol) in dry toluene (150 mL) under an atmosphere of N$_2$ at −15° C. (salt/ice/acetone) was added 1-naphthaleneacetyamide (5.45 g, 23.80 mmol) solution in toluene (50 mL) dropwise over 20 min. The resulting solution was stirred at −15° C. for 1 h and then quenched with 1 N HCl (50 mL) at −15° C. The reaction mixture was extracted with EtOAc (2×300 ml), and the combined extracts were washed with saturated NaHCO$_3$ (100 mL) and brine (50 mL), dried (MgSO$_4$), and evaporated under vaccum to give 1-naphthyl-2-butanone (4.60 g, 97%): $^1$H-NMR (400 MHz, CDCl$_3$) δ 7.92–7.78 (m, 3 H), 7.55–7.37 (m, 4 H), 4.11 (s, 2 H), 2.43 (q, 2 H), 0.99 (t, 3 H).

Step 4: 1-Naphthalen-1-ylmethyl-propanol

Sodium borohydride (1.80 g, 47.4 mmol) was added portion wise at 0° C. to a solution of 1-naphthyl-2-butanone (4.70 g, 23.7 mmol) in CH$_3$OH (100 mL). The mixture was stirred at 0° C. for 3 h. A solution of 1 N HCl (10 mL) was added, and the solvent was removed in vacuo. Water (50 mL) was added to the residue, and the aqueous was extracted with EtOAc (300 mL). The combined organic extracts were washed with the H$_2$O (100 mL) and brine (50 mL), and the solvent was removed by rotary evaporation. Silica gel flash chromatography (10% EtOAc in hexanes) yielded 4.10 g (86%) of 1-naphthalen-1-ylmethyl-propanol as a colorless oil: $^1$H-NMR (400 MHz, CDCl$_3$) δ 8.04 (dd, 1 H), 7.85 (dd, 1 H), 7.74 (dd, 1 H), 7.54–7.43 (m, 2 H), 7.41–7.24 (m, 2 H), 3.93–3.87 (m, 1 H), 3.36 (dd, 1 H), 3.05 (dd, 1H), 1.71–1.57 (m, 2 H), 1.45 (br s, 1 H), 1.05 (t, 3 H).

EXAMPLE 21

Route F

Step 1: 2-(2-Naphthalen-1-yl-ethoxy)-4-nitro-aniline

To a solution of 2-hydroxy-4-nitro-aniline (9.24 g, 60 mmol), 1-naphthyleneethanol (8.61 g, 50 mmol) and triphenylphosphine (19.7 g, 75 mmol) in dry THF (200 mL) was added diethylazodicarboxylate at 0° C. under an atmosphere of dry nitrogen. The reaction mixture was allowed to warm to room temperature and was stirred at room temperature overnight. The solvent was evaporated and the residue was taken up in chloroform (250 mL) and filtered. The chloroform solution was applied to a pad of silica (900 g) and the product eluted with an additional 2000 mL chloroform. The combined eluant was evaporated and the residue was triturated with ether (75 mL). The resulting solid was collected by filtration, washed with ether and dried under vacuum to give pure 2-(2-naphthalen-1-yl-ethoxy)-4-nitro-aniline (8.75 g). Mp=151–153° C.

Analysis calculated for C$_{18}$H$_{16}$N$_2$O: C, 70.12; H, 5.23; N, 9.09.

Found: C, 69.85; H, 5.29; N, 8.99.

Step 2: 2-(2-Naphthalen-1-yl-ethoxy)-4-nitro-benzenesulfonyl chloride

A solution of 2-(2-naphthalen-1-yl-ethoxy)-4-nitro-aniline (3.6 g) in dioxane (60 mL) and glacial acetic acid (30 mL) and a solution of sodium nitrite (1 g) in water (5 mL) were added alternately and in small portions to a solution of conc. HCl (50 mL) and glacial acetic acid (50 mL) at −10° C. The reaction mixture was stirred at −10° C. for 30 minutes and then was allowed to warm to 10° C. It was poured into a solution of SO$_2$ (45 mL) in dioxane (40 mL) and glacial acetic acid (40 mL) containing LiCl (1 g) and CuCl (500 mg) at 0° C. The reaction mixture was stirred at 0° C. for 1 h and at 50° C. for 90 minutes. The reaction mixture was cooled and poured into a mixture of ether (800 mL) and water (800 mL). The organic layer was collected and washed with water (5×400 mL) and brine (200 mL). The ether layer was evaporated to give crude 2-(2-naphthalen-1-yl-ethoxy)-4-nitro-benzenesulfonyl chloride (4.06 g) which was not purified, but used directly in the next reaction. A pure sample was obtained by crystallization from toluene.

Step 3: N-Methoxy-N-methyl-3-[2-(2-naphthalen-1-yl-ethoxy)-4-nitro-benzenesulfonylamino]-succinamic acid tert-butyl ester A solution of 3-amino-N-methoxy-N-methyl-succinamic acid tert-butyl ester (2.5 g, 3.3 mmol), 2-(2-naphthalen-1-yl-ethoxy)-4-nitro-benzenesulfonyl chloride (4.0 g, 3.3 mmol) and pyridine (2.5 mL, 10 mmol) in methylene chloride (100 mL) was stirred at room temperature overnight and the solvent was evaporated. The residue was taken up in ether (300 mL), washed with 1 N HCl (5×100 mL). Removal of the solvent provided crude sulfonamide, which was purified by flash chromatography (silica) eluting first with chloroform to remove a high Rf impurity, followed 25% ethyl acetate/chloroform to elute the desired N-methoxy-N-methyl-3-[2-(2-naphthalen-1-yl-ethoxy)-4-nitro-benzenesulfonylamino]-succinamic acid tert-butyl ester (3.5 g).

Analysis calculated for C$_{28}$H$_{33}$N$_3$O$_9$S.0.25H$_2$O: C, 56.79; H, 5.70; N, 7.10.

Found: C, 56.64; H, 5.64; N, 6.83.

Step 4: 3-[4-Amino-2-(2-naphthalen-1-yl-ethoxy)-benzenesulfonylamino]-N-methoxy-N-methyl-succinamic acid tert-butyl ester A solution of N-methoxy-N-methyl-3-[2-(2-naphthalen-1-yl-ethoxy)-4-nitro-benzenesulfonylamino]-succinamic acid tert-butyl ester (0.52 g) in tetrahydrofuran (35 mL) and ethanol (35 mL) was treated with RaNi (0.3 g) and hydrogenated at 50 psi. The solution was filtered through Celite and evaporated to give the desired aniline derivative 3-[4-amino-2-(2-naphthalen-1-yl-ethoxy)-benzenesulfonylamino]-N-methoxy-N-methyl-succinamic acid tert-butyl ester (0.45 g) as an amorphous foam.

Analysis calculated for C$_{28}$H$_{35}$N$_3$O$_7$S.0.5H$_2$O: C, 59.35; H, 6.40; N, 7.42; S, 5.66.

Found: C, 59.20; H, 6.15; N, 7.18; S, 5.50.

Step 5: 3-(4-Acetylamino-2-(2-naphthalen-1-yl-ethoxy)-benzenesulfonylamino)-N-methoxy-N-methyl-succinamic acid tert-butyl ester To a solution of 3-[4-amino-2-(2-naphthalen-1-yl-ethoxy)-benzenesulfonylamino]-N-methoxy-N-methylsuccinamic acid tert-butyl ester (300 mg, 0.54 mmol) and acetyl chloride (45 mg, 0.57 mg) in methylene chloride (10 mL) was added triethylamine (58 mg, 0.57 mmol) and the reaction mixture was stirred at room temperature overnight. The solvent was evaporated and the residue was taken up in ethyl acetate (50 mL). The resulting solution was extracted with 0.1N HCl (50 mL) and brine (50 mL), dried (MgSO$_4$), and evaporated to give 3-(4-acetylamino-2-(2-naphthalen-1-yl-ethoxy)-benzenesulfonylamino)-N-methoxy-N-methyl-succinamic acid tert-butyl ester (300 mg) as an amorphous solid.

Analysis calculated for $C_{30}H_{35}N_3O_8S\cdot0.5H_2O$: C, 59.39; H, 5.98; N, 6.93; S, 5.28.

Found: C, 59.77; H, 6.21; N, 6.53; S, 5.14.

Step 6: 3-[Acetylamino-2-(2-naphthalen-1-yl-ethoxy)-benzenesulfonylamino]-4-oxo-butyric acid tert-butyl ester A solution of lithium aluminum hydride (1.45 mL, 1.0 M in ether) was added in 3 portions over a period of 35 minutes to a solution of 3-(4-acetylamino-2-(2-naphthalen-1-yl-ethoxy)-benzenesulfonylamino)-N-methoxy-N-methyl-succinamic acid tert-butyl ester (270 mg, 0.45 mmol) in dry ether (12 mL) and tetrahydrofuran (2 mL) at −65° C. under an atmosphere of dry nitrogen. The reaction mixture was stirred at −65° C. for an additional 10 minutes followed by the careful, dropwise addition of 0.3 N KHSO$_4$ (10 mL) at −65° C. The reaction mixture was allowed to warm to room temperature and 0.1 N HCl (20 mL) was added. The organic layer was collected, dried (MgSO$_4$) and evaporated to give the crude aldehyde (230 mg). Flash chromatography (silica, 2:1 ethyl acetate/hexane) provided pure 3-[4-acetylamino-2-(2-naphthalen-1-yl-ethoxy)-benzenesulfonylamino]-4-oxo-butyric acid tert-butyl ester (140 mg).

Analysis calculated for $C_{28}H_{32}N_2O_7S\cdot0.9H_2O$: C, 60.40; H, 6.12; N, 5.03.

Found: C, 60.63; H, 6.13; N, 4.67.

Step 7: 3-[4-Acetylamino-2-(2-naphthalen-1-yl-ethoxy)-benzenesulfonylamino]-4-oxo-butyric acid A solution of 3-[4-acetylamino-2-(2-naphthalen-1-yl-ethoxy)-benzenesulfonylamino]-4-oxo-butyric acid tert-butyl ester (110 mg) in methylene chloride (6 mL) and trifluoroacetic acid (3 mL) was stirred at room temperature for 4 hours. The solvent was evaporated. The residue was triturated with ether and the resulting amorphous solid (58 mg) was collected by filtration.

Analysis calculated for $C_{24}H_{24}N_2O_7S\cdot0.5H_2O$ (493.54): C, 58.41; H, 5.11; N, 5.68; S, 6.50.

Found: C, 58.54; H, 5.25; N, 5.61; S, 7.10.

EXAMPLE 22

3-[4-Isobutoxy-2-(2-naphthalen-1-yl-ethoxy)-benzenesulfonylamino]-4-oxo-butyric acid trifloroacetate salt Synthesized by Route A and lyophilized as a white solid.

Analysis calculated for $C_{26}H_{29}N_1O_7S_1\cdot0.02H_2O\cdot0.29$ TFA: C, 52.92; H, 5.55; N, 2.63.

Found: C, 59.92; H, 5.45; N, 2.46. MS(APCI) m/z 500.0 (M+1)

EXAMPLE 23

3-[2-(2-Isoquinolin-4-yl-ethoxy)-benzenesulfonylamino]-4-oxo-butyric acid trifluoroacetate salt
Route B Synthesis
Step 1: 2-Benzyloxy-benzenesulfonyl chloride To 2-benzyloxy-1-bromo benzene (4.0 g, 15.2 mmol) in diethyl ether/THF (1:1, 100 mL) at −78° C. was added n-butyllithium (2 equiv.). After 30 min sulfur dioxide/THF (1:1, 40 mL) was added. The reaction warmed to room temperature over 1.5 h and the solvent was removed under reduced pressure. Hexanes (75 mL) was added and the reaction was cooled to 0° C. prior to adding sulfuryl chloride (2 equiv.). After 15 min the reaction was poured into water, washed with brine and dried over magnesium sulfate to give a colorless oil. Chromatography silica gel, eluting with 1:1 hexanes/diethyl ether gave 2-benzyloxy-benzenesulfonyl chloride (3.11 g, 72%) as a colorless solid. $^1$H NMR (CDCl$_3$) 8.00(d,1H), 7.65(t,1H), 7.54(d,2H), 7.38(m,3H), 7.12(m,2H), 5.37 (s,2H).

Step 2: (S)-3-(2-Benzyloxy-benzenesulfonylamino)-N-methoxy-N-methyl-succinamic acid tert-butyl ester To 2-benzyloxy-benzenesulfonyl chloride (3.11 g, 11 mmol) in dichloromethane (50 mL) and pyridine (2.6 mL, 3 equiv) was added 3-amino-N-methoxy-N-methyl-succinamic acid tert-butyl ester (1 equiv). The reaction stirred for 16 h and was washed with 10% sulfuric acid, water, and then brine. To give (S)-3-(2-benzyloxy-benzenesulfonylamino)-N-methoxy-N-methyl-succinamic acid tert-butyl ester as a yellow oil (4.82 g, 92%) that was sufficiently pure for further use. $^1$H NMR (CDCl$_3$) 7.88(d, 1H), 7.57(d,2H), 7.40(m,3H), 7.17(d,1H), 7.03(m,2H), 5.92 (d,1H), 5.25(s,2H), 4.73(bs,1H), 3.57(s,3H), 2.86(s,3H), 2.63–2.39(AB quartet, 2H), 1.40(s,9H).

Step 3: (S)-3-(2-Hydroxy-benzenesulfonylamino)-N-methoxy-N-methyl-succinamic acid tert-butyl ester (S)-3-(2-Benzyloxy-benzenesulfonylamino)-N-methoxy-N-methyl-succinamic acid tert-butyl ester (3.54 g) in TBF (50 mL) was treated with 20% Pd/C (0.30 g) at 50 psi hydrogen until uptake was complete. The reaction was filtered and the filtrate was evaporated to give (S)-3-(2-hydroxy-benzenesulfonylamino)-N-methoxy-N-methyl-succinamic acid tert-butyl ester as a colorless oil (3.01 g, 100%). $^1$H NMR (CDCl$_3$) 8.82(s,1H), 7.63(d,1H), 7.44(t, 1H), 6.98(m,2H), 5.95(d,1H), 4.62(bs,1H), 3.62(s,3H), 3.03 (s,3H), 2.65–2.40(AB quartet, 2H), 1.43(s,9H).

Step 4: (S)-3-[2-(2-Isoquinolin-4-yl-ethoxy)-benzenesulfonylamino]-N-methoxy-N-methyl-succinamic acid tert-butyl ester To (S)-3-(2-hydroxy-benzenesulfonylamino)-N-methoxy-N-methyl-succinamic acid tert-butyl ester (194 mg, 0.50 mmol), 2-isoquinolin-4-yl-ethanol (108 mg, 0.625 mmol), triphenyl phosphine (197 mg, 0.75 mmol) in THF(5 mL) was added diethyl azodicarboxylate (133 μL, 0.85 mmol). After 16 h the solvent was removed under reduced pressure, the residue was chromatographed on silica gel 20% THF in dichloromethane to give (S)-3-[2-(2-isoquinolin-4-yl-ethoxy)-benzenesulfonylamino]-N-methoxy-N-methyl-succinamic acid tert-butyl ester as a colorless foam (394 mg, contaminated with triphenyl phosphine oxide). MS (APCI) m/z 544.1 (M+1).

4-Isoquinolyl-2-ethanol used in the synthesis of 3-[2-(2-isoquinolin-4-yl-ethoxy)-benzenesulfonylamino]-4-oxo-butyric acid was prepared in a single step from 4-bromoisoquinoline. To n-butyllithium (40 mmol) in tetrahydrofuran-ether (1:1,180 mL) at −78° C. was added 4-bromoisoquinoline in tetrahydrofuran (20 mL) after 30 minutes ethylene oxide (3 mL) was added and the reaction was allowed to warn to room temperature. The reaction was quenched by the addition of methanol and was poured into water and ethyl acetate. The organic layer was washed with brine and dried over magnesium sulfate to give an orange oil that was chromatographed on silica gel (5% methanol/dichloromethane) to give product as a red oil (948 mg, 27%). $^1$H NMR (CDCl$_3$) 3.32(t,2H), 4.02(t,2H), 7.63(t,1H), 7.75 (t,1H), 7.95(d,1H), 8.05(d,1H), 8.22(s,1H),9.11(s,1H).

Step 5: (S)-3-[2-(2-Isoquinolin-4-yl-ethoxy)-benzenesulfonylamino]-4-oxo-butyric acid tert-butyl ester To lithium aluminum hydride (0.45 mL of 1.0 M solution in diethyl ether) in diethyl ether (7 mL) at −65° C. was added (S)-3-[2-(2-isoquinolin-4-yl-ethoxy)-benzenesulfonylamino]-N-methoxy-N-methyl-succinamic acid tert-butyl ester in 1:1 THF/diethylether (4 mL). After 1 hour, the reaction was quenched by addition of 1.0N sodium hydroxide (2 mL) and the reaction was warmed to room temperature. The organic layer was separated and evaporated. The resulting residue was chromatographed on silica gel eluting with 10% diethyl ether in ethyl acetate to give (S)-3-[2-(2-isoquinolin-4-yl-ethoxy)-benzenesulfonylamino]-4-oxo-butyric acid tert-butyl ester as a colorless foam (39 mg). MS (APCI) m/z 485.1 (M+1).

Step 6: 3-[2-(2-Isoquinolin-4-yl-ethoxy)-benzenesulfonylamino]-4-oxo-butyric acid trifluoro-acetate salt To (S)-3-[2-(2-isoquinolin-4-yl-ethoxy)-benzenesulfonylamino]-4-oxo-butyric acid tert-butyl ester was added 3:1 dichloromethane/trifluoroacetic acid (20 mL) and water (200 µL). After 2 h at room temperature, toluene (20 ml) was added and the solvent was removed under reduced pressure to give 3-[2-(2-isoquinolin-4-yl-ethoxy)-benzenesulfonylamino]-4-oxo-butyric acid trifluoro-acetate salt as a colorless foam (36 mg). MS (APCI) m/z 429.1 (M+1).

EXAMPLE 24

3-[4-Methoxy-2-(1-methyl-2-naphthalen-1-yl-ethoxy)-benzenesulfonylamino]-4-oxo-butyric acid Route A using the $BF_3$ etherate/tert-butyl nitrite diazotization described in Route D. Low $R_f$ diastereomer, as a colorless solid 95 mg. The alcohol, 1-(2-hydroxy-1-propyl)naphthalene, used in the synthesis is known: Barcus, R. L., Wright, B. B., Platz, M. S., Scaiano, J. C. *Tet. Lett.* 1983, 24, 3955–3958.

Analysis calculated for $C_{24}H_{25}N_1O_7S_1$: C, 61.13; H, 5.34; N, 2.97.

Found: C, 60.92; H, 6.56; N, 2.61.

EXAMPLE 25

3-[2-(2-Benzoimidazol-1-yl-ethoxy)-benzenesulfonylamino]-4-oxo-butyric acid trifloroacetate salt (1:1)

Route B. Analysis calculated for $C_{19}H_{19}N_3O_6S_1 \cdot 1.18\, CF_3CO_2H$ (551.98): C, 46.58; H, 3.70; N, 7.64.

Found: C, 46.94; H, 3.88; N, 6.89.

EXAMPLE 26

(S)-3-{2-[2-(3H-Benzimidazol-4-yl)-ethoxy]-benzenesulfonylamino}-4-oxo-butyric acid Prepared according to Route B to yield after prep HPLC and lyophylization (51 mg, 64%) as a fluffy off-white solid. MS (APCI) m/z 416 (M−1) Synthesis of 1-tert-Butoxycarbonyl-4-hydroxyethyl benzamidazole Prepared from 1-tert-Butoxycarbonyl-4-allylbenzamidazole whose preparation is described in Tett. Lett. 34(43), 6849–6852, (1993). This compound (260 mg, 1 mmol) was dissolved in $CH_2Cl_2$:EtOH (2:1, 3 mL) and cooled to −78° C. Ozone was bubbled through and the reaction mixture was monitored by TLC. When complete the reaction was purged with $N_2$ then $NaBH_4$ (38 mg, 1 mmol) was added in small portions and the reaction mixture was allowed to warm slowly to room temperature and stirred overnight. The reaction was quenched with $H_2O$, diluted with EtOAc (200 mL), and washed with 2×50 mL each of 5% citric acid, sat. $NaHCO_3$, and sat. NaCl. The organic layer was then dried over anh. $Na_2SO_4$, filtered and concentrated. Purification by flash chromatography ($SiO_2$, hexane:EtOAc, 2:1, then 1:1) gave the desired alcohol (146 mg, 68%) as a pale yellow oil. $^1H$ NMR (400 MHz) $CDCl_3$ δ 8.44 (s, 1H), 7.89 (d, 1H), 7.34 (t, 1H) 7.19 (d, 1H), 3.99 (t, 2H), 3.29 (t, 2H).

EXAMPLE 27

4-Oxo-3-[2-(2-quinolin-5-yl-ethoxy)-benzenesulfonylamino]-butyric acid trifloroacetate salt (1:1)

Synthesized by Route B as an off white solid. Analysis calculated for $C_{21}H_{20}N_2O_6S \cdot 1.07\, C_2F_3CO_2H$ (550.473): C, 50.50; H, 4.12; N, 4.78. Found: C, 50.49; H, 3.86; N, 5.09.

EXAMPLE 28

(S)-4-Oxo-3-[2-(2-quinolin-4-yl-ethoxy)-benzenesulfonylamino]-butyric acid

The synthesis of 4-(γ-Hydroxyethyl)-quinoline employed in the synthesis of (S)-4-Oxo-3-[2-(2-quinolin-4-yl-ethoxy)-benzenesulfonylamino]-butyric acid:

Step 1: 4-(Bis-ethoxycarbonyl methyl)-quinoline

4-Methylquinoline (4.62 mL, 35.0 mmol) was mixed with freshly distilled THF (17 mL) in an argon-purged, round-bottom flask and was chilled to 0° C. Lithium diisopropyl amide (19.25 mL of 2.0M solution in diethyl ether, 38.5 mmol) was added via syringe. The reaction was stirred for ten minutes at 0° C. and then was cooled to −78° C. The chilled anion solution was cannula transferred to a −78° C. solution of ethyl chloroformate (10.0 mL, 105 mmol) in freshly distilled THF (17 mL) in an argon-purged, round-bottom flask. The reaction was stirred at −78° C. for fifteen minutes and then was quenched with saturated aqueous $NH_4Cl$ (5 mL). The quenched reaction was allowed to warm to room temperature. The mixture was diluted with $H_2O$ and was extracted three times with EtOAc. The organic extracts were combined, washed with brine solution, dried over $Na_2SO_4$, filtered through celite, and concentrated. Purification by flash chromatography ($SiO_2$, 20% EtOAc-hexane) gave 4-(bis-ethoxycarbonyl methyl)-quinoline (6.02 g, 21.0 mmol) in 60% yield. MS (APCI) m/z 288.1 (M+H). $^1H$ NMR (300 MHz) $CDCl_3$ 8.46 (d, J=8.7 Hz, 1H), 7.86 (d, J=8.1 Hz, 1H), 7.65 (m, 2H), 7.46 (m, 1H), 7.28 (m, 1H), 5.97 (s, 1H), 4.42 (q, J=7.1 Hz, 2H), 4.21 (q, J=7.1 Hz), 1.42 (t, J=7.1 Hz, 3H), 1.32 (t, J=7.2 Hz, 3H).

Step 2: 4-(Ethoxycarbonyl methyl)-quinoline 4-(Bis-ethoxycarbonyl methyl)-quinoline (5.05 g, 17.6 mmol), NaCl (2.06 g, 35.2 mmol), and $H_2O$ (0.63 mL, 35 mmol) were combined with DMSO (22 mL) in a round-bottom flask fitted with a reflux condenser. The heterogeneous mixture was stirred and heated to 160° C. for 90 minutes. TLC analysis (silca, 20% EtOAc-hexanes) indicated complete consumption of the starting material. The reaction was allowed to cool to room temperature and then was diluted with $H_2O$. The dilution was extracted three times with EtOAc. The organic extracts were combined, washed with brine solution, dried over $Na_2SO_4$, filtered through celite, and concentrated. Purification by gradient elution chromatography ($SiO_2$, 20% EtOAc-hexanes to 30% EtOAc-hexanes) gave 4-(ethoxycarbonyl methyl)-quinoline (1.81 g, 8.40 mmol) in 48% yield. MS (APCI) m/z 216.1 (M+H). $^1H$ NMR (300 MHz) $CDCl_3$ δ 8.87 (d, J=4.4 Hz, 1H), 8.14 (d, J=8.0 Hz, 1H), 8.00 (d, J=8.4 Hz, 1H), 7.73 (m, 1H), 7.60 (m, 1H), 7.34 (d, J=4.5 Hz, 1H), 4.17 (q, J=7.1 Hz, 2H), 4.07 (s, 2H), 1.23 (t, J=7.2 Hz, 3H).

Step 3: 4-(γ-Hydroxyethyl)-quinoline 4-(Ethoxycarbonyl methyl)-quinoline (1.8 g, 8.4 mmol) was dissolved in diethyl ether (42 mL) in an argon-purged, round-bottom flask. The mix was chilled to −78° C. then $LiAlH_4$ (636 mg, 16.74 mmol) was added. The reaction was stirred at −78° C. for fifteen minutes and then at room temperature for 60 minutes. The reaction was cooled back to −78° C. and was slowly quenched with saturated aqueous KHSO$_4$. The quenched reaction was allowed to warm to room temperature and then was diluted with H$_2$O. The dilution was extracted three times with EtOAc and once with CH$_2$Cl$_2$. The organic extracts were combined, washed with brine solution, dried over Na$_2$SO$_4$, filtered through celite, and concentrated. Purification by gradient elution chromatography (SiO$_2$, 10% acetone in CH$_2$Cl$_2$ to 25% acetone to 5% MeOH in CH$_2$Cl$_2$) gave 4-(γ-hydroxyethyl)-quinoline in 54% yield. MS (APCI) m/z 174.1 (M+H). $^1$H NMR (300 MHz) CDCl$_3$ δ 8.59 (d, J=4.4 Hz, 1H), 8.03 (m, 2H), 7.66 (m, 1H), 7.54 (m, 1H), 7.23 (d, J=4.4 Hz, 1H), 4.07 (t, J=6.5 Hz, 3H), 3.3 (t, J=6.3 Hz, 3H).

(S)-4-Oxo-3-[2-(2-quinolin-4-yl-ethoxy)-benzenesulfonylamino]-butyric acid was then synthesized via Route B. MS (APCI) m/z 429.1 (M+H). $^1$H NMR (300 MHz) CD$_3$OD 9.09 (t, J=5.0 Hz, 1H), 8.65 (d, J=8.8 Hz, 1H, 8.20 (m, 3H), 8.02 (t, J=7.8 Hz, 1H), 7.77 (d, J=7.8 Hz, 1H), 7.56 (m, 1H), 7.21 (d, J=8.4 Hz, 1H), 7.07 (t, J=7.4 Hz, 1H), 4.68 (m, 2H), 4.38 (d, J=4 Hz, 0.5H, acetal diastereomer), 4.27 (d, J=3.2 Hz, 0.5H, acetal diastereomer), 4.03 (m, 2H), 3.49 (m, 1H), 2.36 (m, 2H).

EXAMPLE 29

(S)-3-{2-[1-Methyl-2-(2-methyl-naphthalen-1-yl)-ethoxy]-benzenesulfonylamino}-4-oxobutyric acid Step 1: (2-Methyl-naphthalen-1-yl)-acetonitrile 1-Chloromethyl-2-methylnaphthalene (5.00 g, 26.3 mmol) and KCN (5.12 g, 78.8 mmol) were combined in H$_2$O (20 mL) and EtOH (40 mL) in a round bottom flask fitted with a reflux condenser. The mix was stirred at 80° C. for 18 hours. TLC analysis (silica, 10% acetone-hexanes) indicated consumption of the starting chloromethylnaphthalene. The reaction was allowed to cool to room temperature and then was diluted with H$_2$O. The dilution was extracted three times with EtOAc. The organic extracts were combined, washed with brine solution, dried over Na$_2$SO$_4$, decanted, and concentrated to give (2-methyl-naphthalen-1-yl)-acetonitrile in quantitative yield. MS (APCI) m/z 180.1 (M−H). $^1$H NMR (400 MHz) CDCl$_3$ δ 7.96 (d, J=8.4 Hz, 1H), 7.85 (d, J=8.2 Hz, 1H), 7.77 (d, J=8.4 Hz, 1H), 7.61 (m ,1H), 7.50 (m, 1H), 7.34 (d, J=8.4, 1H), 4.07 (s, 2H), 2.58 (s, 3H).

Step 2: (2-Methyl-naphthalen-1-yl)-acetic acid (2-Methyl-naphthalen-1-yl)-acetonitrile (4.9 g, 27 mmol) was stirred with H$_2$SO$_4$ (50 mL) and H$_2$O (50 mL) at 150° C. for 25 minutes in a round-bottom flask fitted with a condenser. TLC analysis (silica, 20% acetone-hexanes) indicated complete consumption of the starting material. The reaction was allowed to cool to room temperature and then was carefully diluted with H$_2$O. The acidic dilution was extracted three times with EtOAc. The organic extracts were combined and extracted twice with aqueous 10% NaOH. The basic H$_2$O extracts were combined, acidified to pH<3 with 1N HCl, and extracted three times with EtOAc. The organic extracts were combined, washed with brine solution, dried over Na$_2$SO$_4$, decanted, and concentrated to give (2-methyl-naphthalen-1-yl)-acetic acid (3.6 g, 18 mmol) in 67% yield. MS (APCI) m/z 199.1 (M−H). $^1$H NMR (300 MHz) CDCl$_3$ 7.97 (d, J=8.6 Hz, 1H), 7.81 (d, J=8.7 Hz, 1H), 7.71 (d, J=8.4 Hz, 1H), 7.47 (m, 2H), 7.33 (d, J=8.2 Hz, 1H), 4.13 (s, 2H), 2.53 (s, 3H).

Step 3: N-Methoxy-N-methyl-2-(2-methyl-naphthalen-1-yl)-acetamide (2-Methyl-naphthalen-1-yl)-acetic acid (3.55 g, 17.8 mmol) was stirred with N-methylpiperidine (2.48 mL, 21.4 mmol) in CH$_2$Cl$_2$ in an argon-purged, round-bottom flask. The mixture was chilled to −78° C. Isobutylchloroformate (2.53 mL, 19.5 mmol) was added via syringe. The reaction was stirred at −78° C. for twenty minutes and then a mixture of N,O-dimethylhydroxylamine hydrochloride (2.08 g, 21.3 mmol) and N-methylpiperidine (2.67 mL, 22.0 mmol) in CH$_2$Cl$_2$ (2 mL) was added via syringe. The reaction was stirred at −78° C. for five minutes and was then allowed to warm to room temperature. The reaction was quenched with 1N HCl (~5 mL) and was diluted with H$_2$O. The dilution was extracted three times with EtOAc. The organic extracts were combined, washed with brine solution, dried over Na$_2$SO$_4$, filtered through celite, and concentrated to give N-methoxy-N-methyl-2-(2-methyl-naphthalen-1-yl)-acetamide in quantitative yield. $^1$H NMR (300 MHz) CDCl$_3$ δ 7.94 (d, J=8.8 Hz, 1H), 7.80 (d, J=8.7 Hz, 1H), 7.69 (d, J=8.4 Hz, 1H), 7.44 (m, 2H), 7.34 (d, J=8.2 Hz, 1H), 4.26 (s, 2H), 3.67 (s, 3H), 3.23 (s, 3H), 2.51 (s, 3H).

Step 4: 1-(2-Methyl-naphthalen-1-yl)-propan-2-one

N-methoxy-N-methyl-2-(2-methyl-naphthalen-1-yl)-acetamide (1.01 g, 4.16 mmol) was dissolved in freshly distilled THF (17 mL) in an argon-purged, round-bottom flask. The mixture was chilled to 0° C. and methyl magnesium bromide (2.08 mL of 3.0 M soln in Et$_2$O, 6.23 mmol) was added via syringe. The reaction was stirred at 0° C. for 75 minutes. TLC analysis (silica, 20% acetone-hexanes) indicated complete consumption of the starting material. The reaction was carefully quenched with a mixture of AcOH (1 mL) in EtOAc (5 mL). The quenched reaction was diluted with H$_2$O and extracted three times with EtOAc. The organic extracts were combined, washed with brine solution, dried over Na$_2$SO$_4$, filtered through celite, and concentrated. Purification by flash chromatography (SiO$_2$, 20% EtOAc-hexane) gave 1-(2-methyl-naphthalen-1-yl)-propan-2-one (343 mg, 1.73 mmol) in 41% yield. MS (APCI) m/z 199.1 (M+H). $^1$H NMR (300 MHz) CDCl$_3$ δ 7.85 (m, 2H), 7.72 (d, J=9.4 Hz, 1H), 7.47 (m, 2H), 7.36 (d, J=8.2 Hz, 1H), 4.18 (s, 2H), 2.51 (s, 3H), 2.10 (s, 3H).

Step 5: 1-(2-Methyl-naphthalen-1-yl)-propan-2-ol 1-(2-Methyl-naphthalen-1-yl)-propan-2-one (1.14 g, 5.76 mmol) was dissolved in Et$_2$O (30 mL) in an argon-purged, round-bottom flask. The mixture was chilled to −78° C. and LiAlH$_4$ (438 mg, 11.52 mmol) was added. The reaction was stirred at −78° C. for five minutes and then at room temperature for twenty minutes. TLC analysis (silica, 20% EtOAc-hexanes) indicated the reaction was complete. The reaction was chilled again to −78° C. and was carefully quenched with saturated aqueous KHSO$_4$ (~2 mL). The mixture was warmed to room temperature, diluted with H$_2$O, and extracted three times with EtOAc. The organic extracts were combined, washed with brine solution, dried over Na$_2$SO$_4$, filtered through celite, and concentrated to give 1-(2-methyl-naphthalen-1-yl)-propan-2-ol in quantitative yield. MS (APCI) m/z 200.2 (M−H).

Step 6: 2-Methyl-1-[2-(2-nitro-phenoxy)-propyl]-naphthalene 1-(2-Methyl-naphthalen-1-yl)-propan-2-ol (1.2 g, 6.0 mmol) was dissolved in freshly distilled THF (15 mL) in a round bottom flask fitted with a reflux condenser. Potassium tert-butoxide (739 mg, 6.60 mmol) was added and the reaction was stirred at room temperature for 30 minutes. 2-fluoronitrobenzene (0.70 mL, 6.60 mmol) was added via syringe. The reaction was stirred at vigorous reflux for 18 hours. The reaction mixture was allowed to cool to room temperature and then was concentrated. The residue was diluted with saturated aqueous NaHCO$_3$ and was extracted three times with EtOAc. The organic extracts were combined, washed with brine, dried over Na$_2$SO$_4$, filtered through celite, and concentrated. The crude product was purified by flash chromatography ($SiO_2$, 20% $CH_2Cl_2$-hexanes) to give 2-methyl-1-[2-(2-nitro-phenoxy)-propyl]-naphthalene (1.51 g, 4.72 mmol) in 79% yield as an oil that solidified on standing. $^1$H NMR (300 MHz) $CDCl_3$ δ 8.03 (d, J=8.4 Hz, 1H), 7.79 (d, J=8.8 Hz, 1H), 7.67 (m, 2H), 7.49 (m, 1H), 7.40 (m, 1H), 7.29 (m, 2H), 6.90 (m, 1H), 6.75 (d, J=8.6 Hz, 1H), 4.93 (m, 1H), 3.67 (dd, J=7.5, 14.5 Hz, 1H), 3.46 (dd, J=5.7, 14.4 Hz, 1H), 2.56 (s, 3H), 1.46 (d, J=6.0 Hz, 3H).

Step 7: 2-[1-Methyl-2-(2-methyl-naphthalen-1-yl)-ethoxy]-phenylamine

2-Methyl-1-[2-(2-nitro-phenoxy)-propyl]-naphthalene (1.51 g, 4.70 mmol) was shaken with Rainey nickel (0.5 g) in THF (50 mL) at 49.0 psi $H_2$ for 5.4 hours. TLC analysis (silica, $CH_2Cl_2$) indicated complete consumption of starting material. The reaction mixture was filtered and concentrated to give 2-[1-methyl-2-(2-methyl-naphthalen-1-yl)-ethoxy]-phenylamine in quantitative yield. MS (APCI) m/z 292.1 (M+H).

Step 8: (S)—N-Methoxy-N-methyl-3-{2-[1-methyl-(2-methyl-naphthalen-1-yl)-ethoxy]-benzenesulfonylamino}-succinamic acid tert-butyl ester $BF_3 \cdot Et_2O$ (1.27 mL, 10.3 mmol) was added to a solution of 2-[1-methyl-2-(2-methyl-naphthalen-1-yl)-ethoxy]-phenylamine (1.00 g, 3.44 mmol) in 5 mL $CH_2Cl_2$ chilled to −15° C. in an ice/acetone bath. t-Butylnitrite (0.49 mL, 4.1 mmol) dissolved in 1 mL $CH_2Cl_2$ was added dropwise and the mixture was stirred at −15° C. for thirty minutes. Hexane (40 mL), chilled to 0° C., was added and a brown tar oiled out of solution onto the walls of the flask. The mother liquor was decanted. The remaining residue was dissolved in a minimum amount of dioxane. CuCl (113 mg, 1.14 mmol), LiCl (873 mg, 20.6 mmol), and $SO_2$ (~20 mL) were added to 20 mL solution of 1:1 acetic acid-dioxane in a separate 3-neck flask fitted with a cold-finger. The solution was chilled to −15° C. The diazonium residue-dioxane solution from above was added to the mixture. The reaction was stirred at −15° C. for 90 minutes and then at 50° C. for 90 minutes. The reaction was allowed to cool to room temperature and then was diluted with about 40 mL saturated aqueous $NaHCO_3$ and was extracted with ethyl acetate. The aqueous portion was diluted with one half volume of 10% aqueous NaOH and was reextracted with ethyl acetate. The organic extracts were combined, washed with brine, dried over $Na_2SO_4$, filtered through celite, and concentrated to give the desired sulfonyl chloride product. $^1$H NMR (300 MHz) $CDCl_3$ 8.06 (d, J=8.4 Hz, 1H), 7.91 (d, J=8.1 Hz, 1H), 7.81 (d, J=7.5 Hz, 1H), 7.66 (d, J=8.1 Hz, 1H), 7.53 (m, 1H), 7.43 (m, 2H), 7.29 (d, J=8.4 Hz, 1H), 6.96 (m, 1H), 6.68 (d, J=8.4 Hz, 1H), 5.18 (m, 1H), 3.78 (dd, J=6.4, 15.0 Hz, 1H), 5.08 (dd, J=6.3, 14.4 Hz, 1H), 2.60 (s, 3H), 1.49 (d, J=6.2, 3H).

The sulfonyl chloride product was immediately combined with (S)-3-amino-N-methoxy-N-methyl-succinamic acid tert-butyl ester (974 mg, 4.20 mmol) and pyridine (5 mL, 60 mmol) in 13 mL $CH_2Cl_2$. The mixture was stirred at room temperature for 16 hours and then was diluted with aqueous 10% citric acid. The dilution was extracted with $CH_2Cl_2$. The organic extracts were combined, washed with brine, dried over $Na_2SO_4$, filtered through celite, and concentrated. The crude product was purified by gradient elution flash chromatography ($SiO_2$, 10% EtOAc-hexanes to 20% EtOAc-hexanes) to give 100 mg of the high $R_f$ diastereomer and 122 mg of the low $R_f$ diastereomer and 248 mg of a diastereomeric mixture (24% yield) of (S)—N-methoxy-N-methyl-3-{2-[1-methyl-(2-methyl-naphthalen-1-yl)-ethoxy]-benzenesulfonylamino}-succinamic acid tert-butyl ester as an orange oil. MS (APCI) m/z 569.4 (M−1).

Step 9: (S)-3-{2-[1-Methyl-2-(2-methyl-naphthanen-1-yl)-ethoxy]-benzenesulfonylamino}-4-oxo-butyric acid tert-butyl ester (S)—N-Methoxy-N-methyl-3-{2-[1-methyl-(2-methyl-naphthalen-1-yl)-ethoxy]-benzenesulfonylamino}-succinamic acid tert-butyl ester (95 mg, 0.17 mmol) was dissolved in $Et_2O$ (1 mL) in a round bottom flask. The mixture was chilled to −65° C. in a dry-ice/chloroform bath. $LiAlH_4$ (12.7 mg, 0.334 mmol) was added and the reaction was stirred at −65° C. for one hour. TLC analysis (silica, 20% EtOAc-hexanes) indicated the reduction was complete. The reaction was quenched with 15 drops of saturated aqueous $KHSO_4$ and was allowed to warm to room temperature. The mixture was diluted with $H_2O$ and extracted three times with EtOAc. The organic extracts were combined, washed with brine, dried over $Na_2SO_4$, filtered through celite, and concentrated to give (S)-3-{2-[1-methyl-2-(2-methyl-naphthanen-1-yl)-ethoxy]-benzenesulfonylamino}-4-oxo-butyric acid tert-butyl ester in quantitative yield. $^1$H NMR (300 MHz) $CDCl_3$ δ 9.51 (s, 1H), 8.15 (d, J=8.6 Hz, 1H), 7.88 (d, J=7.7 Hz, 1H), 7.82 (d, J=7.87 Hz, 1H), 7.68 (d, J=8.4 Hz, 1H), 7.52 (m, 1H), 7.43 (m, 1H), 7.33 (d, J=8.4 Hz, 1H), 7.00 (m, 1H), 6.87 (d, J=8.4 Hz, 1H), 6.37 (d, J=7.50 Hz, 1H), 5.03 (m, 1H), 4.01 (m, 1H).

Step 10: 3-{2-[1-Methyl-2-(2-methyl-naphthalen-1-yl)-ethoxy]-benzenesulfonylamino}-4-oxo-butyric acid (S)-3-{2-[1-Methyl-2-(2-methyl-naphthanen-1-yl)-ethoxy]-benzenesulfonylamino}-4-oxo-butyric acid tert-butyl ester (92 mg, 0.18 mmol) was stirred in a mixture of $H_2O$ (1 drop), TFA (0.5 mL), and $CH_2Cl_2$ (2 mL) at room temperature for three hours. The reaction mixture was concentrated. Residual TFA was azeotroped with toluene. The crude product was purified by preparative scale HPLC to give the desired product (17 mg, 0.037 mmol) in 21% yield. MS (APCI) m/z 454.0 (M−H).

EXAMPLE 30

3-[2-(2-Naphthalen-1-yl-ethoxy)-4-propionylamino-benzenesulfonylamino]-4-oxo-butyric acid Synthesized as in Route F only propionyl chloride was used in step 5, the title compound was isolated as a cream colored powder. Analysis calculated for $C_{25}H_{26}N_2O_7S \cdot 0.5H_2O$ (507.58): C, 59.16; H, 5.36; N, 5.52; S, 6.32. Found: C, 59.32; H, 5.35; N, 5.44; S, 6.08.

(S)-1-Isoquinolin-4-yl-propan-2-ol used in this synthesis was made as described for 4-isoquinolyl-2-ethanol, except S-propylene oxide was used as the electrophile. $^1$H NMR ($CDCl_3$) 1.36(d,3H), 3.17(m,2H), 4.20(m,2H), 7.61(t,1H), 7.75(t,1H), 7.97(d,1H), 8.03(d,1H), 8.41(s,1H), 9.13(s,1H).

EXAMPLE 31

3-[2-(2-Isoquinolin-4-yl-1-methyl-ethoxy)-benzenesulfonylamino]-4-oxo-butyric acid trifloroacetate salt (1:1)

Route B, as a colorless solid 43 mg. Analysis calculated for $C_{22}H_{22}N_2O_6S_1 \cdot 0.04$ water.1.19 TFA: C, 50.55; H, 4.05; N, 4.84. Found: C, 50.55; H, 4.00; N, 4.45.

EXAMPLE 32

3-[2-(2-Isoquinolin-4-yl-1-methyl-ethoxy)-4-methoxy-benzenesulfonylamino]-4-oxo-butyric acid Route B, as a colorless solid 41 mg. The alcohol, 4-isoquinoline-1-propan-2-ol, used in this synthesis was previously described. Analysis calculated for $C_{23}H_{24}N_2O_7S_1 \cdot 1.03$ water.155 TFA: C, 46.96; H, 4.17; N, 4.20. Found: C, 46.96; H, 4.17; N, 4.43

EXAMPLE 33
3-[4-(3-Methyl-ureido)-2-(2-naphthalen-1-yl-ethoxy)-benzenesulfonylamino]-4-oxo-butyric acid Synthesized as in Route F only methyl isocyanate was used in step 5. The title compound was isolated as an off-white powder. Analysis calculated for $C_{24}H_{25}N_3O_7S_1 \cdot H_2O \cdot 0.1$ TFA: C, 54.95; H, 5.16; N, 7.94. Found: C, 55.13; H, 5.08; N, 7.85.

EXAMPLE 34
3-[4-(3-Methyl-thioureido)-2-(2-naphthalen-1-yl-ethoxy)-benzenesulfonylamino]-4-oxo-butyric acid Synthesized as in Route F only methyl isothiocyanate was used in step 5. The title compound was isolated as an off-white powder. Analysis calculated for $C_{24}H_{25}N_3O_6S_2 \cdot H_2O$: C, 54.02; H, 5.10; N, 7.87. Found: C, 53.79; H, 4.95; N, 7.72.

EXAMPLE 35
3-[4-Methoxy-2-(2-quinolin-5-yl-ethoxy)-benzenesulfonylamino]-4-oxo-butyric acid trifloroacetate salt (1:1)

Synthesized by Route B as an off white solid. Analysis calculated for $C_{22}H_{22}N_2O_7S_1 \cdot 1.18\ C_2F_3CO_2H$: C, 49.34; H, 3.94; N, 4.72. Found: C, 49.35; H, 4.07; N, 4.49.

EXAMPLE 36
3-[4-Acetylamino-2-(2-quinolin-5-yl-ethoxy)-benzenesulfonlamino]-4-oxo-butyric acid trifloroacetate salt (1:1)

Step 1: 2-Benzyloxycarbonylamino-N-methoxy-N-methyl-succinamic acid 4-tert-butyl ester The 2-benzyloxycarbonylamino-succinic acid 4-tert-butyl ester (52.53 g, 0.1625 mol) was dissolved in 250 mL of methylene chloride and cooled in an ice/acetone bath. Then 4-methylmorpholine (42 mL) was added slowly, followed by the isobutylchloroformate (25 mL), keeping the temperature below 0° C. The reaction was stirred for 20 min, and the N,O-dimethylhydroxylamine hydrochloride was added and the reaction stirred overnight, allowing it to come to room temperature.

The solvent was stripped off, and replaced with diethyl ether. The crude mixture was washed once with 5% NaHCO₃, then twice with 5% HCl, and twice with brine, dried over MgSO₄, filtered and rotovapped. The product was recrystallized in ether/hexane to give 2-benzyloxycarbonylamino-N-methoxy-N-methyl-succinamic acid 4-tert-butyl ester (47 g, 79%) as a fluffy white solid. $^1$H NMR (CDCl₃) 7.4–7.3 (m, 5H), 5.64 (br, 1H), 5.2–5.0 (m, 3H), 3.78 (s, 3H), 3.22 (s, 3H), 2.8–2.6 (m, 1H), 2.6–2.5 (m, 1H), 1.42 (s, 9H).

Step 2: 2-Amino-N-methoxy-N-methyl-succinamic acid 4-tert-butyl Ester

The 2-benzyloxycarbonylamino-N-methoxy-N-methyl-succinamic acid 4-tert-butyl ester is dissolved in THF and 20% Pd/C is added, then the solution is placed under 50 psi of hydrogen for approximately 4 hours. The reaction is filtered and the solvent stripped off with minimal heating. The 2-amino-N-methoxy-N-methyl-succinamic acid 4-tert-butyl ester is used crude. $^1$H NMR (CDCl₃) 4.13 (m, 1H), 3.77 (s, 3H), 3.22 (s, 3H), 2.72–2.6 (dd, 1H), 2.45–2.36 (dd, 1H), 1.46 (s, 9H).

Step 3: 2-Benzyloxy-4-nitro-phenylamine

The starting 2-amino-5-nitrophenol (21.2 g, 0.14 mol) was dissolved in 350 mL THF. Solid potassium t-butoxide (15.85 g, 0.141 mol) was added slowly, with vigorous stirring. Then a solution of benzylbromide (in 150 mL THF) was added slowly and stirred at room temperature for 2 days.

The solvent was removed and the crude oil poured into water (ca. 500 mL) and 3:1 ethyl acetate/methylene chloride (ca. 200 mL). The solid precipitate was filtered off and dried, then recrystallized in toluene to give 2-benzyloxy-4-nitro-phenylamine (9.1 g). The aqueous and organic layers were separated and the aqueous layer was extracted twice with 3:1 ethyl acetate/methylene chloride. The combined organic layers were washed with 5% sodium hydroxide (which formed three layers, and the middle layer contained the desired material by TLC), then the desired layer was washed twice with water, then brine, and dried over anhydrous magnesium sulfate, filtered and the solvent removed. The solid was recrystallized in toluene, filtered and dried to yield 12 g of 2-benzyloxy-4-nitro-phenylamine. (The total yield was 62%.). $^1$H NMR (CDCl₃) 7.9–7.7 (m, 2H), 7.5–7.3 (m, 5H), 6.65 (d, 1H, J=8.68 Hz), 5.15 (s, 2H), 4.57 (br, 2H).

Step 4: 2-Benzyloxy-4-nitro-benzenesulfonyl chloride

The 2-benzyloxy-4-nitro-phenylamine (9.09 g, 37.2 mmol) was dissolved in 200 mL methylene chloride (stored over sieves) and cooled in an ice/acetone bath. Then BF₃-etherate (14 mL in 50 mL methylene chloride) was added slowly, keeping the temperature below 0° C. Then tert-butylnitrite (6.5 mL in 50 mL methylene chloride) was added slowly, keeping the temperature below 0° C., and stirred for 1 hour. Hexane (200 mL) was added and most of the solvent was removed under reduced pressure with minimal external heating. More hexane was added, and decanted off. The crude diazo salt was dissolved in 50 mL acetonitrile and diluted with 100 mL dioxane, and this solution was used directly.

CuCl (1.02 g, 10.3 mmol) was suspended in 125 mL glacial acetic acid, and LiCl (9.54 g, 225 mmol) was added, resulting in a yellow solution. This solution was diluted with 125 mL dioxane, and cooled in an ice/acetone bath. Appoximately 50 mL of liquid SO₂ was then added (add the SO₂ before the acetic acid/dioxane mixture starts to freeze). The diazo salt solution was added slowly, making sure that the solution never rose above 5° C. After the addition was complete, the solution is placed in a 50° C. oil bath for 1 hour. The solvents were stripped off, and the solution was poured into water and extracted three times with ether. The combined ether layers were washed with water, 5% NaOH, and then 5% NaHCO₃. The solution was dried over MgSO₄, filtered and the solvent stripped off. The crude 2-benzyloxy-4-nitro-benzenesulfonyl chloride was used directly in the next step. $^1$H NMR (CDCl₃) 8.19 (1H, d, J=8.7 Hz), 8.1–7.9 (2H, m), 7.6–7.3 (5H, m), 5.47 (2H, s). MS (M−Cl)=292.

Step 5: 3-(2-Benzyloxy-4nitro-benzenesulfonylamino)-N-methoxy-N-methyl-succinamic acid 4-tert-butyl ester The 2-benzyloxy-4-nitro-benzenesulfonyl chloride (37 mmol crude) and the 2-amino-N-methoxy-N-methyl-succinamic acid 4-tert-butyl ester (37 mmol crude) were both combined in methylene chloride (200 mL) and pyridine (25 mL) was added. The reaction was stirred overnight at room temperature. The solvent was stripped off and the crude product was chromatographed with 7.5% ethyl acetate/chloroform (the desired material has an $R_f$=0.2.). The solvent was removed to give 3-(2-benzyloxy-4-nitro-benzenesulfonylamino)-N-methoxy-N-methyl-succinamic acid tert-butyl ester (6.98 g, 36% yield from the starting aniline) as a foam. $^1$H NMR (CDCl₃) 8.02 (1H, d), 7.9–7.8 (2H, m), 7.6–7.3 (5H, m), 6.05 (1H, d), 5.36 (2H, m), 4.8–4.7 (1H, m), 3.61 (3H, s), 2.91 (3H, s), 2.7–2.58 (1H, m), 2.5–2.4 (1H, m), 1.40 (9H, s). MS (m/z) (M−1)=5.22.

Step 6: 3-(4-amino-2-benzyloxy-benzenesulfonylamino)-N-methoxy-N-methyl-succinamic acid tert-butyl ester The 3-(2-benzyloxy-4-nitro-benzenesulfonylamino)-N-methoxy-N-methyl-succinamic acid tert-butyl ester was dissolved in 1:1 THF/MeOH, and Raney Ni added. The solution was hydrogenated at 30 psi. When the reaction was complete, the solvent was removed to give the crude give 3-(4-amino-2-benzyloxy-benzenesulfonylamino)-N-methoxy-N-methyl-succinamic acid tert-butyl ester. The product can be used crude, or chromatographed with 7.5% methanol/ethyl acetate. $^1$H NMR (CDCl$_3$) 7.65–7.3 (8H, m), 6.2 (2H, m), 5.78 (2H, d, J=9.76 Hz), 5.2–5.1 (2H, m), 4.8–4.7 (1H, m), 4.2–4.0 (2H, br), 3.59 (3H, s), 2.56 (3H, s), 2.6–2.4 (2H, m), 1.41 (9H, s). MS (m/z) (M+1)=494.

Step 7: 3-(4-acetylamino-2-benzyloxy-benzenesulfonylamino)-N-methoxy-N-methyl-succinamic acid 4-tert butyl ester The 3-(4-amino-2-benzyloxy-benzenesulfonylamino)-N-methoxy-N-methyl-succinamic acid tert-butyl ester (5.56 g, 11.3 mmol) was dissolved in 100 mL methylene chloride, and triethylamine (2.8 mL) is added. One equivalent of acetyl chloride was added and stirred at room temperature. Additional portions of acetyl chloride were added approximately every 30 min until the starting material was consumed. (A total of 1.5 equivalents of acetyl chloride was used over about 2 hours.) The solvent was removed and replaced with ethyl acetate. The organic solution was washed twice with 5% cold HCl, then once with water, once with saturated potassium carbonate, then once with brine. The solution was dried over anhydrous magnesium sulfate, filtered and the solvent removed. The product was chromatographed with 30% chloroform/ethyl acetate, to yield 5.16 g (85%) of 3-(4-acetylamino-2-benzyloxy-benzenesulfonylamino)-N-methoxy-N-methyl-succinamic tert-butyl ester acid as a yellow foam. $^1$H NMR (CDCl$_3$) 7.73 (1H, d, J=8.42 Hz), 7.6–7.5 (4H, m), 7.5–7.3 (3H, m), 6.9 (1H, d, J=8.6 Hz), 5.85 (1H, d, J=9.52), 5.3–5.1 (2H, m), 4.8–4.6 (1H, m), 3.56 (3H, s), 2.92 (3H, s), 2.7–2.38 (2H, m), 2.14 (3H, s), 1.40 (9H, s).

Step 8: 3-(4-Acetylamino-2-hydroxy-benzenesulfonylamino)-N-methoxy-N-methyl-succinamic acid tert-butyl ester 3-(4-Acetylamino-2-benzyloxy-benzenesulfonylamino)-N-methoxy-N-methyl-succinamic acid tert-butyl ester (0.99 g, 1.8 mmol) was dissolved in 50 mL methanol and 20% Pd/C (0.09 g) is added. The reaction was placed under 50 psi of hydrogen for approximately 1 hour. The reaction was filtered and concentrated in vacuo. The crude product was chromatographed with 2:1 ethyl acetate/hexane to yield 3-(4-acetylamino-2-hydroxy-benzenesulfonylamino)-N-methoxy-N-methyl-succinamic acid tert-butyl ester 0.7 g (85%) of an brown solid. MS (APCI) m/z 444.2 (M−1).

Step 9: 3-[4-Acetylamino-2-(2-quinolin-5-yl-ethoxy)-benzenesulfonylamino]-N-methoxy-N-methyl-succinamic acid tert-butyl ester 3-(4-Acetylamino-2-hydroxy-benzenesulfonylamino)-N-methoxy-N-methyl-succinamic acid tert-butyl ester (0.40 g, 0.9 mmol) was combined with 2-Quinolin-5-yl-ethanol (0.155 g, 0.9 mmol) and triphenyl phosphine (355 mg, 1.3 mmol) in 15 mL THF. The solution was cooled to 0° C. DEAD (0.21 mL, 1.3 mmol) was added. The reaction was slowly warmed to room temperature, and stirred overnight. The reaction mixture was concentrated in vacuo. The crude product was chromatorgraphed using 1:1 ethyl acetate/hexanes followed by ethyl acetate, and then 10% methanol in ethyl acetate to yield 3-[4-acetylamino-2-(2-quinolin-5-yl-ethoxy)-benzenesulfonylamino]-N-methoxy-N-methyl-succinamic acid tert-butyl ester 450 mg (83%) of an off-white solid. MS (APCI) m/z 601.2 (M+1).

Synthesis of: 2-Quinolin-5-yl-ethanol
5-Bromo-quinoline

Sodium nitrite (2.5 g, 41.8 mmol) was dissolved in 15 mL water. Copper (I) bromide (6.0 g, 41.8 mmol) was dissolved in 38 mL of 48% HBr and heated to 75° C. The 5-aminoquinoline (5.0 g, 34.7 mmol) was suspended in 15 mL water and 18 mL 48% HBr and cooled to 0° C. The sodium nitrite solution was added to the 5-aminoquinoline solution at 0° C. The resulting diazonium solution was added slowly to the warmed CuBr solution. The reaction mixture was stirred at room temperature for 2 hr. The reaction mixture was basified with sodium hydroxide, then filtered through celite. The solid was washed with methylene chloride, and the aqueous material was extracted with methylene chloride. The organic layers were combined, dried with Na$_2$SO$_4$, and concentrated in vacuo. The crude product was chromatographed with 2:1 hexane/ethyl acetate to yield 5.7 g (80%) of 5-bromo-quinoline as a yellow oil. MS (APCI) m/z 208.0 (M+1).

5-Allyl-quinoline

5-Bromo-quinoline (5.6 g, 27 mmol) was dissolved in 40 mL toluene. BHT (50 mg) was added, along with allyl tributyl stannane (9.3 mL, 30 mmol), and tetrakis(triphenyl) phospine palladium (600 mg, 0.52 mmol). The reaction was refluxed overnight, then cooled. Potassium fluoride solution (1.0 g, in 18 mL H$_2$O) was added. The reaction was stirred for 3 hours, then filtered. The reaction mixture was concentrated in vacuo. It was chromatographed in 3:1 hexane/ethyl acetate to yield 4.38 g (95%) of 5-allyl-quinoline as a yellow oil. MS (APCI) m/z 170.1 (M+1).

2-Quinolin-5-yl-ethanol

5-Allyl-quinoline (3.12 g, 18.4 mmol) was dissolved in 40 mL methanol and 40 mL methylene chloride and cooled to −78° C. Ozone was bubbled in until a green solution was seen. Sodium borohydride (1.4 g, 36.8 mmol) was added. The reaction was warmed to room temperature and stirred for 2 hours. The reaction was quenched with water. A saturated solution of KHPO$_4$ was added and the mixture extracted with methylene chloride. The organic extracts were dried with Na$_2$SO$_4$, filtered, and concentrated in vacuo. The crude product was chromatographed with ethyl acetate to yield 1.6 g (50%) of 2-quinolin-5-yl-ethanol as a yellow solid. MS (APCI) m/z 174.1 (M+1).

Step 10: 3-[4-Acetylamino-2-(2-quinolin-5-yl-ethoxy)-benzenesulfonylamino]-4-oxo-butyric acid tert-butyl ester Lithium aluminum hydride solution (0.9 mL of a 1.0 M solution in ether) was dissolved in 15 mL diethyl ether and cooled to 65° C. 3-[4-Acetylamino-2-(2-quinolin-5-yl-ethoxy)-benzenesulfonylamino]-N-methoxy-N-methyl-succinamic acid tert-butyl ester (180 mg, 0.3 mmol) was dissolved in 5 mL THF and added to the LiAlH$_4$ solution via canula. The reaction was stirred for 10 minutes at 65° C. and then warmed to −44° C. for 15 minutes. The reaction was cooled to −65° C. and saturated Rochelle's salt was added. The reaction was warmed to room temperature, and then extracted with ethyl acetate. The extract was dried with sodium sulfate, and then concentrated in vacuo. The crude product was chromatographed with 5% methanol in ethyl acetate to yield 3-[4-acetylamino-2-(2-quinolin-5-yl-ethoxy)-benzenesulfonylamino]-4-oxo-butyric acid tert-butyl ester 130 mg (80%) of a light brown solid.

MS (APCI) m/z 542.2 (M+1).

Step 11: 3-[4-Acetylamino-2-(2-quinolin-5-yl-ethoxy)-benzenesulfonylamino]-4oxo-butyric acid trifloroacetate salt (1:1)

3-[4-Acetylamino-2-(2-quinolin-5-yl-ethoxy)-benzenesulfonylamino]-4-oxo-butyric acid tert-butyl ester (130 mg, 0.24 mmol) was dissolved in 2 mL methylene chloride and 2 mL trifluoroacetic acid. The reaction was stirred at room temperature for 90 minutes. The reaction was concentrated in vacuo, and chased with toluene to yield 110 mg (68%) of the desired product.

Analysis calculated for $C_{23}H_{23}N_3O_7S.1.34\ C_2F_3CO_2H$: C, 48.32; H, 3.84; N, 6.58.

Found: C, 48.30; H, 3.95; N, 6.47.

EXAMPLE 37

4-Oxo-3-{2-[2-(5,6,7,8-tetrahdro-quinolin-5-yl)-ethoxy]-benzenesulfonlamino}-butyric acid Route B, colorless solid. Analysis: Calcd for $C_{21}H_{24}N_2O_6S_1.0.40\ CH_2Cl_2$: C, 55.10; H, 5.36; N, 6.00. Found: C, 55.30; H, 5.38; N, 5.99. MS (APCI) m/z 433.1 (M+1).

EXAMPLE 38

3-[4-Acetylamino-2-(2-isoquinolin-4-yl-ethoxy)-benzenesulfonylamino]-4-oxo-butyric acid trifloroacetate salt (1:1)

Route B, as an off white solid: mp 112–118° C. (decomp.). MS (APCI) m/z 486.1 (M+1). $^1$H NMR (400 MHz) $CD_3OD$ 9.60 (s, 1H), 8.66 (s, 1H), 8.56 (d, J=8.3 Hz, 1H), 8.46 (d, J=8.1 Hz, 1H), 8.25 (t, J=8.0 Hz, 1H), 8.00 (t, J=7.8 Hz, 1H), 7.74 (s, 1H), 7.65 (d, J=8.6 Hz, 1H), 6.90 (m, 1H), 4.55 (m, 2H), 3.80 (m, 2H), 3.45 (m, 1H), 2.25–2.45 (m, 2H), 2.10 (s, 3H).

EXAMPLE 39

3-[4-Acetylamino-2-(2-isoquinolin-4-yl-1-methyl-ethoxy)-benzenesulfonylamino]-4-oxo-butyric acid trifloroacetate salt (1:1)

Route B. Analysis calculated for $C_{24}H_{25}N_3O_7S_1.1.34\ CF_3CO_2H$: C, 49.12; H, 4.07; N, 6.44. Found: C, 49.03; H, 4.46; N, 6.26.

EXAMPLE 40

(S)-3-[4-Dimethylamino-2-(2-isoquinolin-4-yl-ethoxy)-benzenesulfonylamino]-4-oxo-butyric acid Route E. MS(APCI) m/z 470.1 (M−1).

EXAMPLE 41

(S)-3-[4-Dimethylamino-2-(2-quinolin-5-yl-ethoxy)-benzenesulfonylamino]-4-oxo-butyric acid Route E.

Step 1: (S)-2-(4-Dimethylamino-2-benzyloxy-benzenesulfonylamino)-N-methoxy-N-methyl-succinamic acid tert-butyl ester A solution of 3-(4-amino-2-benzyloxy-benzenesulfonylamino)-N-methoxy-N-methyl-succinamic acid, from Route D Step 6 (1.82 g, 3.70 mmol) in MeOH (90.0 mL) and formaldehyde (37% in $H_2O$ solution, 10.0 mL) was shaken with Raney nickel (1.0 g) under $H_2$ (55 psi) for 19 h using a Parr apparatus. The reaction mixture was filtered through celite and concentrated. The crude product was purified by silica gel chromatography (25% EtOAc in hexanes) to afford the (S)-2-(4-dimethylamino-2-benzyloxy-benzenesulfonylamino)-N-methoxy-N-methyl-succinamic acid tert-butyl ester as a white solid (1.20 g, 75%). MS (APCI) m/z 431.50 (M−1).

Step 2: (S)-2-(Dimethylamino-hydroxy-benzenesulfonylamino)-N-methoxy-N-methyl-succinamic acid tert-butyl ester A solution of (S)-2-(4-dimethylamino-2-benzyloxy-benzenesulfonylamino)-N-methoxy-N-methyl-succinamic acid tert-butyl ester (0.50 g, 1.0 mmol) in THF:MeOH (50 mL) was shaken with 20% Pd/C (0.10 g) under $H_2$ (50 psi) for 2.5 h using a Parr apparatus. The reaction mixture was filtered through celite and concentrated. The crude (S)-2-(dimethylamino-hydroxy-benzenesulfonylamino)-N-methoxy-N-methyl-succinamic acid tert-butyl ester was obtained (0.35 g, 86%) as an off white solid. MS (APCI) m/z 402.0 (M−1) and was used without purification.

Step 3: (S)-2-[4-Dimethylamino-2-(2-quinolin-5-yl-ethoxy)-benzenesulfonylamino]-N-methoxy-N-methyl-succinamic acid tert-butyl ester To a solution of (S)-2-(dimethylamino-hydroxy-benzenesulfonylamino)-N-methoxy-N-methyl-succinamic acid tert-butyl ester (0.53 g, 1.20 mmol) in dry THF (30 mL) at 0° C. was added 2-quinolin-5-yl-ethanol (0.22 g, 1.20 mmol) and $Ph_3P$ (0.63 g, 2.40 mmol) then followed by drop wise addition of diethyl azodicarboxylate (0.40 mL, 2.40 mmol). The reaction mixture was allowed to warm up to room temperature and stirred for 12 h. The solvent was removed and the crude product was purified using silica gel flash chromatography (20% EtOAc in hexanes). (S)-2-[4-Dimethylamino-2-(2-quinolin-5-yl-ethoxy)-benzenesulfonylamino]-N-methoxy-N-methyl-succinamic acid tert-butyl ester was obtained (0.57 g, 80%) as an off white foam. MS (APCI) m/z 585.2 (M−1).

Step 4: (S)-3-[4-Dimethylamino-2-(2-quinolin-5-yl-ethoxy)-benzenesulfonylamino]-4-oxo-butyric acid tert-butyl ester To (S)-2-[4-dimethylamino-2-(2-quinolin-5-yl-ethoxy)-benzenesulfonylaino]-N-methoxy-N-methyl-succinamic acid tert-butyl ester (0.57 g, 1.0 mmol) solution in dry $THF:Et_2O$ (1:2, 30 mL) at −65° C. was added $LiAlH_4$ (0.056 g, 1.5 mmol). The reaction temperature was maintained for 2 h. The excess hydride was quenched by the addition of potassium hydrogen sulfate (2 equiv) dissolved in water. After warming to room temperature, $Et_2O$ was added (100 mL) and the organic layer was washed with water and then with brine. The solvent was dried ($MgSO_4$), filtered, and evaporated to dryness. The resulting crude product was purified via silica gel flash chromatography (25% EtOAc in hexanes) to give (S)-3-[4-dimethylamino-2-(2-quinolin-5-yl-ethoxy)-benzenesulfonylamino]-4-oxo-butyric acid tert-butyl ester as a off white foam (0.33 g, 62%). MS (APCI) m/z 526.1 (M−1).

Step 5: (S)-3-[4-Dimethylamino-2-(2-quinolin-5-yl-ethoxy)-benzenesulfonylamino]-4-oxo-butyric acid A solution of (S)-3-[4-dimethylamino-2-(2-quinolin-5-yl-ethoxy)-benzenesulfonylamino]-4-oxo-butyric acid tert-butyl ester (0.33 g, 0.60 mmol) in TFA (2 mL) and $CH_2Cl_2$ (20 mL) was stirred for 3 h. After the solvent was removed under vacuum, the residue was subjected to preparative reverse-phase HPLC (VYDAC, C18) using a linear gradient of (A) water containing 0.1% TFA and (B) acetonitrile containing 0.1% TFA (20–65% B, in 120 min) at a flow rate of 15 mL/min. Fractions containing the major peak were pooled and lyophilized to yield 0.260 g (92%) of (S)-3-[4-dimethylamino-2-(2-quinolin-5-yl-ethoxy)-benzenesulfonylamino]-4-oxo-butyric acid. MS (APCI) m/z 470.1 (M−1).

EXAMPLE 42

(S)-3-[4-Acetylamino-2-(2-quinolin-5-yl-propoxy)-benzenesulfonylamino]-4-oxo-butyric acid The synthesis of 2-(5-quinolyl)-1-propanol employed in the synthesis of (S)-3-[4-acetylamino-2-(2-quinolin-5-yl-propoxy)-benzenesulfonylamino]-4-oxo-butyric acid:

Step 1: [(E)-1-Methoxy-1-propenyl]oxy(trimethyl)silane

Synthesized from commercially available methyl propionate following the procedure of Tamura et al. *Tet. Lett.* 44, 4311–4314, 1979. [(E)-1-Methoxy-1-propenyl]oxy(trimethyl)silane was 60% pure by NMR. $^1$H-NMR ($CDCl_3$) 3.7 (q, 1H), 3.5 (s, 3H), 1.5 (d, 3H), 0.2 (s, 9H).

Step 2: 5-Quinolyl trifluoromethanesulfonate

To a 0° C. solution of 5-hydroxyquinoline(1 g, 6.9 mmol) in pyridine(20 mL) was added triflic anhydride (1.3 mL, 7.6 mmol). This mixture was stirred at 0° C. for one hour and the solvent was removed under reduced pressure. The residue was azeotroped with toluene(25 mL) and triturated with hot heptane(25 mL) to give 5-quinolyl trifluoromethanesulfonate (1.9 g, 99% yield) HPLC (10% to 90% acetonitrile in 0.1N aqueous ammonium acetate over 10 min at 2 mL/min using a Waters Symmetry C18, 150×4.6 mm column) 8.36 min.

Step 3: Methyl 2-(5-quinolyl)propanoate

A solution of tris(dibenzylideneacetone)-dipalladium (65 mg, 0.14 mmol), 1,1'-bis(diphenylphosphino)ferrocene(155 mg, 0.28 mmol) and lithium acetate(2.8 g, 27.6 mmol) in THF (50 mL) was stirred at room temperature for 5 minutes. To this mixture was added 5-quinolyl trifluoromethanesulfonate and [(E)-1-methoxy-1-propenyl]oxy(trimethyl) silane. The resulting mixture was heated at reflux for 24 hours and then allowed to cool to room temperature. The mixture was filtered, the residue was washed with THF(50 mL) and the solvent was removed under reduced pressure. Following a short silica column and aqueous workup, methyl 2-(5-quinolyl)propanoate was purified by HPLC yield 250 mg, 17%. HPLC (10% to 90% acetonitrile in 0.1N aqueous ammonium acetate over 10 min at 2 mL/min using a Waters Symmetry C18, 150×4.6 mm column) 6.89 min.

Step 4: 2-(5-Quinolyl)-1-propanol

Methyl 2-(5-quinolyl)propanoate (100 mg, 0.47 mmol) was dissolved in dry THF(10 mL) and cooled to −78° C. on a dry ice/acetone bath. Lithium aluminum hydride (1M in ether, 0.93 mL, 0.93 mmol) was added dropwise. The mixture stirred for 10 minutes while warming to 0° C. The reaction was quenched with $KHSO_4$(1M aq., 1 mL). The mixture was made basic with NaOH(1M aq) and extracted into ethyl acetate. The organics were washed with brine, dried over $MgSO_4$ and then removed under reduced pressure to give 2-(5-quinolyl)-1-propanol (65 mg, 74%). HPLC (10% to 90% acetonitrile in 0.1N aqueous ammonium acetate over 10 min at 2 mL/min using a waters Symmetry C18, 150×4.6 mm column) 2.96 min.

Route D, HPLC (10% to 90% acetonitrile in 0.1 N aqueous ammonium acetate over 10 min at 2 mL/min using a waters Symmetry C18, 150×4.6 mm column) 5.65 min. MS (APCI) m/z 500 (M+1).

EXAMPLE 43

3-[4-Carbamoyl-2-(2-naphthalen-1-yl-ethoxy)-benzenesulfonylamino]-4-oxo-butyric acid Route G

Step 1: 3-Fluoro-4-nitrobenzamide

To a solution of 3-fluoro-4-nitrobenzoic acid, J. Am. Chem. Soc. 66, 1631–1632 (1944), (2.0 g, 10.81 mmol) in tetrahydrofuran (100 mL) at 0° C. was added 4-methyl morpholine (1.78 mL, 16.21 mmol), 1-hydroxybenzotriazole (2.18 g, 16.21 mmol), followed by 1-(3 dimethylaminopropyl)-3-ethylcarbodiimide hydrochloride (3.10 g, 16.21 mmol). The reaction was stirred for 1 hour at 0° C., then concentrated ammonium hydroxide was added (2.19 mL, 16.21 mmol). The reaction was allowed to warm slowly to room temperature and stirred overnight. The reaction was then diluted with ethyl acetate and washed with 5% citric acid (50 mL), saturated sodium bicarbonate (50 mL), and saturated sodium chloride (50 mL), dried over magnesium sulfate, filtered and concentrated under reduced pressure to yield a pale yellow powder. The powder was collected and washed with ether, followed by drying under reduced pressure to yield 3-fluoro-4-nitro-benzamide 1.22 g (69%). MS(APCI) m/z 183.0 (M−H). Anal. Calcd. for $C_7H_5N_2O_3F_1$: C, 45.66; H, 2.74; N, 15.21. Found: C, 46.03; H, 2.75; N, 15.02.

Step 2: 3-(2-Naphthalen-1-yl-ethoxy)-4-nitro-benzamide

To a solution of 3-fluoro-4-nitro-benzamide (1.0 g, 5.43 mmol) in tetrahydrofuran (55 mL) at room temperature was added 1-napthaleneethanol (1.02 g, 5.97 mmol) followed by potassium tert-butoxide (0.67 g, 5.97 mmol). The reaction was allowed to stir overnight at room temperature. The reaction was then diluted with ethyl acetate and washed with 1N hydrochloric acid (50 mL), saturated sodium bicarbonate (50 mL), and saturated sodium chloride (50 mL), dried over magnesium sulfate, filtered and concentrated under reduced pressure to yield a pale yellow solid. The powder was collected and washed with ether, followed by drying under reduced pressure to yield 3-(2-naphthalen-1-yl-ethoxy)-4-nitro-benzamide 1.09 g (60%). $^1$HNMR(300 MHz, DMSO) 8.13 (d, 2H), 7.91 (t, 2H), 7.88 (dd, 1H), 7.72(s, 1H), 7.64 (s, 1H), 7.41 (m, 5H), 4.50 (t, 2H), 3.54 (t, 2H). MS(APCI) m/z 335.1 (M−H). Anal. Calcd. for $C_{19}H_{16}N_2O_4$: C, 67.85; H, 4.79; N, 8.33. Found: C, 67.35; H, 4.53; N, 8.06.

Step 3: 4-Amino-3-(2-naphthalen-1-yl-ethoxy)-benzamide

To a solution of 3-(2-naphthalen-1-yl-ethoxy)-4-nitrobenzamide (0.500 g, 1.48 mmol) in 75 mL of tetrahydrofuran at room temperature was added Raney Nickel (0.50 g). The reaction was pressurized to 50 psi of hydrogen for 18 hours. The reaction was then filtered through celite and washed with tetrahydrofuran. The filtrate was then concentrated in vacuo to dryness to yield 4-amino-3-(2-naphthalen-1-yl-ethoxy)-benzamide 455 mg (100%) of a white solid. $^1$HNMR(300 MHz, DMSO) 8.26 (d, 1H), 7.99 (d, 1H), 7.98 (d,1H), 7.68(m, 5H), 7.33 (m, 2H), 6.93 (bs, 1H), 6.62 (d, 1H), 4.89 (s, 2H), 5.16 (s, 2H), 4.34 (t, 2H), 3.63 (t, 2H). MS(APCI) m/z 307.1 (M+H).

Step 4: 4-Diazo-3-(2-naphthalen-1-yl-ethoxy)-benzamide fluoroborate

To a solution of 4-amino-3-(2-naphthalen-1-yl-ethoxy)-benzamide (0.450 g, 1.47 mmol) in 15 mL of dichloromethane at −15° C. (ice-acetone) was added boron trifluoride diethyl etherate (0.54 mL, 4.41 mmol). tert-Butyl nitrite (0.21 mL, 1.76 mmol) in dichloromethane (1 mL) was added dropwise over 5 minutes. Following the complete addition, the reaction was stirred for 30 minutes at −15° C. Cold pentane (100 mL) was then added to the reaction to precipitate the tetrafluoroborate salt. The 4-diazo-3-(2-naphthalen-1-yl-ethoxy)-benzamide fluoroborate was collected and washed with pentane and air-dried. $^1$HNMR(300 MHz, $CDCl_3$) 8.21 (d, 1H), 8.09 (bs, 1H), 7.79 (d, 1H), 7.70 (s, 1H), 7.53 (m, 3H), 7.19 (m, 5H), 4.50 (t, 2H), 3.42 (t, 2H).

Step 5: 4-(Chlorosulfonyl)-3-(2-naphthalen-1-yl-ethoxy)-benzamide

To a solution of acetic acid (8 mL) and dioxane (8 mL) at 0° C. was added lithium chloride (0.36 g, 8.46 mmol) and copper (I) chloride (0.042 g, 0.42 mmol). Sulfur dioxide (40 mL) was then condensed into this mixture by means of a cold finger at −78° C. A solution of 4-diazo-3-(2-naphthalen-1-yl-ethoxy)-benzamide fluoroborate in dioxane (20 mL) and acetonitrile (5 mL) was added in one portion to the sulfur dioxide mixture. The reaction was stirred at 0° C. for 3 hours and then heated to 65° C. overnight. The reaction was then cooled to room temperature and poured onto ethyl acetate (500 mL) and washed with water (50 mL), 1N sodium hydroxide (50 mL), saturated sodium bicarbonate (50 mL), and saturated sodium chloride (50 mL), dried over magnesium sulfate, filtered and concentrated under reduced pressure to yield 4-(chlorosulfonyl)-3-(2-naphthalen-1-ylethoxy)-benzamide as an orange oil. $^1$HNMR(300 MHz, CDCl$_3$) 8.00 (d, 1H), 7.87 (d, 1H), 7.78 (d, 1H), 7.68 (d, 1H), 7.57 (s, 1H), 7.40 (m, 4H), 6.21 (bs, 1H), 4.49 (t, 2H), 3.64 (t, 2H).

Step 6: 3-[4-Carbamoyl-2-(2-naphthalen-1-yl-ethoxy)-benzenesulfonylamino]-N-methoxy-N-methyl-succinamic acid tert-butyl ester To a solution of 4-(chlorosulfonyl)-3-(2-naphthalen-1-yl-ethoxy)-benzamide (0.55 g, 1.41 mmol) in dichloromethane (14 mL) was added (S)-2-amino-N-methoxy-N-methyl-succinamic acid-4-tert-butyl ester (0.33 g, 1.41 mmol) followed by pyridine (0.34 mL, 4.23 mmol). The reaction was allowed to stir over night at room temperature. The reaction was then diluted with ethyl acetate and washed with 5% citric acid (50 mL), saturated sodium bicarbonate (50 mL), and saturated sodium chloride (50 mL), dried over magnesium sulfate, filtered and concentrated under reduced pressure to yield a orange oil. The crude residue was chromatographed (silica gel, 75% ethyl acetate-24% hexanes-1% acetic acid) to give 3-[4-carbamoyl-2-(2-naphthalen-1-yl-ethoxy)-benzenesulfonylamino]-N-methoxy-N-methyl-succinamic acid tert-butyl ester a white foam (0.25 g, 30%). $^1$HNMR(300 MHz, DMSO) 8.27 (d, 1H), 8.01 (s, 1H), 7.93 (d, 1H), 7.83 (d, 1H), 7.76 (d, 1H), 7.50 (m, 8H), 4.42 (m, 3H), 3.73 (m, 2H), 3.48 (bs, 3H), 2.81 (bs, 3H), 2.49 (dd, 1H), 2.36 (dd, 1H), 1.32 (s, 9H). MS(APCI) m/z 584.1 (M−H).

Step 7: 3-[4-Carbamoyl-2-(2-naphthalen-1-yl-ethoxy)-benzenesulfonylamino]-4-oxo-butyric acid tert-butyl ester To a 65° C. solution of lithium aluminum hydride (0.37 ml, 1M in diethyl ether) in diethyl ether (5 mL) was added a solution of 3-[4-carbamoyl-2-(2-naphthalen-1-yl-ethoxy)-benzenesulfonylamino]-N-methoxy-N-methyl-succinamic acid tert-butyl ester (0.20 g, 0.34 mmol) in diethyl ether (5 mL). The reaction was stirred at −65° C. for 4.5 hours. The reaction was then diluted with ethyl acetate (100 mL) and washed with 10% potassium hydrogen sulfate (25 mL) and saturated sodium chloride (25 mL), dried over magnesium sulfate, filtered and concentrated under reduced pressure to yield 3-[4-carbamoyl-2-(2-naphthalen-1-yl-ethoxy)-benzenesulfonylamino]-4-oxo-butyric acid tert-butyl ester as a clear oil. MS(APCI) m/z 525.1(M−H)

Step 8: 3-[4-Carbamoyl-2-(2-naphthalen-1-yl-ethoxy)-benzenesulfonylamino]-4-oxo-butyric acid To a solution of 3-[4-carbamoyl-2-(2-naphthalen-1-yl-ethoxy)-benzenesulfonylamino]-4-oxo-butyric acid tert-butyl ester (0.18 g, 0.34 mmol) in dichloromethane (10 mL) and water (0.1 mL) was added trifluoroacetic acid (1 mL). The reaction was stirred for 2 hours at room temperature. The reaction was then concentrated under reduced pressure to yield a colorless oil. The residue was purified by HPLC using a gradient of 10% to 50% acetonitrile containing 0.1% TFA and water at containing 0.1% TFA over 140 minutes to yield 3-[4-carbamoyl-2-(2-naphthalen-1-yl-ethoxy)-benzenesulfonylamino]-4-oxo-butyric acid as a lyophilized as a white solid (0.045 g, 28%). MS(APCI) m/z 471.0 (M+1).

EXAMPLE 44

3-[4-Dimethylamino-2-(2 isoquinolin-4-yl-1-methyl-ethoxy)-benzenesulfonylamino]-4oxo-butyric acid trifloroacetate salt (1:X)

Route E. MS (APCI) m/z 486.1 (M+1)

EXAMPLE 45

3-[4-Acetylamino-2-(2-adamantan-1-yl-ethoxy)-benzenesulfonylamino]-4-oxo-butyric acid Route B. MS (APCI) m/z 436 (M+1).

EXAMPLE 46

3-[4-Dimethylamino-2-(1-methyl-2-naphthalen-1-yl-ethoxy)-benzenesulfonylamino]-4-oxo-butyric acid trifloroacetate salt (1:X)

Route E. MS (APCI) m/z 482.9 (M+1).

EXAMPLE 47

3-[4-(3-Methyl-thioureido)-2-(2quinolin-5-ethoxy)-benzenesulfonylamino]-4-oxo-butyric acid trifloroacetate salt Route D.

Step 1: 3-(4-Amino-2-hydroxy-benzenesulfonylamino)-N-methyl-succinamic acid tert-butyl ester A mixture of 1.0 g (1.91 mmol) 3-(2-benzyloxy-4-nitro-benzenesulfonylamino)-N-methyl-succinamic acid tert-butyl ester from Route D, 0.2 g 20% Pd/C, and 75 mL of a 1:1 mixture of THF:MeOH was shaken under 50 psi H$_2$ gas for 4.5 h. TLC analysis showed reaction complete. The reaction was filtered to remove catalyst and the solvent evaporated under reduced pressure to give 3-(4-amino-2-hydroxy-benzenesulfonylamino)-N-methyl-succinamic acid tert-butyl ester 0.78 g (100%) as a light yellow foam. MS (APCI) m/z 402 (M−1).

Step 2: 3-(4-Amino-2-(2-quinolin-5-yl-ethoxy)-benzenesulfonylamino)-N-methyl-succinamic acid tert-butyl ester A mixture of 0.167 g (0.972 mmol) 2-quinolin-5-yl-ethanol, 0.48 g (1.94 mmol) triphenyl phosphine, and 0.392 g (0.972 mmol) 3-(4-amino-2-hydroxy-benzenesulfonylamino)-N-methyl-succinamic acid tert-butyl ester was stirred in 25 mL THF at room temperature under a nitrogen atmosphere. 0.31 mL (1.94 mmol) diethyl azodicarboxylate was added dropwise and the mixture stirred 18 h. TLC anaylsis indicated complete reaction. The solvent was evaporated under reduced pressure and the residue purified on silica eluting with 1:1 hexanes:EtOAc to EtOAc yielding 0.23 g (43%) of 3-(4-amino-2-(2-quinolin-5-yl-ethoxy)-benzenesulfonylamino)-N-methyl-succinamic acid tert-butyl ester as a colorless foam. MS (APCI) m/z 559 (M+1).

Step 3: N-Methoxy-N-methyl-3-[4-(3-methyl-thioureido)-2-(2-quinolin-5-yl-ethoxy)-benzenesulfonylamino]-succinamic acid tert-butyl ester A mixture of 0.2 g (0.36 mmol) 3-(4-amino-2-(2-quinolin-5-yl-ethoxy)-benzenesulfonylamino)-N-methyl-succinamic acid tert-butyl ester and 15 mL pyridine was heated to 80° C. Methyl isothiocyanate 0.5 g (6.8 mmol) was added and the mixture was heated to reflux for 1.5 h. TLC anaylsis indicated complete reaction. The solvent was evaporated under reduced pressure to give a yellow residue. The residue was passed through a short silica plug eluting with EtOAc to give 0.18 g (80%) of N-methoxy-N-methyl-3-[4-(3-methyl-thioureido)-2-(2-quinolin-5-yl-ethoxy)-benzenesulfonylamino]-succinamic acid tert-butyl ester as a yellow film. MS (APCI) m/z 632 (M+1).

Step 4: 3-[4-(3-Methyl-thioureido)-2-(2-quinolin-5-yl-ethoxy)-benzenesulfonylamino]-4-oxo-butyric acid tert-butyl ester A mixture of 2 mL THF and 0.8 mL 1M LiAlH$_4$ solution in ether was cooled to −65° C. in a chloroform/dry ice bath. A mixture if 0.18 g (0.29 mmol) N-methoxy-N-methyl--3-[4-(3-methyl-thioureido)-2-(2-quinolin-5-yl-ethoxy)-benzenesulfonylamino]-succinamic acid tert-butyl ester in 3 mL THF was added dropwise and the reaction mixture was stirred 30 min at −65° C. TLC analysis showed starting material consumed. The reaction was quenched cold with 1 mL 1M aqueous potassium sodium tartrate solution and allowed to reach room temperature. The product was partioned between 75 mL brine and 50 mL EtOAc. The product was extracted with 50 EtOAc, the combined organic extracts dried over anhydrous magnesium sulfate, filtered, concentrated and purified on silica with 1:1 EtOAc:hexanes to give 0.84 g (52%) of 3-[4-(3-methyl-thioureido)-2-(2-quinolin-5-yl-ethoxy)-benzenesulfonylamino]-4-oxo-butyric acid tert-butyl ester as a colorless glass. MS (APCI) m/z 573 (M+1).

Step 5: 3-[4(3-Methyl-thioureido)-2-(2-quinolin-5-yl-ethoxy)-benzenesulfonylamino]-4-oxo-butyric acid trifluoroacetate salt A mixture of 0.084 g (0.147 mmol) 3-[4-(3-methyl-thioureido)-2-(2-quinolin-5-yl-ethoxy)-benzenesulfonylamino]-4-oxo-butyric acid tert-butyl ester and 20 mL (3:1 $CH_2Cl_2$:TFA) was stirred 2 h at room temperature. TLC analysis indicated starting material consumed. The solvent was removed under reduced pressure. To the residue was added 25 mL $CH_2Cl_2$ and the solvent removed under reduced pressure. The residue was triturated with 15 mL ether and the solid was filtered, washed with ether and dried at 40° C. 36 h to give 0.087 g (94%) of 3-[4-(3-methyl-thioureido)-2-(2-quinolin-5-yl-ethoxy)-benzenesulfonylamino]-4-oxo-butyric acid trifluoroacetate salt as a beige solid. MS (APCI) m/z 517 (M+1).

Analysis calculated for $C_{23}H_{24}N_4O_6S_2$.1.55 TFA: C, 45.21; H, 3.71; N, 8.08. Found: C, 44.82; H, 3.97; N, 7.79.

EXAMPLE 48

3-[2-(2-Isoquinolin-4-yl-ethoxy)-4-(3-methyl-thioureido)-benzenesulfonylamino]-4-oxo-butyric acid trifloroacetate salt (1:1)

Route D; a beige solid. mp 92–98° C. (dec.) MS (APCI) m/z 517.2 (M+1). $^1$H NMR (400 MHz) $CD_3OD$ 9.60 (s, 1H), 8.65 (s, 1H), 8.55 (m, 1H), 8.45 (m, 1H), 8.25 (m, 1H), 8.00 (m, 1H), 7.90 (m, 1H), 7.65 (m, 1H), 6.80 (m, 1H), 4.55 (m, 1H), 3.85 (m, 2H), 3.00 (s, 3H), 2.25–2.50 (m, 2H).

Analysis calculated for $C_{23}H_{24}N_4O_6S_2$.2.14 $C_2HF_3O_2$: C, 43.59; H, 3.71; N, 7.19.

Found: C, 43.80; H, 3.61; N, 6.82.

EXAMPLE 49

3-[4-(3-Methyl-ureido)-2-(2-quinolin-5-yl-ethoxy)-benzenesulfonlamino]-4-oxo-butyric acid trifloroacetate salt (1:2)

Synthesized by Route D; an off white solid. Analysis calculated for $C_{23}H_{24}N_4O_7S$.1.51 $C_2F_3CO_2H$: C, 46.46; H, 3.82; N, 8.33. Found: C, 46.73; H, 4.05; N, 7.94.

EXAMPLE 50

3-[2-(2-Isoquinolin-4-yl-1-methyl-ethoxy)-4-(3-methyl-thioureido)-benzenesulfonyl-amino]-4-oxo-butyric acid trifloroacetate salt (1:2).

Route D; an off-white powder. mp 95–100° C. (dec.) MS (APCI) m/z 531 (M+1). $^1$H NMR (400 MHz) $CD_3OD$ 9.52 (s, 1H), 8.60–8.65 (m, 1H), 8.53 (d, J=8.5 Hz, 1H), 8.23 (t, J=7.4 Hz, 1H), 7.97 (t, J=7.4 Hz, 1H), 7.80 (m, 1H), 7.60 (m, 1H), 6.75 (bs, 1H), 5.00 (m, 1H), 3.55–3.80 (m, 3H), 2.95 (s, 3H), 2.30–2.65 (m, 2H), 1.60 (m, 3H).

Analysis calculated for $C_{24}H_{26}N_4O_6S_2$.1.56 $C_2HF_3O_2$: C, 45.97; H, 3.92; N, 7.91.

Found: C, 45.60; H, 4.09; N, 7.70.

EXAMPLE 51

3-[4-(3-Ethyl-thioureido)-2-(2-quinolin-5-yl-ethoxy)-benzenesulfonylamino]-4-oxo-butyric acid trifloroacetate salt (1:X)

Route D. MS (APCI) m/z 531.2 (M+1).

EXAMPLE 52

3-[4-(3-Isopropyl-thioureido)-2-(2-quinolin-5-yl-ethoxy)-benzenesulfonylamino]-4-oxo-butyric acid brifloroacetate salt (1:X).

Route D. MS (APCI) m/z 545.3 (M+1).

EXAMPLE 53

3-[2-(2-Benzoimidazol-1-yl-1-methyl-propoxy)-benzenesulfonylamino]-4-oxo-butyric acid trifloroacetate salt (1:X), Route B, as a Colorless Solid 44 mg Analysis calculated for $C_{21}H_{23}N_3O_6S_1$.2.44 water.1.64 TFA: C, 45.97; H, 4.69; N, 7.93. Found: C, 45.97; H, 4.69; N, 7.93.

EXAMPLE 54

3-[4-Acetylamino-2-(2-benzoimidazol-1-yl-1-methyl-ethoxy)-benzenesulfonylamino]-4-oxo-butyric acid trifloroacetate salt (1:X)

Route B; a colorless solid. MS(APCI) m/z 489.1(M+1).

(S)-1-(3H benzimidazol-1-yl)-propan-2-ol used in the synthesis of 3-[4-acetylamino-2-(2-benzoimidazol-1-yl-1-methyl-ethoxy)-benzenesulfonylamino]-4-oxo-butyric acid trifloroacetate salt was made in one step as follows: to a solution of benzimidazole (945 mg, 8.0 mmol) in THF/tert-butanol (1:10, 25 mL) was added potassium tert-butoxide (898 mg, 8.0 mmol) and (S)-propylene oxide (0.56 mL, 8.0 mmol). The reaction was stirred 24 h at room temperature and was poured into water, extracted with ethyl acetate and dried over magnesium sulfate. Evaporation gave product (1.37 g) as a 7:1 mixture of product to benzimidazole as a brown oil which was used in Route B with out purification. $^1$H NMR (CDCl$_3$) 1.35(d,3H), 4.00 (m,1H), 4.18(d,1H), 4.26(m,1H), 7.07(t,1H), 7.15–7.27(m,2H), 7.40(d,1H), 7.78 (s,1H).

EXAMPLE 55

3-[4-Acetylamino-2-(1-methyl-2-quinolin-5-yl-ethoxy)-benzenesulfonylamino]-4-oxo-butyric acid trifloroacetate salt (1:1)

Route B. Analysis calculated for $C_{24}H_{25}N_3O_7S_1$.1.51 $CF_3CO_2H$: C, 46.58; H, 3.70; N, 7.64. Found: C, 46.94; H, 3.88; N, 6.89.

EXAMPLE 56

(S)-3-[6-Methoxy-2-(2-quinolin-4-yl-ethoxy)-pyridin-3-sulfonylamino]-4-oxo-butyric acid Step 1: 2-Benzyloxy-6-methoxy-3 nitro-pyridine Potassium tert-butoxide (4.28 g, 38.2 mmol) was added to a solution of benzyl alcohol (3.29 mL, 31.8 mmol) in 66 mL anhydrous THF. The mixture was stirred at room temperature for 20 minutes. 2-Chloro-6-methoxy-3-nitropyridine (5.00 g, 26.5 mmol) was added and the reaction was stirred at vigorous reflux for 18 h. TLC analysis (silica, 1:1 $CH_2Cl_2$-hexanes) indicated no unreacted starting material. The reaction mix was diluted with 200 mL $H_2O$ and 20 mL 10% aqueous NaOH. The dilution was extracted with ethyl acetate (75 mL) and then with $CH_2Cl_2$ (50 mL). The organic extractions were combined, washed with brine (100 mL), dried over $Na_2SO_4$, filtered through celite, and concentrated. The crude product was purified by flash chromatography ($SiO_2$, 1:1.5 $CH_2Cl_2$-hexanes) to give 3.41 g (13.1 mmol, 49%) of 2-benzyloxy-6-methoxy-3 nitro-pyridine. MS (APCI) m/z 261.1 (M+1).

Step 2: 2-Benzyloxy-6-methoxy-pyridin-3-ylamine

2-Benzyloxy-6-methoxy-3 nitro-pyridine (3.41 g, 13.1 mmol) was shaken with 1 g Rainey nickel in 100 mL THF in a Parr hydrogenation apparatus at 48 psi $H_2$ for 20 h. TLC analysis (silica, $CH_2Cl_2$) indicated complete consumption of starting material. The reaction mixture was filtered and concentrated. The crude product was purified by gradient elution flash chromatography ($SiO_2$, 1:1 $CH_2Cl_2$/hexanes to 3:1 $CH_2Cl_2$/hexanes to 100% $CH_2Cl_2$) to give 1.65 g (7.17 mmol, 55%) of 2-benzyloxy-6-methoxy-pyridin-3-ylamine. MS (APCI) m/z 231.2 (M+1). $^1$H NMR (300 MHz) CDCl$_3$ 7.29–7.48 (m, 5H), 6.98 (d, J=8.1 Hz, 1H), 6.19 (d, J=8.1 Hz, 1H), 5.42 (s, 2H), 3.84 (s, 3H).

Step 3: (S)-3-(2-Benzyloxy-6-methoxy-pyridin-3-sulfonylamino)-N-methoxy-N-methyl-succinic acid tert-butyl ester BF$_3$.Et$_2$O (2.63 mL, 21.4 mmol) was added to a solution of 2-benzyloxy-6-methoxy-pyridin-3-ylamine (1.64 g, 7.13 mmol) in 10 mL CH$_2$Cl$_2$ chilled to −15° C. in an ice/acetone bath. t-butylnitrite (1.02 mL, 8.56 mmol) dissolved in 1 mL CH$_2$Cl$_2$ was added dropwise and the mix was stirred at −15° C. for one hour. Hexane (40 mL) chilled to 0° C. were added and a brown tar oiled out of solution onto the walls of the flask. The mother liquor was decanted. The remaining residue was dissolved in a minimum of dioxane. CuCl (0.234 g, 2.37 mmol), LiCl (1.81 g, 42.78 mmol), and SO$_2$ (~30 mL) were combined in a 40 mL solution of 1:1 acetic acid-dioxane in a separate 3-neck flask fitted with a cold-finger. The solution was chilled to −15° C. The residue-dioxane solution from above was added to the mixture. The reaction was stirred at −15° C. for 90 minutes and then at 50° C. for 90 minutes. The mixture was allowed to cool to room temperature and then was diluted with 75 mL saturated aqueous NaHCO$_3$. The dilution was extracted with ethyl acetate. The aqueous portion was diluted with one half volume of 10% aqueous NaOH and was reextracted with ethyl acetate. The organic extracts were combined, washed with brine, dried over Na$_2$SO$_4$, filtered through celite, and concentrated to give the desired sulfonyl chloride. $^1$H NMR (300 MHz) CDCl$_3$ 8.08 (d, J=8.4 Hz, 1H), 7.30–7.54 (m, 5H), 6.40 (d, J=8.7 Hz, 1H), 5.64 (s, 2H), 3.98 (s, 3H).

Step 4

The sulfonyl chloride product from step 3 was immediately combined with (S)-3-amino-N-methoxy-N-methyl-succinamic acid tert-butyl ester (2.15 g, 9.27 mmol) and pyridine (5 mL, 60 mmol) in 17 mL CH$_2$Cl$_2$. The mixture was stirred at room temperature for 16 h and then was diluted with 50 mL H$_2$O. The dilution was extracted with CH$_2$Cl$_2$. The organic extracts were combined, washed with brine, dried over Na$_2$SO$_4$, filtered through celite, and concentrated. The crude product was purified by gradient elution flash chromatography (SiO$_2$, 1:9 acetone/hexanes to 1:5 acetone/hexanes) to give 2.19 g (4.30 mmol, 60%) of(S)-3-(2-benzyloxy-6-methoxy-pyridin-3-sulfonylamino)-N-methoxy-N-methyl-succinic acid tert-butyl ester as an orange oil. MS (APCI) m/z 510.2 (M+1). $^1$H NMR (300 MHz) CDCl$_3$ 7.99 (d, J=8.4 Hz, 1H), 7.29–7.59 (m, 5H), 6.33 (d, J=8.4 Hz, 1H), 5.83 (d, J=9.9 Hz, 1H), 5.61 (d, J=12.6 Hz, 1H), 5.46 (d, J=12.3 Hz, 1H), 4.68 (m, 1H), 3.92 (s, 3H), 3.61 (bs, 3H), 2.96 (bs, 3H), 2.59 (dd, J=15.3 and 6 Hz, 1H), 2.44 (dd, J=15.6 and 6.8 Hz, 1H), 1.40 (s, 9H).

Step 5: (S)-3-(2-Hydroxy-6-methoxy-pyridin-3-sulfonylamino)-N-methoxy-N-methyl-succinic acid tert-butyl ester Compound from step 4 (2.18 g, 4.28 mmol) was stirred with 20% Pd/C (0.24 g) in THF at room temperature under a hydrogen balloon for 2.5 h. TLC analysis (silica, 1:4 acetone/hexanes) indicated complete consumption of the starting material. The reaction mixture was filtered through celite and concentrated. The crude product was purified by flash chromatography (SiO$_2$, 1:4 acetone/hexanes) to give (S)-3-(2-hydroxy-6-methoxy-pyridin-3-sulfonylamino)-N-methoxy-N-methyl-succinic acid tert-butyl ester (1.39 g, 77%). MS (APCI) m/z 418.1 (M−1). $^1$H NMR (300 MHz) CDCl$_3$ 8.02 (d, J=8.4 Hz, 1H), 6.09 (m, 1H), 5.89 (d, J=7.8 Hz, 1H), 4.81 (m, 1H), 3.96 (s, 2H), 3.73 (s, 3H), 3.09 (bs, 3H), 2.71 (dd, J=15.6 and 6.3 Hz, 1H), 2.51 (dd, J=15.5 and 6.7, 1H), 1.42 (s, 9H).

Step 6: (S)-N-Methoxy-3[6-methoxy-2-(2-quinolin-4-yl-ethoxy)-pyridin-3-sulfonylamino]-N-methoxy-N-methyl-succinic acid tert-butyl ester (S)-3-(2-Hydroxy-6-methoxy-pyridin-3-sulfonylamino)-N-methoxy-N-methyl-succinic acid tert-butyl ester (0.30 g, 0.72 mmol) was combined and stirred for 18 h with 4-quinoline ethanol (0.14 g, 0.79 mmol), triphenylphosphine (0.33 g, 1.25 mmol), and diethyl azodicarboxylate (0.21 mL, 1.36 mmol) in 3 mL THF at room temperature. TLC analysis (silica, 1:2.3 ethyl acetate/hexanes) indicated the reaction was complete. The reaction mixture was concentrated. The product was isolated by flash chromatography (SiO$_2$, 1:4 ethyl acetate/hexanes) to give 0.220 g (0.383 mmol, 54%) of (S)-N-methoxy-3-[6-methoxy-2-(2-quinolin-4-yl-ethoxy)-pyridin-3-sulfonylamino]-N-methoxy-N-methyl-succinic acid tert-butyl ester. MS (APCI) m/z 545.2 (M+1). $^1$H NMR (300 MHz) CDCl$_3$ 7.35 (d, J=4.5 Hz, 1H), 8.22 (d, J=7.5 Hz, 1H), 8.13 (d, J=8.4 Hz, 1H), 7.76 (d, J=8.4 Hz, 1H), 7.41–7.56 (m, 3H), 6.30 (d, J=8.4 Hz, 1H), 5.89 (d, J=9.6 Hz, 1H), 4.79 (m, 2H), 4.58 (m, 1H), 3.82 (s, 3H), 3.68 (m, 2H), 3.56 (s, 3H), 2.90 (s, 3H), 2.54 (dd, J=15.5 and 5.6, 1H), 2.38 (dd, J=15.5 and 7.0, 1H), 1.40 (s, 9H).

Step 7: (S)-3-[6-Methoxy-2-(2-quinolin-4-yl-ethoxy)-pyridin-3-sulfonylamino]-4-oxo-butyric acid tert-butyl ester (S)-N-Methoxy-3-[6-methoxy-2-(2-quinolin-4-yl-ethoxy)-pyridin-3-sulfonylamino]-N-methoxy-N-methyl-succinic acid tert-butyl ester (0.22 g, 0.38 mmol) was dissolved in 0.4 mL freshly distilled THF and then was diluted with 1.5 mL ether. The solution was chilled to −65° C. in a dry-ice/chloroform bath. LiAlH$_4$ (0.76 mL 1.0M soln in Et$_2$O, 0.76 mmol) was added dropwise via syringe and the reaction was stirred at −65° C. for 1 h. TLC analysis (silca, 1:1 ethylacetate/hexanes) indicated complete consumption of starting material. The reaction was quenched with 1 mL saturated aqueous KHSO$_4$ and allowed to warm to room temperature. The quench was diluted with H$_2$O (15 mL) and was extracted with ethyl acetate and then CH$_2$Cl$_2$. The organic extracts were combined, washed with brine, dried over Na$_2$SO$_4$, filtered through celite, and concentrated to give 0.19 g of (S)-3-[6-methoxy-2-(2-quinolin-4-yl-ethoxy)-pyridin-3-sulfonylamino]-4-oxo-butryric acid tert-butyl ester as a yellow glass. MS (APCI) m/z 516.2 (M+1).

Step 8: (S)-3-[6-Methoxy-2-(2-quinolin-4-yl-ethoxy)-pyridin-3-sulfonylamino]-4-oxo-butyric acid (S)-3-[6-Methoxy-2-(2-quinolin-4-yl-ethoxy)-pyridin-3-sulfonylamino]-4-oxo-butyric acid tert-butyl ester (0.18 g, 0.35 mmol) was stirred in 5 mL of a solution of 25% TFA in CH$_2$Cl$_2$ at room temperature for 2 h. Analytical HPLC indicated the reaction was complete. The reaction mixture was concentrated. Residual TFA was azeotroped with toluene. The crude product was purified by preparative-scale reverse phase HPLC (0 to 30% acetonitrile in H$_2$O with 0.1% TFA over 2.5 hours at 15 mL/min on Vydac 2.5×25 cm C18 column) to give 0.053 g (0.12 mmol, 33%) of (S)-3-[6-methoxy-2-(2-quinolin-4-yl-ethoxy)-pyridin-3-sulfonylamino]-4-oxo-butyric acid as a fluffy white solid. MS (APCI) m/z 460.2 (M+1). $^1$H NMR (300 MHz) CD$_3$OD 9.03 (m, 1H), 8.63 (d, J=8.4 Hz, 1H), 7.94–8.23 (m, 5H), 6.39 (d, J=8.4 Hz, 1H), 4.97 (m, 2H), 4.43 (dd, 1H), 3.96 (m, 2H), 3.88 (d, 3H), 3.48 (m, 1H), 2.46–2.60 (m, 1H), 2.24–2.38 (m, 1H)

EXAMPLE 57

(S)-3-[4-Carbamoyl-2-(1-methyl-2-naphthalen-1-yl-ethoxy)-benzenesulfonylamino]-4-oxo-butyric acid Route I, lyophilized as a white solid. MS(APCI) m/z 485.2 (M+1), m/z 483.2 (M−1).

EXAMPLE 58
(S)-3-(2-{2-[4-(2-Dimethylamino-ethylcarbamoyl)-naphthalen-1-yl]-ethoxy}-benzenesulfonylamino)-4-oxo-butyric acid Synthesized employing Route M, using (S)-3-(2-hydroxybenzensufonylamino)-4,4-diethoxy-butryric acid tert-butyl ester as the starting material. Colorless foam, MS(APCI) m/z 542.2 (+1).

EXAMPLE 59
(S)-3-[2-(2-Naphthalen-1-yl-ethoxy)-4-piperidin-1-yl-benzenesulfonylamino]-4-oxo-butyric acid Route H, tan foam, MS(APCI) m/z 495.1 (M−OH+1).

EXAMPLE 60
(S)-3-[4-((S)-1-Carboxy-ethylcarbamoyl)-2-(2-naphthalen-1-yl-ethoxy)-benzenesulfonylamino]-4-oxo-butyric acid. Route I, Lyophilized as a White Solid. MS(APCI) m/z 543.1 (M+1), 541.1 (M−1).

EXAMPLE 61
(S)-3-[4-Acetylamino-2-((1R,2S)-2-benzimidazol-1-yl-1-methyl-propoxy)-benzenesulfonylamino]-4-oxo-butyric acid Route B; colorless solid (45 mg). MS (APCI) m/z 489.1 (M+1).

(1S,2S)-2-benzimidazol-1-yl-1-methyl-propanol employed in the synthesis of (S)-3-[4-Acetylamino-2-((1R, 2S)-2-benzimidazol-1-yl-1-methyl-propoxy)-benzenesulfonylamino]-4-oxo-butyric acid was prepared as follows:

Step 1: (1R,2S)-2-benzimidazol-1-yl-1-methyl-propanol

Benzimidazole (950 mg, 8.0 mmol) in THF was added to tert-butanol (20 mL) and THF (2.5 mL) containing potassium tert-butoxide (900 mg, 8.0 mmol). 2R,3R-butene oxide (500 mg, ~1 equiv) was added. The reaction was heated in a sealed tube at 60° C. for 2 days. After cooling to room temperature, the reaction was poured into water, extracted with ethyl acetate, washed with 1.0N sodium hydroxide, then brine. To give (1R,2S)-2-benzimidazol-1-yl-1-methyl-propanol 1.27 g (84%) as a yellow oil. MS (APCI) m/z 191.2 (M+1).

Step 2: (1S,2S)-2-Benzimidazol-1-yl-1-methyl-propanol

To (1R,2S)-2-benzimidazol-1-yl-1-methyl-propanol (1.27 g, 6.68 mmol), triphenylphosphine (1.19 g, 1.1 equiv), and 4-nitrobenzoic acid (1.22 g, 1.1 equiv) in THF (20 mL) was added diethyl azodicarboxylate (1.15 mL, 1.1 equiv). After stirring 12 h, the solvent was removed, and chromatographed on silica gel eluting with ethyl acetate to give the intermediate 4-nitrobenzoate and triphenylphosphine oxide as a mixture. This mixture was directly hydrolyzed with 1.0N sodium hydroxide (20 mL) in THF/methanol for 3 h. The solvent was partially removed and the reaction diluted with water and extracted with ethyl acetate. The crude product was chromatographed on silica gel eluting with 7%(8:1, ethanol/ammonium hydroxide) in dichloromethane. (1S,2S)-2-benzimidazol-1-yl-1-methyl-propanol was isolated as a colorless solid 552 mg (44%). $^1$H NMR (CDCl$_3$) 8.00(s,1H), 7.69(d,1H), 7.43(d,1H), 7.24(M, 2H), 4.36(m, 1H), 4.27(m,1H), 1.33(d,3H), 1.22(d,3H).

EXAMPLE 62
(S)-3-[2-((1R,2S)-2-Benzimidazol-1-yl-1-methyl-propoxy-4-methoxy-benzenesulfonylamino)-4-oxo-butyric acid Route B, Colorless solid (25 mg) MS APCI m/z 476.2 (M+1).

EXAMPLE 63
3-(4-Acetylamino-2-[2-(2-chloro-quinolin-5-yl)-ethoxy]-benzenesulfonylamino)-4-oxo-butyric acid Route B; off white solid: MS (APCI) m/z 520 (M, 100% abundance), 522 (M+2, 31% abundance). Analysis calculated for $C_{23}H_{22}N_3O_7SCl \cdot 0.20\ C_2HF_3O_2$: C, 51.85; H, 4.13; N, 7.66. Found: C, 52.24; H, 4.61; N, 7.36.

2-(2-Chloro-quinolin-5-yl)-ethanol employed in the synthesis of 3-(4-acetylamino-2-[2-(2-chloro-quinolin-5-yl)-ethoxy]-benzenesulfonylamino)-4-oxo-butyric acid was prepared as follows:

Step 1: 1-(2-Chloro-quinolin-5-yl)-2-diazo-ethanone

A mixture of 2.0 g (10.6 mmol) of 2-oxo-1,2-dihydro-quinoline-5-carboxylic acid, synthesized according to M. Tominaga et al. Chem Pharm Bull (1986) 34(2) 682, and 30 mL thionyl chloride was brought to reflux under a nitrogen atmosphere for 3 h. The excess thionyl chloride was concentrated leaving a brown residue. The residue was suspended in 25 mL toluene and the solvent concentrated under reduced pressure. This step was repeated. The resulting brown residue was dried under vaccuum 1 h. The product was then stirred in 40 mL dioxane and 1.4 mL (11.0 mmol) N-ethylmorpholine was added to the mixture. The resulting solution was added in 10 mL portions to a polished 500 mL erlenmeyer flask containing 80 mL 0.4M diazomethane in ether at 0° C., in an ice/water bath. The resulting reaction mixture was stirred 30 min at 0° C. and then 2 h at room temperature. After TLC analysis (1:1 hexanes/ethyl acetate, R$_f$ prod 0.4) showed starting material was consumed, 1 mL acetic acid was added to quench excess diazomethane. The solvent was removed under reduced pressureand the residue purified on 150 g 230–400 mesh silica eluting with 1:1 hexanes/ethyl acetate yeilding 1.2 g (5.63 mmol, 53%) of 1-(2-chloro-quinolin-5-yl)-2-diazo-ethanone as a white solid. $^1$H NMR (400 MHz) CDCl$_3$ 8.95 (m, 1H), 8.15 (m, 1H), 7.75 (m, 2H), 7.50 (m, 1H), 5.80 (bs, 1H).

Step 2: (2-Chloro-quinolin-5-yl)-acetic acid methyl ester

A mixture of 2.17 g (9.37 mmol) 1-(2-chloro-quinolin-5-yl)-2-diazo-ethanone and 20 mL methanol was brought to reflux. A solution of 0.20 g (0.87 mmol) silver benzoate in 1 mL triethylamine was added to the reaction mixture. After 10 min at reflux, TLC analysis (ethyl acetate, silica, R$_f$ prod 0.8) showed starting material consumed. The solvent was removed under reduced pressure and the resulting black residue was purified on 100 g 230–400 mesh silica eluting with 1:1 hexanes/ethyl acetate to give 1.20 g (5.09 mmol, 55%) of (2-chloro-quinolin-5-yl)-acetic acid methyl ester as a white amorphous solid. MS (APCI) m/z 236 (M, 100% abundance), 238 (M+2, 32% abundance). $^1$H NMR (400 MHz) CDCl$_3$ 8.31 (d, J=8.9 Hz, 1H), 7.98 (d, J=8.5 Hz, 1H), 7.74 (m, 1H), 7.49 (d, J=7.2 Hz, 1H), 7.44 (d, J=8.9 Hz, 1H), 4.05 (s, 2H), 3.68 (s, 3H).

Step 3: 2-(2-Chloro-quinolin-5-yl)-ethanol

A mixture of 0.35 g (1.46 mmol) (2-chloro-quinolin-5-yl)-acetic acid methyl ester and 10 mL anhydrous THF was cooled to −20° C. in a dry ice/acetone bath. 1.4 mL (1.4 mmol) IM LiAlH$_4$ solution in ether was added dropwise. After 10 min, TLC analysis (ethyl acetate, silica, R$_f$ prod 0.3) showed starting material consumed. The reaction was quenched with 1 mL of 1M aqueous potassium sodium tartrate solution. The product was partitioned between ethyl acetate and 10 ml brine and the product extracted with three 25 mL portions of ethyl acetate. The combined organic extracts were washed with 25 mL of brine, dried over magnesium sulfate, filtered, and the solvent removed under reduced pressure to yield 0.29 g (1.37 mmol 99.9%) of 2-(2-chloro-quinolin-5-yl)-ethanol as a white solid.

MS(APCI) m/z 208 (M, 100% abundance), 210 (M+2, 32% abundance). $^1$H NMR (400 MHz) CDCl$_3$ 8.38 (d, J=8.9 Hz, 1H), 7.92 (d, J=8.5 Hz, 1H), 7.70 (m, 1H), 7.46 (d, J=7.2 Hz, 1H), 7.41 (d, J=8.9 Hz), 3.97 (m, 2H), 3.32 (t, J=6.5 Hz, 2H), 1.45 (m, 1H).

EXAMPLE 64

S)-3-[2-(2-naphthalen-1-yl-ethoxy)-pyrrolidin-1-yl-phenylsulfanylamino]-4-oxo-butyric acid Step 1: 1-[2-(5-Fluoro-2-nitro-phenoxy)-ethyl]-naphthalene To a solution of 4-fluoro-2-nitrophenol (20.0 g, 127.3 mmol) in dry THF (100 mL) at 0° C. was added 2-naphthalen-1-yl-ethanol (21.93 g, 127.3 mmol) and triphenyl phosphine (50.0 g, 191.0 mmol) then followed by drop wise addition of diethyl azodicarboxylate (30.0 mL, 191.0 mmol). The reaction mixture was allowed to warm up to room temperature and stirred for 12 h. The solvent was removed and the crude product was purified using silica gel flash chromatography (15% EtOAc in hexanes). 1-[2-(5-Fluoro-2-nitro-phenoxy)-ethyl]-naphthalene was obtained (32.0 g, 81%) as a pale yellow solid. $^1$H NMR (CDCl$_3$, 300 MHz) 8.06 (d, 1H), 7.94–7.80 (m, 2H), 7.77 (d, 1H), 7.58–7.42 (m, 4H), 6.71–6.64 (m, 2H), 4.36 (t, 2H), 3.65 (t, 2H).

Step 2: 4-Fluoro-2-(2-naphthalen-1-yl-ethoxy)-phenylamine

A solution of 1-[2-(5-fluoro-2-nitro-phenoxy)-ethyl]-naphthalene (24.63 g, 79.10 mmol) in THF (200 mL) was shaken with Raney nickel (3.0 g) under H$_2$ (55 psi) for 2 h using Parr apparatus. The reaction mixture was filtered through celite and concentrated. 4-Fluoro-2-(2-naphthalen-1-yl-ethoxy)-phenylamine (21.0 g, 94%) was obtained as a light-yellow solid. $^1$H NMR (CDCl$_3$, 400 MHz) 8.12 (d, 1H), 7.84 (d, 1H), 7.77 (d, 1H), 7.57–7.42 (m, 4H), 6.60–6.45 (m, 3H), 4.31 (t, 2H), 3.59 (t, 2H).

Step 3: 4-Fluoro-2-(2-naphthalen-1-yl-ethoxy)-benzenesulfonyl chloride

To a –10° C. (acetone/ice/sodium chloride) CH$_2$Cl$_2$ solution of 4-fluoro-2-(2-naphthalen-1-yl-ethoxy)-phenylamine (15.0 g, 53.30 mmol) was added boron trifluoride diethyl etherate (19.7 mL, 160.0 mmol) dropwise. Tert-Butyl nitrite (8.30 mL, 69.3 mmol) was then slowly added dropwise. The reaction mixture was allowed to stirred at –10° C. for 30 min. Chilled pentane (150 mL) was then added to precipitate the diazo-salt from CH$_2$Cl$_2$. The diazo-salt was then dissolved in dioxane:acetonitrile (3:1, 150 mL) kept at 0° C. In a three-necked flask to a solution of dioxane (150 mL) and acetic acid (150 mL) at –10° C. was added copper (I) chloride (1.60 g, 16.0 mmol) and LiCl (33.0 g, 319 mmol). Sulfur dioxide (~100 mL) was then condensed into this solution using a –78° C. cold finger. The above diazo-salt solution was then poured into this solution. The reaction was kept at 0° C. for 2 h and then placed into a preheated oil bath at 65° C. for 12 h. The reaction was then cooled and poured into EtOAc (500 mL) and washed with water, and 1 N sodium hydroxide. The organic layer was then dried (MgSO$_4$), filtered and concentrated under reduced pressure to yield 4-fluoro-2-(2-naphthalen-1-yl-ethoxy)-benzenesulfonyl chloride as a yellowish foam (19.90 g, 98%). $^1$H NMR (CDCl$_3$, 400 MHz) 8.05 (d, 1H), 7.90 (d, 1H), 7.87 (d, 1H), 7.78 (d, 1H), 7.60–6.42 (m, 4H), 6.78–6.64 (m, 2H), 4.21 (t, 2H), 3.79 (t, 2H).

Step 4: (S)-3-[4-Fluoro-2-(2-naphthalen-1-yl-ethoxy)-benzenesulfonyl amino]-N-methoxy-N methyl-succinamic acid tert-butyl ester To a room temperature CH$_2$Cl$_2$ solution (50 mL) of 4-fluoro-2-(2-naphthalen-1-yl-ethoxy)-benzenesulfonyl chloride (19.90 g, 54.60 mmol) was added 2-amino-N-methoxy-N-methyl succinamic acid 4-tert-butyl ester (13.0 g, 54.60 mmol) and pyridine (17.60 mL, 218.40 mmol). The reaction mixture was allowed to stir for 12 h at room temperature. The reaction was then diluted with ethyl acetate (200 mL) and washed with 5% citric acid and then saturated NaHCO$_3$. The organic phase was dried (MgSO$_4$), and then the solvent was removed under vacuum. The resulting crude product was purified using silica gel flash chromatography (20% EtOAc in hexanes). S)-3-[4-Fluoro-2-(2-naphthalen-1-yl-ethoxy)-benzenesulfonyl amino]-N-methoxy-N methyl-succinamic acid tert-butyl ester was obtained in 66% yield (20.0 g) as a off white foam. MS (APCI) m/z 559.1 (M–1).

Step 5: (S)-N-Methoxy-N-methyl-3-[2-(2-naphthalen-1-yl-ethoxy)-4-pyrrolidin-1-yl-benzenesulfonyl amino]-succinamic acid tert-butyl ester A solution of S)-3-[4-fluoro-2-(2-naphthalen-1-yl-ethoxy)-benzenesulfonyl amino]-N-methoxy-N methyl-succinamic acid tert-butyl ester (1.10 g, 2.0 mmol) in pyrollidine (10 mL) was heated at 50° C. for 5 h. The reaction mixture was allowed to cool and then was added EtOAc (150 mL). The resulting solution was washed sequentially with the following solutions: 5% citric acid, saturated NaHCO$_3$, and brine. The organic phase was dried (MgSO$_4$), and then the solvent was removed under vacuum. The resulting crude product was purified using flash silica gel chromatography (25% EtOAc in hexanes). (S)-N-Methoxy-N-methyl-3-[2-(2-naphthalen-1-yl-ethoxy)-4-pyrrolidin-1-yl-benzenesulfonyl amino]-succinamic acid tert-butyl ester was obtained in 81% yield (1.0 g) as a off white foam. MS (APCI) m/z 610.3 (M–1).

Step 6: (S)-3-[2-(2-Naphthalen-1-yl-ethoxy)-4-pyrrolidin-1-yl-benzenesulfonyl amino]-4-oxo-butyric acid tert-butyl ester To (S)-N-methoxy-N-methyl-3-[2-(2-naphthalen-1-yl-ethoxy)-4-pyrrolidin-1-yl-benzenesulfonylamino]-succinamic acid tert-butyl ester (1.0 g, 1.60 mmol) solution in dry THF/Et$_2$O (2:1, 30 mL) at –65° C. was added LiAlH$_4$ (6.50 mL, 6.5 mmol, 1.0 M solution in Et$_2$O). The reaction mixture temperature was maintained for 2 h. The excess hydride was quenched by the addition of potassium hydrogen sulfate (2 equiv) dissolved in water. After warming to room temperature, Et$_2$O was added (100 mL) and the organic layer was washed with water and then with brine. The solvent was dried (MgSO$_4$), filtered, and evaporated to dryness. The resulting crude product was purified on silica gel flash chromatography (25% EtOAc in hexanes) to give (S)-3-[2-(2-naphthalen-1-yl-ethoxy)-4-pyrrolidin-1-yl-benzenesulfonyl amino]-4-oxo-butyric acid tert-butyl ester as a off white foam (0.60 g, 68%). MS (APCI) m/z 551.3 (M–1).

Step 7: (S)-3-[2-(2-Naphthalen-1-yl-ethoxy)-4-pyrrolidin-1-yl-benzenesulfonyl amino]-4-oxo-butyric acid A solution of (S)-3-[2-(2-naphthalen-1-yl-ethoxy)-4-pyrrolidin-1-yl-benzenesulfonylamino]-4-oxo-butyric acid tert-butyl ester (0.60 g, 1.10 mmol) in TFA (2 mL) and CH$_2$Cl$_2$ (20 mL) was stirred for 3 h. After the solvent was removed under vacuum, the residue was subjected to preparative reverse-phase HPLC (VYDAC, C18) using linear gradient of water containing 0.1% TFA and acetonitrile containing 0.1% TFA (20–65% acetonitrile, in 120 min) at a flow rate of 20 mL/min. Fractions containing the major peak were pooled and lyophilized to yield 0.190 g (60%) of (S)-3-[2-(2-naphthalen-1-yl-ethoxy)-4-pyrrolidin-1-yl-benzenesulfonyl amino]-4-oxo-butyric acid. MS (APCI) m/z 496.1 (M+1).

EXAMPLE 65
3-[4-Morpholin-4-yl-2-(2-naphthalen-1-yl-ethoxy)-benzenesulfonylamino]-4-oxo-butyric acid Route H, as an off white solid. MS (APCI) m/z 513.1 (M+1).

EXAMPLE 66
(S)-3-[4-Carbamoyl-2-(2-quinolin-5-yl-ethoxy)-benzenesulfonylamino]-4-oxo-butyric Route I Step 1: 3-Benzyloxy-4-[(S)-2-tert-butoxycarbonyl-1-(methoxy-methyl-carbamoyl)-ethylsulfamoyl]-benzoic acid methyl ester To a solution of 3-benzyloxy-4-chlorosulfonyl-benzoic acid methyl ester (9.25 g, 27.1 mmol) in dichloromethane (270 mL) was added (S)-3-amino-N-methoxy-N-methyl-succinamic acid tert-butyl ester (6.30 g, 27.1 mmol) followed by pyridine (6.59 mL, 81.4 mmol). The reaction was allowed to stir over night at room temperature. The reaction was then diluted with ethyl acetate (500 mL) and washed sequentially with 5% citric acid, saturated sodium bicarbonate, and saturated sodium chloride, dried over magnesium sulfate, filtered and concentrated under reduced pressure to yield an orange oil. The crude residue was chromatographed (silica gel, 40% ethyl acetate-60% hexane) to give 3-benzyloxy-4-[(S)-2-tert-butoxycarbonyl-1-(methoxy-methyl-carbamoyl)-ethylsulfamoyl]-benzoic acid methyl ester as a white foam (8.20 g, 56%). $^1$H NMR(300 MHz, DMSO) 7.84 (d, 1H), 7.60 (m, 1H), 7.57 (m, 2H), 7.52 (d, 2H), 7.36 (t, 2H), 7.28 (t, 1H), 5.35 (s, 2H), 4.60 (m, 1H), 3.81 (s, 3H), 3.48 (bs, 3H), 2.82 (bs, 3H), 2.46 (dd, 1H), 2.33 (dd, 1H), 1.27 (s, 9H). MS(APCI) m/z 535.2 (M−H).

Step 2: 3-Benzyloxy-4-[(S)-2-tert-butoxycarbonyl-1-(methoxy-methyl-carbamoyl)-ethylsulfamoyl]-benzoic acid To a solution of 3-benzyloxy-4-[(S)-2-tert-butoxycarbonyl-1-(methoxy-methyl-carbamoyl)-ethylsulfamoyl]-benzoic acid methyl ester (8.20 g, 15.3 mmol) in tetrahydrofuran (150 mL) at room temperature was added 1N lithium hydroxide (30.5 mL, 15.3 mmol). The reaction was stirred at room temperature for 3.5 h. The reaction was then diluted with ethyl acetate (300 mL) and acidified to pH 2 with 5% citric acid. The organic layer was then washed with saturated sodium chloride, dried over magnesium sulfate, filtered and concentrated under reduced pressure to yield 3-benzyloxy-4-[(S)-2-tert-butoxycarbonyl-1-(methoxy-methyl-carbamoyl)-ethylsulfamoyl]-benzoic acid as a white foam (2.9 g, 100%). MS(ACI) m/z 521.1 (M−H).

Step 3: 3-(2-Benzyloxy-4-carbamoyl-benzenesulfonylamino)-N-methoxy-N-methyl-succinamic acid tert-butyl ester To a solution of 3-benzyloxy-4-[(S)-2-tert-butoxycarbonyl-1-(methoxy-methyl-carbamoyl)-ethylsulfamoyl]-benzoic acid (8.0 g, 15.3 mmol) in tetrahydrofuran (150 ml) at 0° C. was added 4-methyl morpholine (2.5 ml, 22.9 mmol), 1-hydroxybenzotriazole (3.09 g, 22.90 mmol), followed by 1-(3-dimethylaminopropyl)-3-ethylcarbodiimide hydrochloride (4.40 g, 22.90 mmol). The reaction was stirred for 1 h at 0° C., then concentrated ammonium hydroxide was added (3.1 ml, 22.9 mmol). The reaction was allowed to warm slowly to room temperature and stirred overnight. The reaction was then diluted with ethyl acetate and washed sequentially with 5% citric acid, saturated sodium bicarbonate, and saturated sodium chloride, dried over magnesium sulfate, filtered and concentrated under reduced pressure to yield a pale oil. The crude residue was chromatographed (silica gel with a gradient of 50% ethyl acetate/49% hexane/1% acetic acid to 99% ethyl acetate/1% acetic acid) to give 3-(2-benzyloxy-4-carbamoyl-benzenesulfonylamino)-N-methoxy-N-methyl-succinamic acid tert-butyl ester as a white foam (6.57 g, 82%). $^1$H NMR(300 MHz, DMSO) 8.12 (s, 1H), 7.76 (d, 1H), 7.38 (m, 9H), 5.34 (dd, 2H), 4.60 (m, 1H), 3.50 (bs, 3H), 2.58 (bs, 3H), 2.55 (dd, 1H), 2.34 (dd, 1H), 1.30 (s, 9H). MS(APCI) m/z 522.2 (M+1), 520.2 (M−H).

Step 4: 3-(4-Carbamoyl-2-hydroxy-benzenesulfonylamino)-N-methoxy-N-methyl-succinamic acid tert-butyl ester To a solution of 3-(2-benzyloxy-4-carbamoyl-benzenesulfonylamino)-N-methoxy-N-methyl-succinamic acid tert-butyl ester (1.0 g, 1.9 mmol) in ethyl acetate (20 mL) was added 20% Pd/C (0.10 g). The mixture was then fitted with a hydrogen balloon. The reaction was kept under an atmosphere of hydrogen for 2 h. The reaction mixture was then filtered through a pad of celite. The celite cake was washed with ethyl acetate (50 mL). The solution was then concentrated under reduced pressure to yield 3-(2-benzyloxy-4-carbamoyl-benzenesulfonylamino)-N-methoxy-N-methyl-succinamic acid tert-butyl ester as a foam (0.80 g, 100%). $^1$H NMR(300 MHz, DMSO) 10.93 (bs, 1H), 8.02 (bs, 1H), 7.47 (m, 5H), 4.64 (m, 1H), 3.55 (bs, 3H), 2.89 (bs, 3H), 2.56 (dd, 1H), 2.32 (dd, 1H), 1.31 (s, 9H). MS(APCI) m/z 430.1 (M−H). Anal. Calcd. for $C_{17}H_{25}N_3O_8S_1$: C, 47.32; H, 5.84; N, 9.74. Found: C, 47.17; H, 5.78; N, 9.46.

Step 5: 3-[4-Carbamoyl-2-(2-quinolin-5-yl-ethoxy)-benzenesulfonylamino]-N-methoxy-N-methyl-succinamic acid tert-butyl ester To a methylene chloride solution of 3-(4-carbamoyl-2-hydroxy-benzenesulfonylamino)-N-methoxy-N-methyl-succinamic acid tert-butyl ester at room temperature was added triphenylphosphine (0.25 g, 0.95 mmol), 2-quinolin-5-yl-ethanol (0.11 g, 0.66 mmol) and diethyl azodicarboxylate (0.17 ml, 1.12 mmol). The reaction was stirred at room temperature for 3 days. The reaction was then concentrated under reduced pressure. The crude residue was chromatographed [silica gel with a gradient of 100% ethyl acetate to 10% (1:9 NH$_4$OH/ethanol) in ethyl acetate] to give 3-[4-carbamoyl-2-(2-quinolin-5-yl-ethoxy)-benzenesulfonylamino]-N-methoxy-N-methyl-succinamic acid tert-butyl ester as a white foam (0.27 g, 69%). $^1$H NMR(300 MHz, DMSO) 8.90 (d, 1H), 8.73 (d, 1H), 8.08 (s, 1H), 7.93 (d, 1H), 7.62 (m, 8H), 4.43 (m, 3H), 3.71 (m, 2H), 3.47 (bs, 3H), 2.77 (bs, 3H), 2.54 (dd, 1H), 2.34 (dd, 1H), 1.31 (s, 9H). MS(APCI) m/z 585.1 (M−H), 587.1 (M+1).

Step 6: (S)-3-[4-Carbamoyl-2-(2-quinolin-5-yl-ethoxy)-benzenesulfonylamino]-4-oxo-butyric acid tert-butyl ester To a −65° C. solution of lithium aluminum hydride (0.51 mL, 1M in diethyl ether) in diethyl ether (5 mL) was added a solution of 3-[4-carbamoyl-2-(2-quinolin-5-yl-ethoxy)-benzenesulfonylamino]-N-methoxy-N-methyl-succinamic acid tert-butyl ester (0.10 g, 0.17 mmol) in diethyl ether (5 mL). The reaction was stirred at −65° C. for 2 h. The reaction was then diluted with ethyl acetate (100 mL) and washed with 10% potassium hydrogen sulfate and then saturated sodium chloride, dried over magnesium sulfate, filtered and concentrated under reduced pressure to yield (S)-3-[4-carbamoyl-2-(2-quinolin-5-yl-ethoxy)-benzenesulfonylamino]-4-oxo-butyric acid tert-butyl ester as a clear oil. MS(APCI) m/z 528.1 (M−H).

Step 7: 3-[4-Carbamoyl-2-(2-quinolin-5-yl-ethoxy)-benzenesulfonylamino]-4-oxo-butyric acid To a solution of (S)-3-[4-carbamoyl-2-(2-quinolin-5-yl-ethoxy)-benzenesulfonylamino]-4-oxo-butyric acid tert-butyl ester (0.08 g, 0.15 mmol) in dichloromethane (10 mL)

and water (0.1 ml) was added trifluoroacetic acid (1 mL). The reaction was stirred for 1 h at room temperature. The reaction was then concentrated under reduced pressure to yield a clear oil. The residue was purified by reverse phase high-pressure liquid chromatograph using a gradient of 0% to 30% acetonitrile containing 0.1% TFA and water containing 0.1% TFA over 140 minutes to yield 3-[4-carbamoyl-2-(2-quinolin-5-yl-ethoxy)-benzenesulfonylamino]-4-oxo-butyric acid as a white solid (0.01 g, 14%). MS(APCI) m/z 472.1 (M+1)

EXAMPLE 67

(S)-3-[2-(2-Benzimidazol-1-yl-ethoxy)-4-dimethylamino-benzenesulfonylamino]-4-oxo-butyric acid Route E; colorless solid, MS(APCI) m/z 461.1 (M+1).

EXAMPLE 68

(S)-3-[2-((1R,2S)-2-Benzimidazol-1-yl-1-methyl-propoxy)-4-dimethylamino-benzenesulfonylamino]-4-oxo-butyric acid Route E, colorless solid, MS(APCI) m/z 489.1 (M+1).

EXAMPLE 69

(S)-3-[4-(2-Dimethylamino-ethylcarbamoyl)-2-(2-naphthalen-1-yl-ethoxy)-benzenesulfonylamino]-4-oxo-butyric acid Route P; colorless solid (151 mg), MS(APCI) m/z 598.3 (M+1).

EXAMPLE 70

(S)-3-[4-[(2-Dimethylamino-ethyl)-methyl-amino]-2-(2-naphthalen-1-yl-ethoxy)-benzenesulfonylamino]-4-oxo-butyric acid Route H, tan powder, MS(APCI) m/z 528.2 (M+1).

EXAMPLE 71

3-(2-{2-[2-(2-Dimethylamino-ethoxy)-naphthalen-1-yl]-ethoxy}-benzenesulfonylamino)-4-oxo-butyric acid Step 1: (1-Bromo-naphthalen-2-yloxy)-triisopropyl-silane 1-Bromo-2-naphthol (5.00 g, 22.4 mmol) was mixed with triisopropylsilyl chloride (7.2 mL, 33.6 mmol), DMAP (402 mg, 3.30 mmol), imidazole (3.81 g, 56.0 mmol), and pyridine (6 mL) in $CH_2Cl_2$ (50 mL). The reaction was refluxed for two hours. TLC analysis (silica, 15% EtOAc-hexanes) indicated the reaction was complete. The reaction was allowed to cool to room temperature and then was diluted with $H_2O$. The dilution was extracted three times with $CH_2Cl_2$. The organic extracts were combined, washed with brine solution, dried over $Na_2SO_4$, filtered through celite, and concentrated. The crude product was purified by flash chromatography (SiO2, 100% hexanes) to give (1-bromo-naphthalen-2-yloxy)-triisopropyl-silane (8.4 g, 22.2 mmol) as a colorless oil in 99% yield. $^1$H NMR (300 MHz) $CDCl_3$ 8.21 (d, J=7.5 Hz, 1H), 7.76 (d, J=8.5 Hz, 1H), 7.68 (d, J=8.8 Hz, 1H), 7.54 (m, 1H), 7.38 (m, 1H), 7.15 (d, J=8.8 Hz, 1H), 1.38 (m, 3H), 1.16 (d, J=7.1 Hz, 18H).

Step 2: 2-(2-Triisopropylsilanyloxy-naphthalen-1-yl)-ethanol n-Butyllithium (16.4 mL of 1.6 M soln in hexanes, 26.3 mmol) was stirred with $Et_2O$ (60 mL) at −78° C. in an argon-purged, round-bottom flask. A solution of (1-bromo-naphthalen-2-yloxy)-triisopropyl-silane (7.10 g, 18.8 mmol) in $Et_2O$ (~5 ml) was added dropwise to the stirring n-BuLi solution. The reaction was stirred at −78° C. for ten minutes and then a solution of ethylene oxide (1.41 mL, 28.2 mmol) and $BF_3$-$Et_2O$ (3.81 mL, 31.0 mmol) in $Et_2O$ (~5 ml) was added via syringe. The reaction was stirred at −78° C. for one hour and then at room temperature for two hours. The reaction was carefully quenched with $H_2O$ and was extracted three times with EtOAc. The organic extracts were combined, washed with brine solution, dried over $Na_2SO_4$, filtered through celite, and concentrated. The crude product was purified by gradient elution flash chromatography ($SiO_2$, 100% hexanes to 10% EtOAc-hexanes) to give 2-(2-triisopropylsilanyloxy-naphthalen-1-yl)-ethanol (3.41 g, 9.91 mmol) as a colorless oil in 53% yield. MS (APCI) m/z 343.2 (M−1).

Step 3: N-Methoxy-N-methyl-3-{2-[2-(2-triisopropylsilanyloxy-naphthalen-1-yl)-ethoxy]-benzenesulfonylamino}-succinamic acid tert-butyl ester 2-(2-Triisopropylsilanyloxy-naphthalen-1-yl)-ethanol (1.0 g, 2.91 mmol) was mixed with (S)-3-(2-hydroxy-benzenesulfonylamino)-N-methoxy-N-methyl-succinamic acid tert-butyl ester (1.13 g, 2.91 mmol), diethylazodicarboxylate (0.92 mL, 5.8 mmol), and triphenyl phosphine (1.52 g, 5.82 mmol) in THF (18.6 mL) at room temperature for 16 h. The reaction mixture was concentrated onto $SiO_2$ (~3 g) and then was chromatographed over $SiO_2$ with 20% EtOAc/hexane to give N-methoxy-N-methyl-3-{2-[2-(2-triisopropylsilanyloxy-naphthalen-1-yl)-ethoxy]-benzenesulfonylamino}-succinamic acid tert-butyl ester (1.45 g, 2.03 mmol) as an oil in 69% yield. MS (APCI) m/z 715.4 (M+1).

Step 4: 3-{2-[2-(2-Hydroxy-naphthalen-1-yl)-ethoxy]-benzenesulfonylamino}-N-methoxy-N-methyl-succinamic acid tert-butyl ester N-Methoxy-N-methyl-3-{2-[2-(2-triisopropylsilanyloxy-naphthalen-1-yl)-ethoxy]-benzenesulfonylamino}-succinamic acid tert-butyl ester (270 mg, 0.38 mmol) was stirred with TBAF (0.45 mL of 1.0 M soln in THF, 0.45 mmol) in freshly distilled THF (1.45 mL) at 0° C. for fifteen minutes and then at room temperature for 1.5 h. The reaction mix was diluted with saturated aq. $NH_4Cl$ and was extracted three times with EtOAc. The organic extracts were combined, washed with brine solution, dried over $Na_2SO_4$, filtered through celite, and concentrated. The crude product was purified by flash chromatography ($SiO_2$, 50% EtOAc-hexanes) to give 3-{2-[2-(2-hydroxy-naphthalen-1-yl)-ethoxy]-benzenesulfonylamino}-N-methoxy-N-methyl-succinamic acid tert-butyl ester in quantitative yield. MS (APCI) m/z 557.3 (M−1).

Step 5: 3-(2-{2-[2-(2-Dimethylamino-ethoxy)-naphthalen-1-yl]-ethoxy}-benzenesulfonylamino)-N-methoxy-N-methyl-succinamic acid tert-butyl ester 3-{2-[2-(2-Hydroxy-naphthalen-1-yl)-ethoxy]-benzenesulfonylamino}-N-methoxy-N-methyl-succinamic acid tert-butyl ester (176 mg, 0.32 mmol) was combined with dimethylamino ethanol (0.063 mL, 0.63 mmol), triphenyl phosphine (165 mg, 0.63 mmol), and diethylazodicarboxylate (0.10 mL, 0.63 mmol) in freshly distilled THF (1.6 mL). The reaction was stirred at room temperature for eighteen hours. TLC analysis (silica, 50% EtOAc/hexanes) indicated consumption of the starting naphthol. The reaction mixture was concentrated and purified by gradient elution flash chromatography ($SiO_2$, 30% EtOAc/hexanes to 50% EtOAc/hexanes to 80% EtOAc/hexanes to 100% EtOAc to 10% MeOH/$CH_2Cl_2$) to give 3-(2-{2-[2-(2-dimethylamino-ethoxy)-naphthalen-1-yl]-ethoxy}-benzenesulfonylamino)-N-methoxy-N-methyl-succinamic acid tert-butyl ester (75 mg, 0.12 mmol) in 38% yield. MS (APCI) m/z 630.2 (M+1).

Step 6: 3-(2-{2-[2-(2-Dimethylamino-ethoxy)-naphthalen-1-yl]-ethoxy}-benzenesulfonylamino)-4-oxo-butyric acid tert-butyl ester 3-(2-{2-[2-(2-Dimethylamino-ethoxy)-naphthalen-1-yl]-ethoxy}-benzenesulfonylamino)-N-methoxy-N-methylsuccinamic acid tert-butyl ester (230 mg, 0.366 mmol) was dissloved in a mixture of freshly distilled THF (0.85 mL) and ether (1.35 mL). The mix was chilled to −65° C. in a dry-ice/chlorofrom bath. LiAlH$_4$ solution (1.23 mL of 1.0 M solution in ether, 1.23 mmol) was added via syringe. The reaction became heterogeneous. Acetonitrile (0.2 mL) and CH$_2$Cl$_2$ (0.2 mL) were added to aid dissolution. The reaction was stirred at −65° C. for 1.25 hours. TLC analysis (5% MeOH/CH$_2$Cl$_2$, silca) indicated the reaction was complete. The reaction was carefully quenched with saturated aqueous KHSO$_4$ (2 mL) and was allowed to warm to room temperature. The reaction was diluted with saturated aqueous NaHCO$_3$ and was extracted three times with EtOAc. The organic extracts were combined, dried over Na$_2$SO$_4$, decanted, and concentrated to give 3-(2-{2-[2-(2-dimethylamino-ethoxy)-naphthalen-1-yl]-ethoxy}-benzenesulfonylamino)-4-oxo-butyric acid tert-butyl ester (202 mg, 0.35 mmol) in 97% yield. MS (APCI) m/z 571.1 (M+1).

Step 7: 3-(2-{2-[2-(2-Dimethylamino-ethoxy)-naphthalen-1-yl]-ethoxy}-benzenesulfonylamino)-4-oxo-butyric acid 3-(2-{2-[2-(2-Dimethylamino-ethoxy)-naphthalen-1-yl]-ethoxy}-benzenesulfonylamino)-4-oxo-butyric acid tert-butyl ester (190 mg, 0.33 mmol) was stirred with trifluoroacetic acid (0.4 mL) in CH$_2$Cl$_2$ (1.2 mL) at room temperature for 1 h. Analytical HPLC analysis indicated the reaction was complete. The reaction mixture was concentrated. Residual trifluoroacetic acid was azeotroped with toluene. The crude product was purified by preparative HPLC to give 3-(2-{2-[2-(2-Dimethylamino-ethoxy)-naphthalen-1-yl]-ethoxy}-benzenesulfonylamino)-4-oxo-butyric acid (31 mg, 0.060 mmol) as a white solid in 18% yield. MS (APCI) m/z 515.1 (M+1).

EXAMPLE 72

(S)-3-[4-Acetylamino-2-(2-quinolin-5-yl-ethoxy)-benzenesulfonylamino]-3-cyano-propionic acid Route O.

Step 1: 3-benzyloxycarbonylamino-succinamic acid tert-butyl ester

To a solution of (S)-2-benzyloxycarbonylamino-succinic acid-4-tert-butyl ester (20.0 g, 61.9 mmol) in CH$_2$Cl$_2$ (100 mL) at −10° C. in a salt/ice/water bath was added N-methylmorpholine (8.20 mL, 74.20 mmol). This was followed by dropwise addition of isobutyl chlorofomate (9.63 mL, 74.20 mmol), over 20 min. After 30 min of stirring at −10° C., ammonium hydroxide solution (28% w/w ammonia, 100 mL) was added portionwise over 5 min. The reaction mixture was stirred for another 8 h then followed by removal of the CH$_2$Cl$_2$ in vacuo. The remaining solution was extracted with EtOAc. The combined extracts were washed with 100 mL of each of the following: 5% citric acid, saturated NaHCO$_3$, and brine. Drying and removal of solvents under vacuum gave crude oil which crystallized from Et$_2$O/hexanes mixture. 3-benzyloxycarbonylamino-succinamic acid tert-butyl ester was obtained in 95% yield (19.0 g). MS (APCI) m/z 323.2 (M+1).

Step 2: (S)-3-Amino-succinamic acid tert-butyl ester

To a solution 3-benzyloxycarbonylamino-succinamic acid tert-butyl ester (5.0 g, 15.50 mmol) in THF (20 mL) was added 20% Pd/C (150 mg), and the mixture was stirred for 4 h under H$_2$ atmosphere at 50 psi. The catalyst was filtered and the solvent removed. The resulting oil solidifies upon the addition of ether. The solid was dried to give 2.90 g (98%) of (S)-3-amino-succinamic acid tert-butyl ester as an off white solid. The solid was used immediately in the next step. MS (APCI) m/z 189.1 (M+1).

Step 3: (S)-3-(2-Benzyloxy-4-nitro-benzenesulfonylamino)-succinamic acid tert-butyl ester To a room temperature CH$_2$Cl$_2$ solution (50 mL) of 2-benzyloxy-4-nitro-benzenesulfonyl chloride from Route J (2.62 g, 8.0 mmol) was added (S)-3-amino-succinamic acid tert-butyl ester (1.50 g, 8.0 mmol) and pyridine (2.60 mL). The reaction mixture was allowed to stir for 12 h at room temperature. The reaction was then diluted with ethyl acetate (200 mL) and washed with 5% citric acid and then saturated NaHCO$_3$. The organic phase was dried (MgSO$_4$), and then the solvent was removed under vacuum. The resulting crude product was purified using silica gel flash chromatography (40% hexanes in EtOAc). (S)-3-(2-Benzyloxy-4-nitro-benzenesulfonylamino)-succinamic acid tert-butyl ester was obtained in 43% yield (1.66 g) as an off white foam. MS (APCI) m/z 478.3 (M−1).

Step 4: (S)-3-(4-Amino-2-benzyloxy-benzenesulfonylamino)-succinamic acid tert-butyl ester A solution of (S)-3-(2-benzyloxy-4-nitro-benzenesulfonylamino)-succinamic acid tert-butyl ester (1.30 g, 2.70 mmol) in THF (75 mL) was shaken with Raney Nickel (0.50 g) under H$_2$ (33 psi) for 18 h using a Parr apparatus. The reaction mixture was filtered through celite and concentrated. (S)-3-(4-Amino-2-benzyloxy-benzenesulfonylamino)-succinamic acid tert-butyl ester was obtained (1.20 g, 98%) as an off white solid. MS (APCI) m/z 448.1 (M−1).

Step 5: (S)-3-(4-Acetylamino-2-benzyloxy-benzenesulfonylamino)-succinamic acid tert-butyl ester To a solution of (S)-3-(4-amino-2-benzyloxy-benzenesulfonylamino)-succinamic acid tert-butyl ester (1.41 g, 3.10 mmol) in methylene chloride (100 mL) and Et$_3$N (0.44 mL, 3.10 mmol) was added acetyl chloride (0.25 mL, 3.1 mmol). The reaction was stirred for 3 h. The solvent was removed and replaced with EtOAc (150 mL). The organic solution was washed twice with 5% citric acid, saturated NaHCO$_3$, water, and brine. The solution was dried over MgSO$_4$, filtered, and the solvent was removed. The resulting crude product was purified using silica gel flash chromatography (20% hexanes in EtOAc). (S)-3-(4-Acetylamino-2-benzyloxy-benzenesulfonylamino)-succinamic acid tert-butyl ester was obtained in 63% yield (0.96 g) as an off white foam. MS (APCI) m/z 490.2 (M−1).

Step 6: (S)-3-(4-Acetylamino-2-hydroxy-benzenesulfonylamino)-succinamic acid tert-butyl ester A solution of (S)-3-(4-acetylamino-2-benzyloxy-benzenesulfonylamino)-succinamic acid tert-butyl ester (0.92 g, 2.0 mmol) in THF (50 mL) was shaken with 20% Pd/C (0.090 g) under H$_2$ (50 psi) for 5 h using Parr apparatus. The reaction mixture was filtered through celite and concentrated. (S)-3-(4-acetylamino-2-hydroxy-benzenesulfonylamino)-succinamic acid tert-butyl ester was obtained (0.85 g, 98%) as an off white solid. MS (APCI) m/z 400.1 (M−1).

Step 7: (S)-3-[4-Acetylamino-2-(2-quinolin-5-yl-ethoxy)-benzenesulfonylamino]-succinamic acid tert-butyl ester To a solution of (S)-3-(4-acetylamino-2-hydroxy-benzenesulfonylamino)-succinamic acid tert-butyl ester (0.40 g, 1.0 mmol) in dry THF (50 mL) at 0° C. was added 2-quinolin-5-yl-ethanol (0.17 g, 1.0 mmol) and triphenyl phosphine (0.53 g, 2.0 mmol) then followed by drop wise addition of diethyl azodicarboxylate (0.39 mL, 2.0 mmol). The reaction mixture was allowed to warm up to room temperature and stirred for 12 h. The solvent was removed and the crude product was purified using silica gel flash chromatography (3% MeOH in CH$_2$Cl$_2$). (S)-3-[4-Acetylamino-2-(2-quinolin-5-yl-ethoxy)- benxenesulfonylamino]-succinamic acid tert-butyl ester was obtained (0.24 g, 43%) as an off white foam. MS (APCI) m/z 555.0 (M−1).

Step 8: (S)-3-[4-Acetylamino-2-(2-quinolin-5-yl-ethoxy)-benzenesulfonylamino]-3-cyano-propionic acid tert-butyl ester To a solution of (S)-3-[4-acetylamino-2-(2-quinolin-5-yl-ethoxy)-benzenesulfonylamino]-succinamic acid tert-butyl ester (0.24 g, 0.40 mmol) in dry THF (10 mL) at 0° C. was added Et$_3$N (0.14 mL, 1.0 mmol). A solution of trifluoroacetic anhydride in THF (0.5 M, 0.50 mmol) was added to the solution dropwise. After 30 min of stirring at 0° C., the ice bath was removed. The reaction mixture was allowed to warm up to room temperature over 4 h. The reaction mixture was worked up by addition of EtOAc (100 mL) then followed by washing the organic phase with saturated NaHCO$_3$. Drying and removal of solvents under vacuum gave 0.20 g (92%) of (S)-3-[4-acetylamino-2-(2-quinolin-5-yl-ethoxy)-benzenesulfonylamino]-3-cyano-propionic acid tert-butyl ester as a tan solid. MS (APCI) m/z 539.1 (M+1).

Step 9: (S)-3-[4-Acetylamino-2-(2-quinolin-5-yl-ethoxy)-benzenesulfonylamino]-3-cyano-propionic acid A solution of (S)-3-[4-acetylamino-2-(2-quinolin-5-yl-ethoxy)-benzenesulfonylamino]-3-cyano-propionic acid tert-butyl ester (0.20 g, 0.40 mmol) in TFA (2 mL) and CH$_2$Cl$_2$ (20 mL) was stirred for 9 h. After the solvent was removed under vacuum, the residue was subjected to preparative reverse-phase HPLC (VYDAC, C18) using a linear gradient of (A) water containing 0.1% TFA and (3) acetonitrile containing 0.1% TFA (0–40% B, in 120 min) at a flow rate of 15 mL/min. Fractions containing the major peak were pooled and lyophilized to yield 50 mg (26%) of (S)-3-[4-acetylamino-2-(2-quinolin-5-yl-ethoxy)-benzenesulfonylamino]-3-cyano-propionic acid. MS (APCI) m/z 483.1 (M+1).

EXAMPLE 73

(S)-3-[4-(4-Methyl-piperazin-1-yl-2-(2-naphthalen-1-yl-ethoxy)-benzenesulfonylamino]-4-oxo-butyric acid Route E, as an off white solid. MS (APCI) m/z 524.1 (M−1).

EXAMPLE 74

3-[4-Acetylamino-2-(2-benzimidazol-1-yl-ethoxy)-benzenesulfonylamino]-4-oxo-butyric acid Route B, colorless solid, MS(APCI) m/z 475.1 (M+1).

EXAMPLE 75

3-(4-Acetylamino-2-{2-[4-(2-dimethylamino-ethylcarbamoyl)-naphthalen-1-yl]-ethoxy}-benzenesulfonylamino)-4-oxo-butyric acid Route M, pink solid, MS(APCI) m/z 599.1 (M+1).

EXAMPLE 76

3-(2-{2-[4-(N',N'-Dimethyl-hydrazinocarbonyl)-naphthalen-1-yl]-ethoxy}-benzenesulfonylamino)-4-oxo-butyric acid Route M, using (S)-3-(2-hydroxybenzenesufonylamino)-4,4-diethoxy-butryric acid tert-butyl ester as the starting material. Colorless solid (47 mg), MS(APCI) m/z 514.0 (M+1).

EXAMPLE 77

(S)-4-Oxo-3-{2-[2-(1-oxy-quinolin-5-yl)-ethoxy]-benzenesulfonylamino}-butyric acid Step 1: 1-Bromo-2-benzyloxy-benzene A mixture of 42 g (242 mmol) 2-bromophenol, 100 g (726 mmol) potassium carbonate and 45.6 g (266.4 mmol) benzyl bromide in 500 mL absolute ethanol was heated to reflux for 18 h. The reaction mixture was cooled to 5° C. in an ice/water bath and filtered. The filtered solid was washed with 200 mL dichloromethane. The filtrate was concentrated and the residue purified over silica eluting with hexanes to give 54 g (205 mmol, 85%) of 1-bromo-2-benzyloxy-benzene as a colorless oil. $^1$H NMR (400 MHz) CDCl$_3$ 7.54–7.56 (d, 1H), 7.46–7.48 (d, 2H), 7.28–7.40 (m, 3H), 6.90–6.93 (d,1H), 6.81–6.85 (t, 1H), 5.14 (s, 2H).

Step 2: 2-Benzyloxy benzenesulfonyl chloride

A mixture of 19 g (72.2 mmol) 1-bromo-2-benzyloxy-benzene and 100 mL tetrahydrofuran was stirred under a nitrogen atmosphere at −78° C. n-Butyllithium (46 mL (72 mmol),1.6 M in tetrahydrofuran) was then added at a rate such that the temperature did not reach above −65° C. The resulting mixture was stirred 15 min. This mixture was then transferred via cannula to a solution of 50 mL condensed sulfur dioxide in 100 mL tetrahydrofuran at −78° C. The resulting mixture was stirred 1 h while the temperature was allowed to warm to room temperature. 250 mL ether was then added and the voluminous white precipitate which formed was filtered, washed with ether and dried at 40° C. overnite to give 17 g (66.9 mmol) of lithium sulfinate salt. The salt was then added to a mixture of 300 mL hexanes and 6 mL (73.5 mmol) sulfuryl chloride at 0° C., under a nitrogen atmosphere and stirred 30 min. The solid was filtered and washed with 60 mL hexanes, and dried at 35° C. 18 h to give 20.3 g (71.7 mmol, 99%) of 2-benzyloxy benzenesulfonyl chloride, contaminated with lithium chloride. $^1$H NMR (400 MHz) CDCl$_3$ 7.96–7.97 (d, 1H), 7.57–7.61 (t, 1H), 7.48–7.50 (d, 2H), 7.28–7.39 (m, 3H), 7.04–7.11 (m, 2H), 5.33 (s, 2H).

Step 3: (S)-3-(2-Benzyloxy-benzenesulfonylamino)-N-methoxy-N-methyl-succinamic acid tert-butyl ester A mixture of 3.87 g (16.66 mmol) (S)-2-amino-N-methoxy-N-methyl-succinamic acid-4-tert-butyl ester, from Route D step 2, 2 mL (18.33 mmol) N-methyl morpholine, and 100 mL dichloromethane was stirred under nitrogen atmosphere at 0° C. 5.04 g (16.66 mmol) of 2-benzyloxy benzenesulfonyl chloride was added and the mixture was allowed to stir at room temperature 48 h. Ethyl acetate (100 mL) was added and the mixture was cooled to 0° C. in an ice/water bath. The mixture was then filtered, concentrated, redissolved in 100 mL ethyl acetate, washed with 150 mL saturated sodium hydrogen carbonate, 150 mL saturated potassium dihydrogen phosphate, 150 mL brine, dried over anhydrous magnesium sulfate, filtered, and concentrated. The product was purified over silica eluting with 1:1 ethyl acetate:hexanes to afford 6.9 g (14.42 mmol, 87%) (S)-3-(2-benzyloxy-benzenesulfonylamino)-N-methoxy-N-methyl-succinamic acid tert-butyl ester as a thick colorless oil. $^1$H NMR (400 MHz) CDCl$_3$ 7.82–7.84 (d, 1H), 7.52–7.54 (d, H), 7.29–7.45 (m, 5H), 6.95–6.99 (m, 2H), 5.86–5.89 (d, 1H), 5.21 (s, 2H), 4.66 (bm, 1H), 3.52 (s, 3H), 2.83 (s, 3H), 2.52–2.57 (m, 1H), 2.36–2.41 (m, 1H), 1.36 (s, 9H).

Step 4: (S)-3-(2-Hydroxy-benzenesulfonylamino)-N-methoxy-N-methyl-succinamic acid tert-butyl ester A mixture of 22.52 g (47.05 mmol) (S)-3-(2-benzyloxy-benzenesulfonylamino)-N-methoxy-N-methyl-succinamic acid tert-butyl ester, 1 g 20% Pd on charcoal, 250 mL tetrahydrofuran and 250 mL ethanol was shaken under a 50 psig. hydrogen atmosphere for 26 h. The mixture was filtered through a pad of celite and concentrated. The residue was passed through a 100 g plug of silica eluting with 6:4 ethyl acetate:hexanes to give 17.5 g (45.05 mmol, 95.7%) of (S)-3-(2-hydroxy-benzenesulfonylamino)-N-methoxy-N- methyl-succinamic acid tert-butyl ester as a thick colorless oil. MS (APCI) m/z 387.0 (M−1).

Step 5: (S)—N-Methoxy-N-methyl-3-[2-(2-quinolin-5-yl-ethoxy)benzenesulfonylamino]-succinamic acid tert-butyl ester To a solution of S)-3-(2-hydroxy-benzenesulfonylamino)-N-methoxy-N-methyl-succinamic acid tert-butyl ester (2.0 g, 5.15 mmol), quinoline ethanol (0.892 g, 5.15 mmol) and triphenylphospine (2.02 g, 7.73 mmol) in 80 mL of THF at 0° C. was slowly added DEAD (1.22 mL, 7.73 mmol). The reaction was stirred for 17 h with slow warming to RT before removing the solvent. The residue was chromatographed (250 g $SiO_2$-50% EtOAC/Hex) to afford 3.55 g of (S)—N-methoxy-N-methyl-3-[2-(2-quinolin-5-yl-ethoxy)benzenesulfonylamino]-succinamic acid tert-butyl ester (contaminated with some triphenylphosphine oxide). $^1$H NMR (400 MHz, $CDCl_3$) 8.90(d, 1H, J=4 Hz), 8.61(d, 1H, J=8 Hz), 8.04(d, 1H, J=8 Hz), 7.81(d, 1H, J=8 Hz), 7.69(t, 1H, J=8 Hz), 7.65(t, 1H, J=8 Hz), 7.51(t, 1H, J=8 Hz), 7.49(d, 1H, J=8 Hz), 6.95(t, 1H, J=8 Hz), 6.85(d, 1H, J=8 Hz), 5.90(d, 1H, J=10 Hz), 4.38(m, 1H), 3.90–3.65(m, 2H), 3.45(s, 3H), 2.80(s, 3H), 2.40(ABX, AB portion, 2H, $J_{AB}$=15, $J_{AX}$=6, $J_{BX}$=7, $\Delta v_{AB}$=50.3 Hz), 1.41(s, 9H).

Step 6: (S)-4-Hydroxy-3-{2-[2-(1-oxy-quinolin-5-yl)-ethoxy]-benzenesufonylamino}-butyric acid tert-butyl ester To a solution of $LiAlH_4$ (11.0 mL, 1.0 M in $Et_2O$, 11.0 mmol) in a total of 150 mL of $Et_2O$ at −78° C. was added a solution of (S)—N-methoxy-N-methyl-3-[2-(2-quinolin-5-yl-ethoxy)benzenesulfonylamino]-succinamic acid tert-butyl ester (2.00 g, 3.68 mmol) in 20 mL of THF via cannula. After 15 min the reaction was warmed to −42° C. for 60 min before recooling to −78° C. and quenching with 200 mL of a sat. Na—K-tartrate solution. The aqueous phase was extracted 3× with EtOAc and the combined extracts were washed 1× with brine, dried ($Na_2SO_4$), filtered and concentrated to yield the intermediate aldehyde.

To the above aldehyde in 25 mL of EtOH at −78° C. was added $NaBH_4$ (0.140 g, 3.68 mmol). The reaction was stirred for 2 h before quenching with 10% citric acid solution and warming to RT. This mixture was diluted with EtOAc, washed 1× with $H_2O$, 1× with brine, dried ($Na_2SO_4$), filtered and concentrated to yield an intermediate alcohol.

To the above alcohol in 30 mL of $CH_2Cl_2$ at 0° C. was added mCPBA (1.58 g, 5.52 mmol). The reaction was stirred for 4 h with slow warming to RT before diluting with EtOAc. This mixture was washed 1× with $NaHCO_3$, 1× with brine, dried ($Na_2SO_4$), filtered and concentrated. Chromatography (100 g $SiO_2$-400 mL $Et_2O$, 400 mL EtOAc and 10% MeOH/$CH_2Cl_2$) afforded (S)-4-hydroxy-3-{2-[2-(1-oxy-quinolin-5-yl)-ethoxy]-benzenesulfonylamino}-butyric acid tert-butyl ester 0.973 g (49%). MS: AP+ mode 503.2 (m+1, 100%); AP− mode 501.2 (m−1, 100%).

Step 7: (S)-4-Oxo-3-{2-[2-(1-oxy-quinolin-5-yl)-ethoxy]-benzenesulfonylamino}-butyric acid To a solution of (S)-4-hydroxy-3-{2-[2-(1-oxy-quinolin-5-yl)-ethoxy]-benzenesulfonylamino}-butyric acid tert-butyl ester (0.91 g, 1.82 mmol) and $Et_3N$ (2.53 mL, 18.2 mmol) in 10 mL of DMSO was added a solution of $SO_3$-Pyr (0.87 g, 5.46 mmol) in 10 mL of DMSO via cannula. The reaction was stirred for 4 h before diluting with EtOAc. This mixture was washed with $H_2O$, with brine, dried ($Na_2SO_4$), filtered and concentrated to afford 0.62 g of aldehyde.

The above aldehyde was stirred for 1 h in a mixture of 10 mL $CH_2Cl_2$ and 4 mL TFA. The solvent was removed and the crude product purified by recrystalization (3×) from $CH_2Cl_2$/$Et_2O$ to afford (S)-4-oxo-3-{2-[2-(1-oxy-quinolin-5-yl)-ethoxy]-benzenesulfonylamino}-butyric acid as a tan solid 0.36 g (65%). Anal. Calcd for $C_{21}H_{20}N_2O_7S$.0.03 TFA: C, 56.48; H, 4.51; N, 6.25. Found C, 56.17; H, 4.72; N, 6.05.

EXAMPLE 78

3-[4-Acetylamino-2-((1R,2R)-1-methyl-2-naphthalen-1-yl-propoxy)-benzenesulfonylamino]-4-oxo-butyric acid Route J, MS (APCI) 513 (M+1).

EXAMPLE 79

(S)-3-[2-((1R,2S)-2-Benzimidazol-1-yl-1-methyl-propoxy)-4-(2-dimethylamino-ethylcarbamoyl)-benzenesulfonylamino]-4-oxo-butyric acid Route P, MS (APCI) 560.1 (M+1).

EXAMPLE 80

(S)-3-[4-((S)-1-Carbamoyl-ethylcarbamoyl)-2-(2-quinolin-5-yl-ethoxy)-benzenesulfonylamino]-4-oxo-butyric acid Route P, Lyophilized as a white solid. MS(APCI) m/z 544.0 (M+1), 542.0 (M−1).

EXAMPLE 81

(S)-3-[4-((S)-1-Carbamoyl-ethylcarbamoyl)-2-(2-naphthalen-1-yl-ethoxy)-benzenesulfonylamino]-4-oxo-butyric acid Route P, Lyophilized as a white solid. MS(APCI) m/z 542.1 (M+1).

EXAMPLE 82

N-[3-[(R)-2-(5-Chloro-imidazo[4,5-b]pyridin-3-yl)-1-methyl-ethoxy]-4-(2-ethoxy-5-oxo-tetrahydro-furan-3-ylsulfamoyl)-phenyl]-acetamide (S)-2-(5-Chloro-imidazo[4,5-b]pyridin-3-yl)-1-methyl-ethanol was synthesized via the method used for (S)-1-Methyl-2-(6-methyl-benzimidazol-1-yl)-ethanol giving a tan solid. MS (APCI) m/z 212 (M). This fragment was used in the synthesis of N-[3-[(R)-2-(5-Chloro-imidazo[4,5-b]pyridin-3-yl)-1-methyl-ethoxy]-4-(2-ethoxy-5-oxo-tetrahydro-furan-3-ylsulfamoyl)-phenyl]-acetamide, which was synthesized via route J; a white solid, MS (APCI) m/z 552 (M). Analysis calculated for $C_{23}H_{26}N_5O_7SCl$ (552.010): C, 50.05; H, 4.75; N, 12.69. Found: C, 50.40; H, 4.87; N, 11.99.

EXAMPLE 83

N-[4-(2-Ethoxy-5-oxo-tetrahydro-furan-3-ylsulfamoyl)-3-((R)-2-imidazo[4,5-b]pyridin-3-yl-1-methyl-ethoxy)-phenyl]-acetamide Route J, a white solid, MS (APCI) m/z 518 (M+1). Analysis calculated for $C_{23}H_{27}N_5O_7S$ (517.565): C, 53.38; H, 5.26; N, 13.53. Found: C, 53.42; H, 5.44; N, 12.72.

(S)-2-imidazo[4,5-b]pyridin-3-yl-1-methyl-ethanol employed in the synthesis of N-[4-(2-ethoxy-5-oxo-tetrahydro-furan-3-ylsulfamoyl)-3-((R)-2-imidazo[4,5-b]pyridin-3-yl-1-methyl-ethoxy)-phenyl]-acetamide was synthesized via the method used for (S)-1-Methyl-2-(6-methyl-benzimidazol-1-yl)-ethanol giving a tan waxy solid. MS (APCI) m/z 178.1 (M+1).

EXAMPLE 84

N-{4-(2-Ethoxy-5-oxo-tetrahydro-furan-3-ylsulfamoyl)-3-[(R)-2-(5-methoxy-imidazo[4,5-b]pyridin-3-yl)-1-methyl-ethoxy]-phenyl}-acetamide Route J, a white solid, MS (APCI) m/z 548.1 (M+1). Analysis calculated for $C_{24}H_{29}N_5O_8S$ (547.591): C, 52.64; H, 5.34; N, 12.79. Found: C, 52.45; H, 5.58; N, 12.17.

(S)-2-(5-methoxy-imidazo[4,5-b]pyridin-3-yl)-1-methyl-ethanol employed in the synthesis of N-{4-(2-ethoxy-5-oxo-tetrahydro-furan-3-ylsulfamoyl)-3-[(R)-2-(5-methoxyimidazo[4,5-b]pyridin-3-yl)-1-methyl-ethoxy]-phenyl}-acetamide was synthesized via the method used for (S)-1-methyl-2-(6-methyl-benzimidazol-1-yl)-ethanol giving a white solid. MS (APCI) m/z 208.1 (M+1).

EXAMPLE 85
N-{4-(2-Ethoxy-5-oxo-tetrahydro-furan-3-ylsulfamoyl-3-[(R)-1-methyl-2-(6-methyl-benzimidazol-1-yl)-ethoxy]-phenyl}-acetamide Route J, a white solid, MS (APCI) m/z 531.1 (M+1). Analysis calculated for $C_{25}H_{30}N_4O_7S$ (530.604): C, 56.59; H, 5.70; N, 10.56. Found: C, 55.84; H, 5.68, N, 10.53.

(S)-1-Methyl-2-(6-methyl-benzimidazol-1-yl)-ethanol used in the synthesis of N-{4-(2-ethoxy-5-oxo-tetrahydro-furan-3-ylsulfamoyl)-3-[(R)-1-methyl-2-(6-methyl-benzimidazol-1-yl)-ethoxy]-phenyl}-acetamide was made as follows: A mixture 0.98 g (6.3 mmol) 2-fluoro-4-methylnitrobenzene, 0.3 mL (6.35 mmol) (S)-1-amino-2-propanol and 0.9 mL (7 mmol) triethylamine was stirred in 25 mL DMF at 60° C. 18 h. The solvent was removed in vacuo, the residue was partitioned between 75 mL ethyl acetate and 50 mL water, and the organic layer was washed with another 50 mL portion of water, 50 mL brine, dried over anydrous magnesium sulphate, filtered, concentrated and purified over silica eluting with 1:1 ethyl acetate:hexanes to afford 0.87 g (4.14 mmol, 66%) of the nitro aniline as an orange solid MS (APCI) m/z 209 (M−1). The nitro aniline was shaken with 0.5 g Raney Ni, 50 mL THF and 50 psig. $H_2$ (g) for 1 h. The catalyst was filtered, and the solvent removed in vacuo to yield 0.75 g (4.14 mmol, 100%) of the dianiline as a lavender solid. MS (APCI) m/z 181 (M+1). The dianiline was stirred at reflux in 50 mL 88% formic acid for 4 h. The solvent was removed in vacuo, the residue partitioned between 50 mL ethyl acetate and 50 mL saturated sodium hydrogen carbonate. The aqueous layer was washed with another 50 mL portion of ethyl acetate, the organic washes were combined, washed with brine, dried over anhydrous magnesium sulfate, filtered and concentrated. The residue was purified over silica eluting with 9:1 ethyl acetate:methanol to afford 0.45 g (2.37 mmol, 53%) of the title compound, (S)-1-methyl-2-(6-methyl-benzimidazol-1-yl)-ethanol as a white solid. MS (APCI) m/z 191 (M+1).

EXAMPLE 86
N-[3-((R)-2-Indazol-1-yl-1-methyl-ethoxy)-4-(2-ethoxy-5-oxo-tetrahydro-furan-3-ylsulfamoyl)-phenyl]-acetamide Synthesized via Route J, a white solid, MS (APCI) m/z 517.1 (M+1). Analysis calculated for $C_{24}H_{28}N_4O_7S$ (516.577): C, 55.80; H, 5.46; N, 10.85. Found: C, 55.82; H, 5.52; N, 10.37.

EXAMPLE 87
3-[4-Acetylamino-2-((R)-2-indazol-1-yl-1-methyl-ethoxy)-benzenesulfonylamino]-4-oxo-butyric acid hydrochloric acid salt Route J, a white solid, MS (APCI) m/z 489.0 (M+1). Analysis calculated for $C_{22}H_{24}N_4O_7S \cdot 0.91$ HCl(521.700): C, 50.65; H, 4.81; N, 10.74. Found: C, 50.27; H, 5.01; N, 10.40.

EXAMPLE 88
(S)-3-[4-(2-Dimethylamino-ethylcarbamoyl)-2-(2-quinolin-5-yl-ethoxy)-benzenesulfonylamino]-4-oxo-butyric acid Route P.

Synthesis of: 3-Benzyloxy-4-chlorosulfonyl-benzoic acid methyl ester

Step 1: 3-Benzyloxy-4-nitro-benzoic acid methyl ester

REFERENCE: *J. Med Chem.* 1997, 40, 105–111. To an acetone solution (500 mL) of methyl 3-hydroxy-4-nitrobenzoate (25.0 g, 126.8 mmol) was added cesium carbonate (61.9 g, 190.2 mmol) followed by benzyl bromide (15.0 mL, 126.8 mmol). The reaction was heated to reflux and monitored by TLC. The reaction was judged complete in approximately 7 h. The reaction was then cooled to room temperature and concentrated under reduced pressure to approximately 20 mL. The residue was diluted with ethyl acetate (700 mL) and washed in succession with 1N hydrochloric acid, 1N sodium hydroxide, 1N hydrochloric acid and finally with saturated aqueous sodium chloride. The organic layer was then dried over magnesium sulfate, filtered and concentrated under reduced pressure to yield 3-benzyloxy-4-nitro-benzoic acid methyl ester as a solid. $^1$H NMR (CDCl$_3$) 7.83(m,2H), 7.70(dd, 1H), 7.50–7.30(m,5H), 5.28(s,2H), 3.96(s,3H).

Step 2: 4-Amino-3-benzyloxy-benzoic acid methyl ester

To a tetrahydrofuran solution (100 mL) of 3-benzyloxy-4-nitro-benzoic acid methyl ester(10.0 g, 34.9 mmol) was added Raney Nickel (wet) (2.0 g). The reaction was pressured to approximately 50 psi at left to shake at room temperature for 5.5 h. An aliquot was removed and TLC deemed the reaction complete. The reaction was filtered through celite and then concentrated under reduced pressure to yield 4-amino-3-benzyloxy-benzoic acid methyl ester as a solid (8.7 g, 97%). $^1$H NMR (CDCl$_3$) 7.58(m,2H), 7.50–7.30(m,5H), 6.70(d,1H), 5.14(s,2H), 4.84(s,3H).

Step 3: 3-Benzyloxy-4-chlorosulfonyl-benzoic acid methyl ester

REFERENCE: *J. Org. Chem,* 1979, 44, 1572–1574. To a −10° C. (acetone/ice/sodium chloride) methylene chloride solution of 4-amino-3-benzyloxy-benzoic acid methyl ester (8.7 g, 33.8 mmol) was added boron trifluoride diethyl etherate (12.4 mL, 101.5 mmol) dropwise. A methylene chloride solution (5.2 mL) of tert-butyl nitrite (4.8 mL, 40.5 mmol) was then slowly added dropwise. The reaction was allowed to stir at −10° C. for approximately 30 min. At this point a small aliquot (2 mL) was removed and concentrated under reduced pressure. $^1$H NMR showed that the reaction was complete. Chilled pentane (125 mL) was then added to precipitate the diazo-salt from the methylene chloride. The 3-benzyloxy-4-diazenyl-benzoic acid methyl ester was then dissolved in dioxane (~150 mL) and acetonitrile (~50 mL) and used without any further manipulation. To a −10° C. (acetone/ice/sodium chloride) solution of dioxane (150 mL) and acetic acid (150 mL) was added copper (I) chloride (0.99 g, 10.5 mmol) and lithium chloride (8.5 g, 201 mmol). Sulfur dioxide (~150 mL) was then condensed into this solution using a −78° C. cold finger. The above solution of 3-benzyloxy-4-diazenyl-benzoic acid methyl ester was then poured into this solution. The reaction was kept at 0° C. for 4–5 h and then placed into a preheated oil bath at 65° C. overnight. The reaction was then cooled and poured into ethyl acetate (600 mL) and washed in succession with water and 1N sodium hydroxide. A final wash with saturated aqueous sodium chloride was done and the organic layer was then dried over magnesium sulfate, filtered and concentrated under reduced pressure to yield 3-benzyloxy-4-chlorosulfonyl-benzoic acid methyl ester as a foam. This was used in the next step without further purification. The product moved on TLC to a $R_f$ of 0.5 in 30% ethyl acetate/hexane. $^1$H NMR (CDCl$_3$) 8.00(d,1H), 7.75(s,1H), 7.67(d,1H), 7.49(d,2H), 7.35(m,3H), 5.35(s,2H), 3.91(s, 3H).

Synthesis of: (S)-3-Amino-4,4-diethoxy-butryic acid tert-butyl ester

Step 1: (S)-3-Benzyloxycarbonylamino-4-hydroxy-butyric acid tert-butyl ester

To a solution of (S)-2-benzyloxycarbonylamino-succinic acid 4-tert-butyl ester (47.56 g, 147 mmol) in 600 mL of THF at 0° C. was added NMM (1.2 eq, 19.4 mL) and IBCF (1.1 eq, 21.0 mL). The reaction was stirred for 15 min before adding this solution via cannula to a suspension of NaBH$_4$ (2.0 eq, 11.2 g) in 1000 mL of THF and 300 mL of MeOH at −78° C. (2×50 mL THF wash). The reaction was stirred for 2 h before quenching with 30 mL of AcOH and removing the solvent (rotovap). The residue was diluted with EtOAc washed with sat. NaHCO$_3$, with brine, dried (Na$_2$SO$_4$), filtered and concentrated. Afforded (S)-3-benzyloxycarbonylamino-4-hydroxy-butryic acid tert-butyl ester 49.86 g (wet with EtOAc) which was used in next step.

MS (APCI) m/z 310.2 (M+1)

Step 2: (S)-3-Benzyloxycarbonylamino-4-oxo-butryic acid tert-butyl ester

A solution of (S)-3-benzyloxycarbonylamino-4-hydroxy-butryic acid tert-butyl ester (17.0 g 1.0 eq) in 150 mL of DMSO was added IBX (21.6 g, 1.4 eq). The reaction was stirred at RT for 3 h (all solids dissolved after 30 min) before pouring into 600 mL of H$_2$O (a white solid formed) and stirring for an additional 60 min. The reaction was filtered, washed with H$_2$O and then with 1000 mL of Et$_2$O. The aqueous phase was extracted with Et$_2$O and with EtOAc. The combined organic phases were washed with H$_2$O, with brine, dried (Na$_2$SO$_4$), filtered and concentrated. (S)-3-Benzyloxycarbonylamino-4-oxo-butryric acid tert-butyl ester was carried on to next step without purification. $^1$H NMR (CDCl$_3$, 400 MHz) 9.63 (s, 1H), 7.31 (m, 5H), 5.87 (d, 1H, J=8 Hz), 5.11 (m, 2H), 4.37 (m, 1H), 2.83 (ABX, AB portion, 2H, J$_{AB}$=17, J$_{AX}$=5, J$_{BX}$=4, Δv$_{AB}$=79 Hz), 1.39 (s, 9H).

Step 3: (S)-3-Benzyloxycarbonylamino-4,4-diethoxy-butryic acid tert-butyl ester

To a solution of (S)-3-benzyloxycarbonylamino-4-oxo-butryric acid tert-butyl ester (23.2 g, 1.0 eq) in 300 mL of EtOH was added triethylorthoformate (125 mL, 10 eq) and TsOH—H$_2$O (1.44 g, 0.1 eq). The reaction was stirred at RT for 17 h before removing the solvent. The residue was diluted with EtOAc, washed with NaHCO$_3$, with H$_2$O, and with brine, dried (Na$_2$SO$_4$), filtered and concentrated. The crude product was purified by SiO$_2$ chromatography (10% EtOAc-Hex). MS (APCI) 280.0 (M−101, 100%); $^1$H NMR (CDCl$_3$, 400 MHz) 7.32 (m, 5H), 5.26 (d, 1H, J=9 Hz), 5.06 (AB quartet, 2H, J$_{AB}$=12, Δv$_{AB}$=18 Hz), 4.45 (m, 1H), 4.19 (m, 1H), 3.67 (m, 2H) 3.50 (m, 2H), 2.48 (m, 2H), 1.39 (s, 9H), 1.16 (t, 3h, J=7 Hz).

Step 4: (S)-3-Amino-4,4-diethoxy-butyric acid tert-butyl ester (S)-3-Benzyloxycarbonylamino-4,4-diethoxy-butyric acid tert-butyl ester (12 g, 31.5 mmol) was shaken with 20% palladium on carbon (1 g), under H$_2$ (50 psi) for 3.5 hours using a Parr apparatus. Mass spectrometry and NMR analysis indicated complete consumption of the starting material. The reaction mixture was filtered through celite and concentrated to yield (8.76 g, 35.4 mmol) a colorless oil. $^1$H NMR (400 MHz, CD$_3$OD) 4.55 (d,1H), 3.71 (q, 2H), 3.592 (m, 2H), 3.41 (m, 1H), 2.67 (dd, 1H), 2.55 (dd, 1H), 1.45 (s, 9H), 1.22 (t, 6H).

(S)-3-[4-(2-Dimethylamino-ethylcarbamoyl)-2-(2-quinolin-5-yl-ethoxy)-benzenesulfonylamino]-4-oxo-butyric acid Employing (S)-3-amino-4,4-diethoxy-butyric acid tert-butyl ester and 3-Benzyloxy-4-chlorosulfonyl-benzoic acid methyl ester From Above Step 1: 3-Benzyloxy-4-(1-tert-butoxycarbonylmethyl-2,2-diethoxy-ethylsulfamoyl)-benzoic acid methyl ester To a solution of (S)-3-amino-4,4-diethoxy-butyric acid tert-butyl ester (3.38 g, 13.7 mmol) in anhydrous methylene chloride (130 mL) was added pyridine (3.3 mL, 41 mmol) followed by 3-benzyloxy-4-chlorosulfonyl-benzoic acid methyl ester (4.66 g, 13.7 mmol). The reaction was allowed to stir at room temperature overnight. Mass spectrometry and TLC analysis showed presence of starting material. An additional 2 equivalents of pyridine (2.2 mL, 27.3 mmol) was added and allowed to stir overnight. TLC analysis showed the reaction to be completed. The methylene chloride was evaporated and the reaction mixture was dissolved in ether and 5% aqueous citric acid. The organic layer was collected and washed with 5% citric acid and then brine, dried over magnesium sulfate, filtered, and concentrated to yield 3-benzyloxy-4-(1-tert-butoxycarbonylmethyl-2,2-diethoxy-ethylsulfamoyl)-benzoic acid methyl ester (6.82 g, 12.4 mmol, 90%) as an orange tar. MS (APCI) m/z 550.3 (M−1).

Step 2: 3-Benzyloxy-4-(1-tert-butoxycarbonylmethyl-2,2-diethyoxy-ethylsulfamoyl)-benzoic acid 3-Benzyloxy-4-(1-tert-butoxycarbonylmethyl-2,2-diethoxy-ethylsulfamoyl)-benzoic acid methyl ester (6.82 g, 12.4 mmol) was combined and stirred with 1M lithium hydroxide (26 mL, 26 mmol) in tetrahydrofuran (250 mL) at room temperature overnight. The reaction mixture was diluted with ethyl acetate and acidified with 1M HCl (26 mL). The organic layer was collected and extracted with water, brine, dried over magnesium sulfate, filtered, and concentrated under reduced pressure to give 3-benzyloxy-4-(1-tert-butoxycarbonylmethyl-2,2-diethyoxy-ethylsulfamoyl-)benzoic acid (4.32 g, 8.0 mmol, 65%). MS (APCI) m/z 536.3 (M−1).

Step 3: 3-[2-Benzyloxy-4-(2-dimethylamino-ethylcarbomoyl)-benzenesulfonylamino]-4,4-diethyoxy-butyric acid tert-butyl ester To a solution of 3-benzyloxy-4-(1-tert-butoxycarbonylmethyl-2,2-diethyoxy-ethylsulfamoyl-)benzoic acid (392 mg, 0.73 mmol) in freshly distilled tetrahydrofuran (6 mL) was added 4-methyl piperidine (120 µL, 2.2 mmol), 1-hydroxybenzotriazole (148 mg, 1.1 mmol), 2-dimethylaminoethylamine (120 µL, 1.1 mmol), followed by (1-(3-dimethylaminopropyl)-3-ethylcarbodiimide hydrochloride (210 mg, 1.1 mmol). The reaction was stirred overnight at room temperature. The reaction was diluted with water. The dilution was extracted into ethyl acetate. The organic extracts were washed with brine, dried over magnesium sulfate, filtered, and concentrated under reduced pressure to yield 3-[2-benzyloxy-4-(2-dimethylamino-ethylcarbomoyl)-benzenesulfonylamino]-4, 4-diethyoxy-butyric acid tert-butyl ester (316 mg, 71%). MS (APCI) m/z 608.2 (M+1).

Step 4: 3-[4-(2-Dimethylamino-ethylcarbamoyl)-2-hydroxy-benzenesulfonylamino]-4,4-diethoxy-butyric acid tert-butyl ester 3-[2-Benzyloxy-4-(2-dimethylamino-ethylcarbomoyl)-benzenesulfonylamino]-4,4-diethyoxy-butyric acid tert-butyl ester (316 mg, 0.52 mmol) was stirred with 20% palladium on carbon (60 mg), under H$_2$ (1 atm) for 15 h. Mass spectrometry and NMR analysis indicated complete consumption of the starting material. The reaction mixture was filtered through celite and concentrated to yield 3-[4-(2-dimethylamino-ethylcarbamoyl)-2-hydroxy-benzenesulfonylamino]-4,4-diethoxy-butyric acid tert-butyl ester (280 mg, 100%). MS (APCI) m/z 518.2 (M+1).

Step 5: (S)-3-[4-(2-Dimethylamino-ethylcarbamoyl)-2-(2-quinolin-5-yl-ethoxy)-benzenesulfonylamino]-4,4-diethoxy-butryic acid tert-butyl ester To 3-[4-(2-dimethylamino-ethylcarbamoyl)-2-hydroxy-benzenesulfonylamino]-4,4-diethoxy-butyric acid tert-butyl ester (140 mg, 0.27 mmol) in dichloromethane (3 mL) was added 2-quinolin-5-yl-ethanol (56 mg, 0.32 mmol), triphenyl phosphine (107 mg, 0.41 mmol) and diethylazodicarboxylate (63 µL, 0.41 mmol). The reaction was stirred at room temperature for 2 h and loaded directly on a column. Chromatography with silica gel eluting with 10%(8:1, ethanol/ammonium hydroxide) in dichloromethane gave (S)-3-[4-(2-dimethylamino-ethylcarbamoyl)-2-(2-quinolin-5-yl-ethoxy)-benzenesulfonylamino]-4,4-diethoxy-butryic acid tert-butyl ester as a colorless oil (101 mg, 56%) MS (APCI) m/z 673.1 (M+1).

Step 6: (S)-3-[4-(2-Dimethylamino-ethylcarbamoyl)-2-(2-quinolin-5-yl-ethoxy)-benzenesulfonylamino]-4-oxo-butryic acid To (S)-3-[4-(2-dimethylamino-ethylcarbamoyl)-2-(2-quinolin-5-yl-ethoxy)-benzenesulfonylamino]-4,4-diethoxy-butryic acid tert-butyl ester (101 mg) in dichloromethane (20 mL) was added trifluoroacetic acid (5 mL) and water (250 µL). The reaction was stirred 2 h. Toluene (100 mL) was added and the reaction was evaporated to dryness. The residue was taken up in 1:1 water/acetonitrile (20 mL) and trifluoroacetic acid (2.5 mL) was added. After stirring overnight, the reaction was diluted with water (100 mL) and lyopholized to give (S)-3-[4-(2-dimethylamino-ethylcarbamoyl)-2-(2-quinolin-5-yl-ethoxy)-benzenesulfonylamino]-4-oxo-butryic acid as a colorless foam (110 mg) MS (APCI) m/z 543.1 (M+1).

EXAMPLE 89

(S)-3-[4-(2-Dimethylamino-ethylcarbamoyl)-2-((R)-1-methyl-2-naphthalen-1-yl-ethoxy)-benzenesulfonylamino]-4-oxo-butyric acid Route P, colorless solid (74 mg), MS(APCI) m/z 556.1 (M+1).

EXAMPLE 90

(S)-3-[2-((S)-1-Ethoxycarbonyl-2-naphthalen-1-yl-ethoxy)-benzenesulfonylamino]-4oxo-butyric acid Synthesized as in Route M, but employing (S)-3-(2-hydroxybenzenesulfonylamino)-4,4-diethoxybutyric acid (see Example 98) and (2-hydroxy-3-naphthalen-1-yl-propionic acid ethyl ester) as starting materials. The product was lyophilized to give a white solid. MS(APCI) m/z 500.1 (M+1), 498.1 (M−1).

2-Hydroxy-3-naphthalen-1-yl-propionic acid ethyl ester Employed in the Synthesis of: (S)-3-[2-((S)-1-Ethoxycarbonyl-2-naphthalen-1-yl-ethoxy)-benzenesulfonylamino]-4-oxo-butyric acid Step 1: 3-Naphthalen-1-yl-oxirane-2-carboxylic acid ethyl ester To a −78° C. solution of 1-naphthaldehyde (13.0 mL, 96.1 mmol) and ethyl chloroacetate (10.3 mL, 96.1 mmol) in tetrahydrofuran (900 mL) was added (1.0 M in tetrahydrofuran) sodium bis(trimethylsilyl)amide (96.1 ml, 96.1 mmol) dropwise. The reaction mixture was stirred at −78° C. for 30 minutes and then warmed to 0° C. The reaction was then quenched with water (200 mL). The reaction mixture was then diluted with ethyl acetate (800 mL). The organic reaction layer was then washed in succession with water and saturated sodium chloride, the organic layer was then dried over magnesium sulfate, filtered and concentrated under reduced pressure to yield a pale oil. The crude residue was chromatographed (silica gel with 5% ethyl acetate-95% hexane) to give 3-naphthalen-1-yl-oxirane-2-carboxylic acid ethyl ester as a clear oil. $^1$H NMR(300 MHz, DMSO) 8.12 (d, 1H), 7.95 (m, 2H), 7.51 (m, 4H), 4.77 (d, 1H), 4.24 (q, 2H), 3.72 (d, 1H), 1.27 (t, 3H). MS(APCI) m/z 241.1 (M−H). Anal. Calcd. for $C_{15}H_{14}O_3$: C, 74.36; H, 5.82. Found: C, 74.47; H, 5.87.

Step 2: 2-Hydroxy-3-naphthalen-1-yl-propionic acid ethyl ester

To an ethanol (400 mL) solution of 3-naphthalen-1-yl-oxirane-2-carboxylic acid ethyl ester (21.26 g, 87.8 mmol) was added 5% palladium hydroxide on carbon (1.0 g). The reaction was then pressurized to 50 psi with hydrogen for 2 h. The reaction was then filtered through a celite pad. The cake was washed with ethanol (100 mL). The reaction was then concentrated under reduced pressure to yield 2-hydroxy-3-naphthalen-1-yl-propionic acid ethyl ester as an oil. $^1$H NMR(300 MHz, DMSO) 8.05 (d, 1H), 7.89(d, 1H), 7.79(d, 1H), 7.34 (m, 4H), 5.58 (d, 1H), 4.32 (dd, 1H), 4.04 (q, 2H), 3.44 (dd, 1H), 3.24 (dd, 1H), 1.05 (t, 3H).

EXAMPLE 91

3-[4-Acetylamino-2-((R)-2-indazol-1-yl-1-methyl-ethoxy)-benzenesulfonylamino]-4-oxo-butyric acid hydrochloric acid salt Route J Step 1: 2-Bromo-5-nitrophenol A mixture of 29.1 g (125.6 mmol) of 2-bromo-5-nitroanisole and 250 mL $CH_2Cl_2$ was stirred at −44° C. in a dry ice acetonitrile bath under a nitrogen atmosphere. Boron tribromide (18 mL) was added dropwise to the reaction mixture. The resulting black reaction was stirred while allowing the cooling bath to slowly rise to room temperature over 20 h. TLC analysis indicated complete reaction, so the reaction mixture was transferred to an addition funnel and added cautiously to a mixture of ice, water and 75 g solid $KH_2PO_4$. The layers were separated, the aqueous layer was washed with $CH_2Cl_2$, the combined organic extracts were washed with brine, dried over anhydrous magnesium sulfate, filtered, concentrated to give 27.4 g (125.6 mmol, 100%) of 2-bromo-5-nitrophenol as a black solid. $^1$H NMR (400 MHz) $CDCl_3$ 7.85 (s, 1H), 7.62–7.70 (m, 2H), 5.88 (s, 1H).

Step 2: 2-bromo-5-nitro-O-benzylphenol

A mixture of 27.4 g (125.6 mmol) of 2-bromo-5-nitrophenol, 26 g (188.4 mmol) potassium carbonate, and 250 mL DMF were stirred 15 min at room temperature. 16.4 mL (138 mmol) of benzyl bromide was added in one portion to the reaction mixture and the mixture was heated to 90° C. TLC analysis indicated complete reaction, so the reaction mixture was cooled to 5° C. in an ice/water bath, filtered and concentrated. 300 mL water was added to the reaction mixture and the black precipitate was filtered and air dried. The crude product was taken up in dichloromethane and purified over silica eluting with 35% hexanes in dichloromethane, to give 2-bromo-5-nitro-O-benzylphenol 35.5 g (115.2 mmol, 91.7%) as an ivory solid. $^1$H NMR (400 MHz) $CDCl_3$ 7.78 (s, 1H), 7.72 (s, 2H), 7.46–7.48 (m, 2H), 7.38–7.42 (m, 2H), 7.32–7.35 (1H), 5.23 (s, 2H).

Step 3: 2-Benzyloxy-4-nitro-S-benzylthiophenol

A mixture of 35.5 g (115.2 mmol) 2-bromo-5-nitro-O-benzylphenol, 26.3 g (190 mmol) potassium carbonate, 15 mL (127 mmol) benzyl mercaptan, and 200 mL DMF were stirred at room temperature 18 h. TLC analysis indicated a complete reaction, so the thick reaction mixture was transferred to a 2 L Erlenmeyer containing 1 L water and the resulting mixture was stirred in a ice/water bath 30 min. The precipitate was filtered, washed with three 300 mL portions of water, dried at 40° C. 18 h under vacuum to give 2-benzyloxy-4-nitro-S-benzylthiophenol 40.5 g (115.2 mmol, 100%) as a yellow solid.

MS (APCI) m/z 352 (M+1).

Step 4: 2-Benzyloxy-4-nitro-benzenesulfonyl chloride

A mixture of 40.5 g (115.2 mmol) 2-benzyloxy-4-nitro-S-benzylthiophenol, 100 mL acetic acid, and 100 mL water was stirred in an ice/water bath to an internal temperature of 3° C. The starting material did not dissolve into the solvent. Chlorine gas was bubbled through a gas dispersion tube into the mixture for 20 min. The internal temperature exothermed to 15° C. and then fell back to 5° C. over the 20 min time period. The solid in the reaction flask became very clumpy and as the reaction cooled, the solid broke up into finer particles. An aliquot was filtered and NMR analysis indicated complete reaction. The solid precipitate was filtered, washed with 100 mL cold water and dried at 40° C. 18 h to yield 37.75 g (115 mmol, 100%) 2-benzyloxy-4-nitro-benzenesulfonyl chloride as a fine yellow precipitate. $^1$H NMR (400 MHz) CDCl$_3$ 8.15–8.18 (d, 1H), 7.98 (s, 1H), 7.91–7.93 (m, 1H), 7.51–7.53 (m, 2H), 7.34–7.46 (m, 3H), 5.44 (s, 2H).

Step 5: (S)-3-(2-Benzyloxy-4-nitro-benzenesulfonylamino)-4,4-diethoxy-butyric acid tert-butyl ester A mixture of 7.69 g (31 mmol) 3-amino-4,4-diethoxy-butyric acid tert-butyl ester, 4.2 mL (33 mmol) N-ethylmorpholine, 0.37 g (3 mmol) N N-dimethylaminopyridine was stirred in 75 mL dichloromethane and cooled to 0° C. in an ice/water bath. 10.1 g (31 mmol) of % 2-benzyloxy-4-nitro-benzenesulfonyl chloride was added in one portion and the resulting mixture was stirred at room temperature 18 h. TLC analysis indicated complete reaction. The reaction mixture was transferred to a separatory funnel and washed with water and then brine. The organic layer was dried over anhydrous magnesium sulfate, filtered, and concentrated in vacuo to a pale yellow oil. The oil was purified over silica eluting with 1:1 ethyl acetate:hexanes to give 11.7 g (21.7 mmol, 70%) (S)-3-(2-benzyloxy-4-nitro-benzenesulfonylamino)-4,4-diethoxy-butyric acid tert-butyl ester as a pale yellow oil. MS (APCI) m/z 538.1 (M–1).

Step 6: (S)-3-(4-Amino-2-benzyloxy-benzenesulfonylamino)-4,4-diethoxy-butyric acid tert-butyl ester A mixture of 11.7 g (21.72 mmol) of (S)-3-(2-benzyloxy-4-nitro-benzenesulfonylamino)-4,4-diethoxy-butyric acid tert-butyl ester, 2 g Raney Ni, and 200 mL tetrahydrofuran was shaken under a 50 psi hydrogen atomosphere for 16 h at room temperature. TLC analysis indicated complete reaction. The catalyst was filtered and the resulting solution was concentrated to give 11.2 g (21.72 mmol, 100%) of (S)-3-(4-amino-2-benzyloxy-benzenesulfonylamino)-4,4-diethoxy-butyric acid tert-butyl ester as a brown oil. MS (APCI) m/z 507 (M–1).

Step 7: (S)-3-(4-Acetylamino-2-benzyloxy-benzenesulfonylamino)-4,4diethoxy-butyric acid tert-butyl ester A mixture of 11.2 g (21.7 mmol) (S)-3-(4-amino-2-benzyloxy-benzenesulfonylamino)-4,4-diethoxy-butyric acid tert-butyl ester and 50 mL dichloromethane and cooled to 0° C. in an ice/water bath. 3.2 mL (25 mmol) N-ethylmorpholine was added, followed by dropwise addition of 1.71 mL (24 mmol) acetyl chloride. After 10 min reaction time, TLC analysis showed complete reaction. The mixture was transferred to a separatory funnel and washed with 50 mL water, 50 mL brine, dried over anhydrous magnesium sulfate, filtered and concentrated to give 12 g (21.8 mmol, 100%) of (S)-3-(4-acetylamino-2-benzyloxy-benzenesulfonylamino)-4,4-diethoxy-butyric acid tert-butyl ester as a brown oil. MS (APCI) m/z 549.1 (M–1), 459.1 (M-CH$_2$Ph).

Step 8: (S)-3-(4-Acetylamino-2-hydroxy-benzenesulfonylamino)-4,4-diethoxy-butyric acid tert-butyl ester 11.4 g (20.7 mmol) (S)-3-(4-Acetylamino-2-benzyloxy-benzenesulfonylamino)-4,4-diethoxy-butyric acid tert-butyl ester, 1 g 20% Pd/C, and 100 mL tetrahydrofuran was shaken under a 50 psi hydrogen atmosphere for 19 h. TLC analysis indicated incomplete reaction, so an additional 1 g 20% Pd/C was added and the reaction shaken an additional 20 h under a 50 psig hydrogen atmosphere. TLC showed complete reaction. The catalyst was filtered and the resulting solution was concentrated to give an oil. The product was purified over silica eluting with ethyl acetate to yield 9.37 g (20.34 mmol, 98.3%) of (S)-3-(4-acetylamino-2-hydroxy-benzenesulfonylamino)-4,4-diethoxy-butyric acid tert-butyl ester as an ivory-yellow solid. MS (APCI) m/z 459.1 (M–1).

Step 9: (S)-3-[4-Acetylamino-2-((R)-2-indazol-1-yl-1-methyl-ethoxy)-benzenesulfonylamino]-4,4-diethoxy-butyric acid tert-butyl ester A mixture of 0.25 g (0.54 mmol) (S)-3-(4-acetylamino-2-hydroxy-benzenesulfonylamino)-4,4-diethoxy-butyric acid tert-butyl ester, 0.096 g (0.54 mmol) (S)-2-indazol-1-yl-1-methyl-ethanol, 0.285 g (1.08 mmol) triphenylphosphine, and 40 mL dry tetrahydrofuran was stirred at room temperature. Diethyl azodicarboxylate 0.2 mL (1.08 mmol) was added dropwise and the resulting yellow solution was stirred 18 h at room temperature. TLC analysis indicated complete reaction. The reaction mixture was concentrated in vacuo to give a deep yellow oil. The product ether was purified over silica eluting with ethyl acetate to 9:1 ethyl acetate:methanol to yield 0.298 g (0.48 mmol, 89%) of (S)-3-[4-acetylamino-2-((R)-2-indazol-1-yl-1-methyl-ethoxy)-benzenesulfonylamino]-4,4-diethoxy-butyric acid tert-butyl ester as a colorless foam.

MS (APCI) m/z 617.2 (M–1).

Synthesis of (S)-2-Indazol-1-yl-1-methyl-ethanol

A mixture of 0.5 g (4.23 mmol) indazole, 0.3 mL (S)-propylene oxide (4.4 mmol), 0.53 g potassium t-butoxide (4.3 mmol) and 15 mL of 25:1 t-BuOH:THF was stirred in a sealed tube at 70° C. overnite. The solvent was removed in vacuo, 50 mL ethyl acetate was added to the residue, the mixture was filtered, concentrated and the residue purified by chromatography over silica eluting with 1:1 EtOAc:hexanes to yield 0.250 g (1.42 mmol, 67%) of the title compound as a viscous oil. MS (APCI) m/z 177 (M+1).

Step 10: N-[3-((R)-2-Indazol-1-yl-1-methyl-ethoxy)-4-(2-ethoxy-5-oxo-tetrahydro-furan-3-ylsulfamoyl)-phenyl]-acetamide 0.298 g (0.48 mmol) (S)-3-[4-acetylamino-2-((R)-2-indazol-1-yl-1-methyl-ethoxy)-benzenesulfonylamino]-4,4-diethoxy-butyric acid tert-butyl ester was stirred in 15 mL of a 3:1 mixture of dichloromethane:trifluoroacetic acid at room temperature 2 h. TLC analysis indicated complete reaction. The solvent was removed in vacuo to give an oil. The product was partitioned between 75 mL ethyl acetate and 75 mL saturated sodium hydrogen carbonate. The layers were separated, the aqueous layer was washed with ethyl acetate. The combined organic extracts were washed with brine, and concentrated in vacuo. The product was purified over silica eluting with 95:5 ethyl acetate:methanol to give 0.162 g product. The product was triturated with ether, filtered and dried at 40° C. 18 hr to give 0.118 g (0.228 mmol, 47%) of N-[3-((R)-2-indazol-1-yl-1-methyl-ethoxy)-4-(2-ethoxy-5-oxo-tetrahydro-furan-3-ylsulfamoyl)-phenyl]-acetamide as a white solid. Analysis calculated for $C_{24}H_{28}N_4O_7S$ (516.577): C, 55.80; H, 5.46; N, 10.85. Found: C, 55.82; H, 5.52; N, 10.37.

Step 11: 3-[4-Acetylamino-2-((R)-2-indazol-1-yl-1-methyl-ethoxy)-benzenesulfonylamino]-4-oxo-butyric acid hydrochloric acid salt 0.103 g (0.199 mmol) N-[3-((R)-2-Indazol-1-yl-1-methyl-ethoxy)-4-(2-ethoxy-5-oxo-tetrahydro-furan-3-ylsulfamoyl)-phenyl]-acetamide was stirred in 10 mL of a mixture of 1:1 5% HCl (aq):acetonitrile at room temperature 18 hr. TLC analysis indicated complete reaction. The solvent was removed under a nitrogen flow for 5 hr. The yellow residue was triturated with a 2:1 mixture of acetone:ether. The precipitate was filtered and dried at 35° C. 18 hr to yield 0.059 g (0.113 mmol, 65.5%) of 3-[4-acetylamino-2-((R)-2-indazol-1-yl-1-methyl-ethoxy)-benzenesulfonylamino]-4-oxo-butyric acid hydrochloric acid salt. Analysis calculated for $C_{22}H_{24}N_4O_7S.0.91$ HCl (521.70): C, 50.33; H, 4.80; N, 10.67. Found: C, 50.27; H, 5.01; N, 10.40.

EXAMPLE 92

(S)-3-[4-Acetylamino-2-(2-methyl-butoxy)-benzenesulfonylamino]-4-oxo-butyric acid Route J, white solid (86 mg, 64%). MS (APCI) m/z 399 (M−1).

EXAMPLE 93

(S)-3-(2-{2-[3-(2-Dimethylamino-ethylcarbamoyl)-naphthalen-1-yl]-ethoxy}-benzenesulfonylamino)-4-oxo-butyric acid Route M, but employing (S)-3-(2-hydroxybenzenesufonylamino)-4,4-diethoxy-butryric acid tert-butyl ester and ethyl 4-(2-hydroxyethyl)-naphthalene-2-carboxylate as starting materials, white solid (88 mg, 97%). MS (APCI) m/z 540 (M−1).

Synthesis of (S)-3-(2-hydroxybenzenesulfonylamino)-4,4-diethoxy-butyric acid tert-butyl ester employed in the synthesis of (S)-3-(2-{2-[3-(2-Dimethylamino-ethylcarbamoyl)-naphthalen-1-yl]-ethoxy}-benzenesulfonylamino)-4-oxo-butyric acid.

Step 1: (S)-3-(2-Benzyloxybenzenesulfonylamino)-4,4-diethoxy-butyric acid tert-butyl ester 2-Benzyloxy-benzenesulfonyl chloride (see Example 23, step 1) (1.7 g, 6 mmol) and (S)-3-amino-4,4-diethoxy-butyric acid tert-butyl ester (see Example 93) (1.5 g, 6 mmol) and pyridine (1.9 g, 30 mmol) were dissolved in chloroform (150 mL) and stirred at room temperature for 3 days. The reaction was diluted with ethyl acetate (500 mL) and washed with 5% citric acid, sat. sodium bicarbonate, and sat. sodium chloride. The organic layer was then dried over anhydrous sodium sulfate, filtered, and concentrated. Purification by flash chromatography ($SiO_2$, hexane:ethyl acetate, 8:1, then 4:1) gave the desired product (2.7 g, 91%) as a colorless oil. $^1$H NMR (400 MHz) $CDCl_3$ δ 7.92 (m, 1H), 7.52 (d, 2H), 7.47 (t, 1H), 7.40 (t, 2H), 7.34 (d, 1H), 7.04 (t, 2H), 5.61 (d, 1H), 5.23 (q, 2H), 4.30 (d, 1H), 3.77 (m, 1H), 3.47 (m, 2H), 3.36 (m, 1H), 3.15 (m, 1H), 2.45 (t, 2H), 1.37 (s, 9H), 1.02 (t, 3H), 0.92 (t, 3H).

Step 2: (S)-3-(2-Hydroxybenzenesulfonylamino)-4,4-diethoxy-butyric acid tert-butyl ester (S)-3-(2-Benzyloxybenzenesulfonylamino)-4,4-diethoxy-butyric acid tert-butyl ester (863 mg, 1.75 mmol) was hydrogenated (see Example 96, step 8) to give the desired product (727 mg, 104%) as a colorless oil. $^1$H NMR (400 MHz) $CDCl_3$ δ 8.68 (m, 1H), 7.68 (d, 1H), 7.45 (t, 1H), 7.01 (d, 1H), 6.98 (d, 1H), 5.54 (d, 1H), 4.34 (d, 1H), 3.73 (m, 1H), 3.58 (m, 2H), 3.44 (m, 1H), 3.28 (m, 1H), 2.48 (t, 2H), 1.42 (s, 9H), 1.13 (t, 3H), 1.08 (t, 3H).

Synthesis of Ethyl 4-(2-hydroxyethyl)-naphthylene-2-carboxylate employed in the synthesis of (S)-3-(2-{2-[3-(2-Dimethylamino-ethylcarbamoyl)-naphthalen-1-yl]-ethoxy}-benzenesulfonylamino)-4-oxo-butyric acid.

Step 1: 3-Amino-4-bromo-2-naphthylene carboxylic acid

3-Amino-2-naphthylene carboxylic acid (9.4 g, 50 mmol) was dissolved in $CHCl_3$ (250 mL) and bromine (2.7 mL, 53 mmol) in $CHCl_3$ (50 mL) was added dropwise over ~20 min. The reaction was further stirred for 2 h and was complete by HPLC. The reaction mixture was filtered and washed with $Et_2O$ and $CHCl_3$ to yield a crude brown solid. This solid was then dissolved in 1N NaOH and then re-acidified with HOAc until acidic (pH ~4–5). A yellow-brown-green solid precipitated and was collected by filtration. This solid was recrystallized from EtOH to yield (4.6 g, 34%) of a green-gold solid. $^1$H NMR (400 MHz) DMSO 8.55 (s, 1H), 7.89 (d, 1H), 7.84 (d, 1H), 7.59 (t, 1H), 7.26 (t, 1H).

Step 2: Methyl 4-bromo-2-naphthylene carboxylate

3-Amino-4-bromo-2-naphthylene carboxylic acid (6.8 g, 26 mmol) as a slurry in HOAc (50 mL) was added slowly in portions to a solution of $NaNO_2$ (2.2 g, 31 mmol) in $H_2SO_4$ (25 mL) and HOAc (25 mL) at 0° C. The reaction was then warmed to 10–15° C. and stirred for 3 h. This reaction mixture was then slowly added to a suspension of $CuO_2$ (11 g, 77 mmol) in MeOH (150 mL). (Caution, the reaction fizzed violently.) The reaction was heated at 55° C. for 1 h more, then cooled to room temperature and filtered through celite to remove copper salts. The reaction mixture was concentrated to remove MeOH and then diluted with EtOAc, washed with $H_2O$, and saturated NaCl. The organic layer was then dried over $Na_2SO_4$, filtered and concentrated.

The crude acid was then dissolved in MeOH (100 mL) and $H_2SO_4$ (2 mL) and then refluxed for 5 h. The reaction was concentrated to remove MeOH and then dissolved in EtOAc (400 mL) and washed with 1N NaOH (50 mL), 5% citric acid (50 mL), and sat. NaCl (50 mL). The organic layer was then dried over anh. $Na_2SO_4$, filtered and concentrated to yield a yellow oil (5.0 g, 73%) $^1$H NMR (400 MHz) $CDCl_3$ 8.55 (s, 1H), 8.36 (s, 1H), 8.26 (d, 1H), 7.94 (d, 1H), 7.70 (t, 1H), 7.60 (t, 1H), 3.99 (s, 3H)

Step 3: Ethyl 4-(2-hydroxyethyl)-naphthylene-2-carboxylate

Methyl 4-bromo-2-naphthylene carboxylate was converted to the title compound as previously described in Route M for the synthesis of 4-(2-hydroxyethyl)-naphthalene-1-carboxylic acid methyl ester to yield the product as colorless oil (362 mg, 63%) $^1$H NMR (400 MHz) $CDCl_3$ δ 8.52 (s, 1H), 8.09 (d, 1H), 7.98 (d, 1H), 7.97 (s, 1H), 7.64 (t, 1H), 7.56 (t, 1H), 4.44 (q, 2H), 4.03 (t, 2H), 3.40 (t, 2H),1.45 (t, 3H).

EXAMPLE 94

N1-(3-(((1R)-2-(1H-Benzo[d]imidazol-1-yl)-1-methylethyl)oxy)-4-(((2-ethoxy-5-oxotetrahydro-3-furanyl)amino)sulfonyl)phenyl)acetamide Route J, (90 mg), RP-HPLC (100%, pH 4.5 50 mM ammonium acetate to 100% $CH_3CN$ in 4.5 minutes with a 0.5 minute hold at 3.5 mL/min using a Perkin Elmer Pecosphere 3 μm C18 (33×4.6 mm) column) 2.02 min, MS m/z 517 (M+1).

Synthesis of (S)-Benzimidazol-1-yl-1-methyl-ethanol employed in the synthesis of N1-(3-(((1R)-2-(1H-benzo[d]imidazol-1-yl)-1-methylethyl)oxy)-4-(((2-ethoxy-5-oxotetrahydro-3-furanyl)amino)sulfonyl)phenyl)acetamide. To a mixture of benzimidazole (40 mg, 0.34 mmol) and potassium carbonate (50 mg, 0.36 mmol) in dimethylformamide (2 mL) was added S-propylene oxide (200 uL, 2.8 mmol). This mixture was mixed on a shaker for 4 days at room temperature. The reaction mixture was filtered and the solvent evaporated to give (S)-benzimidazol-1-yl-1-methyl-ethanol (57 mg, 94%) of sufficient purity for further use MS m/z 177 (M+1).

EXAMPLE 95
3-[(4-(Acetylamino)-2-[(1R)-2-(1H-benzo[d]imidazol-1-yl)-1-methylethyl]oxyphenyl)sulfonyl]amino-4-oxobutanoic acid Route J, as an off white solid 65 mg, MS m/z 489 (M+1).

EXAMPLE 96
N1-(3-[(1R)-2-(5,6-Dimethyl-1H-benzo[d]imidazol-1-yl)-1-methylethyl]oxy-4-[(2-ethoxy-5-oxotetrahydro-3-furanyl)amino]sulfonylphenyl)acetamide Route J, MS m/z 545 (M+1).

(2S)-1-(5,6-Dimethyl-1H-benzo[d]imidazol-1-yl)propan-2-ol employed in the synthesis of N1-(3-[(1R)-2-(5,6-dimethyl-1H-benzo[d]imidazol-1-yl)-1-methylethyl]oxy-4-[(2-ethoxy-5-oxotetrahydro-3-furanyl)amino]sulfonylphenyl)acetamide was synthesized in a manner analogous to that used for (S)-benzimidazol-1-yl-1-methyl-ethanol, MS m/z 205 (M+1).

EXAMPLE 97
(S)-3-[4-(2-Dimethylamino-ethylcarbamoyl)-2-((R)-2-isoquinolin-4-yl-1-methyl-ethoxy)-benzenesulfonylamino]-4-oxo-butyric acid Route P, yellow solid (54 mg), MS(APCI) m/z 557.1 (M+1).

EXAMPLE 98
N1-[4-[(2-Ethoxy-5-oxotetrahydro-3-furanyl)amino]sulfonyl-3-((1R)-1-methyl-2-[2-(1,3-thiazol-4-yl)-1H-benzo[d]imidazol-1-yl]ethyloxy)phenyl]acetamide Route J, MS m/z 600 (M+1).

(2S)-1-[2-(1,3-Thiazol-4-yl)-1H-benzo[d]imidazol-1-yl]propan-2-ol employed in the synthesis of N1-[4-[(2-ethoxy-5-oxotetrahydro-3-furanyl)amino]sulfonyl-3-((1R)-1-methyl-2-[2-(1,3-thiazol-4-yl)-1H-benzo[d]imidazol-1-yl]ethyloxy)phenyl]acetamide was synthesized in a manner analogous to that used for (S)-benzimidazol-1-yl-1-methyl-ethanol, MS m/z 260 (M+1).

EXAMPLE 99
N1-4-[(2-Ethoxy-5-oxotetrahydro-3-furanyl)amino]sulfonyl-3-[((1R)-2-2-[(imidazo[2,1-b][1,3]thiazol-6ylmethyl)sulfanyl]-1H-benzo[d]imidazol-1-yl-1-methylethyl)oxy]phenylacetamide Route J, MS m/z 685 (M+1).

(2S)-1-2-[(Imidazo[2,1-b][1,3]thiazol-5-ylmethyl)sulfanyl]-1H-benzo[d]imidazol-1-ylpropan-2-ol emplyed in the synthesis of N1-4-[(2-ethoxy-5-oxotetrahydro-3-furanyl)amino]sulfonyl-3-[((1R)-2-2-[(imidazo[2,1-b][1,3]thiazol-6-ylmethyl)sulfanyl]-1H-benzo[d]imidazol-1-yl-1-methylethyl)oxy]phenylacetamide was synthesized in a manner analogous to that used for (S)-benzimidazol-1-yl-1-methyl-ethanol, MS m/z 345 (M+1).

EXAMPLE 100
3-([4-(acetylamino)-2-((1R)-1-methyl-2-[2-(1,3-thiazol-4-yl)-1H-benzo[d]imidazol-1-yl]ethyloxy)phenyl]sulfonylamino)-4-oxobutanoic acid Route J, MS m/z 572 (M+1).

(2S)-1-[2-(1,3-Thiazol-4-yl)-1H-benzo[d]imidazol-1-yl]propan-2-ol) employed in the synthesis of 3-([4-(acetylamino)-2-((1R)-1-methyl-2-[2-(1,3-thiazol-4-yl)-1H-benzo[d]imidazol-1-yl]ethyloxy)phenyl]sulfonylamino)-4-oxobutanoic acid was synthesized in a manner analogous to that used for (S)-benzimidazol-1-yl-1-methyl-ethanol, MS m/z 260 (M+1)

EXAMPLE 101
3-[4-(acetylamino)-2-[((1,R)-2-2-[(imidazo[2,1-b][1,3]thiazol-6-ylmethyl)sulfanyl]-1H-[d]imidazol-1-yl-1-methylethyl)oxy]phenylsulfonyl)amino]-4-oxobutanoic acid Route J, MS m/z 657 (M+1).

(2S)-1-2-[(Imidazo[2,1-b][1,3]thiazol-5-ylmethyl)sulfanyl]-1H-benzo[d]imidazol-1-ylpropan-2-ol employed in the synthesis of 3-[(4-(acetylamino)-2-[((1R)-2-2-[(imidazo[2,1-b][1,3]thiazol-6-ylmethyl)sulfanyl]-1H-benzo[d]imidazol-1-yl-1-methylethyl)oxy]phenylsulfonyl)amino]-4-oxobutanoic acid was synthesized in a manner analogous to that used for (S)-benzimidazol-1-yl-1-methylethanol, MS m/z 345 (M+1).

EXAMPLE 102
3-[4-(acetylamino)-2-((1R)-2-[2-(4-methoxyanilino)-1H-benzo[d]imidazol-1-yl]-1-methylethyloxy phenyl]sulfonylamino)-4-oxobutanoic acid Route J, MS m/z 610 (M+1).

(2S)-1-[2-(4-Methoxyanilino)-1H-benzo[d]imidazol-1-yl]propan-2-ol employed in the synthesis of 3-([4-(acetylamino)-2-((1R)-2-[2-(4-methoxyanilino)-1H-benzo[d]imidazol-1-yl]-1-methylethyloxy)phenyl]sulfonylamino)-4-oxobutanoic acid was synthesized in a manner analogous to that used for (S)-benzimidazol-1-yl-1-methyl-ethanol, MS m/z 298 (M+1).

EXAMPLE 103
(S)-3-[4-((S)-1-Carboxy-ethylcarbamoyl)-2-(2-quinolin-5-yl-ethoxy)-benzenesulfonylamino]-4-oxo-butyric acid Route P, lyophilized as a white solid. MS(APCI) m/z 544.1 (M+1), 542.0 (M–1).

EXAMPLE 104
(S)-3-[2-((1R, 2S)-2-Benzoimidazol-1-yl-1-methyl-propoxy)-4-carbamoyl-benzenesulfonylamino]-4-oxo-butyric acid Route P, lyophilized as a white solid. MS(APCI) m/z 489.1 (M+1), 487.1 (M–1).

EXAMPLE 105
(S)-3-(2-{2-[3-(N',N'-Dimethyl-hydrazinocarbonyl)-naphthalen-1-yl]-ethoxy}-benzenesulfonylamino)-4-oxo-butyric acid Route M, except (S)-3-(2-hydroxybenzenesufonylamino)-4,4-diethoxy-butryric acid tert-butyl ester was employed as starting material (see Example 98) to yield after prep HPLC and lyophylization (52 mg, 60%) as a fluffy white solid. MS (APCI) m/z 512 (M–1).

EXAMPLE 106
(S)-3-[4-(2-Dimethylamino-1-methyl-ethylcarbamoyl)-2-(2-quinolin-5-yl-ethoxy-benzenesulfonylamino]-4-oxo-butyric acid Route P, colorless solid (169 mg), MS (APCI) m/z 557.2 (M+1).

EXAMPLE 107
N-{4-(2-Ethoxy-5-oxo-tetrahydro-furan-3-ylsulfamoyl)-3-[(R)-2-(5-fluoro-benzimidazol-1-yl)-1-methyl-ethoxy]-phenyl}-acetamide Route J, a white solid, MS (APCI) m/z 535.1 (M+1). Analysis calculated for $C_{24}H_{27}N_4O_7S$ (534.568): C, 53.93; H, 5.09; N, 10.48. Found: C, 54.10; H, 5.26; N, 9.60.

(S)-2-(5-fluoro-benzimidazol-1-yl)-1-methyl-ethanol employed in the synthesis of N-{4-(2-ethoxy-5-oxo-tetrahydro-furan-3-ylsulfamoyl)-3-[(R)-2-(5-fluoro-benzimidazol-1-yl)-1-methyl-ethoxy]-phenyl}-acetamide was synthesized via the method used for (S)-1-methyl-2-(6-methyl-benzimidazol-1-yl)-ethanol giving a clear viscous oil MS (APCI) m/z 195.1 (M+1).

EXAMPLE 108
N-[3-[(R)-2-(5-Bromo-benzimidazol-1-yl)-1-methyl-ethoxy]-4-(2-ethoxy-5-oxo-tetrahydro-furan-3-ylsulfamoyl)-phenyl]-acetamide Route J, a white solid, MS (APCI) m/z 596 (M, 100% abundance), 598 (M+2, 98% abundance).

(S)-2-(5-Bromo-benzimidazol-1-yl)-1-methyl-ethanol employed in the synthesis of N-[3-[(R)-2-(5-bromo-benzimidazol-1-yl)-1-methyl-ethoxy]-4-(2-ethoxy-5-oxo-tetrahydro-furan-3-ylsulfamoyl)-phenyl]-acetamide was synthesized via the method used for (S)-1-methyl-2-(6-methyl-benzimidazol-1-yl)-ethanol giving a tan solid. MS (APCI) m/z 255 (M, 100% abundance), 257 (M+2, 98% abundance).

EXAMPLE 109
N-{4-(2-Ethoxy-5-oxo-tetrahydro-furan-3-ylsulfamoyl)-3-[(R)-1-methyl-2-(5-trifluoromethyl-benzimidazol-1-yl)-ethoxy]-phenyl}-acetamide Route J, a white solid, MS (APCI) m/z 585 (M+1).

(S)-1-Methyl-2-(5-trifluoromethyl-benzimidazol-1-yl)-ethanol employed in the synthesis of N-{4-(2-ethoxy-5-oxo-tetrahydro-furan-3-ylsulfamoyl)-3-[(R)-1-methyl-2-(5-trifluoromethyl-benzimidazol-1-yl)-ethoxy]-phenyl}-acetamide was synthesized via the method used for (S)-1-methyl-2-(6-methyl-benzimidazol-1-yl)-ethanol giving a white solid. MS (APCI) m/z 245.1 (M+1).

EXAMPLE 110
N-[3-[(R)-2-(6-Chloro-benzimidazol-1-yl)-1-methyl-ethoxy]-4-(2-ethoxy-5-oxo-tetrahydro-furan-3-ylsulfamoyl)-phenyl]-acetamide Route J, a white solid, MS (APCI) m/z 551 (M, 100% abundance), 553 (M+2, 33% abundance).

(S)-2-(5-Chloro-imidazo[4,5-b]pyridin-3-yl)-1-methyl-ethanol employed in the synthesis of N-[3-[(R)-2-(6-chloro-benzimidazol-1-yl)-1-methyl-ethoxy]-4-(2-ethoxy-5-oxo-tetrahydro-furan-3-ylsulfamoyl)-phenyl]-acetamide was synthesized via the method used for (S)-1-methyl-2-(6-methyl-benzimidazol-1-yl)-ethanol giving a tan solid. MS (APCI) m/z 212 (M, 100% abundance), 214 (M+2, 33% abundance).

EXAMPLE 111
N-[3-[(R)-2-(5-Acetyl-benzimidazol-1)-yl)-1-methyl-ethoxy]-4-(2-ethoxy-5-oxo-tetrahydro-furan-3-ylsulfamoyl)-phenyl]-acetamide Route J, a white solid, MS (APCI) m/z 559.1 (M+1).

(S)-2-(5-Acetyl-benzimidazol-1-yl)-1-methyl-ethanol employed in the synthesis of N-[3-[(R)-2-(5-acetyl-benzimidazol-1-yl)-1-methyl-ethoxy]-4-(2-ethoxy-5-oxo-tetrahydro-furan-3-ylsulfamoyl)-phenyl]-acetamide was synthesized via the method used for (S)-1-Methyl-2-(6-methyl-benzimidazol-1-yl)-ethanol giving a white solid. MS (APCI) m/z 219.1 (M+1).

EXAMPLE 112
3-{4-Acetylamino-2-[(R)-2-(5-fluoro-benzimidazol-1-yl)-1-methyl-ethoxy]-benzenesulfonylamino}-4-oxo-butyric acid hydrochloric acid salt Route J, a white solid, MS (APCI) m/z 507.1 (M+1).

EXAMPLE 113
3-{4-Acetylamino-2-[(R)-2-(5-bromo-benzimidazol-1-yl)-1-methyl-ethoxy]-benzenesulfonylamino}-4-oxo-butyric acid Route J. Analysis calculated for $C_{22}H_{23}N_4O_7SBr.0.88$ HCl (599.496): C, 44.08; H, 4.01; N, 9.35. Found: C, 44.45; H, 4.23; N, 8.88.

(S)-1-(5-Bromo-benzoimidazol-1-yl)-propan-2-ol employed in the synthesis of 3-{4-acetylamino-2-[(R)-2-(5-bromo-benzoimidazol-1-yl)-1-methyl-ethoxy]-benzenesulfonylamino}-4-oxo-butyric acid was synthesized by Route I, MS (APCI) m/z 255 (M, 91% abundance), 257 (M+2, 100% abundance).

EXAMPLE 114
3-{4-Acetylamino-2-[(R)-1-methyl-2-(5-trifluoromethyl-benzoimidazol-1-yl)-ethoxy]-benzenesulfonylamino}-4-oxo-butyric acid Route J. Analysis calculated for $C_{23}H_{23}N_4O_7SF_3.1.43$ HCl (608.65): C, 45.39; H, 4.05; N, 9.21. Found: C, 45.78; H, 4.24; N, 8.64.

(S)-1-(5-Trifluoromethyl-benzoimidazol-1-yl)-propan-2-ol employed in the synthesis of 3-{4-acetylamino-2-[(R)-1-methyl-2-(5-trifluoromethyl-benzoimidazol-1-yl)-ethoxy]-benzenesulfonylamino}-4-oxo-butyric acid was synthesized by Route I, MS (APCI) m/z 245.1 (M+1).

EXAMPLE 115
3-{4-Acetylamino-2-[(R)-2-(6-chloro-benzoimidazol-1-yl)-1-methyl-ethoxy]-benzenesulfonylamino}-4-oxo-butyric acid Route J. Analysis calculated for $C_{24}H_{26}N_4O_8S.2.5$ HCl (620.61): C, 46.45; H, 4.62; N, 9.03. Found: C, 46.07; H, 4.91; N, 9.34.

(S)-1-(6-Chloro-benzoimidazol-1-yl)-propan-2-ol employed in the synthesis of 3-{4-acetylamino-2-[(R)-2-(6-chloro-benzoimidazol-1-yl)-1-methyl-ethoxy]-benzenesulfonylamino}-4-oxo-butyric acid was synthesized by Route I; MS (APCI) m/z 211 (M, 100% abundance), 213 (M+2, 33% abundance).

EXAMPLE 116
3-[4-(2-Dimethylamino-ethylcarbamoyl)-2-((1R,2R)-1-methyl-2-naphthalen-1-yl-propoxy)-benzenesulfonylamino]-4-oxo-butyric acid Route P, MS (APCI) m/z 570 (M+1).

EXAMPLE 117
3-{4-Acetylamino-2-[2-(2-oxo-1,2-dihydro-quinolin-5-yl)-ethoxy]-benzenesulfonylamino}-4-oxo-butyric acid Synthesized via Route J, except an intermediate benzyl ether deprotection step was required: The benzyl ether was dissolved in ethanol, Pd/C, and treated with hydrogen. The solution was filtered, and the solvent stripped off. The product was chromatographed on silica with a gradient 5% (8:1 ethanol/ammonium hydroxide)/methylene chloride and going to 10% (8:1 ethanol/ammonium hydroxide)/methylene chloride to give 0.025 g of desired material. NMR (CDCl$_3$): 10.8 (1H, br), 8.15–8.13 (1H, d, J=9.9 Hz), 7.8–7.7 (2H, m), 7.6–7.4 (2H, m), 7.3–7.2(2H, m), 6.8–6.6 (2H, m), 5.68–5.66 1 h, d, J=8.0 Hz), 4.4–4.2 (3H, m), 3.8–3.2 (8H, m), 2.4 (2H, d, J=6.5 Hz), 2.19 (3H, s), 1.39 (9H, s), 1.1–1.05 (3H, t, J=7.0 Hz), 1.0–0.95 (3H, t, J=7.0 Hz). MS m/z 630(M+1). 3-{4-Acetylamino-2-[2-(2-oxo-1,2-dihydro-quinolin-5-yl)-ethoxy]-benzenesulfonylamino}-4-oxo-butyric acid was isolated as a white solid MS m/z 502(M+1).

Synthesis of (2-benzyloxy-quinolin-5-yl)-ethanol employed in the synthesis of 3-{4-acetylamino-2-[2-(2-oxo-1,2-dihydro-quinolin-5-yl)-ethoxy]-benzenesulfonylamino}-4-oxo-butyric acid.

Step 1: (2-Benzyloxy-quinolin-5-yl)-acetic acid methyl ester
(2-Chloroquinolin-5-yl)-acetic acid methyl ester (0.198 g, 1.01 mmol), whose synthesis was previously described, and benzyl alcohol (0.722 g, 6.67 mmol) were dissolved in anhydrous THF, and NaH (60% in oil, 0.244 g, 6.10 mmol) was added. The reaction was stirred at room temperature overnight. The solution was poured into ethyl acetate and water and the layers were separated. The organic layer was washed twice with water, then washed with brine, dried over magnesium sulfate, filtered and rotovapped to give the excess starting benzyl alcohol. The basic aqueous layer was acidified with 5% citric acid solution and extracted three times with ethyl acetate. The combined organic layers were washed with brine, dried over magnesium sulfate, filtered and rotovapped. The crude product was dissolved in ether and treated with freshly prepared diazomethane (14 mmol) in ether. The diazomethane solution was treated with acetic acid (1 mL). The solvent was stripped off, toluene was added and stripped off. Traces of toluene were removed by azeotroping with acetonitrile. (2-Benzyloxy-quinolin-5-yl)-acetic acid methy ester was used without further purification. MS m/z 308 (M+1).

Step 2: (2-Benzyloxy-quinolin-5-yl)-ethanol (2-Benzyloxy-quinolin-5-yl)-acetic acid methyl ester (0.198 g, 0.64 mmol) was dissolved in 10 mL of anhydrous ether, and cooled to −10° C. Lithium aluminum hydride (1.0M solution in ether, 0.5 mL, 0.5 mmol) was added and stirred at −10° C. for 1 h. The reaction was quenched with 0.5 mL water, then 0.5 mL 15% NaOH, then 1.5 mL water. A solution of Na, K tartrate was added to help solublized the salts. Ethyl acetate was added and the layers were separated. The aqueous layer was washed with ethyl acetate. The combined organic layers were washed with brine, dried over magnesium sulfate, filtered, and rotovapped. (2-Benzyloxy-quinolin-5-yl)-ethanol (0.140 g, 78%) was used without further purification. MS m/z 280 (M+1).

EXAMPLE 118

N1-[4-[(2-Ethoxy-5-oxotetrahydro-3-furanyl)amino] sulfonyl-3-((1R)-1-methyl-2-[2-(methylsulfanyl)-1H-benzo [d]imidazol-1-yl]ethyloxy)phenyl]acetamide Route J, MS m/z 563 (M+1).

(2S)-1-[2-(Methylsulfanyl)-1H-benzo[d]imidazol-1-yl] propan-2-ol employed in the synthesis of N1-[4-[(2-ethoxy-5-oxotetrahydro-3-furanyl)amino]sulfonyl-3-((1R)-1-methyl-2-[2-(methylsulfanyl)-1H-benzo[d]imidazol-1-yl] ethyloxy)phenyl]acetamide was synthesized via the method used for (S)-benzimidazol-1-yl-1-methyl-ethanol, MS m/z 223 (M+1).

EXAMPLE 119

N1-[4-[(2-Ethoxy-5-oxotetrahydro-3-furanyl)amino] sulfonyl-3-((1R)-1-methyl-2-[2-(2-thienyl)-1H-benzo[d] imidazol-1-yl]ethyloxy)phenyl]acetamide Route J, MS m/z 599 (M+1).

(2S)-1-[2-(2-Thienyl)-1H-benzo[d]imidazol-1-yl]propan-2-ol employed in the synthesis of N1-[4-[(2-ethoxy-5-oxotetrahydro-3-furanyl)amino]sulfonyl-3-((1R)-1-methyl-2-[2-(2-thienyl)-1H-benzo[d]imidazol-1-yl]ethyloxy) phenyl]acetamide was synthesized via the method used for (S)-benzimidazol-1-yl-1-methyl-ethanol, RP-HPLC 6.55 min (10 to 90% acteonitrile in 0.1N aqueous ammonium acetate over 10 min at 2 mL/min using a Waters Symmetry C18, 150×4.6 mm column).

EXAMPLE 120

N1-[4-[(2-Ethoxy-5-oxotetrahydro-3-furanyl)amino] sulfonyl-3-((1R)-2-[2-(2-furyl)-1H-benzo[d]imidazol-1-yl]-1-methylethyloxy)phenyl]

Route J, MS m/z 583 (M+1).

(2S)-1-[2-(2-Furyl)-1H-benzo[d]imidazol-1-yl]propan-2-ol employed in the synthesis of N1-[4-[(2-ethoxy-5-oxotetrahydro-3-furanyl)amino]sulfonyl-3-((1R)-2-[2-(2-furyl)-1H-benzo[d]imidazol-1-yl]-1-methylethyloxy) phenyl] was prepared via the method used for (S)-benzimidazol-1-yl-1-methyl-ethanol, MS m/z 243 (M+1).

EXAMPLE 121

3-(4-Acetylamino-2-{2-[4-(N',N'-dimethyl-hydrazinocarbonyl)-naphthalen-1-yl]-ethoxy}-benzenesulfonylamino)-4-oxo-butyric acid Route M.

Synthesis of: 4-(2-hydroxyethyl-naphthlene-1-carboxylic acid methyl ester employed in the synthesis of 3-(4-acetylamino-2-{2-[4-(N',N'-dimethyl-hydrazinocarbonyl)-naphthalen-1-yl]-ethoxy}-benzenesulfonylamino)-4-oxo-butyric acid Step 1: 4-Bromo-naphthylene-1-carboxylic acid 1-Bromo-4-methyl-naphthalene (20.0 g, 90.4 mmol), sodium dichromate dihydrate (94 g, 0.32 mol) and water (180 mL) were sealed in a 2 L Parr bottle, stirred and heated to 250° C. for 10 h. The green sludge was rinsed from the reaction with $H_2O$. The green hydrated chromium oxide in the reaction mixture was separated on a large Buchner funnel and washed with warm water until the filtrate was colorless. The combined filtrates were acidified with 6N HCl. The acidified mixture was allowed to cool to room temperature. The 1-bromo-4-naphthoic acid that precipitated was collected on a large Buchner funnel, washed with water until colorless, and dried to constant weight on vacuum pump to yield 8.6 g white paste (38%). MS m/z 250.9 (M−1) $^1$HNMR (400 MHz, $CD_3OD$) 8.96(dd, 1H), 8.32(dd, 1H), 8.05(d, 1H), 7.85(d, 1H), 7.67(dd, 2H).

Step 2: 4-Bromo-naphthalene-1-carboxylic acid methyl ester

To a solution of 4-Bromo-naphthylene-1-carboxylic acid (8.6 g, 34.3 mmol) in MeOH (175 mL) at room temperature was added concentrated sulfuric acid (3.5 mL). The reaction was heated to reflux for 7 h. The reaction was then cooled to room temperature and the methanol partially evaporated. The reaction mixture was diluted with 300 mL $H_2O$. The dilution was extracted with ethyl acetate and then with ether. The organic extractions were combined and washed with saturated sodium bicarbonate and brine, dried over $MgSO_4$, filtered and concentrated to yield 8.86 g of a light yellow liquid (97%). $^1$H NMR (400 mHz) $CDCl_3$ 8.86 (m, 1H), 8.31 (m, 1H), 7.98 (d, 1H), 7.87 (d, 1H), 7.66 (m, 2H), 3.97 (s, 3H).

Step 3: 4-Allylnaphthalene-1-carboxylic acid methyl ester

To a solution of 4-bromo-naphthalene-1-carboxylic acid methyl ester (2.0 g, 7.9 mmol) in toluene (20 mL) was added allyltributyltin (2.7 mL), tetrakis(triphenylphosphine) palladium(0) (183 mg, 0.16 mmol) and 2 crystals of BHT. The system was purged under vacuum and nitrogen and allowed to heat to 120° C. under $N_2$ for 4 h. TLC analysis (silica, 1:1 ethyl acetate-hexanes) showed the reaction to be completed with only one new fluorescent spot present. The mixture was diluted with ether, washed with $H_2O$, 10% HCl, and then saturated sodium bicarbonate, dried over magnesium sulfate, filtered, and concentrated under reduced pressure. The crude product was purified by flash chromatography ($SiO_2$, 9:1 hexanes-ether) to give (1.6 g, 89%) 4-allylnaphthalene-1-carboxylic acid methyl ester as a colorless liquid. MS m/z 227.1 (M+1). $^1$H NMR (400 mHz) $CDCl_3$ 8.95(d 1H), 8.11(d, 1H), 8.08(d, 1H), 7.58(m, 2H), 7.37(d, 1H), 6.09(m, 1H), 5.11(m, 2H), 3.99(s, 3H), 3.88(d, 2H).

Step 4: 4-(2-Hydroxyethyl)-naphthlene-1-carboxylic acid methyl ester

4-Allylnaphthalene-1-carboxylic acid methyl ester was dissolved in a 1:1 mixture of $CH_2Cl_2$ and MeOH and cooled in an ice bath to −78° C. Ozone was bubbled into the solution for 15 minutes. The appearance of a light yellow tint to the colorless solution indicated a reaction had occurred. Sodium borohydride (0.53 g, 14 mmol) was then added and the flask removed from the ice bath. The solution was allowed to slowly warm to room temperature. The reaction was diluted with 10% sulfuric acid and was extracted into methylene chloride. The organic extracts were combined and washed with $H_2O$, brine, and then dried over magnesium sulfate, filtered, and concentrated to yield 1.4 g light yellow liquid. The crude product was purified by flash chromatography ($SiO_2$, 2:1 ethyl acetate-hexanes) to give (0.80 g, 49%) of 4-(2-hydroxyethyl)-naphthlene-1-carboxylic acid methyl ester as a colorless liquid. MS m/z 231.1 (M+1). $^1$H NMR (400 mHz) $CDCl_3$ 8.96(d, 1H), 8.10(d, 1H), 8.10(d, 1H), 7.60(m, 2H), 7.42(d, 1H), 4.02(t, 2H), 3.99(s, 3H), 3.40(t, 2H).

Step 1: 4-{2-[5-Acetylamino-2-(1-tert-butoxycarbonylmethyl-2,2-diethoxy-ethylsulfamoyl)-phenoxy]-ethyl}-naphthalene-1-carboxylic acid methyl ester Synthesized by the Mitsunobu reaction between (S)-3-(4-Acetylamino-2-benzyloxy-benzenesulfonylamino)-4,4-diethoxy-butyric acid tert-butyl ester from step 8 of Route J and 4-(2-hydroxyethyl)-naphthlene-1-carboxylic acid methyl ester from above. $^1$H NMR (400 MHz, $CD_3OD$) 8.96(d, 1H), 8.16(dd, 2H), 7.71(d, 2H), 7.61(m, 2H), 7.55(d, 1H), 6.69(d, 1H), 5.57(d, 1H), 4.42(t, 2H), 4.21(d, 1H), 3.98(s, 3H), 3.72(t, 2H) 3.62(m, 1H), 3.42(m, 2H), 3.40(m, 1H), 3.14(m, 1H), 2.37(d, 2H), 2.16(s, 3H), 1.37(s, 9H), 1.00(t, 3H), 0.90(t, 3H).

Step 2: 4-{2-[5-Acetylamino-2-(1-tert-butoxycarbonylmethyl-2,2-diethoxy-ethylsulfamoyl)-phenoxy]-ethyl}-naphthalene-1-carboxylic acid To a solution of 4-{2-[5-acetylamino-2-(1-tert-butoxycarbonylmethyl-2,2-diethoxy-ethylsulfamoyl)-phenoxy]-ethyl}-naphthalene-1-carboxylic acid methyl ester (0.97 g, 1.44 mmol) in THF (20 mL) was added 1M lithium hydroxide (3.2 mL, 3.2 mmol) and stirred at room temperature overnight. The reaction mixture was then diluted with ethyl acetate, acidified with 1M HCl (3.2 mL), and washed with $H_2O$, brine, dried over magnesium sulfate, filtered and concentrated under reduced pressure to yield (0.6 g, 0.91 mmol, 63%) of 4-{2-[5-acetylamino-2-(1-tert-butoxycarbonylmethyl-2,2-diethoxy-ethylsufamoyl)-phenoxy]-ethyl}-naphthalene-1-carboxylic acid as a white solid. MS m/z 657.2 (M−1).

Step 3: 3-(4-Acetylamino-2-{2-[4-(N',N'-dimethyl-hydrazinocarbonyl)-naphthalen-1-yl]-ethoxy}-benzenesulfonylamino)-4,4-diethyoxy-butyric acid tert-butyl ester To a solution of 4-{2-[5-acetylamino-2-(1-tert-butoxycarbonylmethyl-2,2-diethoxy-ethylsulfamoyl)-phenoxy]-ethyl}-naphthalene-1-carboxylic acid (0.28 g, 0.43 mmol), in freshly distilled tetrahydrofuran (5 mL) was added 4-methyl piperidine (0.16 mL, 1.28 mmol), 1-hydroxybenzotriazole (0.086 g, 0.64 mmol), 1,1-dimethylhydrazine (0.05 mL, 0.64 mmol), followed by (1-(3 dimethylaminopropyl)-3-ethylcarbodiimide hydrochloride (0.12 g, 0.64 mmol). The reaction was stirred overnight at room temperature. The reaction was then diluted with water. The dilution was extracted with ethyl acetate. The organic extracts were washed with brine, dried over magnesium sulfate, filtered, and concentrated under reduced pressure to yield 0.26 g yellow solid. The crude product was purified by flash chromatography ($SiO_2$, 1:1 ethyl acetate-acetone) to give (0.12 g, 0.17 mmol, 40%) of 3-(4-acetylamino-2-{2-[4-(N',N'-dimethyl-hydrazinocarbonyl)-naphthalen-1-yl]-ethoxy}-benzenesulfonylamino)-4,4-diethyoxy-butyric acid tert-butyl ester as a white solid. MS m/z 699.23 (M−1).

Step 4: 3-(4-Acetylamino-2-{2-[4-(N',N'-dimethyl-hydrazinocarbonyl)-naphthalen-1-yl]-ethoxy}-benzenesulfonylamino)-4-oxo-butyric acid 3-(4-Acetylamino-2-{2-[4-(N',N'-dimethyl-hydrazinocarbonyl)-naphthalen-1-yl]-ethoxy}-benzenesulfonylamino)-4,4-diethyoxy-butyric acid tert-butyl ester (0.12 g, 0.17 mmol) was stirred in 12 mL of a solution of 17% TFA in $CH_2Cl_2$ at room temperature for 2 h. Analytical HPLC indicated the reaction was complete. The reaction mixture was concentrated. Residual TFA was azeotroped with toluene. Half of the product was lyophilized to give (0.06 g, 54%). The second half of the crude product was stirred with 22 mL of a solution of 10% TFA in 1:1 acetonitrile/water for 16 h. Analytical HPLC indicated that reaction was complete. The reaction mixture was diluted with $H_2O$ and lyopholized. The crude product was purified by preparative-scale reverse phase HPLC (0 to 30% acetonitrile in $H_2O$ with 0.1% TFA over 2 h at 15 mL/min on Vydac #218TP152022-2.5×25 cm C18 column) and then lyophilized to give (0.035 g, 0.06 mmol, 36%) of 3-(4-Acetylamino-2-{2-[4-(N',N'-dimethyl-hydrazinocarbonyl)-naphthalen-1-yl]-ethoxy}-benzenesulfonylamino)-4-oxo-butyric acid as a fluffy white solid. MS m/z 571 (M+1).

EXAMPLE 122

3-(4-Acetylamino-2-{2-[4-(3-dimethylamino-propylcarbamoyl)-naphthalen-1-yl]-ethoxy}-benzenesulfonylamino)-4-oxo-butyric acid Synthesized employing N1,N1-dimethyl-1,3-propanediamine in step 3 of Route M giving the title compound as a fluffy white solid. The crude product was purified by preparative-scale reverse phase HPLC (0 to 30% acetonitrile in $H_2O$ with 0.1% TFA over 2 hrs at 15 mL/min on Vydac #218TP152022-2.5×25 cm C18 column) and lyophilized to give (0.06 g, 0.10 mmol, 27%). MS m/z 613.4 (M+1).

EXAMPLE 123

3-{4-Acetylamino-2-[(R)-1-methyl-2-(5-methylcarbamoyl-benzimidazol-1-yl)-ethoxy]-benzenesulfonylamino}-4-oxo-butyric acid hydrochloric acid salt Route J, a white solid. Analysis calculated for $C_{24}H_{27}N_5O_8S$.2.82 HCl (647.68): C, 44.46; H, 4.64; N, 10.80. Found: C, 44.06; H, 5.30; N, 11.16.

(S)-1-Methyl-2-(5-methylcarbamoyl-benzimidazol-1-yl)-ethanol employed in the synthesis of 3-{4-acetylamino-2-[(R)-1-methyl-2-(5-methylcarbamoyl-benzimidazol-1-yl)-ethoxy]-benzenesulfonylamino}-4-oxo-butyric acid hydrochloric acid salt was synthesized as follows: A mixture of 2.0 g (10.8 mmol) 4-fluoro-3-nitrobenzoic acid, 2.11 g (11 mmol) 1-(3-dimethylaminopropyl)-3-ethylcarbodiimide hydrochloride, and 25 mL dichloromethane was stirred at room temperature 15 min. Then, 5.42 mL (10.85 mmol) of a 2.0 M solution of methyl amine in tetrahydrofuran was added and the reaction mixture was stirred 3 days at room temperature. TLC analysis showed complete reaction. The reaction mixture was concentrated in vacuo, and the product purified over silica eluting with 9:1 ethyl acetate:methanol to yield 1.81 g (9.13 mmol, 84.6%) of the amide as a yellow solid. MS m/z 197.1 (M−1). A mixture of 1.81 g (9.1 mmol) amide, 0.8 mL (10 mmol) (S)-1-amino-2-propanol, 5 mL (39.3 mmol) N-ethylmorpholine, and 10 mL dimethylformamide was stirred at 60° C. 2 h. TLC analysis indicated reaction complete. The reaction mixture is concentrated in vacuo, partitioned between ethyl acetate and water. The aqueous layer is washed with ethyl acetate. The combined organic extracts were washed with brine, dried over anhydrous magnesium sulfate, filtered and concentrated in vacuo to give 2.3 g (9.13 mmol, 100%) of the nitro aniline alcohol as a yellow solid. MS m/z 254.1 (M+1). A mixture of 2.3 g (9.1 mmol) nitro aniline, 1.0 g Raney Ni, and 50 mL methanol was shaken under a 50 psig atmosphere of hydrogen for 20 min. TLC indicated complete reaction. The catalyst was filtered and the solvent was removed in vacuo to give a dark foam. The product was stirred at reflux in 50 mL 88% formic acid for 3 h. TLC analysis indicated complete reaction. The solvent was removed in vacuo and the residue was stirred in 50 mL 1 M sodium hydroxide for 1 h. The product was extracted with mixture of 2:1 chloroform:isopropyl alcohol. The combined organic extracts were washed with brine, dried over anhydrous magnesium sulfate, filtered and concentrated. The product was precipitated from a mixture of 2:1 ethyl acetate:methanol to give 0.65 g (2.79 mmol, 28%) of (S)-1-methyl-2-(5-methylcarbamoyl-benzimidazol-1-yl)-ethanol as a pale lavendar solid. MS m/z 234.1 (M+1). Analysis calculated for $C_{12}H_{15}N_3O_2$ (233.272): C, 61.79; H, 6.48; N, 18.01. Found: C, 61.82; H, 6.44; N, 17.83.

EXAMPLE 124
3-(4-Acetylamino-2-{(R)-2-[5-(2-dimethylamino-ethylcarbamoyl)-benzimidazol-1-yl]-1-methyl-ethoxy}-benzenesulfonylamino)-4-oxo-butyric acid hydrochloric acid salt Route J, a white solid. Analysis calculated for $C_{27}H34N6O8S.4.4$ HCl (763.11): C, 42.54; H, 5.07; N, 11.02. Found: C, 42.15; H, 5.56; N, 10.81.

(S)-2-[5-(2-Dimethylamino-ethylcarbamoyl)-benzimidazol-1-yl]-1-methyl-ethanol employed in the synthesis of 3-(4-acetylamino-2-{(R)-2-[5-(2-dimethylamino-ethylcarbamoyl)-benzimidazol-1-yl]-1-methyl-ethoxy}-benzenesulfonylamino)-4-oxo-butyric acid hydrochloric acid salt was synthesized via the method used for (S)-1-methyl-2-(5-methylcarbamoyl-benzimidazol-1-yl)-ethanol giving a tan solid. MS m/z 291.1 (M+1).

EXAMPLE 125
3-{4-Acetylamino-2-[(R)-1-methyl-2-(2-methyl-benzimidazol-1-yl)-ethoxy]-benzenesulfonylamino}-4-oxo-butyric acid hydrochloric acid salt Route J, a white solid. Analysis calculated for $C_{23}H_{26}N_4O_7S.1.71$ HCl (564.89): C, 48.90; H, 4.94; N, 9.92. Found: C, 48.53; H, 5.46; N, 9.58.

(S)-1-Methyl-2-(2-methyl-benzimidazol-1-yl-ethanol employed in the synthesis of 3-{4-acetylamino-2-[(R)-1-methyl-2-(2-methyl-benzimidazol-1-yl)-ethoxy]-benzenesulfonylamino}-4-oxo-butyric acid hydrochloric acid salt was synthesized via the method used for (S)-1-methyl-2-(6-methyl-benzimidazol-1-yl)-ethanol utilizing acetic acid instead of formic acid giving a pink solid. MS m/z 191.1 (M+1).

EXAMPLE 126
3-{4-Acetylamino-2-[(R)-2-(2-dimethylaminomethyl-benzimidazol-1-yl)-1-methyl-ethoxy]-benzenesulfonylamino}-4-oxo-butyric acid hydrochloric acid salt Route J, a white solid. Analysis calculated for $C_{25}H_{31}N_5O_7S.3.14$ HCl (660.096): C, 45.49; H, 5.21; N, 10.61. Found: C, 45.09; H, 5.86; N, 11.31.

(S)-2-(2-Dimethylaminomethyl-benzimidazol-1-yl)-1-methyl-ethanol employed in the synthesis of 3-{4-acetylamino-2-[(R)-2-(2-dimethylaminomethyl-benzimidazol-1-yl)-1-methyl-ethoxy]-benzenesulfonylamino}-4-oxo-butyric acid hydrochloric acid salt was synthesized via the method used for (S)-1-methyl-2-(6-methyl-benzimidazol-1-yl)-ethanol utilizing N,N-dimethylglycine instead of formic acid giving a pink solid. MS m/z 234.1 (M+1).

EXAMPLE 127
3-(4-Acetylamino-2-{2-[4-(2-dimethylamino-1-methyl-ethylcarbamoyl)-naphthalen-1-yl]-ethoxy}-benzenesulfonylamino)-4-oxo-butyric acid Synthesized employing N1,N1-dimethyl-1,2-propanediamine in step 3 of Route M.

MS(APCI) m/z 613.3 (M+1).

Synthesis of (S)-3-[4-Carbamoyl-2-(2-quinolin-5-yl-ethoxy)-benzenesulfonylamino]-3-cyano-propionic acid Step 1: 3-Benzyloxy-4-((S)-2-tert-butoxycarbonyl-1-carbamoyl-ethylsulfamoyl)-benzoic acid methyl ester To a room temperature $CH_2Cl_2$ solution (400 mL) of 3-benzyloxy-4-chlorosulfonyl-benzoic acid methyl ester (11.43 g, 33.50 mmol) was added (S)-3-amino-succinamic acid tert-butyl ester (6.32 g, 33.50 mmol) and pyridine (10.80 mL). The reaction mixture was allowed to stir for 12 h at room temperature. The reaction was then diluted with ethyl acetate and washed with 5% citric acid and saturated $NaHCO_3$. The organic phase was dried ($MgSO_4$), and then the solvent was removed under vacuum. The resulting crude product was purified using silica gel flash chromatography (3% MeOH in $CH_2Cl_2$). 3-Benzyloxy-4-((S)-2-tert-butoxycarbonyl-1-carbamoyl-ethylsulfamoyl)-benzoic acid methyl ester was obtained in 45% yield (7.40 g) as an off white foam. MS m/z 491.2 (M−1).

Step 2: 4-((S)-2-tert-Butoxycarbonyl-1-carbamoyl-ethylsulfamoyl)-3-hydroxy-benzoic acid methyl ester A solution of 3-benzyloxy-4-((S)-2-tert-butoxycarbonyl-1-carbamoyl-ethylsulfamoyl)-benzoic acid methyl ester (7.40 g, 15.0 mmol) in EtOH (100 mL) was shaken with 20% Pd/C (1.0 g) under $H_2$ (50 psi) for 1.5 h using a Parr apparatus. The reaction mixture was filtered through celite and concentrated. 4-((S)-2-tert-Butoxycarbonyl-1-carbamoyl-ethylsulfamoyl)-3-hydroxy-benzoic acid methyl ester was obtained (6.03 g, 99%) as an off white foam. MS m/z 401.2 (M−1).

Step 3: 4-((S)-2-tert-Butoxycarbonyl-1-carbamoyl-ethylsulfamoyl)-3-(2-quinolin-5-yl-ethoxy)-benzoic acid methyl ester To a solution of phenol 4-((S)-2-tert-butoxycarbonyl-1-carbamoyl-ethylsulfamoyl)-3-hydroxy-benzoic acid methyl ester (3.0 g, 7.50 mmol) in dry THF (50 mL) at 0° C. was added 2-quinolin-5-yl-ethanol (1.30 g, 7.5.0 mmol) and triphenyl phosphine (3.90 g, 15.0 mmol) then followed by dropwise addition of diethyl azodicarboxylate (2.40 mL, 15.0 mmol). The reaction mixture was allowed to warm up to room temperature and stirred for 12 h. The solvent was removed and the crude product was purified using silica gel flash chromatography (30% hexanes in EtOAc). 4-((S)-2-tert-Butoxycarbonyl-1-carbamoyl-ethylsulfamoyl)-3-(2-quinolin-5-yl-ethoxy)-benzoic acid methyl ester was obtained (1.40 g, 33%) as an off white foam. MS m/z 556.2 (M−1).

Step 4: 4-((S)-2-tert-Butoxycarbonyl-1-cyano-ethylsulfamoyl)-3-(2-quinolin-5-yl-ethoxy)-benzoic acid methyl ester To a solution of 4-((S)-2-tert-butoxycarbonyl-1-carbamoyl-ethylsulfamoyl)-3-(2-quinolin-5-yl-ethoxy)-benzoic acid methyl ester (1.20 g, 2.20 mmol) in dry THF (10 mL) at 0° C. was added $Et_3N$ (0.80 mL, 5.50 mmol). A solution of $(CF_3CO)_2O$ in THF (0.5 M, 0.37 mL, 2.60 mmol) was added to the solution dropwise. After 30 min of stirring at 0° C., the ice bath was removed. The reaction mixture was allowed to warm up to room temperature over 4 h. The reaction mixture was worked up by addition of EtOAc (100 mL) then followed by washing the organic phase with saturated NaHCO$_3$ (50 mL). Drying and removal of solvents under vacuum gave 0.90 g (76%) of 4-((S)-2-tert-butoxycarbonyl-1-cyano-ethylsulfamoyl)-3-(2-quinolin-5-yl-ethoxy)-benzoic acid methyl ester as a tan solid. MS m/z 540.3 (M+1).

Step 5: 4-((S)-2-tert-Butoxycarbonyl-1-cyano-ethylsulfamoyl)-3-(2-quinolin-5-yl-ethoxy)-benzoic acid To a solution of ester 4-((S)-2-tert-butoxycarbonyl-1-cyano-ethylsulfamoyl)-3-(2-quinolin-5-yl-ethoxy)-benzoic acid methyl ester (0.90 g, 1.70 mmol) in THF (10 mL) was added lithium hydroxide monohydrate (0.14 g, 3.40 mmol) in H$_2$O (3 mL). The reaction mixture was allowed to stirred at room temperature for 8 h. H$_2$O (50 mL) was added, and the reaction was washed with Et$_2$O. The aqueous layer was acidified to pH=7 using 5% H$_2$SO$_4$ then extracted with EtOAc. Drying and removal of solvents under vacuum gave 0.60 g (67%) of 4-((S)-2-tert-butoxycarbonyl-1-cyano-ethylsulfamoyl)-3-(2-quinolin-5-yl-ethoxy)-benzoic acid as a tan solid. MS m/z 526.3 (M+1).

Step 6: (S)-3-[4-Carbamoyl-2-(2-quinolin-5-yl-ethoxy)-benzenesulfonylamino]-3-cyano-propionic acid tert-butyl ester To a solution of acid 4-((S)-2-tert-butoxycarbonyl-1-cyano-ethylsulfamoyl)-3-(2-quinolin-5-yl-ethoxy)-benzoic acid (0.60 g, 1.10 mmol) in THF (20 mL) was added EDCI (0.33 g, 1.70 mmol), HOBt (0.23 g, 1.70 mmol), and N-methylmorpholine (1.70 mmol, 0.20 mL). The reaction was allowed to stirred at room temperature for 1 h then followed by addition of NH$_4$OH (10 mL). The mixture was stirred for another 12 h. To reaction was added EtOAc (100 mL) and washed with the 5% citric acid and then saturated NaHCO$_3$. The organic phase was dried (MgSO$_4$), and then the solvent was removed under vacuum. The resulting crude product was purified using silica gel flash chromatography (70% EtOAc in hexanes). (S)-3-[4-Carbamoyl-2-(2-quinolin-5-yl-ethoxy)-benzenesulfonylamino]-3-cyano-propionic acid tert-butyl ester was obtained in 22% yield (0.130 g) as an off white foam. MS (APCI) m/z 525.2 (M+1).

Step 7: (S)-3-[4-Carbamoyl-2-(2-quinolin-5-yl-ethoxy)-benzenesulfonylamino]-3-cyano-propionic acid A solution of (S)-3-[4-carbamoyl-2-(2-quinolin-5-yl-ethoxy)-benzenesulfonylamino]-3-cyano-propionic acid tert-butyl ester (0.13 g, 0.20 mmol) in TFA (2 mL) and CH$_2$Cl$_2$ (20 mL) was stirred for 9 h. Toluene (50 mL) was added and the solvents were removed under vacuum. The residue was lyophilized to yield 100 mg (99%) of (S)-3-[4-carbamoyl-2-(2-quinolin-5-yl-ethoxy)-benzenesulfonylamino]-3-cyano-propionic acid as a pale yellow solid. MS m/z 469.2 (M+1).

EXAMPLE 128

(S)-3-[4-(N',N'-Dimethyl-hydrazinocarbonyl)-2-(2-quinolin-5-yl-ethoxy)-benzenesulfonlamino]-4-oxo-butryic acid Route P, MS (APCI) m/z 515.3 (M+1).

EXAMPLE 129

3-[4-(3-Dimethylamino-propylcarbamoyl)-2-(2-quinolin-5-yl-ethoxy)-benzenesulfonylamino]-4-oxo-butyric acid Route P, colorless foam (116 mg), MS(APCI) m/z 557.3 (M+1).

EXAMPLE 130

(S)-3-[4-[3H-Imidazol-4-ylmethyl)-methyl-carbamoyl]-2-(2-quinolin-5-yl-ethoxy)-benzenesulfonylamino]-4-oxo-butyric acid Route P, yellow glass (178 mg), MS(APCI) m/z 556.3 (M+1).

EXAMPLE 131

(S)-3-[4-(2-Dimethylamino-acetylamino)-2-(2-quinolin-5-yl-ethoxy)-benzenesulfonylamino]-4-oxo-butyric acid Step 1: (S)-3-[2-Benzyloxy-4-(2-chloro-ethanoylamino)-benzenesulfonylamino]-N-methoxy-N-methyl-succinamic acid tert-butyl ester To a solution of 3-(4-amino-2-benzyloxy-benzenesulfonylamino)-N-methoxy-N-methyl-succinamic acid-4-tert butyl ester from Route D step 6 (3.0 g, 6.10 mmol), in anhydrous methylene chloride (20 mL) at 0° C. was added pyridine (1.0 mL, 12.20 mmol) followed by chloroacetyl chloride (0.97 mL, 12.2 mmol) dropwise. The reaction was allowed to stir at 0° C. for 1 h and then allowed to slowly warm to room temperature overnight. The methylene chloride was evaporated and the reaction mixture was dissolved in ethyl acetate and water. The organic layer was collected and washed with 10% sulfuric acid, brine, dried over magnesium sulfate, and concentrated. The crude product was subjected to silica gel flash chromatography (25–40% EtOAc in hexanes) to yield (S)-3-[2-benzyloxy-4-(2-chloro-ethanoylamino)-benzenelsulfonylamino]-N-methoxy-N-methyl-succinamic acid tert-butyl ester 2.85 g (82%) as white solid. MS (APCI) m/z 568.1 (M−1).

Step 2: (S)-3-[2-Benzyloxy-4-(2-dimethylamino-ethanoylamino)-benzenesulfonylamino]-N-methoxy-N-methyl succinamic acid tert-butyl ester To solution of (S)-3-[2-benzyloxy-4-(2-chloro-ethanoylamino)-benzenelsulfonylamino]-N-methoxy-N-methyl-succinamic acid tert-butyl ester (2.85 g, 5.0 mmol) in freshly distilled THF (20 mL) at −10° C. was added cold anhydrous dimethyl amine (20 mL). The reaction mixture was allowed to warm up slowly and stirred at room temperature for 12 h. The dimethyl amine was then allowed to evaporate under nitrogen and the remaining solution was concentrated under reduced pressure. The crude product was purified by flash chromatography (SiO$_2$, 2.5% MeOH in CH$_2$Cl$_2$) to give (S)-3-[2-benzyloxy-4-(2-dimethylamino-ethanoylamino)-benzenesulfonylamino]-N-methoxy-N-methyl succinamic acid tert-butyl ester 2.60 g (90%) MS (APCI) m/z 577.3 (M−1). This compound furnished the final product following the steps employed in Route D.

(S)-3-[4-(2-Dimethylamino-acetylamino)-2-(2-quinolin-5-yl-ethoxy)-benzenesulfonylamino]-4-oxo-butyric acid was synthesized by Route L. Off white solid. MS (APCI) m/z 529.3 (M+1).

EXAMPLE 132

3-[4-(2-Dimethylamino-acetylamino)-2-((1R,2R)-1-methyl-2-naphthalen-1-yl-propoxy)-benzosulfonylamino]-4-oxo-butyric acid Synthesis of: (1R,2R)-1-methyl-2-naphthalen-1-yl-propanol employed in the synthesis of 3-[4-(2-Dimethylamino-acetylamino)-2-((1R,2R)-1-methyl-2-naphthalen-1-yl-propoxy)-benzenesulfonylamino]-4-oxo-butyric acid.

Step 1: (Z)-1-(1-Naphthyl)-propene 1-(1-Naphthyl)-1-propyne was prepared by literature procedures (H. Kouzai, et al, Bull. Chem. Soc. Jpn., (1995), 398.). The 1-(1-naphthyl)-1-propyne (10.8 g, 0.065 mol) was dissolved in THF, Lindlar's catalyst was added, and the solution was placed under a hydrogen atmosphere. After the reduction was complete, the solvent was removed and replaced with ether. The ether solution was filtered though a plug of silica, and the solvent removed to give the (Z)-1-(1-naphthyl)-propene (11.01 g, 0.65 mol). NMR (CDCl$_3$)

8.1–7.7 (3H, m), 7.6–7.3 (4H, m), 7.0–6.8 (1H, m), 6.2–5.9 (1H, m), 1.8–1.7 (3H, dd).

Step 2: (1R, 2S)-1-(1-Naphthyl)-1-propene Oxide (ref. E. Jacobsen, el al; JACS 1991, 7064.) The (Z)-1-(1-naphthyl)-propene (2.06 g, 0.012 mol) was dissolved in methylene chloride, and (R, R)-Jacobsen's catalyst (0.168 g) was added, then cooled to 6° C., and a bleach solution (10 mL, buffered to pH=11.3 with disodium hydrogen phosphate) was added. After 6 h at 6° C., the layers were separated, and the aqueous layer washed with ether. The combined organic layers were washed with water, then brine, dried over magnesium sulfate, filtered and rotovapped. The crude product was chromatographed on silica using 5% ether/pentane, to give the desired (1R, 2S)-1-(1-naphthyl)-1-propene oxide (0.421 g). NMR (CDCl$_3$) 8.1–7.7 (3H, m), 7.6–7.3 (4H, m), 4.6–4.5 (1H, m), 3.7–3.5 (1H, m), 1.0 (3H, d, J=5.3 Hz).

Step 3: (1R,2R)-1-Methyl-2-naphthalen-1-yl-propanol

The (1R, 2S)-1-(1-naphthyl)-1-propene oxide (0.166 g, 0.90 mmol) was dissolved in methylene chloride (20 ml), and cooled to −78° C. Three portions of trimethylaluminum (2M in hexane, 0.68 mL, followed by another 0.22 mL after 15 min, and 0.3 mL after another 2 h) were added, and the reaction stirred overnight at −78° C. The reaction was quenched with excess conc. ammonium hydroxide, and the reaction was warmed to room temperature. The solution was poured into ether, the layers were separated, and the organic layer was washed with ammonium hydroxide, water, and then brine. The solution was dried over magnesium sulfate, filtered and rotovapped. The crude product (0.164 g) was clean by NMR and MS. NMR (CDCl$_3$) 8.18 (1H, d, J=8.4 Hz), 7.86 (1H, d, J=8.0 Hz), 7.8–7.7 (1H, m), 7.6–7.4 (4H, m), 4.2–4.1 (1H, m), 3.8–3.6 (1H, m), 1.36 (3H, d, J=7.0 Hz), 1.28 (3H, d, J=6.0 Hz). MS (APCI) m/z 183 (M(−H$_2$O)+1).

3-[4-(2-Dimethylamino-acetylamino)-2-((1R,2R)-1-methyl-2-naphthalen-1-yl-propoxy)-benzenesulfonylamino]-4-oxo-butyric acid was synthesized via Route L, except employing chloroacetyl chloride. MS (APCI) m/z 556 (M+1).

EXAMPLE 133

(S)-3-[4-(2-Dimethylamino-ethanoylamino)-2-(2-naphthalen-1-yl-ethoxy)-benzenesulfonylamino]-4-oxo-butryic acid Route L, except chloroacetyl chloride was used in step 1, colorless solid (15 mg), MS APCI m/z 528.3 (M+1).

EXAMPLE 134

(S)-3-[4-Acetylamino-2-((1R,2S)-2-indazol-1-yl-1-methyl-propoxy-benzenesulfonylamino]-4-oxo-butyric acid Route J, yellow foam (109 mg), MS(APCI) m/z 503.3 (M+1).

(1S,2S)-2-indazol-1-yl-1-methyl-propanol employed in the synthesis of (S)-3-[4-acetylamino-2-((1R,2S)-2-indazol-1-yl-1-methyl-propoxy)-benzenesulfonylamino]-4-oxo-butyric acid was synthesized in the manner previously described for (1S,2S)-2-benzimidazol-1-yl-1-methyl-propanol only indazole was used instead of benzimidazole. $^1$H NMR(CDCl$_3$) 8.08(s,1H), 7.77(d,1H), 7.42(m,2H), 7.18 (m,1H), 4.55(m,1H), 4.23(m,1H), 1.60(d,3H), 1.13(d,3H).

EXAMPLE 135

N1-(3-[(1R)-2-(2-[2-(dimethylamino)ethyl]sulfanyl-1H-benzo[d]imidazol-1-yl)-1-methylethyl]oxy-4-[(2-ethoxy-5-oxotetrahydro-3-furanyl)amino]sulfonylphenyl)acetamide Route J, MS m/z 620 (M+1).

(2S)-1-(2-[2-(Dimethylamino)ethyl]sulfanyl-1H-benzo[d]imidazol-1-yl)propan-2-ol employed in the synthesis of N1-(3-[(1R)-2-(2-[2-(dimethylamino)ethyl]sulfanyl-1H-benzo[d]imidazol-1-yl)-1-methylethyl]oxy-4-[(2-ethoxy-5-oxotetrahydro-3-furanyl)amino]sulfonylphenyl)acetamide was synthesized via the method used for (S)-benzimidazol-1-yl-1-methyl-ethanol, MS m/z 280 (M+1).

EXAMPLE 136

N1-4-[(2-Ethoxy-5-oxotetrahydro-3-furanyl)amino]sulfonyl-3-[((1R)-1-methyl-2-2-[(2-morpholinoethyl)sulfanyl]-1H-benzo[d]imidazol-1-ylethyl)oxy]phenylacetamide Route J, MS m/z 662 (M+1).

2(S)-1-2-[(2-Morpholinoethyl)sulfanyl]-1H-benzo[d]imidazol-1-ylpropan-2-ol employed in the synthesis of N1-4-[(2-ethoxy-5-oxotetrahydro-3-furanyl)amino]sulfonyl-3-[((1R)-1-methyl-2-2-[(2-morpholinoethyl)sulfanyl]-1H-benzo[d]imidazol-1-ylethyl)oxy]phenylacetamide was synthesized via the method used for (S)-benzimidazol-1-yl-1-methyl-ethanol, MS m/z 322 (M+1).

EXAMPLE 137

N1-4-[(2-Ethoxy-5-oxotetrahydro-3-furanyl amino]sulfonyl-3-[((1R)-2-2-[(2-methoxyethyl sulfanyl]-1H-benzo[d]imidazol-1-yl-1-methylethyl)oxy]phenylacetamide Route J, MS m/z 607 (M+1).

2(S)-1-2-[(2-Methoxyethyl)sulfanyl]-1H-benzo[d]imidazol-1-ylpropan-2-ol employed in the synthesis of N1-4-[(2-ethoxy-5-oxotetrahydro-3-furanyl)amino]sulfonyl-3-[((1R)-2-2-[(2-methoxyethyl)sulfanyl]-1H-benzo[d]imidazol-1-yl-1-methylethyl)oxy]phenylacetamide was synthesized via the method used for (S)-benzimidazol-1-yl-1-methyl-ethanol, MS m/z 267 (M+1).

EXAMPLE 138

3-([4-(Acetylamino)-2-((1R)-1-methyl-2-[2-(methylsulfanyl)-1H-benzo[d]imidazol-1-yl]ethyloxy)phenyl]sulfonylamino)-4-oxobutanoic acid Route J, MS m/z 535 (M+1).

(2S)-1-[2-(Methylsulfanyl)-1H-benzo[d]imidazol-1-yl]propan-2-ol employed in the synthesis of 3-([4-(acetylamino)-2-((1R)-1-methyl-2-[2-(methylsulfanyl)-1H-benzo[d]imidazol-1-yl]ethyloxy)phenyl]sulfonylamino)-4-oxobutanoic acid was synthesized in a manner analogous to that used for (S)-benzimidazol-1-yl-1-methyl-ethanol, MS m/z 223 (M+1).

EXAMPLE 139

3-([4-(Acetylamino)-2-((1R)-2-[2-(2-furyl)-1H-benzo[d]imidazol-1-yl]-1-methylethyloxy)phenyl]sulfonylamino)-4-oxobutanoic acid Route J, MS m/z 555 (M+1).

(2S)-1-[2-(2-Furyl)-1H-benzo[d]imidazol-1-yl]propan-2-ol employed in the synthesis of 3-([4-(acetylamino)-2-((1R)-2-[2-(2-furyl)-1H-benzo[d]imidazol-1-yl]-1-methylethyloxy)phenyl]sulfonylamino)-4-oxobutanoic acid was synthesized in a manner analogous to that used for (S)-benzimidazol-1-yl-1-methyl-ethanol, MS m/z 243 (M+1).

EXAMPLE 140

3-([4-(Acetylamino)-2-((1R)-1-methyl-2-[2-(2-thienyl)-1H-benzo[d]imidazol-1-yl]ethyloxy)phenyl]sulfonylamino)-4-oxobutanoic acid Route J, MS m/z 571(M+1).

(2S)-1-[2-(2-Thienyl)-1H-benzo[d]imidazol-1-yl]propan-2-ol employed in the synthesis of 3-([4-(acetylamino)-2-((1R)-1-methyl-2-[2-(2-thienyl)-1H-benzo[d]imidazol-1-yl]

EXAMPLE 141

3-([4-(Acetylamino)-2-((1R)-2-[2-(benzylsulfanyl)-1H-benzo[d]imidazol-1-yl]-1-methylethyloxy phenyl] sulfonylamino)-4-oxobutanoic acid Route J, MS m/z 611 (M+1).

(2S)-1-[2-(Benzylsulfanyl)-1H-benzo[d]imidazol-1-yl] propan-2-ol employed in the synthesis of 3-([4-(acetylamino)-2-((1R)-2-[2-(benzylsulfanyl)-1H-benzo[d] imidazol-1-yl]-1-methylethyloxy)phenyl]sulfonylamino)-4-oxobutanoic acid was synthesized in a manner analogous to that used for (S)-benzimidazol-1-yl-1-methyl-ethanol, MS m/z 299 (M+1).

EXAMPLE 142

3-[(4-(Acetylamino)-2-[(1R)-2-(2-[2-(dimethylamino) ethyl]sulfanyl-1H-benzo[d]imidazol-1-yl)-1-methylethyl] oxyphenyl)sulfonyl]amino-4-oxobutanoic acid Route J, MS m/z 592 (M+1).

(2S)-1-(2-[2-(Dimethylamino)ethyl]sulfanyl-1H-benzo[d]imidazol-1-yl)propan-2-ol employed in the synthesis of 3-[(4-(acetylamino)-2-[(1R)-2-(2-[2-(dimethylamino)ethyl] sulfanyl-1H-benzo[d]imidazol-1-yl)-1-methylethyl] oxyphenyl)sulfonyl]amino-4-oxobutanoic acid was synthesized in a manner analogous to that used for (S)-benzimidazol-1-yl-1-methyl-ethanol, MS m/z 280 (M+1).

EXAMPLE 143

3-[(4-(Acetylamino)-2-[((1R)-1-methyl-2-2-[(2-morpholinoethyl)sulfanyl]-1H-benzo[d]imidazol-1-ylethyl) oxy]phenylsulfonyl)amino]-4-oxobutanoic acid Route J, MS m/z 634 (M+1).

(2S)-1-2-[(2-Morpholinoethyl)sulfanyl]-1H-benzo[d] imidazol-1-ylpropan-2-ol employed in the synthesis of 3-[(4-(acetylamino)-2-[((1R)-1-methyl-2-2-[(2-morpholinoethyl)sulfanyl]-1H-benzo[d]imidazol-1-ylethyl) oxy]phenylsulfonyl)amino]-4-oxobutanoic acid was synthesized in a manner analogous to that used for (S)-benzimidazol-1-yl-1-methyl-ethanol, MS m/z 322 (M+1).

EXAMPLE 144

3-[(4-(Acetylamino)-2-[(1R)-2-(2-[2-(dimethylamino)-2-oxoethyl]sulfanyl-1H-benzo[d]imidazol-1-yl)-1-methylethyl]oxyphenyl)sulfonyl]amino-4-oxobutanoic acid Route J, MS m/z 606 (M+1).

N1,N1-Dimethyl-2-(1-[(2S)-2-hydroxypropyl]-1H-benzo[d]imidazol-2-ylsulfanyl)acetamide employed in the synthesis of 3-[(4-(acetylamino)-2-[(1R)-2-(2-[2-(dimethylamino)-2-oxoethyl]sulfanyl-1H-benzo[d]imidazol-1-yl)-1-methylethyl]oxyphenyl)sulfonyl]amino-4-oxobutanoic acid was synthesized in a manner analogous to that used for (S)-benzimidazol-1-yl-1-methyl-ethanol, MS m/z 294 (M+1).

EXAMPLE 145

3-([4-(Acetylamino)-2-((1R)-2-[2-(ethylsulfanyl-1H-benzo[d]imidazol-1-yl]-1-methylethyloxy)phenyl] sulfonylamino)-4-oxobutanoic acid Route J, MS m/z 549 (M+1).

(2S)-1-[2-(Ethylsulfanyl)-1H-benzo[d]imidazol-1-yl] propan-2-ol employed in the synthesis of 3-([4-(acetylamino)-2-((1R)-2-[2-(ethylsulfanyl)-1H-benzo[d] imidazol-1-yl]-1-methylethyloxy)phenyl]sulfonylamino)-4-oxobutanoic acid was synthesized in a manner analogous to that used for (S)-benzimidazol-1-yl-1-methyl-ethanol, MS m/z 237 (M+1).

EXAMPLE 146

3-[(4-(Acetylamino)-2-[((1R)-2-2-[(cyclopropylmethyl) sulfanyl]-H-benzo[d]imidazol-1-yl-1-methylethyl)oxy] phenylsulfonyl)amino]-4-oxobutanoic acid Route J, MS m/z 575 (M+1).

(2S)-1-2-[(Cyclopropylmethyl)sulfanyl-1H-benzo[d] imidazol-1-ylpropan-2-ol employed in the synthesis of 3-[(4-(acetylamino)-2-[((1R)-2-2-[(cyclopropylmethyl) sulfanyl]-1H-benzo[d]imidazol-1-yl-1-methylethyl)oxy] phenylsulfonyl)amino]-4-oxobutanoic acid was synthesized in a manner analogous to that used for (S)-benzimidazol-1-yl-1-methyl-ethanol, MS m/z 263 (M+1).

EXAMPLE 147

3-[(4-(Acetylamino)-2-[((1R)-2-2-[(2-methoxyethyl) sulfanyl]-1H-benzo[d]imidazol-1-yl-1-methylethyl)oxy] phenylsulfonyl)amino]-4-oxobutanoic acid Route J, MS m/z 579 (M+1).

(2S)-1-2-[(2-Methoxyethyl)sulfanyl]-1H-benzo[d] imidazol-1-ylpropan-2-ol employed in the synthesis of 3-[(4-(acetylamino)-2-[((1R)-2-2-[(2-methoxyethyl) sulfanyl]-1H-benzo[d]imidazol-1-yl-1-methylethyl)oxy] phenylsulfonyl)amino]-4-oxobutanoic acid was synthesized in a manner analogous to that used for (S)-benzimidazol-1-yl-1-methyl-ethanol, MS m/z 267 (+1).

EXAMPLE 148

3-[(4-(acetylamino)-2-[(1R)-1-methyl-2-(2-[(2-methyl-1,3-thiazol-4-yl)methyl]sulfanyl-1H-benzo[d]imidazol-1-yl) ethyl]oxyphenyl)sulfonyl]amino-4-oxobutanoic acid Route J, MS m/z 632 (M+1).

(2S)-1-(2-[(2-Methyl-1,3-thiazol-4-yl)methyl]sulfanyl-1H-benzo[d]imidazol-1-yl propan-2-ol employed in the synthesis of 3-[(4-(acetylamino)-2-[(1R)-1-methyl-2-(2-[(2-methyl-1,3-thiazol-4-yl)methyl]sulfanyl-1H-benzo[d] imidazol-1-yl)ethyl]oxyphenyl)sulfonyl]amino-4-oxobutanoic acid was synthesized in a manner analogous to that used for (S)-benzimidazol-1-yl-1-methyl-ethanol, MS m/z 320 (M+1).

EXAMPLE 149

3-([4-(Acetylamino)-2-((1R)-2-[2-(isopropylsulfanyl)-1H-benzo[d]imidazol-1-yl]-1-methylethyloxy)phenyl] sulfonylamino)-4-oxobutanoic acid Route J, MS m/z 563 (M+1).

(2S)-1-[2-(Isopropylsulfanyl)-1H-benzo[d]imidazol-1-yl] propan-2-ol employed in the synthesis of 3-([4-(acetylamino)-2-((1R)-2-[2-(isopropylsulfanyl)-1H-benzo [d]imidazol-1-yl]-1-methylethyloxy)phenyl] sulfonylamino)-4-oxobutanoic acid was synthesized in a manner analogous to that used for (S)-benzimidazol-1-yl-1-methyl-ethanol, MS m/z 251 (M+1).

EXAMPLE 150

(S)-3-(2-{2-[3-(3-Dimethylamino-propylcarbamoyl)-naphthalen-1-yl]-ethoxy}-benzenesulfonylamino)-4-oxo butyric acid Prepared according to Route M, only employing (S)-3-(2-hydroxybenzenesulfonylamino)-4,4-diethoxy-butryic acid tert-butyl ester as starting material to yield after prep HPLC and lyophilization (36 mg, ~90%) as a fluffy white solid. MS (APCI) m/z 554 (M−1).

EXAMPLE 151
3-[4-(4-Dimethylamino-butyrylamino)-2-(2-naphthalen-1-yl-ethoxy)-benzenesulfonylamino]-4-oxo-butyric acid Route L as a fluffy cream solid. MS (APCI) m/z 556.3 (M+1), 554.3 (M−1).

EXAMPLE 152
(S)-3-[4-(2-Dimethylamino-ethanoylamino)-2-((R)-2-isoquinolin-4-yl-1-methyl-ethoxy)-benzenesulfonylamino]-4-oxo-butryic acid Route M, only chloroacetyl chloride was employed in step 1. Colorless foam(70 mg), MS(APCI) m/z 543.3 (M+1).

EXAMPLE 153
(S)-3-{4-Acetylamino-2-[(R)-1-methyl-2-(2-methylamino-benzoimidazol-1-yl)-ethoxy]-benzenesulfonylamino-4-oxo-butryic acid Route J, MS (APCI) m/z 518.3 (M+1).

(R)-1-methyl-2-(2-methylamino-benzoimidazol-1-yl)-ethanol employed in the synthesis of (S)-3-{4-acetylamino-2-[(R)-1-methyl-2-(2-methylamino-benzoimidazol-1-yl)-ethoxy]-benzenesulfonylamino-4-oxo-butryic acid was synthesized following a literature procedure: Perkins, J. J., Zartman, A. E., Meissner, R. S. *Tet. Lett.* 1999, 40, 1103–1106.

EXAMPLE 154
(S)3-[4-(4-Dimethylamino-butyrylamino)-2-(2-quinolin-5-yl-ethoxy)-benzenesulfonylamino]-4-oxo-butyric acid Route L Step1 (S)-3-[2-Benzyloxy-4-(4-chloro-butanoylamino)-benzenesulfonylamino]-4,4-diethoxy-butyric acid tert-butyl ester To a solution of (S)-3-(4-amino-2-benzyloxy-benzenesulfonylamino)-4,4-diethoxy-butyric acid tert-butyl ester from Route J step 7 (0.958 g, 1.88 mmol), in anhydrous methylene chloride (20 mL) at 0° C. was added triethylamine (1.32 mL, 9.42 mmol) followed by 4-chlorobutyryl chloride (0.32 ml, 2.83 mmol) dropwise. The reaction was allowed to stir at 0° C. for 1 h and then allowed to slowly warm to room temperature overnight. The methylene chloride was evaporated and the reaction mixture was dissolved in ethyl acetate and water. The organic layer was collected and washed with 10% sulfuric acid, brine, dried over magnesium sulfate, and concentrated to yield (S)-3-[2-benzyloxy-4-(4-chloro-butanoylamino)-benzenesulfonylamino]-4,4-diethoxy-butyric acid tert-butyl ester (1.32 g) as a crude brown oil. MS (APCI) m/z 611.3 (M−1).

Step 2: (S)-3-[2-Benzyloxy-4-(4-dimethylamino-butanoylamino)-benzenesulfonylamino]-4,4-diethoxy-butyric acid tert-butyl ester (S)-3-[2-Benzyloxy-4-(4-chloro-butanoylamino)-benzenesulfonylamino]-4,4-diethoxy-butyric acid tert-butyl ester (1.32 g, 2.1 mmol) was dissolved in freshly distilled tetrohydrofuran (5 mL) and transferred to a presure tube. Anhydrous dimethyl amine was bubbled into the solution for 5 minutes. The tube was sealed and the reaction allowed to stir at room temperature overnight. The dimethyl amine was then allowed to evaporate under nitrogen and the remaining solution concentrated under reduced pressure to give (1.11 g, 83%) of the crude product. (S)-3-[2-benzyloxy-4-(4-dimethylamino-butanoylamino)-benzenesulfonylamino]-4,4-diethoxy-butyric acid tert-butyl ester was purified by flash chromatography (SiO$_2$, 100% ethyl acetate) to give 0.62 g (0.99 mmol, 45%) MS (APCI) m/z 622.5 (M+1).

Step 3: (S)-3-[4-(4-Dimethylamino-butanoylamino)-2-hydroxy-benzensulfonylamino]-4,4-diethoxy-butyric acid tert-butyl ester (S)-3-[2-Benzyloxy-4-(4-dimethylamino-butanoylamino)-benzenesulfonylamino]-4,4-diethoxy-butyric acid tert-butyl ester (0.62 g, 1.0 mmol) was shaken with 20% palladium on carbon (0.06 g) in THF-EtOH (1:1) under H$_2$ (50 psi) for 16 h using a Parr apparatus. Mass spectrometry and NMR analysis indicated only starting material to be present. An additional 0.28 g of 20% Pd/C and EtOH (50 mL) were added and allowed to stir for 19.5 h. TLC analysis showed complete consumption of starting material. The reaction mixture was filtered through celite and concentrated to yield (S)-3-[4-(4-dimethylamino-butanoylamino)-2-hydroxy-benzensulfonylamino]-4,4-diethoxy-butyric acid tert-butyl ester (0.44 g, 0.83 mmol, 83%). MS (APCI) m/z 532.4 (M+1).

Step 4: (S)-3-[4-(4-Dimethylamino-butanoylamino)-2-(2-quinolin-5-yl-ethoxy)benzensulfonylamino]-4,4-diethoxy-butyric acid tert-butyl ester A mixture of 0.22 g (0.41 mmol), (S)-3-[4-(4-dimethylamino-butanoylamino)-2-hydroxy-benzensulfonylamino]-4,4-diethoxy-butyric acid tert-butyl ester, 0.079 g (0.41 mmol), 2-quinolin-5-yl-ethanol, 0.14 g (0.62 mmol) triphenylphosphine, and anhydrous methylene chloride (5 mL) was stirred at room temperature. Diethyl azodicarboxylate 0.1 mL (0.62 mmol) was added dropwise and the resulting orange solution was stirred at room temperature for 24 h. TLC analysis indicated complete reaction. The reaction mixture was concentrated in vacuo to give a deep yellow oil. The product was purified over silica eluting with 10% (8:1 EtOH/NH$_4$OH): 90% methylene chloride to yield 0.115 g (0.17 mmol, 41%) of (S)-3-[4-(4-dimethylamino-butanoylamino)-2-(2-quinolin-5-yl-ethoxy)benzensulfonylamino]-4,4-diethoxy-butyric acid tert-butyl ester as a yellow oil. MS (APCI) m/z 685.5 (M−1).

Step 5: Dimethylamino-N-[4-(S)-2-ethoxy-5-oxo-tetrahydro-furan-3-ylsulfamoyl)-3-(2-quinolin-5-yl-ethoxy)-phenyl]-butyramide (S)-3-[4-(4-Dimethylamino-butanoylamino)-2-(2-quinolin-5-yl-ethoxy) benzensulfonylamino]-4,4-diethoxy-butyric acid tert-butyl ester (0.112 g, 0.163 mmol) was stirred in 13 mL of a solution of 17% TFA in CH$_2$Cl$_2$ at room temperature for 2 h. Analytical HPLC indicated the reaction was complete. Toluene (20 mL) was added to the reaction mixture and the solvent was concentrated under reduced pressure. Residual TFA was azeotroped with toluene. Half of the product was lyophilized to give (0.035 g, 0.04 mmol, 25%) of dimethylamino-N-[4-(S)-2-ethoxy-5-oxo-tetrahydro-furan-3-ylsulfamoyl)-3-(2-quinolin-5-yl-ethoxy)-phenyl]-butyramide. MS (APCI) m/z 557.4 (M+1), 585.4 (M−1).

Step 6: (S)3-[4-(4-Dimethylamino-butyrylamino)-2-(2-quinolin-5-yl-ethoxy)-benzenesulfonylamino]-4-oxo-butyric acid The second half of the crude product from above was stirred with 22 mL of a solution of 10% TFA in 1:1 acetonitrile/water for 24 h. Analytical HPLC indicated that reaction was complete. The reaction mixture was diluted with 100 mL of water and lyopholyzed to give (0.051 g, 0.061 mmol, 38%) of (S)3-[4-(4-dimethylamino-butyrylamino)-2-(2-quinolin-5-yl-ethoxy)-benzenesulfonylamino]-4-oxo-butyric acid as a granular yellow-brown powder. MS (APCI) m/z 557.4 (M+1), 555.3 (M−1).

EXAMPLE 155
C-Dimethylamino-N-{4-((S)-2-ethoxy-5-oxo-tetrahydro-furan-3-ylsulfamoyl)-3-[(R)-1-methyl-2-(2-methylsulfanyl-benzoimidazol-1-yl)-ethoxy]-phenyl}-acetamide and (S)-3-{4-(2-Dimethylamino-ethanoylamino)-2-[(R)-1-methyl-2-

(2-methylsulfanyl-benzoimidazol-1-yl)-ethoxy]-benzenesulfonylamino}-4-oxo-butyric acid Route C Step 1: (S)-3-(2-Benzyloxy-4-nitro-benzenesulfonylamino)-4-oxo-butyric acid tert-butyl ester (S)-3-(2-Benzyloxy-4-nitro-benzenesulfonylamino-N-methoxy-N-methyl succinamic acid tert-butyl ester (530 mg, 1 mmol) was dissolved in anhydrous THF and the mixture was cooled to −78° C. on a dry ice acetone bath. Lithium aluminum hydride 1M in ether (5 ml, 5 mmol) was added dropwise to maintain the internal temperature below −70° C. Following complete addition, the mixture was stirred at −78° C. for 2 h. KHSO4 1M aqueous (5 ml, 5 mmol) was added dropwise to the reaction mixture to maintain the internal temperature below −70° C. Following complete addition the mixture was stirred at −78° C. for 1 h. The mixture was allowed to slowly warm to room temperature. The mixture was extracted with ethyl acetate, the organics were combined, washed with brine and dried over $Na_2SO_4$. The solvent was removed under reduced pressure to give the (S)-3-(2-benzyloxy-4-nitro-benzenesulfonylamino)-4-oxo-butyric acid tert-butyl ester (420 mg, 90%). RP-HPLC (10 to 90% acetonitrile in 0.1 N aqueous ammonium acetate over 10 min at 2 mL/min using a Waters Symmetry C18 150×4.6 mm column) 9.5 min.

Step 2: (S)-3-(2-Benzyloxy-4-nitro-benzenesulfonylamino)-4,4-diethoxy-butyric acid tert-butyl ester (S)-3-(2-Benzyloxy-4-nitro-benzenesulfonylamino)-4-oxo-butyric acid tert-butyl ester (420 mg, 0.9 mmol) was dissolved in ethanol (25 mL). Triethylorthoformate (5 mL, 30 mmol) and and p-toluenesulfonic acid monohydrate (100 mg, 0.5 mmol) were added. This mixture was stirred at room temperature overnight. The ethanol was evaporated and the resulting orange oil was triturated with heptane (3×100 ml). (S)-3-(2-Benzyloxy-4-nitro-benzenesulfonylamino)-4,4-diethoxy-butyric acid tert-butyl ester was purified by silica gel chromatography with ethyl acetate/heptane yield 160 mmol, 33%. RP-HPLC (10 to 90% acetonitrile in 0.1 N aqueous ammonium acetate over 10 min at 2 mL/min using a Waters Symmetry C18 150×4.6 mm column) 11.6 min.

Step 3: (S)-3-(4-Amino-2-hydroxy-benzenesulfonylamino)-4,4-diethoxy-butyric acid tert-butyl ester (S)-3-(2-Benzyloxy-4-nitro-benzenesulfonylamino)-4,4-diethoxy-butyric acid tert-butyl ester (150 mg, 0.28 mmol) was hydrogenated with 10% Pd/C (50 mg) in 1:1 tetrahydrofuran/ethanol (10 mL) at room temperature under 50 psi hydrogen in a Parr shaker for 3 h. The reaction mixture was filtered over a celite pad, the catalyst was washed with ethanol, the organics were combined and the solvent was removed under reduced pressure to give (S)-3-(4-amino-2-hydroxy-benzenesulfonylamino)-4,4-diethoxy-butyric acid tert-butyl ester, 100 mg, 85%. RP-HPLC (10 to 90% acetonitrile in 0.1 N aqueous ammonium acetate over 10 min at 2 mL/min using a Waters Symmetry C18 150×4.6 mm column) 8.3 min.

Step 4: (S)-3-{4-Amino-2-[(R)-1-methyl-2-(2-methylsulfanyl-benzoimidazol-1-yl)-ethoxy]-benzenesulfonylamino-}4,4-diethoxy-butyric acid tert-butyl ester To a 0° C. solution of (S)-3-(4-amino-2-hydroxy-benzenesulfonylamino)-4,4-diethoxy-butyric acid tert-butyl ester (200 mg, 0.48 mmol), (2S)-1-[2-(methylsulfanyl)-1H-benzo[d]imidazol-1-yl]propan-2-ol (150 mg, 0.67 mmol) and resin bound triphenyl phosphine (1 g, 1 mmol) in THF (5 mL) was added diisopropyl azodicarboxylate (600 uL, 3 mmol). This mixture was shaken at room temperature for 2 h. TLC 50% ethyl acetate/heptane shows no phenol rf 0.2.

The reaction mixture was filtered, the resin was washed with dichloromethane, the organics were combined, the solvent was evaporated under reduced pressure. (S)-3-{4-amino-2-[(R)-1-methyl-2-(2-methylsulfanyl-benzoimidazol-1-yl)-ethoxy]-benzenesulfonylamino}-4,4-diethoxy-butyric acid tert-butyl ester was purified by silica gel chromatography ethyl acetate/heptane (132 mg, 44%). RP-HPLC (10 to 90 % acetonitrile in 0.1 N aqueous ammonium acetate over 10 min at 2 mL/min using a Waters Symmetry C18 150×4.6 mm column) 9.8 min.

Step 5: (S)-3-{4-(2-Dimethylamino-ethanoylamino)-2-[(R)-1-methyl-2-(2-methylsulfanyl-benzoimidazol-1-yl)-ethoxy]-benzenesulfonylamino}-4,4-diethoxy-butyric acid tert-butyl ester To a solution of (S)-3-{4-amino-2-[(R)-1-methyl-2-(2-methylsulfanyl-benzoimidazol-1-yl)-ethoxy]-benzenesulfonylamino}-4,4-diethoxy-butyric acid tert-butyl ester (100 mg, 0.16 mmol) in dichloromethane (1 mL) containing pyridine (100 uL, 1.2 mmol) was added chloroacetyl chloride (20 uL, 0.24 mmol) dropwise. The mixture turned orange and it was stirred at room temperature for 30 minutes. The solvent was removed to give an intermediate alkyl chloride 115 mg, 100%. The intermediate alkyl chloride (50 mg, 0.07 mmol) was dissolved in dichloromethane (1 mL) and dimethylamine 2 M in THF (1 mL, 2 mmol) was added. The mixture sat at room temperature for 3 h. TLC 5% methanol in dichloromethane showed no starting material rf 1.0 and a new spot rf 0.3. The mixture was evaporated and (S)-3-{4-(2-dimethylamino-ethanoylamino)-2-[(R)-1-methyl-2-(2-methylsulfanyl-benzoimidazol-1-yl)-ethoxy]-benzenesulfonylamino}-4,4-diethoxy-butyric acid tert-butyl ester was purified by silica gel chromatography 5% methanol in dichloromethane with 0.5% NH4OH. The yield was 26 mg, 46%. RP-HPLC (10 to 90% acetonitrile in 0.1 N aqueous ammonium acetate over 10 min at 2 mL/min using a Waters Symmetry C18 150×4.6 mm column) 8.1 min.

Step 6: C-Dimethylamino-N-{4-((S)-2-ethoxy-5-oxo-tetrahydro-furan-3-ylsulfamoyl)-3-[(R)-1-methyl-2-(2-methylsulfanyl-benzoimidazol-1-yl)-ethoxy]-phenyl}-acetamide Trifluoroacetic acid 25% in dichloromethane (5 mL) was added to (S)-3-{4-(2-dimethylamino-ethanoylamino)-2-[(R)-1-methyl-2-(2-methylsulfanyl-benzoimidazol-1-yl)-ethoxy]-benzenesulfonylamino}-4,4-diethoxy-butyric acid tert-butyl ester (26 mg, 0.04 mmol). This mixture sat at room temperature for 30 minutes. The solvent was removed under reduced pressure and the residue was azeotroped with dichloromethane/toluene. The product was dried under high vacuum to give C-dimethylamino-N-{4-((S)-2-ethoxy-5-oxo-tetrahydro-furan-3-ylsulfamoyl)-3-[(R)-1-methyl-2-(2-methylsulfanyl-benzoimidazol-1-yl)-ethoxy]-phenyl}-acetamide as an off white powder, 26 mg, 100% as the TFA salt, MS m/z 606 (M+1).

Step 7: (S)-3-=55 4-(2-Dimethylamino-ethanoylamino)-2-[(R)-1-methyl-2-(2-methylsulfanyl-benzoimidazol-1-yl)-ethoxy]-benzenesulfonylamino}-4-oxo-butyric acid To C-dimethylamino-N-{4-((S)-2-ethoxy-5-oxo-tetrahydro-furan-3-ylsulfamoyl)-3-[(R)-1-methyl-2-(2-methylsulfanyl-benzoimidazol-1-yl)-ethoxy]-phenyl}-acetamide (20 mg, 0.02 mmol) was added acetonitrile (1 mL) and 10% aqueous HCl (1 mL). This mixture sat at room temperature overnight. The solvent was removed under a stream of nitrogen to give (S)-3-{4-(2-Dimethylamino-ethanoylamino)-2-[(R)-1-methyl-2-(2-methylsulfanyl-benzoimidazol-1-yl)-ethoxy]-benzenesulfonylamino}-4-oxo-butyric acid (12 mg, 100%) as an off white HCl salt MS m/z 578 (M+1).

EXAMPLE 156
N1-[4-[(2-Ethoxy-5-oxotetrahydro-3-furanyl)amino]sulfonyl-3-((1R)-1-methyl-2-[2-(methylsulfanyl)-1H-benzo[d]imidazol-1-yl]ethyloxy)phenyl]-2-(diethylamino)acetamide Route C, MS m/z 634 (M+1).

(2S)-1-[2-(Methylsulfanyl)-1H-benzo[d]imidazol-1-yl]propan-2-ol employed in the synthesis of N1-[4-[(2-ethoxy-5-oxotetrahydro-3-furanyl)amino]sulfonyl-3-((1R)-1-methyl-2-[2-(methylsulfanyl)-1H-benzo[d]imidazol-1-yl]ethyloxy)phenyl]-2-(diethylamino)acetamide was synthesized in a manner analogous to that used for (S)-benzimidazol-1-yl-1-methyl-ethanol, MS m/z 223 (M+1).

EXAMPLE 157
N1-[4-[(2-Ethoxy-5-oxotetrahydro-3-furanyl)amino]sulfonyl-3-((1R)-1-methyl-2-[2-(methylsulfanyl)-1H-benzo[d]imidazol-1-yl]ethyloxy)-2phenyl]-2-tetrahydro-1H-1-pyrrolylacetamide Route C, MS m/z 632 (M+1).

(2S)-1-[2-(Methylsulfanyl)-1H-benzo[d]imidazol-1-yl]propan-2-ol employed in the synthesis of N1-[4-[(2-ethoxy-5-oxotetrahydro-3-furanyl)amino]sulfonyl-3-((1R)-1-methyl-2-[2-(methylsulfanyl)-1H-benzo[d]imidazol-1-yl]ethyloxy)phenyl]-2-tetrahydro-1H-1-pyrrolylacetamide was synthesized in a manner analogous to that used for (S)-benzimidazol-1-yl-1-methyl-ethanol, MS m/z 223 (M+1).

EXAMPLE 158
N1-4-[(2-Ethoxy-5-oxotetrahydro-3-furanyl)amino]sulfonyl-3-[((1R)-2-2-[(2-methoxyethyl)sulfanyl]-1H-benzo[d]imidazol-1-yl-1-methylethyl)oxy]phenyl-2-(dimethylamino)acetamide Route C, MS m/z 650 (M+1).

(2S)-1-2-[(2-Methoxyethyl)sulfanyl]-1H-benzo[d]imidazol-1-ylpropan-2-ol employed in the synthesis of N1-4-[(2-ethoxy-5-oxotetrahydro-3-furanyl)amino]sulfonyl-3-[((1R)-2-2-[(2-methoxyethyl)sulfanyl]-1H-benzo[d]imidazol-1-yl-1-methylethyl)oxy]phenyl-2-(dimethylamino)acetamide was synthesized in a manner analogous to that used for (S)-benzimidazol-1-yl-1-methyl-ethanol, MS m/z 267 (M+1).

EXAMPLE 159
N1-4-[(2-Ethoxy-5-oxotetrahydro-3-furanyl)amino]sulfonyl-3-[((1R)-2-2-[(2-methoxyethyl)sulfanyl]-1H-benzo[d]imidazol-1-yl-1-methylethyloxy]phenyl-2-tetrahydro-1H-1-pyrrolylacetamide Route C, MS m/z 676 (M+1).

(2S)-1-2-[(2-Methoxyethyl)sulfanyl]-1H-benzo[d]imidazol-1-ylpropan-2-ol employed in the synthesis of N1-4-[(2-ethoxy-5-oxotetrahydro-3-furanyl)amino]sulfonyl-3-[((1R)-2-2-[(2-methoxyethyl)sulfanyl]-1H-benzo[d]imidazol-1-yl-1-methylethyl)oxy]phenyl-2-tetrahydro-1H-1-pyrrolylacetamide was synthesized in a manner analogous to that used for (S)-benzimidazol-1-yl-1-methyl-ethanol, MS m/z 267 (M+1).

EXAMPLE 160
N1-4-[(2-Ethoxy-5-oxotetrahydro-3-furanyl)amino]sulfonyl-3-[((1R)-1-methyl-2-2-[(2-morpholinoethyl)sulfanyl]-1H-benzo[d]imidazol-1-ylethyl oxy]phenyl-2-(dimethylamino)acetamide Route C, MS m/z 705 (M+1).

(2S)-1-2-[(2-Morpholinoethyl)sulfanyl]-1H-benzo[d]imidazol-1-ylpropan-2-ol employed in the synthesis of N1-4-[(2-ethoxy-5-oxotetrahydro-3-furanyl)amino]sulfonyl-3-[((1R)-1-methyl-2-2-[(2-morpholinoethyl)sulfanyl]-1H-benzo[d]imidazol-1-ylethyl)oxy]phenyl-2-(dimethylamino)acetamide was synthesized in a manner analogous to that used for (S)-benzimidazol-1-yl-1-methyl-ethanol, MS m/z 322 (M+1).

EXAMPLE 161
N1-4-[(2-Ethoxy-5-oxotetrahydro-3-furanyl)amino]sulfonyl-3-[((1R)-1-methyl-2-2-[(2-morpholinoethyl)sulfanyl]-1H-benzo[d]imidazol-1-ylethyl)oxy]phenyl-2-tetrahydro-1H-1-pyrrolylacetamide Route C, MS m/z 731(M+1).

(2S)-1-2-[(2-Morpholinoethyl sulfanyl]-1H-benzo[d]imidazol-1-ylpropan-2-ol employed in the synthesis of N1-4-[(2-ethoxy-5-oxotetrahydro-3-furanyl)amino]sulfonyl-3-[((1R)-1-methyl-2-2-[(2-morpholinoethyl)sulfanyl]-1H-benzo[d]imidazol-1-ylethyl)oxy]phenyl-2-tetrahydro-1H-1-pyrrolylacetamide was synthesized in a manner analogous to that used for (S)-benzimidazol-1-yl-1-methyl-ethanol, MS m/z 322 (M+1).

EXAMPLE 162
3-([4-[2-(Diethylamino)acetyl]amino-2-((1R)-1-methyl-2-[2-(methylsulfanyl)-1H-benzo[d]imidazol-1-yl]ethyloxyphenyl]sulfonylamino)-4-oxobutanoic acid Route C, MS m/z 606 (M+1).

(2S)-1-[2-(Methylsulfanyl)-1H-benzo[d]imidazol-1-yl]propan-2-ol employed in the synthesis of 3-([4-[2-(diethylamino)acetyl]amino-2-((1R)-1-methyl-2-[2-(methylsulfanyl)-1H-benzo[d]imidazol-1-yl]ethyloxy)phenyl]sulfonylamino)-4-oxobutanoic acid was synthesized in a manner analogous to that used for (S)-benzimidazol-1-yl-1-methyl-ethanol, MS m/z 223 (M+1).

EXAMPLE 163
3-[(2-((1R)-1-Methyl-2-[2-(methylsulfanyl)-1H-benzo[d]imidazol-1-yl]ethyloxy)-4-[(2-tetrahydro-1H-1-pyrrolylacetyl)amino]phenylsulfonyl)amino]-4-oxobutanoic acid Route C, MS m/z 604 (M+1).

(2S)-1-[2-(Methylsulfanyl)-1H-benzo[d]imidazol-1-yl]propan-2-ol employed in the synthesis of 3-[(2-((1R)-1-methyl-2-[2-(methylsulfanyl)-1H-benzo[d]imidazol-1-yl]ethyloxy)-4-[(2-tetrahydro-1H-1-pyrrolylacetyl)amino]phenylsulfonyl)amino]-4-oxobutanoic acid was synthesized in a manner analogous to that used for (S)-benzimidazol-1-yl-1-methyl-ethanol, MS m/z 223 (M+1).

EXAMPLE 164
3-[(4-[2-(Dimethylamino)acetyl]amino-2-[((1R)-2-2-[(2-methoxyethyl)sulfanyl]-1H-benzo[d]imidazol-1-yl-1-methylethyl oxy]phenylsulfonyl)amino]-4-oxobutanoic acid Route C, MS m/z 622(M+1).

(2S)-1-2-[(2-Methoxyethyl)sulfanyl]-1H-benzo[d]imidazol-1-ylpropan-2-ol employed in the synthesis of 3-[(4-[2-(dimethylamino)acetyl]amino-2-[((1R)-2-2-[(2-methoxyethyl)sulfanyl]-1H-benzo[d]imidazol-1-yl-1-methylethyl)oxy]phenylsulfonyl)amino]-4-oxobutanoic acid was synthesized in a manner analogous to that used for (S)-benzimidazol-1-yl-1-methyl-ethanol, MS m/z 267 (M+1).

EXAMPLE 165
3-[(2-[((1R)-2-2-[(2-methoxyethyl)sulfanyl]-1H-benzo[d]imidazol-1-yl-1-methylethyl)oxy]-4-[(2-tetrahydro-1H-1-pyrrolylacetyl)amino]phenylsulfonyl)amino]-4-oxobutanoic acid Route C, MS m/z 648 (M+1).

(2S)-1-2-[(2-Methoxyethyl)sulfanyl]-1H-benzo[d]imidazol-1-ylpropan-2-ol employed in the synthesis of 3-[(2-[((1R)-2-2-[(2-methoxyethyl)sulfanyl]-1H-benzo[d]imidazol-1-yl-1-methylethyl)oxy]-4-[(2-tetrahydro-1H-1-pyrrolylacetyl)amino]phenylsulfonyl)amino]-4-oxobutanoic acid was synthesized in a manner analogous to that used for (S)-benzimidazol-1-yl-1-methyl-ethanol, MS m/z 267 (M+1).

EXAMPLE 166
3-[(4-[2-(Dimethylamino)acetyl]amino-2-[((1R)-1-methyl-2-2-[(2-morpholinoethyl sulfanyl]-1H-benzo[d]imidazol-1-ylethyl oxy]phenylsulfonyl)amino]-4-oxobutanoic acid Route C, MS m/z 677(M+1).

(2S)-1-2-[(2-morpholinoethyl)sulfanyl]-1H-benzo[d]imidazol-1-ylpropan-2-ol employed in the synthesis of 3-[(4-[2-(dimethylamino)acetyl]amino-2-[((1R)-1-methyl-2-2-[(2-morpholinoethyl)sulfanyl]-1H-benzo[d]imidazol-1-ylethyl)oxy]phenylsulfonyl)amino]-4-oxobutanoic acid was synthesized in a manner analogous to that used for (S)-benzimidazol-1-yl-1-methyl-ethanol, MS m/z 322 (M+1).

EXAMPLE 167
3-[(2-[((1R)-1-methyl-2-2-[(2-morpholinoethyl)sulfanyl]-1H-benzo[d]imidazol-1-ylethyl)oxy]-4-[(2-tetrahydro-1H-1-pyrrolylacetyl)amino]phenylsulfonyl)amino]-4-oxobutanoic acid Route C, MS m/z 703(M+1).

(2S)-1-2-[(2-Morpholinoethyl)sulfanyl]-1H-benzo[d]imidazol-1-ylpropan-2-ol employed in the synthesis of 3-[(2-[((1R)-1-methyl-2-2-[(2-morpholinoethyl)sulfanyl]-1H-benzo[d]imidazol-1-ylethyl)oxy]-4-[(2-tetrahydro-1H-1-pyrrolylacetyl)amino]phenylsulfonyl)amino]-4-oxobutanoic acid was synthesized in a manner analogous to that used for (S)-benzimidazol-1-yl-1-methyl-ethanol, MS m/z 322 (M+1).

EXAMPLE 168
3-[4-(2-[[2-(dimethylamino)ethyl](methyl amino]acetylamino)-2-((1R)-1-methyl-2-[2-(methylsulfanyl)-1H-benzo[d]imidazol-1-yl]ethyloxy)phenyl]sulfonylamino)-4-oxobutanoic acid Route C, MS m/z 635(M+1).

(2S)-1-[2-(Methylsulfanyl)-1H-benzo[d]imidazol-1-yl]propan-2-ol employed in the synthesis of 3-([4-(2-[[2-(dimethylamino)ethyl](methyl)amino]acetylamino)-2-((1R)-1-methyl-2-[2-(methylsulfanyl)-1H-benzo[d]imidazol-1-yl]ethyloxy)phenyl]sulfonylamino)-4-oxobutanoic acid was synthesized in a manner analogous to that used for (S)-benzimidazol-1-yl-1-methyl-ethanol, MS m/z 223 (M+1).

EXAMPLE 169
3-[(4-(2-[[2-(dimethylamino)ethyl](methyl)amino]acetylamino)-2-[((1R)-2-2-[(2-methoxyethyl)sulfanyl]-1H-benzo[d]imidazol-1-yl-1-methylethyl)oxy]phenylsulfonyl)amino]-4-oxobutanoic acid Route C, MS m/z 679(M+1).

(2S)-1-2-[(2-Methoxyethyl)sulfanyl]-1H-benzo[d]imidazol-1-ylpropan-2-ol employed in the synthesis of 3-[(4-(2-[[2-(dimethylamino)ethyl](methyl)amino]acetylamino)-2-[((1R)-2-2-[(2-methoxyethyl)sulfanyl]-1H-benzo[d]imidazol-1-yl-1-methylethyl)oxy]phenylsulfonyl)amino]-4-oxobutanoic acid was synthesized in a manner analogous to that used for (S)-benzimidazol-1-yl-1-methyl-ethanol, MS m/z 267 (M+1).

EXAMPLE 170
3-[(4-(2-[[2-(dimethylamino)ethyl](methyl)amino]acetylamino)-2-[((1R)-1-methyl-2-2-[(2-morpholinoethyl)sulfanyl]-1H-benzo[d]imidazol-1-ylethyl)oxy]phenylsulfonyl)amino]-4-oxobutanoic acid Route C, MS m/z 734 (M+1).

(2S)-1-2-[(2-Morpholinoethyl)sulfanyl]-1H-benzo[d]imidazol-1-ylpropan-2-ol employed in the synthesis of 3-[(4-(2-[[2-(dimethylamino)ethyl](methyl)amino]acetylamino)-2-[((1R)-1-methyl-2-2-[(2-morpholinoethyl)sulfanyl]-1H-benzo[d]imidazol-1-ylethyl)oxy]phenylsulfonyl)amino]-4-oxobutanoic acid was synthesized in a manner analogous to that used for (S)-benzimidazol-1-yl-1-methyl-ethanol, MS m/z 322 (M+1).

EXAMPLE 171
4-[3-(2-Dimethylamino-ethyl)-ureido]-N-((S)-2-ethoxy-5-oxo-tetrahdro-furan-3-yl)-2-(2-quinolin-5-yl-ethoxy)-benzenesulfonamide and (S)-3-[4-[3-(2-Dimethylamino-ethyl)-ureido]-2-(2-quinolin-5-yl-ethoxy)-benzenesulfonylamino]-4-oxo-butyric acid Step 1: (S)-3-{2-Benzyloxy-4-[3-(2-dimethylamino-ethyl)-ureido]-benzenesulfonylamino}-4,4-diethoxy-butyric acid tert-butyl ester To (S)-3-(4-amino-2-benzyloxy-benzenesulfonylamino)-4,4-diethoxy-butryic acid tert-butyl ester, from Route J step 7, (2.4 g, 4.7 mmol) in dichloromethane (120 mL) in a 1000 mL separatory funnel was added, in this order, saturated sodium bicarbonate (120 mL) and ice (120 mL) followed by 20% phosgene in toluene (18.4 mL, 7.5 equiv.). The separatory funnel was inverted and vigorously shaken for 10 min while continuously venting. Dichloromethane and water were then added and the organic layer was removed. The aqueous phase was then extracted with dichloromethane. The combined organic layers were washed with brine and dried over magnesium sulfate. The solvent was removed under reduced pressure, to give the crude isocyanate that was taken up in dichloromethane (50 mL). To this solution was added N,N-dimethylethyenediamine (0.77 mL, 7.0 mmol). After 30 min the solvent was removed under reduced pressure and the residue was chromatographed on silica gel 10%(8:1, ethanol/ammonium hydroxide) in dichloromethane to give (S)-3-{2-benzyloxy-4-[3-(2-dimethylamino-ethyl)-ureido]-benzenesulfonylamino}-4,4-diethoxy-butyric acid tert-butyl ester as a yellow foam 1.80 g (62%). MS (APCI) m/z 623.5 (M+1).

Step 2: (S)-3-{4-[3-(2-Dimethylamino-ethyl)-ureido]-2-hydroxy-benzenesulfonylamino}-4,4-diethoxy-butyric acid tert-butyl ester To (S)-3-{2-benzyloxy-4-[3-(2-dimethylamino-ethyl)-ureido]-benzenesulfonylamino}-4,4-diethoxy-butyric acid tert-butyl ester (1.80 g, 2.9 mmol) in ethanol (100 mL) was added 20% Pd on carbon (250 mg) and stirred under 1 atmosphere of hydrogen for 24 h. The reaction was judged complete by thin layer analysis and filtered. The filtrate was evaporated to give (S)-3-{4-[3-(2-dimethylamino-ethyl)-ureido]-2-hydroxy-benzenesulfonylamino}-4,4-diethoxy-butyric acid tert-butyl ester as a colorless foam 1.54 g (100%). MS (APCI) m/z 533.4 (M+1).

Step 3: (S)-3-[4-[3-(2-Dimethylamino-ethyl)-ureido]-2-(2-quinolin-5-yl-ethoxy)-benzenesulfonylamino]-4,4-diethoxy butryric acid tert-butyl ester To (S)-3-{4-[3-(2-dimethylamino-ethyl)-ureido]-2-hydroxy-benzenesulfonylamino}-4,4-diethoxy-butyric acid tert-butyl ester (1.54 g, 2.9 mmol) in dichloromethane (30 mL) was added 2-quinolin-5-yl ethanol (525 mg, 3.0 mmol), triphenyl phosphine (1.13 g, 4.3 mmol), and diethylazodicarboxylate (680 µL, 4.3 mmol). The reaction stirred for 2 h and was loaded directly on to a silica gel column. Elution with 13% (8:1, ethanol/ammonium hydroxide) in dichloromethane provided (S)-3-[4-[3-(2-dimethylamino-ethyl)-ureido]-2-(2-quinolin-5-yl-ethoxy)-benzenesulfonylamino]-4,4-diethoxy butryric acid tert-butyl ester as a yellow foam (1.53 g, 77%). MS (APCI) m/z 688.5 (M+1).

Step 4: 4-[3-(2-Dimethylamino-ethyl)-ureido]-N-((S)-2-ethoxy-5-oxo-tetrahydro-furan-3-yl)-2-(2-quinolin-5-yl-ethoxy)-benzenesulfonamide and (S)-3-[4-[3-(2-Dimethylamino-ethyl)-ureido]-2-(2-quinolin-5-yl-ethoxy)-benzenesulfonylamino]-4oxo-butyric acid To (S)-3-[4-[3-(2-dimethylamino-ethyl)-ureido]-2-(2-quinolin-5-yl-ethoxy)-benzenesulfonylamino]-4,4-diethoxy butryric acid tert-butyl ester (1.53 g, 2.2 mmol) was added 4:1 dichloromethane/trifluoroacteic acid (50 mL). The reaction stirred for 1.5 h and toluene (50 mL) was added the solvent was removed under reduced pressure to give a foam, lyopholyzation from acetonitrile/water gave 4-[3-(2-dimethylamino-ethyl)-ureido]-N-((S)-2-ethoxy-5-oxo-tetrahydro-furan-3-yl)-2-(2-quinolin-5-yl-ethoxy)-benzenesulfonamide as a yellow solid. MS (APCI) m/z 586.4(M+1). Approximately 0.7 mmol of this material was dissolved in 1:1 acetonitrile/water (25 mL) and treated with trifluoroacetic acid (2.5 mL) for 24 h. HPLC analysis indicated the hydrolysis was complete. Water (100 mL) was added and the solution was lyopholyzed to give (S)-3-[4-[3-(2-Dimethylamino-ethyl)-ureido]-2-(2-quinolin-5-yl-ethoxy)-benzenesulfonylamino]-4-oxo-butyric acid as a yellow solid (440 mg). $^1$H NMR (300 mHz, CD$_3$OD) 9.58(d, 1H), 9.20(d,1H), 8.20–8.00(m, 4H), 7.62(d,1H), 7.53(m, 1H), 6.93(dt, 1H), 4.54(m,2H), 4.35(d,1/2H), 4.24(d,1/2H), 3.84(m,2H), 3.58(t,2H), 3.43(m,1H), 2.96(m,6H), 2.44–2.10 (m,2H).

EXAMPLE 172

N1-[4-[(2-Ethoxy-5-oxotetrahydro-3-furanyl]amino]sulfonyl-3-((1R)-1-methyl-2-[2-(methylsulfanyl)-1H-benzo[d]imidazol-1-yl]ethyloxy)phenyl]-2-morpholinoacetamide Route C, MS m/z 648 (M+1).

(2S)-1-[2-(Methylsulfanyl)-1H-benzo[d]imidazol-1-yl]propan-2-ol employed in the synthesis of N1-[4-[(2-ethoxy-5-oxotetrahydro-3-furanyl)amino]sulfonyl-3-((1R)-1-methyl-2-[2-(methylsulfanyl)-1H-benzo[d]imidazol-1-yl]ethyloxy)phenyl]-2-morpholinoacetamide was synthesized in a manner analogous to that used for (S)-benzimidazol-1-yl-1-methyl-ethanol, MS m/z 223 (M+1).

EXAMPLE 173

N1-[4-[(2-Ethoxy-5-oxotetrahydro-3-furanyl)amino]sulfonyl-3-((1R)-1-methyl-2-[2-(methylsulfanyl)-1H-benzo[d]imidazol-1-yl]ethyloxyphenyl]-2-(4-methylpiperazino)acetamide Route C, MS m/z 661 (M+1).

(2S)-1-[2-(Methylsulfanyl)-1H-benzo[d]imidazol-1-yl]propan-2-ol employed in the synthesis of N1-[4-[(2-ethoxy-5-oxotetrahydro-3-furanyl)amino]sulfonyl-3-((1R)-1-methyl-2-[2-(methylsulfanyl)-1H-benzo[d]imidazol-1-yl]ethyloxy)phenyl]-2-(4-methylpiperazino)acetamide was synthesized in a manner analogous to that used for (S)-benzimidazol-1-yl-1-methyl-ethanol, MS m/z 223 (M+1).

EXAMPLE 174

N1-[4-[(2-Ethoxy-5-oxotetrahydro-3-furanyl)amino]sulfonyl-3-((1R)-1-methyl-2-[2-(methylsulfanyl)-1H-benzo[d]imidazol-1-yl]ethyloxy)phenyl]-2-(4-hydroxypiperidino)acetamide Route C, MS m/z 662 (M+1).

(2S)-1-[2-(Methylsulfanyl)-1H-benzo[d]imidazol-1-yl]propan-2-ol employed in the synthesis of N1-[4-[(2-ethoxy-5-oxotetrahydro-3-furanyl)amino]sulfonyl-3-((1R)-1-methyl-2-[2-(methylsulfanyl)-1H-benzo[d]imidazol-1-yl]ethyloxy)phenyl]-2-(4-hydroxypiperidino)acetamide was synthesized in a manner analogous to that used for (S)-benzimidazol-1-yl-1-methyl-ethanol, MS m/z 223 (M+1).

EXAMPLE 175

N1-[4-[(2-Ethoxy-5-oxotetrahydro-3-furanyl)amino]sulfonyl-3-((1R-11-methyl-2-[2-(methylsulfanyl-1H-benzo[d]imidazol-1-yl]ethyloxy)phenyl]-2-[4-(2-hydroxyethyl piperazino]acetamide Route C, MS m/z 691 (M+1).

(2S)-1-[2-(Methylsulfanyl)-1H-benzo[d]imidazol-1-yl]propan-2-ol employed in the synthesis of N1-[4-[(2-ethoxy-5-oxotetrahydro-3-furanyl)amino]sulfonyl-3-((1R)-1-methyl-2-[2-(methylsulfanyl)-1H-benzo[d]imidazol-1-yl]ethyloxy)phenyl]-2-[4-(2-hydroxyethyl)piperazino]acetamide was synthesized in a manner analogous to that used for (S)-benzimidazol-1-yl-1-methyl-ethanol, MS m/z 223 (M+1).

EXAMPLE 176

3-[(2-((1R)-1-Methyl-2-[2-(methylsulfanyl-1H-benzo[d]imidazol-1-yl]ethyloxy)-4-[(2-morpholinoacetyl)amino]phenylsulfonyl)amino]-4-oxobutanoic acid Route C, MS m/z 620(M+1).

(2S)-1-[2-(Methylsulfanyl)-1H-benzo[d]imidazol-1-yl]propan-2-ol employed in the synthesis of 3-[(2-((1R)-1-methyl-2-[2-(methylsulfanyl)-1H-benzo[d]imidazol-1-yl]ethyloxy)-4-[(2-morpholinoacetyl)amino]phenylsulfonyl)amino]-4-oxobutanoic acid was synthesized in a manner analogous to that used for (S)-benzimidazol-1-yl-1-methyl-ethanol, MS m/z 223 (M+1).

EXAMPLE 177

3-[(2-((1R)-1-Methyl-2-[2-(methylsulfanyl)-1H-benzo[d]imidazol-1-yl]ethyloxy)-4-[2-(4-methylpiperazino)acetyl]aminophenyl)sulfonyl]amino-4-oxobutanoic acid Route C, MS m/z 633 (M+1).

(2S)-1-[2-(Methylsulfanyl)-1H-benzo[d]imidazol-1-yl]propan-2-ol emplyed in the synthesis of 3-[(2-((1R)-1-methyl-2-[2-(methylsulfanyl)-1H-benzo[d]imidazol-1-yl]ethyloxy)-4-[2-(4-methylpiperazino)acetyl]aminophenyl)sulfonyl]amino-4-oxobutanoic acid was synthesized in a manner analogous to that used for (S)-benzimidazol-1-yl-1-methyl-ethanol, MS m/z 223 (M+1).

EXAMPLE 178

3-([4-[2-(4-Hydroxypiperidino)acetyl]amino-2-((1R)-1-methyl-2-[2-(methylsulfanyl)-1H-benzo[d]imidazol-1-yl]ethloxyphenyl]sulfonylamino)-4-oxobutanoic acid HPLC 2.23 min method a, MS m/z 634 (M+1).

(2S)-1-[2-(Methylsulfanyl)-1H-benzo[d]imidazol-1-yl]propan-2-ol employed in the synthesis of 3-([4-[2-(4-hydroxypiperidino)acetyl]amino-2-((1R)-1-methyl-2-[2-(methylsulfanyl)-1H-benzo[d]imidazol-1-yl]ethyloxy)phenyl]sulfonylamino)-4-oxobutanoic acid was synthesized in a manner analogous to that used for (S)-benzimidazol-1-yl-1-methyl-ethanol, MS m/z 223 (M+1).

EXAMPLE 179

3-([4-(2-[4-(2-hydroxyethyl piperazino]acetylamino)-2-((1R)-1-methyl-2-[2-(methylsulfanyl)-1H-benzo[d]imidazol-1-yl]ethyloxy)phenyl]sulfonylamino)-4-oxobutanoic acid Route C, MS m/z 663(+1).

(2S)-1-[2-(Methylsulfanyl)-1H-benzo[d]imidazol-1-yl]pro an-2-ol employed in the synthesis of 3-([4-(2-[4-(2- hydroxyethyl)piperazino]acetylamino)-2-((1R)-1-methyl-2-[2-(methylsulfanyl)-1H-benzo[d]imidazol-1-yl]ethyloxy)phenyl]sulfonylamino)-4-oxobutanoic acid was synthesized in a manner analogous to that used for (S)-benzimidazol-1-yl-1-methyl-ethanol, MS m/z 223 (M+1).

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound represented by generalized structure 1:

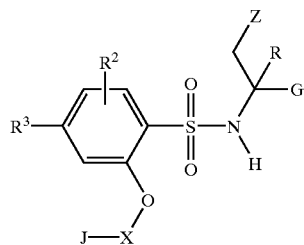

wherein

Z represents carboxylate, alkoxycarbonyl, or aryloxycarbonyl;

G represents formyl or —CN; or

Z, G, and R, together with the carbon atoms in the generalized structure 1 to which they are attached, form a radical of the formula:

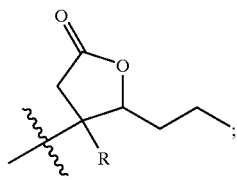

J represents optionally substituted benzimidazolyl, quinolinyl, isoquinolinyl, tetrahydroquinolinyl, adamantyl, azabenzimidazolyl, or indazolyl;

X represents $(C(R)_2)_f$, or $(C(R)_2)_f(C(R)_2)$;

R represents independently for each occurrence H or alkyl;

$R_2$ is absent or present 1, 2, or 3 times;

$R_2$ represents independently for each occurrence alkyl, alkenyl, alkynyl, halogen, formyl, acyl, carboxylate, alkoxycarbonyl, aryloxycarbonyl, carboxamido, alkylamino, acylamino, hydroxyl, alkoxyl, acyloxy, hydroxyalkyl, alkoxyalkyl, aminoalkyl, (alkylamino)alkyl, alkylthio, mercapto, mercaptoalkyl, (alkylthio)alkyl, carbamoyl, ureido, thioureido, sulfonyl, sulfonate, sulfonamido, sulfonylamino, or sulfonyloxy;

$R_3$ represents hydrogen, alkoxyl, amino, alkylamino, dialkylamino, (aminoalkyl)amino, ((alkylamino)alkyl)amino, ((dialkylamino)alkyl)amino, acylamino, (aminoacyl)amino, ((alkylamino)acyl)amino, ((dialkylamino)acyl)amino, (heterocyclyl)acylamino, carboxamido, (aminoalkyl)carboxamido, (alkylamino)alkyl)carboxamido, (dialkylamino)alkyl)carboxamido, sulfonylamino, urea, thiourea, —C(O)N(R)N(R)$_2$, —C(O)N(R)C(R)$_2$CO$_2$H, or —C(O)N(R)C(R)$_2$C(O)N(R)$_2$;

f represents 1, 2, or 3; and the stereochemical configuration at any stereocenter of a compound represented by 1 may be R, S, or a mixture of these configurations, and the pharmaceutically acceptable salts, thereof.

2. The compound of claim 1, wherein Z represents carboxylate.

3. The compound of claim 1, wherein G represents formyl.

4. The compound of claim 1, wherein X represents $(CH(R))_f$.

5. The compound of claim 1, wherein $R^2$ is absent.

6. The compound of claim 1, wherein f is 2.

7. The compound of claim 1, wherein Z represents carboxylate; and G represents formyl.

8. The compound of claim 1, wherein Z represents carboxylate; G represents formyl; and X represents $(CH(R))_f$.

9. The compound of claim 1, wherein Z represents carboxylate; G represents formyl; and $R^2$ is absent.

10. The compound of claim 1, wherein Z represents carboxylate; G represents formyl; and f is 2.

11. The compound of claim 1, wherein Z represents carboxylate; G represents formyl; X represents $(CH(R))_f$; and $R^2$ is absent.

12. The compound of claim 1, wherein Z represents carboxylate; G represents formyl; X represents $(CH(R))_f$; and f is 2.

13. The compound of claim 1, wherein Z represents carboxylate; G represents formyl; $R^2$ is absent; and f is 2.

14. The compound of claim 1, wherein Z represents carboxylate; G represents formyl; X represents $(CH(R))_f$; $R^2$ is absent; and f is 2.

15. A compound represented by generalized structure 2:

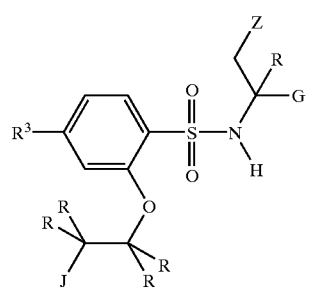

wherein

Z represents carboxylate, alkoxycarbonyl, or aryloxycarbonyl;

G represents formyl or —CN; or

Z, G, and R, together with the carbon atoms in the generalized structure 2 to which they are attached, form a radical of the formula:

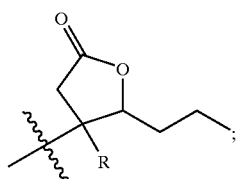

J represents optionally substituted 1-, 4-, or 7-benzimidazolyl, 4-, or 5-quinolinyl, 4-isoquinolinyl, 5-tetrahydroquinolinyl, 1-adamantyl, 4-azabenzimidazol-3-yl, or 1-indazolyl;

R represents independently for each occurrence H or alkyl;

$R_3$ represents hydrogen, alkoxyl, amino, alkylamino, dialkylamino, (aminoalkyl)amino, ((alkylamino)alkyl)amino, ((dialkylamino)alkyl)amino, acylamino, (aminoacyl)amino, ((alkylamino)acyl)amino, ((dialkylamino)acyl)amino, (heterocyclyl)acylamino, carboxamido, (aminoalkyl)carboxamido, ((alkylamino)alkyl)carboxamido, ((dialkylamino)alkyl)carboxamido, sulfonylamino, urea, thiourea, —C(O)N(R)N(R)$_2$, —C(O)N(R)C(R)$_2$CO$_2$H, or —C(O)N(R)C(R)$_2$C(O)N(R)$_2$; and the stereochemical configuration at any stereocenter of a compound represented by 2 may be R, S, or a mixture of these configurations, and the pharmaceutically acceptable salts thereof.

16. The compound of claim 15, wherein $R^3$ is selected from the group consisting of:

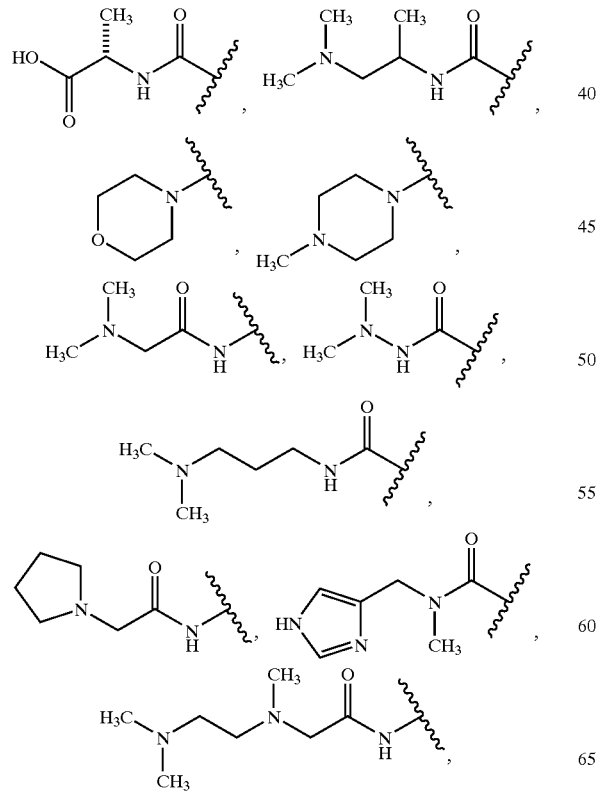

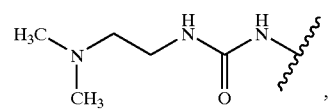

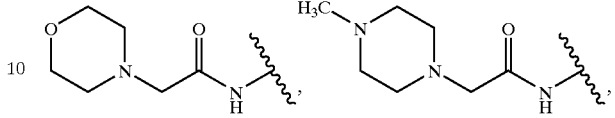

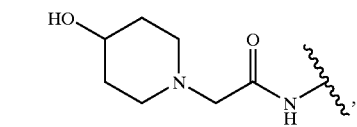

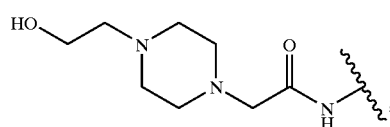

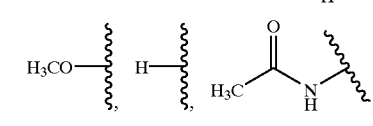

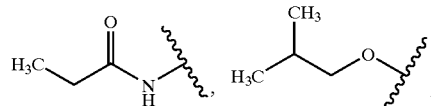

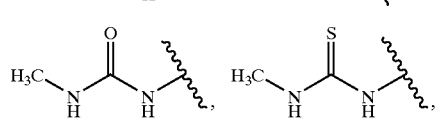

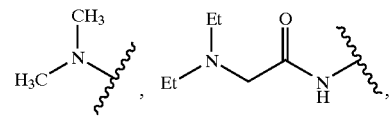

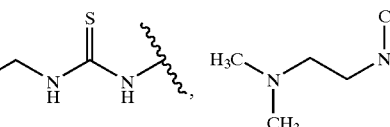

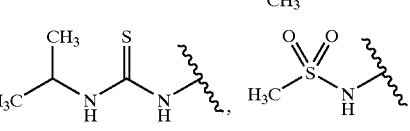

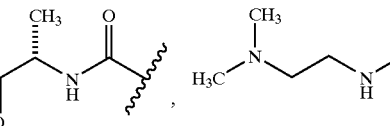

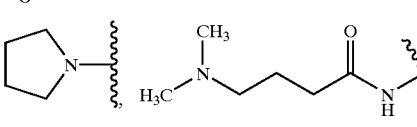

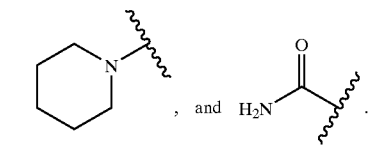

17. The compound of claim 15, wherein J is selected from the group
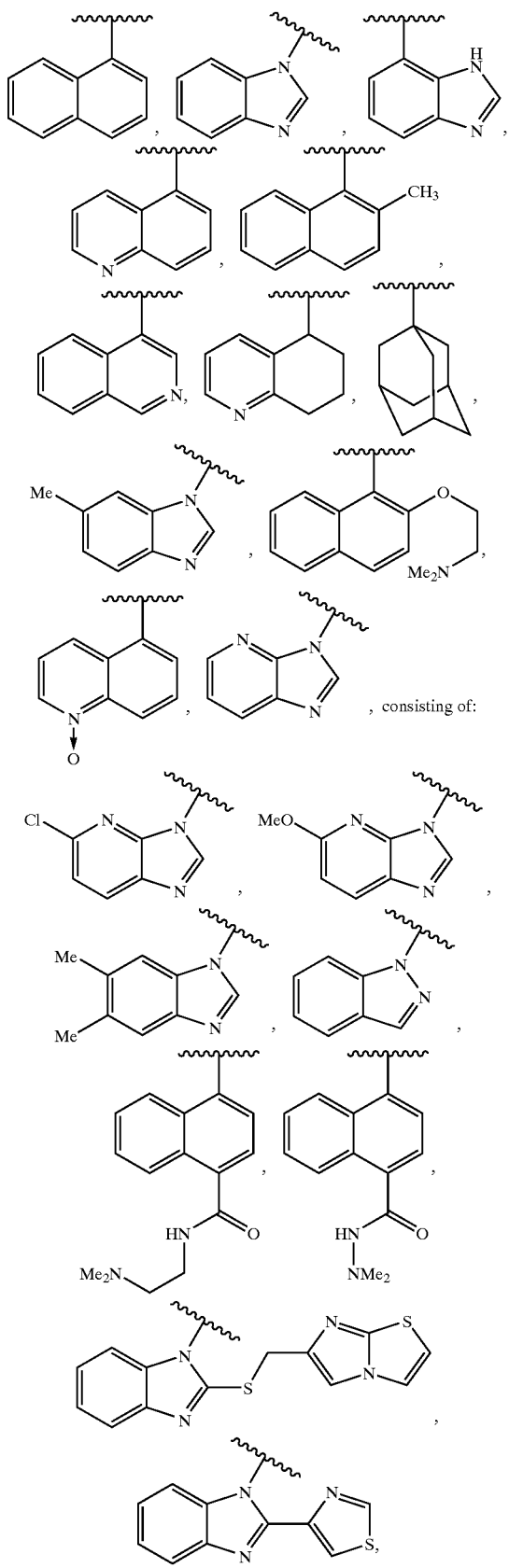
consisting of:
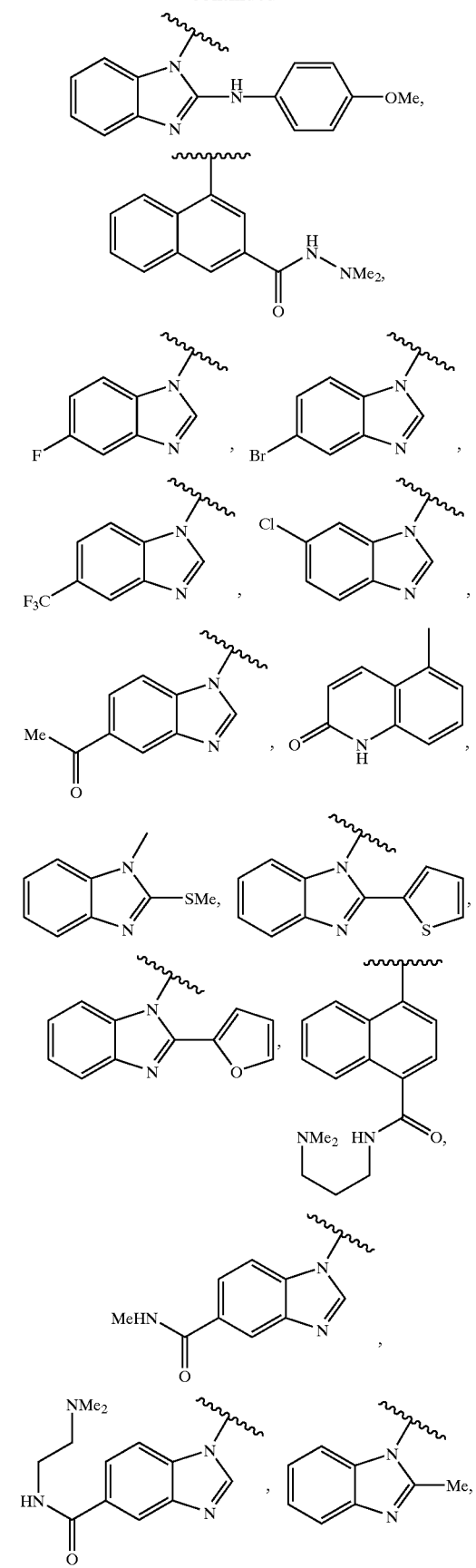

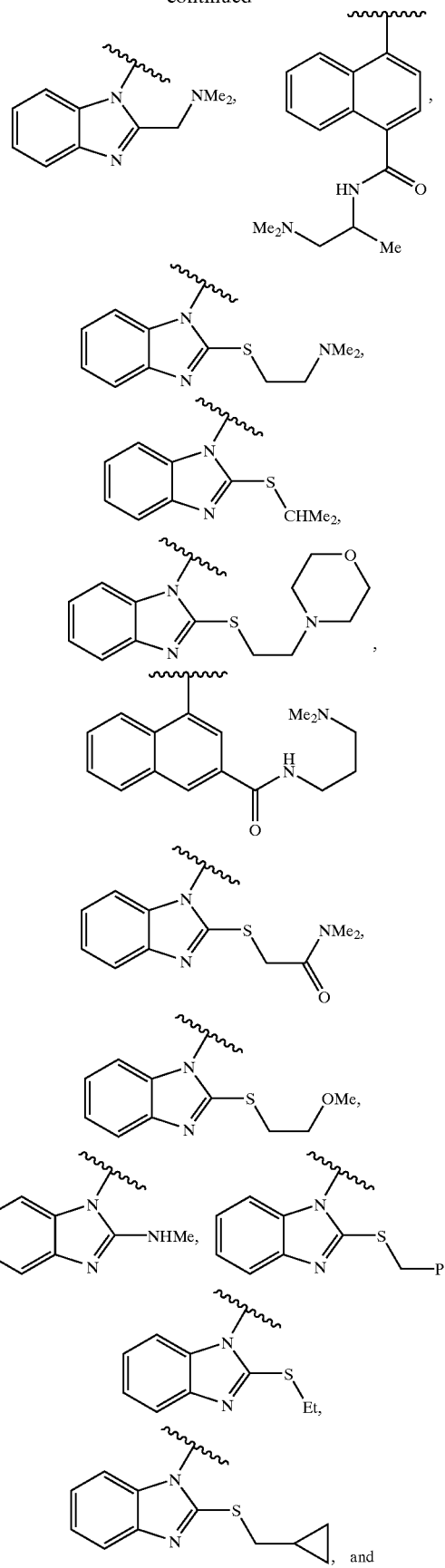
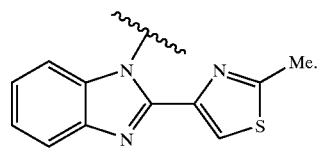
18. The compound of claim 16, wherein J is selected from the group
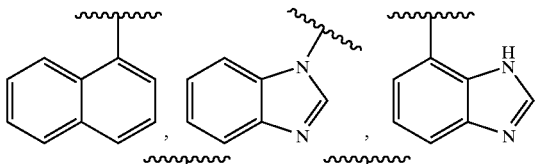
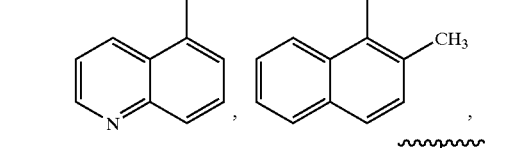
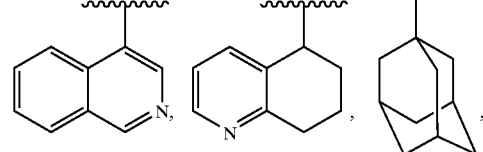
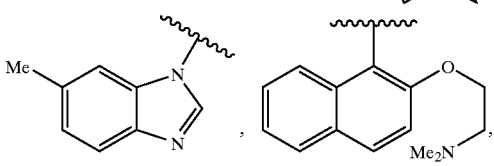
, consisting of:
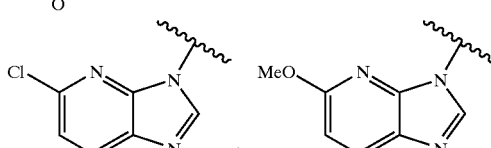
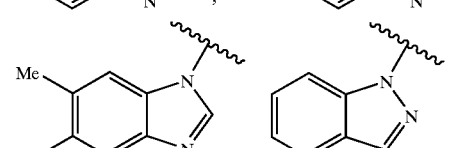
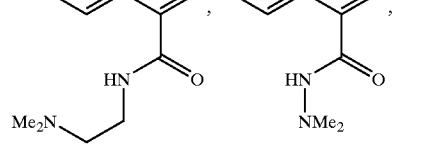

-continued
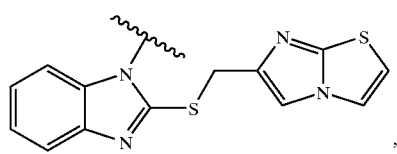,
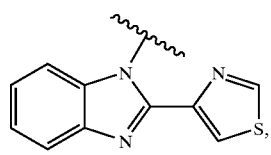,
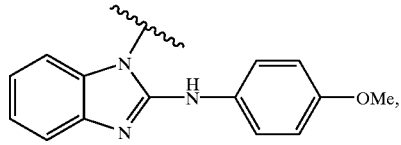,
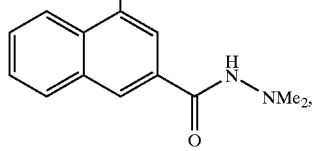,
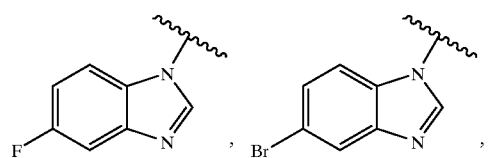,
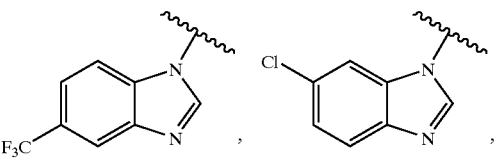,
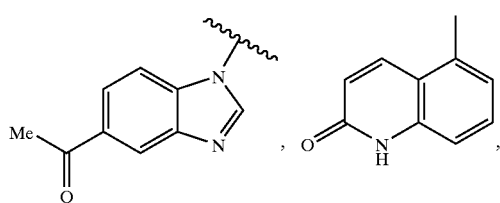,
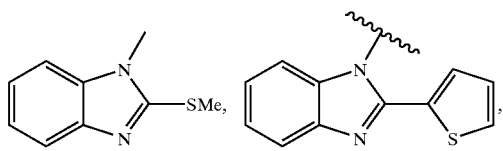,
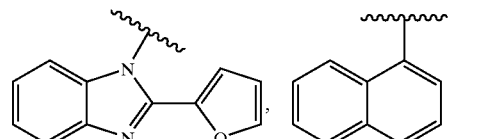,
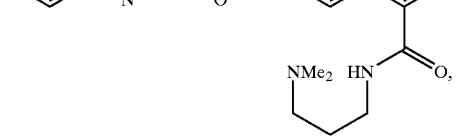,
-continued
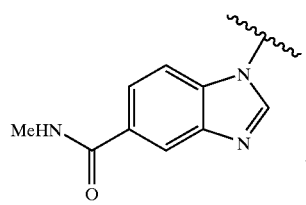,
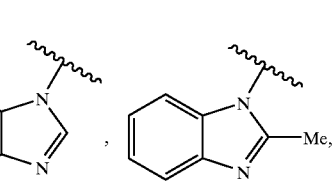,
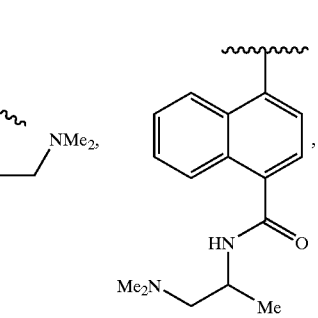,
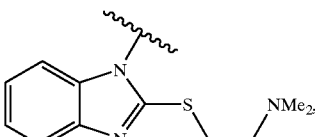,
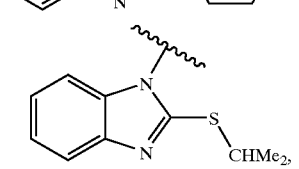,
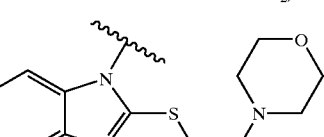,
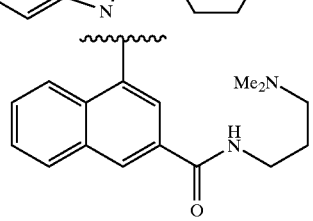,
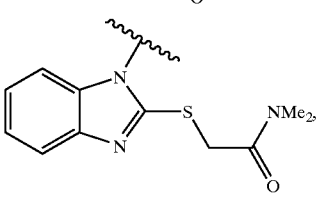,
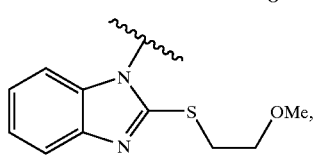,

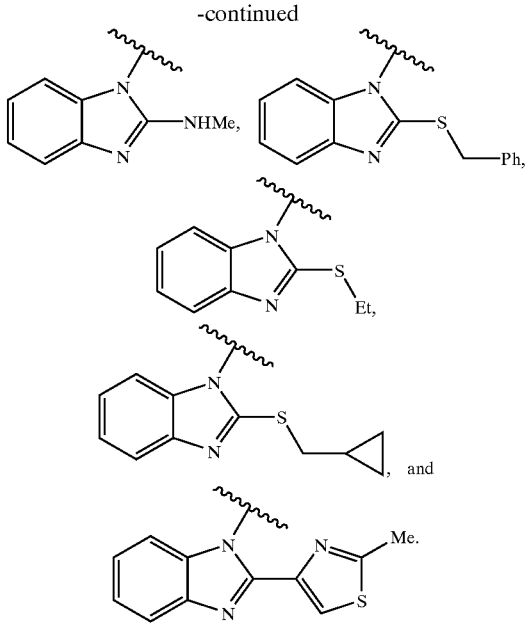

19. The compound of claim 17, wherein Z represents carboxylate.

20. The compound of claim 17, wherein G represents formyl.

21. The compound of claim 17, wherein R represents independently for each occurrence hydrogen or methyl.

22. The compound of claim 17, wherein Z represents carboxylate; and G represents formyl.

23. The compound of claim 17, wherein Z represents carboxylate; G represents formyl; and R represents independently for each occurrence hydrogen or methyl.

24. The compound of claim 1 or 15, wherein said compound has an $IC_{50}$ less than 1 $\mu$M against an interleukin converting enzyme.

25. The compound of claim 1 or 15, wherein said compound has an $IC_{50}$ less than 500 nM against an interleukin converting enzyme.

26. The compound of claim 1 or 15, wherein said compound has an $IC_{50}$ less than 250 nM against an interleukin converting enzyme.

27. A pharaceutical composition comprising a compound of any of claims 1–14 and a pharmaceutically acceptable carrier thereof.

28. A pharmaceutical composition comprising a compound of any of claims 15–23 and a pharmaceutically acceptable carrier thereof.

29. A method of treating arthritis, comprising administrering to a patient having arthritis a therapeutically effective amount of a compound of claim 1 or 15.

* * * * *